US009758481B2

(12) United States Patent
Toretsky et al.

(10) Patent No.: US 9,758,481 B2
(45) Date of Patent: *Sep. 12, 2017

(54) TARGETING OF EWS-FLI1 AS ANTI-TUMOR THERAPY

(71) Applicant: Georgetown University, Washington, DC (US)

(72) Inventors: Jeffrey A. Toretsky, Silver Spring, MD (US); Aykut Uren, Rockville, MD (US); Milton Lang Brown, Brookville, MD (US); Yali Kong, Centerville, VA (US)

(73) Assignee: GEORGETOWN UNIVERSITY, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/696,005

(22) Filed: Apr. 24, 2015

(65) Prior Publication Data

US 2015/0329488 A1 Nov. 19, 2015

Related U.S. Application Data

(63) Continuation of application No. 12/720,616, filed on Mar. 9, 2010, now Pat. No. 9,045,415, which is a continuation of application No. 12/494,191, filed on Jun. 29, 2009, now Pat. No. 8,232,310, which is a continuation-in-part of application No. PCT/US2007/089118, filed on Dec. 28, 2007.

(60) Provisional application No. 60/877,856, filed on Dec. 29, 2006, provisional application No. 61/177,932, filed on May 13, 2009.

(51) Int. Cl.
| | | |
|---|---|---|
| C07D 209/38 | (2006.01) |
| A61K 31/404 | (2006.01) |
| C07D 401/06 | (2006.01) |
| A61K 38/00 | (2006.01) |
| C07K 7/08 | (2006.01) |
| C07K 7/06 | (2006.01) |
| A61K 45/06 | (2006.01) |

(52) U.S. Cl.
CPC .......... *C07D 209/38* (2013.01); *A61K 31/404* (2013.01); *A61K 45/06* (2013.01); *C07D 401/06* (2013.01); *C07K 7/06* (2013.01); *C07K 7/08* (2013.01); *A61K 38/00* (2013.01)

(58) Field of Classification Search
CPC ............................ C07D 209/38; C07D 401/06
See application file for complete search history.

(56) References Cited

U.S. PATENT DOCUMENTS

| 6,969,729 B2* | 11/2005 | Jensen ................. C07D 209/60 514/415 |
| 8,232,310 B2 | 7/2012 | Toretsky et al. |
| 8,232,410 B2 | 7/2012 | Ojima et al. |
| 9,045,415 B2 | 6/2015 | Toretsky et al. |
| 9,290,449 B2 | 3/2016 | Toretsky et al. |
| 9,511,050 B2* | 12/2016 | Toretsky .............. C07D 209/38 |
| 2005/0288244 A1 | 12/2005 | Manoharan et al. |
| 2010/0004179 A1 | 1/2010 | Toretsky et al. |
| 2010/0167994 A1 | 7/2010 | Toretsky et al. |
| 2015/0051260 A1 | 2/2015 | Toretsky et al. |

FOREIGN PATENT DOCUMENTS

| CN | 1365972 A | 8/2002 |
| EP | 0133244 A2 | 2/1985 |
| WO | WO 03/000925 A1 | 1/2003 |
| WO | WO 2006/117414 A1 | 11/2006 |
| WO | WO 2008/083326 | 7/2008 |

OTHER PUBLICATIONS

RN 900016-35-5 (Registry, 2H-Indol-2-one, 7-chloro-1, 3-dihydro-3-hydroxy-3-[2-oxo-2-(3, 4, 5-trimethoxyphenyl) ethyl Aug 9, 2006).*
RN 848688-25-5 (2H-Indol-2-one, 4, 6-dichloro-3-[2-(2, 4-dimethoxyphenyl)-2-oxoethyl]-1, 3- dihydro-3-hydroxy Apr. 18, 2005).*
RN 667914-33-2 (2H-Indol-2-one, 4, 7-dichloro-3-[2-(4-chlorophenyl)-2-oxoethyl]-1, 3-dihydro-3-hydroxy Mar. 26, 2004).*
National Center for Biotechnology Information. (PubChem Substance Database; SID=862348, https://pubchem.ncbi.nlm.nih.gov/substance/862348, downloaded Jan. 2, 2017, available Jun. 29, 2005).*
Database Registry [Online] Chemical Abstracts Service, Columbus, Ohio, US; Oct. 16, 2001 (Oct. 26, 2001), XP00274532, Database accession No. 36506-54-5.
Database Registry [Online] Chemical Abstracts Service, Columbus, Ohio, US; Oct. 16, 2001 (Oct. 16, 2001), XP002745330, Database accession No. 362507-29-7.
Database Registry [Online] Chemical Abstracts Service, Columbus, Ohio, US; May 8, 2009 (May 8, 2009), XP002745331, Database accession No. 1144428-37-4.
Abaan et al., "PTPL1 is a direct transcriptional target of EWS-FLI1 and modulates Ewing's sarcoma tomorigenesis", Oncogene (2005) 24(16): 2715-2722.
Ankhiwala, Studies in Spiroheterocycles. Synthesis and Antimicrobial Activities of Some New Spiro (indoline-3, 5'-pyrazonlin)-1'-phenyl-2-ones and Spiro . . . ; J Indian Chem Soc. (1990) 67: 432-434.
Baer et al., "Profiling and functional annotation of mRNA gene expression in pediatric rhabdomyosarcoma and Ewing's sarcoma", Int J Cancer (2004) 110(5):687-694.
Bayoumy et al., "Studies on Spiroheterocyclic Nitrogen Compounds. Part 1: Synthesis of Some New Spiro Pyrazolines, Isoxazolines and Pyrimidinethiones Containing Benzanilide Moiety", J Indian Chem Soc. (1984) LXI(1):520-522.

(Continued)

*Primary Examiner* — Peter J Redding
(74) *Attorney, Agent, or Firm* — Knobbe, Martens, Olson & Bear LLP

(57) ABSTRACT

Peptides and compounds are provided that function as EWS-FLI1 protein inhibitors. The peptides and compounds have utility in the treatment of Ewing's sarcoma family of tumors. Also provided are methods of preparing the compounds and assays for identifying inhibitors of EWS-FLI1 protein.

20 Claims, 66 Drawing Sheets

(56) References Cited

OTHER PUBLICATIONS

Berg et al., "Small-molecule antagonists of Myc/Max dimerization inhibit Myc-induced transformation of chicken embryo fibroblasts", Proc Natl Acad Sci U S A (2002) 99(6):3830-3835.
Bhalla et al., "Local flexibility in molecular function paradigm", Mol Cell Proteomics (2006) 5:1212-1223.
Bowdish et al., "Immunomodulatory properties of defensins and cathelicidins", Curr Top Microbiol Immunol (2006) 306:27-66.
Braun et al., "Identification of target genes for the Ewing's sarcoma EWS/FLI fusion protein by representational difference analysis", Mol Cell Biol (1995) 15(8):4623-4630.
Carter et al., "Chemotherapy of Cancer", 2nd Edition; John Wiley & Sons, New York (1981), Appendix C—Drug-Tumor Interactions; 5 pages.
Castillero-Trejo et al., "Expression of the EWS/FLI-1 oncogene in murine primary bone-derived cells results in EWS/FLI-1-dependent, Ewing sarcoma-like tumors", Cancer Res (2005) 65(19):8698-8705.
Chen et al., "Specific alterations of U1-C protein or U1 small nuclear RNA can eliminate the requirement of Prp28p, an essential DEAD box splicing factor", Mol Cell (2001) 7(1):227-232.
Database accession No. CID 359736, 3-[2-(4-Amino-phenyl)-2-oxo-ethyl]-3-hydroxy-1,3-dihydro-indol-2-one—Compound Summary; (Mar. 26, 2005) XP-002717179; Database PubChem Compound; pp. 1-5.
Database accession No. CID 326411; NSC297830—Compound summary; XP-002717181; (Mar. 26, 2004) Database PubChem Compound; pp. 1-5.
Database accession No. CID 366668, NSC635343—Compound summary; XP-002717180; (Mar. 26, 2005) Database PubChem Compound; pp. 1-3.
Database accession No. CID 366694, NSC635411—Compound summary; (Mar. 6, 2005) Database PubChem Compound; pp. 1-3.
Database accession No. CID 398900, NC160_038544—Compound summary; (May 30, 2009) Database PubChem Compound; pp. 1-2.
Database accession No. CID 703160, ZINC00085926—Compound summary; (Jul. 8, 2005) Database PubChem Compound; pp. 1-2.
Database accession No. CID 772922, ZINC00257314—Compound summary; (Jul. 8, 2005) Database PubChem Compound; pp. 1-2.
Database accession No. CID 797457, ZINC00302255—Compound summary; (Jul. 9, 2005) Database PubChem Compound; pp. 1-2.
Database accession No. CID 797741, ZINC00302664—Compound summary; (Jul. 9, 2005) Database PubChem Compound; pp. 1-2.
Database accession No. CID 1149577, ZINC00894999—Compound summary; (Jul. 10, 2005) Database PubChem Compound; pp. 1-2.
Database accession No. CID 1517002, ZINC01439946—Compound summary; (Jul. 11, 2005) Database PubChem Compound; pp. 1-2.
Database accession No. CID 51703682, ZINC35686355—Compound summary; (May 5, 2011) Database PubChem Compound; pp. 1-2.
Delattre et al., "The Ewing family of tumors—a subgroup of small-round-cell tumors defined by specific chimeric transcripts" N Engl J Med (1994) 331(5):294-299.
Demichelis et al., TMPRSS2: ERG gene fusion associated with lethal cancer in a watchful waiting cohort, Oncogene (2007)26:4596-4599.
Derossi et al., "The third helix of the Antennapedia homeodomain translocates through biological membranes", J Biol Chem (1994) 269(14):10444-10450.
Erkizan et al., "A small molecule blocking oncogenic protein EWS-FLI1 interaction with RNA helicase a inhibits growth of Ewing's sarcoma", Nat Med. (2009) 15(7): 750-756.
Feldmann et al., "Blockage of hedgehog signaling inhibits pancreatic cancer invasion and metastases: A new paradigm for combination therapy in solid cancers", Cancer Res. (2007) 67:2187-2196.
Frangioni et al., "Use of a general purpose mammalian expression vector for studying intracellular protein targeting: identification of critical residues in the nuclear lamin A/C nuclear localization signal", J Cell Sci (1993) 105(Pt. 2):481-488.
French et al., "Midline carcinoma of children and young adults with NUT rearrangement", J Clin Oncol (2004) 22(20):4135-4139.
Fujii et al., "An antagonist of dishevelled protein-protein interaction suppresses beta-catenin-dependent tumor cell growth", Cancer Res (2007) 67(2):573-579.
Gangwal et al., "Microsatellites as EWS/FLI response elements in Ewing's sarcoma", Proc Natl Acad Sci U S A (2008) 105(29):10149-10154.
Garden et al., "A versatile synthetic methodology for the synthesis of tryptophols", Tetrahedron (2002) 58:8399-8412.
Grier et al., "Addition of ifosfamide and etoposide to standard chemotherapy for Ewing's sarcoma and primitive neuroectodermal tumor of bone", N Engl J Med (2003) 348(8):694-701.
Gyurkocza et al., "Antileukemic activity of shepherdin and molecular diversity of hsp90 inhibitors", J Natl Cancer Inst (2006) 98(15):1068-1077.
Hu-Lieskovan et al., "Sequencespecific knockdown of EWS-FLI1 by targeted, nonviral delivery of small interfering RNA inhibits tumor growth in a murine model of metastatic Ewing's sarcoma", Cancer Res (2005) 65:8984-8992.
Kaiser, J., "First Pass at Cancer Genome Reveals Complex Landscape", Sciene (2006) 313:1370.
Khan et al., "Classification and diagnostic prediction of cancers using gene expression profiling and artificial neural networks", Nat Med (2001) 7(6):673-679.
Kinsey et al., "NROB1 is required for the oncogenic phenotype mediated by EWS/FLI in Ewing's sarcoma", Mol Cancer Res (2006)4(11):851-859.
Knoop et al., "The splicing factor U1C represses EWS/FLI-mediated transactivation", J Biol Chem (2000) 275(32):24865-24871.
Knoop et al., "EWS/FLI alters 5'-splice site selection", J Biol Chem (2001) 276(25):22317-22322.
KOBAYASHI et al., "Studies on indole derivativrs I. Synthesis of 3-phenyl-9h-pyridazino(3,4-b)indole derivatives", Chemical & Pharmaceutical Bulletin (1964) 12(10): 1129-1135
Kovar et al., "EWS/FLI-1 antagonists induce growth inhibition of Ewing tumor cells in vitro", Cell Growth Differ (1996) 7(4):429-437.
Krontiris et al., "Internal Medicine", 4th Edition, Elsevier Science (1994) Chapters 71-72, pp. 699-729.
Lee et al., "RNA helicase A is essential for normal gastrulation", Proc Natl Acad Sci U S A (1998) 95(23):13709-13713.
Leeson et al., "The influence of drug-like concepts on decision-making in medicinal chemistry", Nature reviews (2007) 6(11):881-890.
Lessnick et al., "The Ewing's sarcoma oncoprotein EWS/FLI induces a p53-dependent growth arrest in primary human fibroblasts", Cancer Cell (2002) 1(4):393-401.
Li et al. "Control of apoptosis and mitotic spindle checkpoint by survivin", Nature (1998) 396(6711):580-584.
Lindgren et al., "Translocation properties of novel cell penetrating transportan and penetratin analogues", Bioconjug. Chem (2000) 11(5):619-626.
Mateo-Lozano S, et al., Rapamycin induces the fusion-type independent downregulation of the EWS/FLI-1 proteins and inhibits Ewing's sarcoma cell proliferation; Oncogene. Dec. 18, 2003;22(58):9282-7.
May et al., "Ewing sarcoma 11;22 translocation produces a chimeric transcription factor that requires the DNA-binding domain encoded by FLI1 for transformation", Proc Natl Acad Sci U S A (1993) 90(12):5752-5756.
May et al., "The Ewing's sarcoma EWS/FLI-1 fusion gene encodes a more potent transcriptional activator and is a more powerful transforming gene than FLI-1", Mol Cell Biol (1993) 13(12):7393-7398.
McIntyre et al., "Design and cloning strategies for constructing shRNA expression vectors", BMC Biotechnol. (2006) 6:1.
Merchant et al., "Potential use of imatinib in Ewing's sarcoma: evidence for in vitro and in vivo activity", J Natl Cancer Inst (2002) 94(22):1673-1679.

(56) References Cited

OTHER PUBLICATIONS

Merchant et al., Interferon gamma enhances the effectiveness of tumor necrosis factor-related apoptosis-inducing ligand receptor agonists in a xenograft model of Ewing's sarcoma., Cancer Res (2004) 64(22):8349-8356.
Murray et al., "Targeting protein-protein interactions: lessons from p53/MDM2", Biopolymers (2007) 88(5):657-686.
Myohanen et al., "Sequence-specific DNA binding activity of RNA helicase A to the p16INK4a promoter", J Biol Chem (2001) 276(2):1634-1642.
Nakajima et al., "RNA helicase A mediates assocation of CBP with RNA polymerase II", Cell (1997) 90(6):1107-1112.
Nakatani et al., "Identification of p21WAF1/CIP1 as a direct target of EWS-FLI1 oncogenic fusion protein", J Biol Chem (2003) 278(17):15105-15115.
Ng et al., "Multiple aromatic side chains within a disordered structure are critical for transcription and transforming activity of EWS family oncoproteins", Proc Natl Acad Sci U S A (2007) 104(2):479-484.
Ojida et al., "Highly enantioselective reformatsky reaction of ketones: Chelation-assisted enantio face discrimination", Org Lett (2002) 4(18):3051-3054.
Pajouhesh et al., "Potential anticonvulsants VI: condensation of isatins with cyclohexanone and other cyclic ketones", Journal of Pharmaceutical Sciences (1982) 72(3):318-321.
Palermo et al., "The AF4-mimetic peptide, PFWT, induces necrotic cell death in MV4-11 leukemia cells", Leuk Res. (2008) 32(4):633-42.
Perez et al., "Antennapedia homeobox as a signal for the cellular internalization and nuclear addressing of a small exogenous peptide", J Cell Sci (1992) 102(Pt. 4):717-722.
Petermann et al., "Oncogenic EWS-FLI1 interacts with hsRPB7, a subunit of human RNA polymerase II", Oncogene (1998) 17:603-610.
Plescia et al., "Rational design of shepherdin, a novel anticancer agent", Cancer Cell (2005) 7(5):457-468.
Popp et al., "Synthesis of 3-hydroxy-3-phenacyloxindole analogs", Journal of Pharmaceutical Sciences (1979) 68(4):519-520.
Poppe et al., "Expression analyses identify MLL as a prominent target of 11q23 amplification and support an etiologic role for MLL gain of function in myeloid malignancies", Blood (2004) 103(1):229-235.
Pui et al., "Clinical heterogeneity in childhood acute lymphoblastic leukemia with 11q23 rearrangements", Luekemia (2003) 17(4):700-706.
Pui et al., "Acute lymphoblastic leukemia", N Engl J Med (2004) 350(15):1535-1548.
Rahim et al., YK-4-279 Inhibits ERG and ETV1 Mediated Prostate Cancer Cell Invasion, Apr. 29, 2011, PLoS ONE 6(4); East Carolina University, United States of America.
"Remington's Pharmaceutical Sciences", Mack Publishing Company 19th edition (1995), pp. vii-viii.
Riggi et al., "Ewing's sarcoma-like tumors originate from EWS-FLI-1-expressing mesenchymal progenitor cells", Cancer Res (2006) 66(19):9786.
RN 667914-27-4 (Registry, 2H-Indol-2-one, 3-[2-(4-aminophenyl)-2-oxoethyl]-5, 7-dichloro-1, 3-dihydro-3-hydroxy, Mar. 26, 2004); 1 page.
RN 672338-27-1 (Registry, 2H-Indol-2-one, 4, 6-dichloro-1, 3-dihydro-3-hydroxy-3-[2-(3-nitrophenyl)-2-oxoehyl], Apr. 7, 2004); 1 page.
RN 6938523-27-7 (Registry, 2H-Indol-2-one, 7-bromo-1,3-dihydro-3-hydroxy-3-[2-(4-methoxyphenl)-2-oxoethyl]-5-methyl, Jun. 16, 2004); 1 page.
RN 909225-77-0 (Registry, 2H-Indol-2-one, 7-chloro-3-[2-(4-ethylphenyl)-2-oxoethyl]-1,3-hydroxy, Oct. 2, 2006); 1 page.
RN 692281-43-9 (Registry, 2H-Indol-2-one, 4-chloro-3-[2-(4-fluorophenyl)-2-oxoethyl]-1,3-dihydro-3-hydroxy-7-methyl, Jun. 13, 2004); 1 page.
RN 848755-10-2 (Registry, 2H-Indol-2-one4,6-dichloro-3-[2-(3,4-dimethoxyphenyl)-2-oxoethyl]-1,3-dihydro-3-hydroxy, Apr. 19, 2005); 1 page.
Sanchez et al., "Alteration of cyclin D1 transcript elongation by a mutated transcription factor up-regulates the oncogenic D1b splice isoform in cancer", Proc Natl Acad Sci U S A. (2008) 105(16):6004-6009.
Sillerud et al., "Design and structure of peptide and peptidomimetic antagonists of protein-protein interaction", Curr Protein Pept Sci (2005) 6(2):151-169.
Smith et al., "Expression profiling of EWS/FLI identifies NKX2.2 as a critical target gene in Ewing's sarcoma", Cancer Cell (2006) 9(5):405-416.
Snyder et al., "Treatment of terminal peritoneal carcinomatosis by a transducible p53-activating peptide", PLos Biol (2004) 2(2):0186-0193.
Srinivasan et al., "The synthetic peptide PPWT disrupts AF4-AF9 protein complexes and induces apoptosis in t(4; 11) leukemia cells", Leukemia (2004) 18(8):1364-1372.
Stegmaier et al., "Signature-based small molecule screening identifies cytosine arabinoside as an EWS/FLI modulator in Ewing sarcoma", PLoS medicine (2007) 4(4):e122.
Strigacova, et al.; Novel oxindole derivatives and their biological activity; Folia Microbiol (Praha). 2001;46(3): 187-92.
Subramanian et al., "Gene set enrichment analysis: a knowledge-based approach for interpreting genome-wide expression profiles", Proc Natl Acad Sci U S A. (2005) 102(43):15545-15550.
Tanaka et al., "EWS-Fli1 antisense oligodeoxynucleotide inhibits proliferation of human Ewing's sarcoma and primitive neuroectodermal tumor cells", J Clin Invest (1997) 99(2):239-247.
Tetsuka et al., "RNA helicase A interacts with nuclear factor kappaB p65 and functions as a transcriptional coactivator", Eur J Biochem (2004) 271(18):3741-3751.
Thoren et al., "The antennapedia peptide penetratin translocates across lipid bilayers—the first direct observation", FEBS Lett (2000) 482(3):265-268.
Tiemann et al., "Solid pseudopapillary neoplasms of the pancreas are associated with FLI-1 expression, but not with EWS/FLI-1 translocation." Mod Pathol. (2006) 19(11):1409-1413.
Torchia et al., "EWS/FLI-1 induces rapid onset of myeloid/ erythroid leukemia in mice", Mol Cell Biol (2007) 27(22):7918-7934.
Toretsky et al., "Phosphoinositide 3-hydroxide kinase blockade enhances apoptosis in the Ewing's sarcoma family of tumors", Cancer Res (1999) 59(22):5745-5750.
Toretsky et al., "Oncoprotein EWS-FLI1 activity is enhanced by RNA helicase A", Cancer Res (2006) 66(11):5574-5581.
Üren et al., "Activation of the canonical wnt pathway during genital keratinocyte transformation: a model for cervical cancer progression", Cancer Res (2005) 65(14):6199-6206.
Üren et al., "Recombinant EWS-FLI1 oncoprotein activates transcription", Biochem. (2004) 43(42)13579-13589.
Üren et al., "Ewing's Sarcoma Oncoprotein EWS-FLI1: The Perfect Target without a Therapeutic Agent", Future Onc. (2005) 1(4):521-528.
Üren et al., "Pediatric malignancies provide unique cancer therapy targets", Curr Opin Pediatr. (2005) 17:14-19.
Välineva et al., "Characterization of RNA helicase A as component of STAT6-dependent enhanceosome", Nucleic Acids Res (2006) 34(14):3938-3946.
Velikorodov et al., "Some Condensations of Methyl 4-Acetylphenylcarbamate", Russian J Org Chem (2010) 46(7):971-975.
Velikorodov et al., "Synthesis of New Spiro Compounds Containing a Carbamate Group", Russian J Org Chem. (2010) 46(12):1826-1829.
Velikorodov et al., "Synthesis of 3-Pyrrol-3'-yloxindoles with a Carbamate Function", Russian J Org Chem. (2011) 47(11):1715-1717.
Velikorodov et al., "L-Proline-Catalyzed 1,3-Dipolar Cycloaddition of Some Schiff Bases to Methyl 4-[1-Oxo-2(2-Oxo-2,3-dihydro1*H*-indol-3-ylidene)ethyl]phenylcarbamate", Russian J Org Chem. (2011) 47(10):1596-1597.

(56) References Cited

OTHER PUBLICATIONS

Velikorodov et al., "Three-Component Synthesis of Spiro Compounds with a Carbamate Functionality", Russian J Org Chem. (2011) 47(3):402-404.
Von Hippel et al., "A general model for nucleic acid helicases and their "coupling" within macromolecular machines", Cell (2001) 104(2):177-190
Walensky et al., "Activation of apoptosis in vivo by a hydrocarbon-stapled BH3 helix", Science (2004) 305(5689):1466-1470.
Xie et al., "Functional anthology of intrinsic disorder. 1. Biological processes and functions of proteins with long disordered regions", J Proteome Res. (2007) 6(5):1882-1898.
Yin et al., "Low molecular weight inhibitors of Myc-Max interaction and function", Oncogene (2003) 22(40):6151-6159.
Zhang et al., "Multiple functions of nuclear DNA helicase II (RNA helicase A) in nucleic acid metabolism", Acta Biochim Biophys Sin (Shanghai) (2004) 36(3):177-183.
Zhong et al., "RNA helicase a in the MEF1 transcription factor complex upregulates the MDR1 gene in multidrug—resistant cancer cells", J Biol Chem (2004) 279(17):17134-17141.
International Search Report and Written Opinion dated Sep. 4, 2008 for International Patent Application No. PCT/US07/89118, filed Dec. 28, 2007.
International Preliminary Report on Patentability dated Jun. 30, 2009 for International Patent Application No. PCT/US2007/089118, filed Dec. 28, 2007.
Anderson et al., "BRCA1 protein is linked to the RNA polymerase II holoenzyme complex via RNA helicase A", Nat Genet (1998) 19(3):254-256.
Babu et al., "Heteropolyacid-silica mediated [3+2] cycloaddition of azomethine ylides—a facile multicomponent one-pot synthesis of novel dispiroheterocycles", Tetrahedron Ltt. (2006) 47(52): 9221-9225.
Beccalli et al., "Synthesis of [a]annulated carbazoles from indol-2,3-dione." Tetrahedron (1993) 49(21): 4741-4758.
Cheng et al., "Rational drug design via intrinsically disordered protein", Trends Biotechnol. (2006) 24(10):435-442.
Dandia et al., "Investigation of the Reactions of some New Fluorine containing 3-Aroylmethylene-indol-2-ones with Urea and Thiourea Derivatives", J Indian Chem Soc., (Nov. 1995) 72: 833-835.
Dandia et al., "Facile One Pot Microwave Induced Solvent-Free Synthesis and Antifungal, Antitubercular Screening of Spiro [1,5]-Benzothiazepin-2,3'[3'*H*]indol-2[1'*H*]-ones", Chem Pharm Bull (2003) 51(10): 1137-1141.
Gadek et al., "Small molecule antagonists of proteins", Biochem Pharmacol (2003) 65(1):1-8.
Golub et al., "Molecular Classsification of Cancer: Class Discovery and Class Prediction by Gene Expression Monitoring", Science (1999) 286: 531-537.
Hartman et al., "RNA helicase A is necessary for translation of selected messenger RNAs", Nat Struct Mol Biol. (2006) 13:509-516.
Helman et al., "Mechanisms of sarcoma development", Nat Rev Cancer (2003) 3(9):685-694.
Iost et al., "mRNAs can be stabilized by DEAD-box proteins", Nature (1994) 372(6502):193-196.
Joshi et al., "Synthesis and central nervous system activities of certain fluorine-containing 3-substituted indol-2-ones." Pharmazie (1984) 39(3): 153-155.
Kidwai et al., "Microwave-induced "solvent-free" novel technique for the synthesis of spiro [indole-pyrazole/isoxazole/pyrimidine] derivatives", Oxidation Communications (2001) 24(2): 287-290.
Kovar et al., "Potentials for RNAi in sarcoma research and therapy: Ewing's sarcoma as a model", Semin Cancer Biol. (2003) 13:275-281.
Lala et al., "Role of nitric oxide in tumor progression: Lessons from experimental tumors", Cancer Metastasis Rev. (1998) 17(1): 91-106.
Lambert et al., EWS FLI-1 antisense nanocapsules inhibits Ewing sarcoma-related tumor in mice, Biochem Biophys Res Commun. (2000) 279(2):401-406.
Lang et al., "Identification of peptide mimetics of xenoreactive alpha-Gal antigenic epitope4 by phage display", Biochem Biophys Res Commun (2006) 306:27-66.
Maitra et al., "Detection of t(11;22)(q24;q12) Translation and EWS-FLI-1 Fusion Transcript in a Case of Solid Pseudopapillary Tumor of the Pancreas", Ped Develop Pathol. (2000) 3:603-605.
Maksimenko et al., "Oligonucleotides targeted against a junction oncogene are made efficient by nanotechnologies", Pharm Res (2003) 20(10):1565-1567.
Medlineplus; Cancer [online]; [retrieved on Jul. 6, 2007] URL - http://www.nlm.nik.gov/medlineplus/cancer.html. 10 pages.
Ouchida et al., "Loss of tumorigenicity of Ewing's sarcoma cells expressing antisense RNA to EWS-fusion transcripts", Oncogene (1995) 11(6):1049-1054.
Pagliaro et al., "Emerging classes of protein-protein interaction inhibitors and new tools for their development", Curr Opin Chem Biol. (2004) 8(4):442-449.
Righetti et al., "Heterodiene Syntheses. Part 21. etc.". J Chem Soc., Perkin Transactions I, (1979) 4; 863-868.
Terrone et al., "Penetratin and related cell-penetrating cationic peptides can translocate across lipid bilayers in the presence of a transbilayer potential", Biochem. (2003) 42(47):13787-13799.
Toretsky et al., "Inhibition of EWS-FLI-1 fusion protein with antisense oligodeoxynucleotides", J Neurooncol. (1997) 31(1-2):9-16.
Toretsky et al., "Glypican-3 expression in Wilms tumor and hepatoblastoma", J Pediatr Hematol Oncol. (2001) 23(8):496-499.
Wikipedia—Cancer [online]; [retrieved on Jul. 6, 2007]. URL; http://en.wikipedia.org/wiki/Cancer; 2 pages.

* cited by examiner

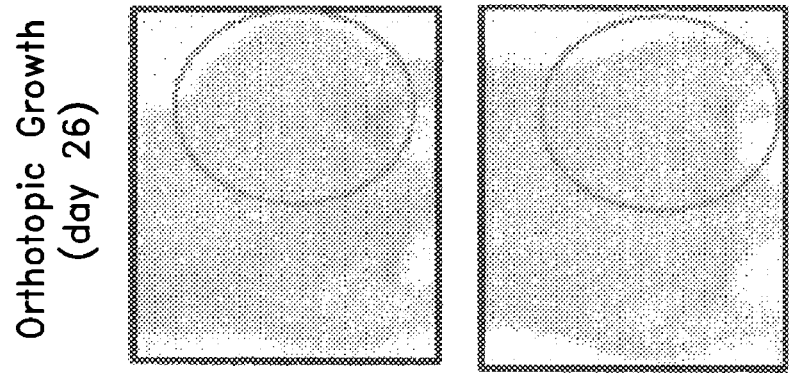
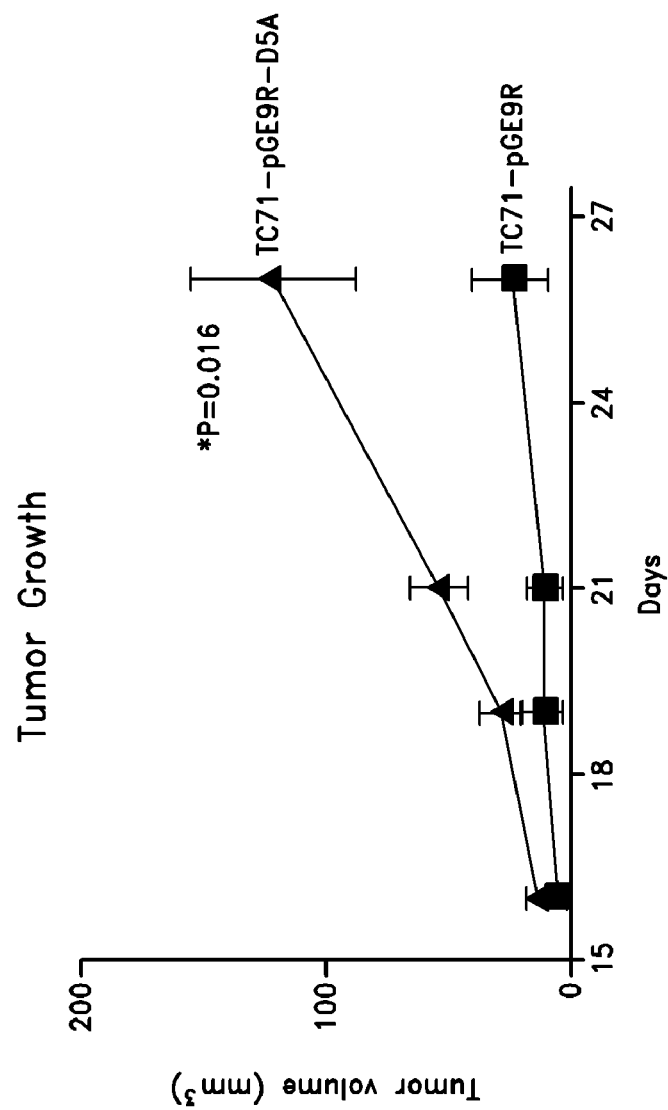
FIG. 10C
FIG. 10B query   1    PPPLDAVIEA   10
1SQC    85   PPDLDTTIEA   94

*FIG. 14A*

| Query   | 1   | PPPLD5   |         |
|---------|-----|----------|---------|
| 1J3W_A  | 53  | PPPLD57  | – 1.46A |
| 1G8Y_A  | 17  | PPPLD21  | – 1.69A |
| 1A9U    | 369 | PPPLD373 | – 0.93A |
| 1WB0_A  | 350 | PPPLD354 | – 0.89A |
| 1CQK A  | 10  | PPPL314  | – 0.62A |

*FIG. 14B*

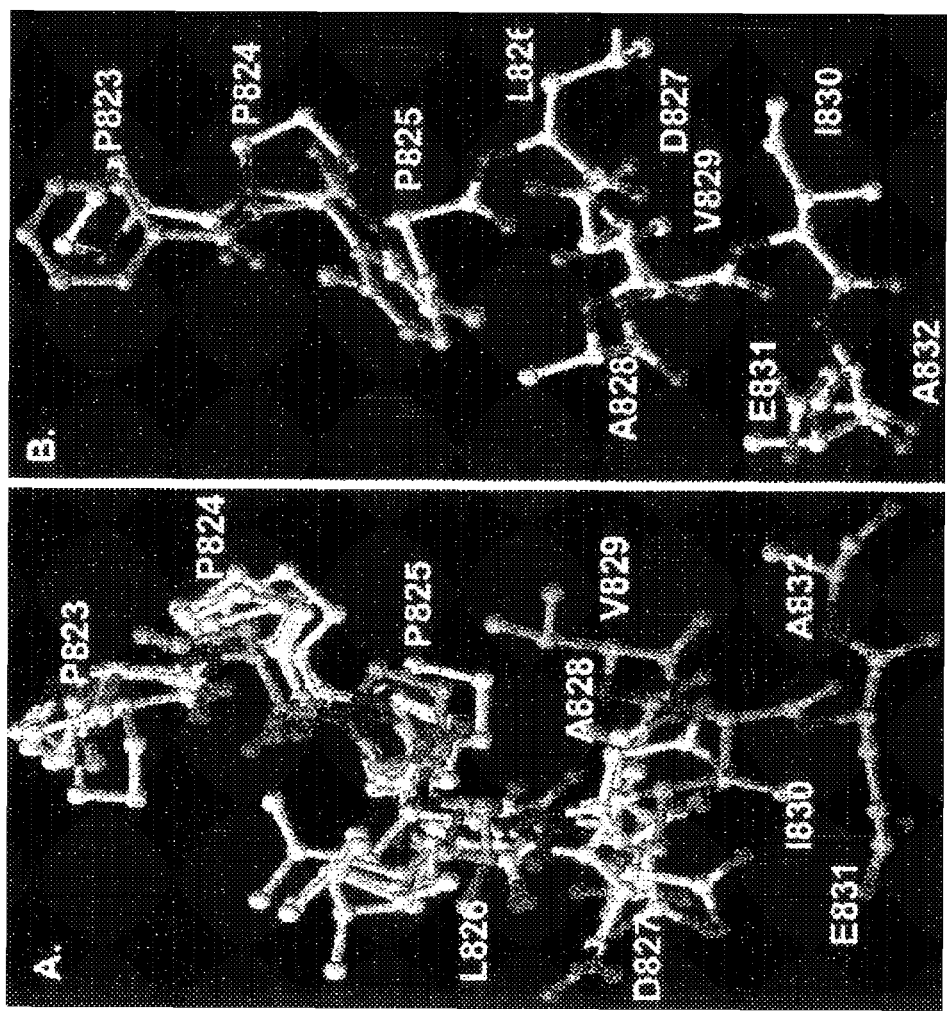

(+)-31: $^1$H NMR (300 MHz, CDCl3) d. 7.39–7.25 (m, 2 H), 7.14–7.02 (t, J=7.5 Hz, 1 H), 6.88–6.76 (d. J=6 Hz, 1 H), 3.93–3.47 (s. 1 H), 3.38–2.97 (s, 3 H), 2.21–1.77 (m, 2 H), 0.93–0.54 (t, J=7.5 Hz 3 H). $^{13}$C NMR (300 MHz, CDCL$_3$) d 179.0, 144.0, 130.5, 130.0, 124.3, 123.6, 106.8, 78.0, 32.1, 26.6, 8.1. HRMS calculated for C$_{11}$H$_{13}$NO$_2$ to be 191.09 (found 191.0950).

FIG. 31B

TARGETING OF EWS-FLI1 AS ANTI-TUMOR THERAPY

CROSS-REFERENCE TO RELATED APPLICATIONS

This application is a continuation of U.S. application Ser. No. 12/720,616 filed Mar. 9, 2010, now issued as U.S. Pat. No. 9,045,415, which is a continuation of U.S. application Ser. No. 12/494,191 filed Jun. 29, 2009 now issued as U.S. Pat. No. 8,232,310 which is a continuation-in-part of PCT International Application No. PCT/US2007/089118 filed Dec. 28, 2007 under the Patent Cooperation Treaty (PCT), which was published by the International Bureau in English, which designates the United States and claims the benefit of U.S. Provisional Application No. 60/877,856 filed Dec. 29, 2006. U.S. application Ser. No. 12/494,191 claims the benefit of U.S. Provisional Application No. 61/177,932 filed May 13, 2009. The disclosures of each of the foregoing applications are hereby expressly incorporated by reference in their entireties.

STATEMENT REGARDING FEDERALLY SPONSORED R&D

This invention was made with government support under NIH Grant/Contract Numbers R01CA138212 and R01CA133662 awarded by the National Institutes of Health of the United States of America. The government has certain rights in the invention.

REFERENCE TO SEQUENCE LISTING

The present application is being filed along with a Sequence Listing in electronic format. The Sequence Listing is provided as a file entitled TOKAS002P1C2.TXT, created Apr. 24, 2015, which is approximately 9 KB in size. The information in the electronic format of the Sequence Listing is incorporated herein by reference in its entirety.

FIELD OF THE INVENTION

Peptides and compounds are provided that function as EWS-FLI1 protein inhibitors. The peptides and compounds have utility in the treatment of cancers including the Ewing's sarcoma family of tumors, pancreatic cancer, prostate cancer, and other cancers comprising translocation gene fusions. Also provided are methods of preparing the compounds and assays for identifying inhibitors of EWS-FLI1 protein.

BACKGROUND OF THE INVENTION

EWS-FLI1 has been identified as a critical target in Ewing's Sarcoma Family of Tumors (ESFT) over 15 years ago, yet no therapies have heretofore moved from bench to bedside that have impacted on the outcome of the disease. While many investigators have recognized the importance of this target, the biochemical nature of EWS-FLI1 presents drug-discovery challenges.

The paradigm of disrupting key protein interactions may have utility in treatment of other diseases including sarcomas (Helman L J, Meltzer P. Mechanisms of sarcoma development. Nat Rev Cancer 2003; 3(9):685-94) with similar translocations, and leukemias with MLL translocations (Pui C H, Relling M V, Downing J R. Acute lymphoblastic leukemia. N Engl J Med 2004; 350(15):1535-48). A recent review suggests that disordered proteins may be excellent therapeutic targets based on their intrinsic biochemical properties (Cheng Y, LeGall T, Oldfield C J, et al. Rational drug design via intrinsically disordered protein. Trends Biotechnol 2006; 24(10):435-42).

Despite years of in vitro and xenograft studies with antisense and siRNA directed towards EWS-FLI1, none of these is heretofore practical as a human therapy based on inadequate delivery and stability. A recent phase II clinical trial using Ara-C was begun in patients with ESFT based on a comparison of cDNA signatures between siRNA reduced EWS-FLI1 and a panel of FDA approved compounds in an ESFT cell line. The recognition that Ara-C may become useful in ESFT therapy is important, however, there are many reasons not to rely on this early result and to pursue more specifically targeted therapy. Ara-C has a broad spectrum of activity that is very dose-dependent and while it may demonstrate activity for ESFT patients, its mechanism of action is more generalized than simply inactivating EWS-FLI1 with broader side effects as well. Ara-C does not represent the kind of specifically targeted therapy that might result in a major breakthrough for ESFT patients (both to improve survival and reduce long term effects of therapy).

SUMMARY OF THE INVENTION

A specific and targeted medicine to inhibit a disordered protein, functioning as a transcription factor, without enzymatic activity is desirable. Therapeutic compounds and novel chemical probes to modulate EWS-FLI1 function are provided that tightly and specifically bind to EWS-FLI1 are also desirable.

Accordingly, in a first aspect, a peptide is provided comprising a sequence selected from the group consisting of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 and 31, preferably SEQ ID NO: 29.

In an embodiment of the first aspect, the peptide further comprises an N-terminal tag comprising a cell-penetrating cationic peptide. The cell-penetrating cationic peptide may comprise the cell-permeable Antennapedia peptide sequence (SEQ ID NO: 34).

In a second aspect the peptide in combination with at least one pharmaceutically acceptable carrier or diluent is provided.

In a third aspect, a method for treating cancer in a mammal, comprising administering to the mammal an effective amount of the peptide of the first aspect is provided.

In an embodiment of the third aspect, the cancer comprises a translocation gene fusion.

In an embodiment of the third aspect, the cancer is selected from the group consisting of Ewing's sarcoma, clear-cell sarcoma, myxoid liposarcoma, desmoplastic small round-cell tumor, myxoid chondrosarcoma, acute myeloid leukemia, congenital fibrosarcoma, prostate cancer and pancreatic cancer.

In an embodiment of the third aspect, the cancer is Ewing's sarcoma.

In an embodiment of the third aspect, the peptide of the first aspect is administered in combination with another pharmaceutically active agent, either simultaneously, or in sequence.

In a fourth aspect, a use of a peptide of the first aspect for the manufacture of a medicament for the treatment of cancer is provided.

In a fifth aspect, a compound is provided having a formula:

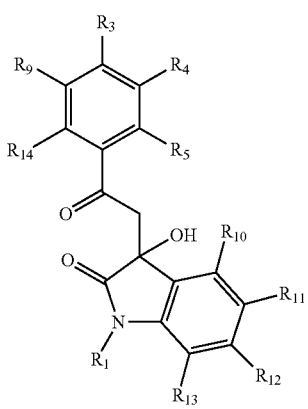

wherein $R_1$ is selected from the group consisting of hydrogen, one amino acid, two amino acids linked together, three amino acids linked together,

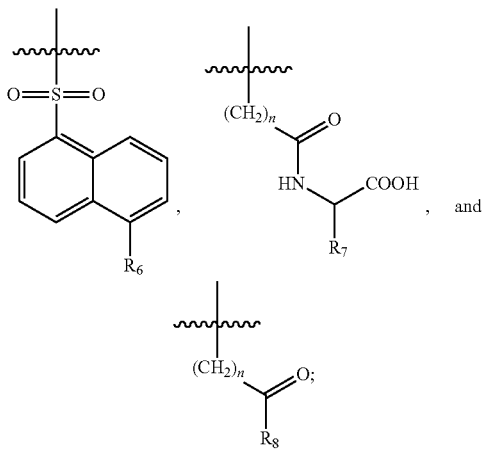

$R_6$ is $C_{1-6}$ dialkyl amine; $R_7$ is selected from the group consisting of hydrogen and $C_{1-6}$ alkyl; $R_8$ is $C_{1-6}$ alkyl; $R_3$, $R_4$, $R_5$, $R_9$, $R_{10}$, $R_{11}$, $R_{12}$, $R_{13}$, and $R_{14}$ are independently selected from the group consisting of hydrogen, halogen, $C_{1-6}$ alkyl, $C_{1-6}$ alkoxy, —C(=O)NH$_2$, —NO$_2$, —NH$_2$, and —OH; and n is an integer from 0 to 4; with the proviso that $R_3$ is not chlorine or fluorine when $R_1$, $R_4$, $R_5$, $R_{11}$, and $R_{12}$ are hydrogen and $R_{10}$ and $R_{13}$ are chlorine.

In an embodiment of the fifth aspect, $R_1$ is hydrogen.

In an embodiment of the fifth aspect, $R_1$ is selected from the group consisting of Leu, Leu-Asp, Leu-Asp-Ala, —CH$_2$—C(=O)—NHCH$_2$COOH, —CH$_2$—C(=O)—(CH$_2$)C(CH$_3$)$_2$,

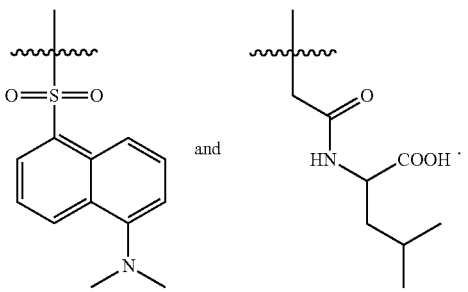 [SMILES: *S(=O)(=O)c1cccc2c(N(C)C)cccc12 ; *CC(=O)NC(CC(C)C)C(=O)O]

In an embodiment of the fifth aspect, $R_3$, $R_4$, $R_5$, $R_9$, $R_{10}$, $R_{11}$, $R_{12}$, $R_{13}$, and $R_{14}$ are independently selected from the group consisting of hydrogen, chlorine, and fluorine.

In a sixth aspect, the compound of the fifth aspect is provided in combination with at least one pharmaceutically acceptable carrier or diluent.

In a seventh aspect, a compound is provided having a formula selected from the group consisting of:

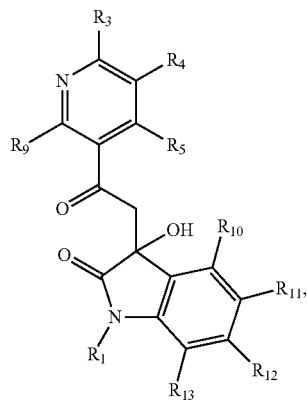

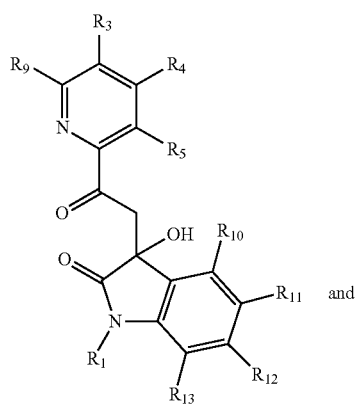 and

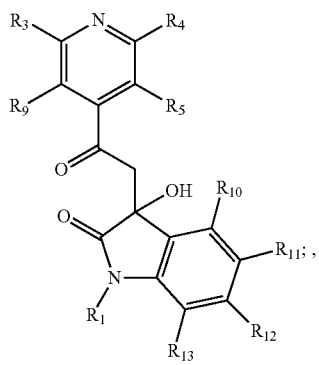

wherein $R_1$ is selected from the group consisting of hydrogen, one amino acid, two amino acids linked together, three amino acids linked together,

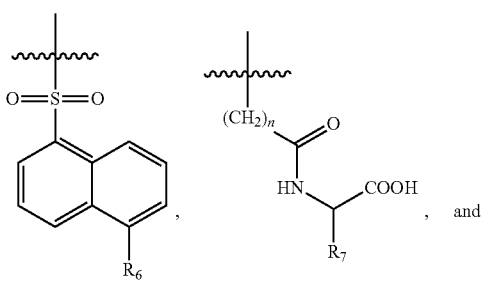

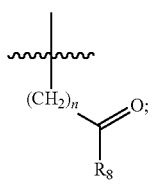

$R_6$ is $C_{1-6}$ dialkyl amine; $R_7$ is selected from the group consisting of hydrogen and $C_{1-6}$ alkyl; $R_8$ is $C_{1-6}$ alkyl; $R_3$, $R_4$, $R_5$, $R_9$, $R_{10}$, $R_{11}$, $R_{12}$, and $R_{13}$ are independently selected from the group consisting of hydrogen, halogen, $C_{1-6}$ alkyl, $C_{1-6}$ alkoxy, —C(=O)NH$_2$, —NO$_2$, —NH$_2$, and —OH; and n is an integer from 0 to 4.

In an embodiment of the seventh aspect, $R_1$ is hydrogen.

In an embodiment of the seventh aspect, $R_1$ is selected from the group consisting of Leu, Leu-Asp, Leu-Asp-Ala, —CH$_2$—C(=O)—NHCH$_2$COOH, —CH$_2$—C(=O)—(CH$_2$)C(CH$_3$)$_2$,

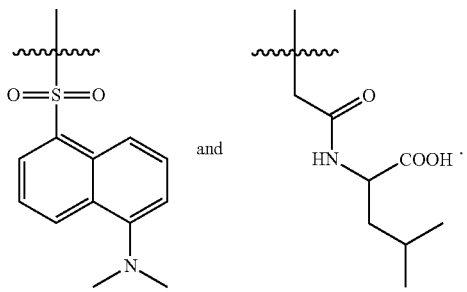 [SMILES: *S(=O)(=O)c1cccc2c(N(C)C)cccc12 ; *CC(=O)NC(CC(C)C)C(=O)O]

In an embodiment of the seventh aspect, $R_3$, $R_4$, $R_5$, $R_9$, $R_{10}$, $R_{11}$, $R_{12}$, $R_{13}$, and $R_{14}$ are independently selected from the group consisting of hydrogen, chlorine, and fluorine.

In an eighth aspect, the compound of the seventh aspect is provided in combination with at least one pharmaceutically acceptable carrier or diluent.

In a ninth aspect, a compound is provided having a formula:

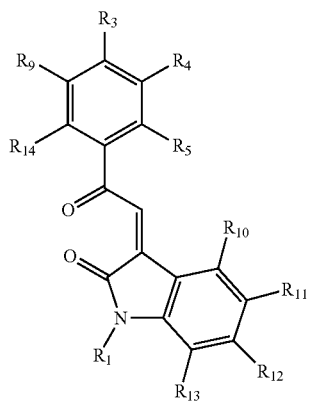

wherein $R_1$ is selected from the group consisting of hydrogen, one amino acid, two amino acids linked together, three amino acids linked together,

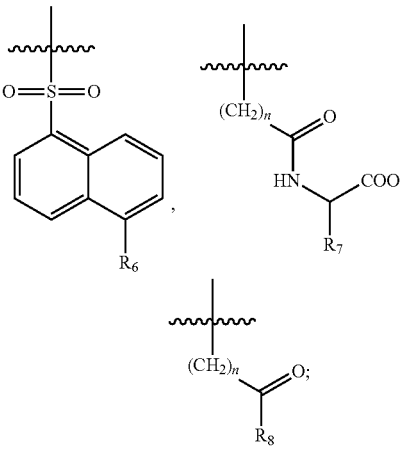

$R_6$ is $C_{1-6}$ dialkyl amine; $R_7$ is selected from the group consisting of hydrogen and $C_{1-6}$ alkyl; $R_8$ is $C_{1-6}$ alkyl; $R_3$, $R_4$, $R_5$, $R_9$, $R_{10}$, $R_{11}$, $R_{12}$, $R_{13}$, and $R_{14}$ are independently selected from the group consisting of hydrogen, halogen, $C_{1-6}$ alkyl, $C_{1-6}$ alkoxy, —C(=O)NH$_2$, —NO$_2$, —NH$_2$, and —OH; and n is an integer from 0 to 4.

In an embodiment of the ninth aspect, $R_1$ is selected from the group consisting of Leu, Leu-Asp, Leu-Asp-Ala, —CH$_2$—C(=O)—NHCH$_2$COOH, —CH$_2$—C(=O)—(CH$_2$)C(CH$_3$)$_2$,

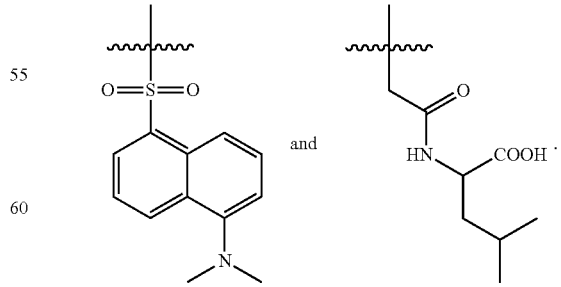

In an embodiment of the ninth aspect, $R_3$, $R_4$, $R_5$, $R_9$, $R_{10}$, $R_{11}$, $R_{12}$, $R_{13}$, and $R_{14}$ are independently selected from the group consisting of hydrogen, chlorine, and fluorine.

In a tenth aspect, the compound of the ninth aspect is provided in combination with at least one pharmaceutically acceptable carrier or diluent.

In an eleventh aspect, a compound is provided having a formula selected from the group consisting of:

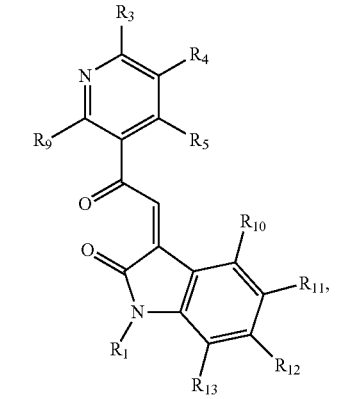

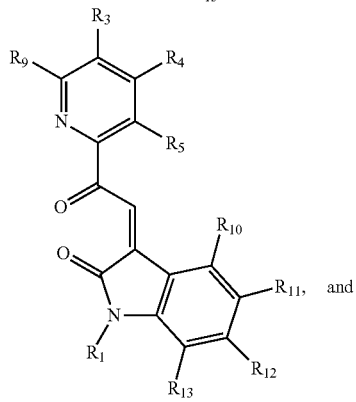

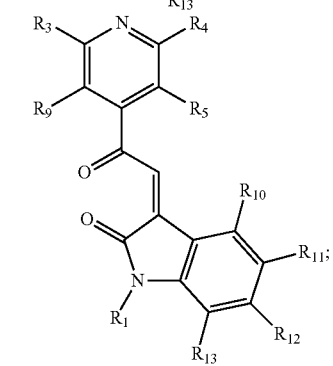

wherein $R_1$ is selected from the group consisting of hydrogen, one amino acid, two amino acids linked together, three amino acids linked together,

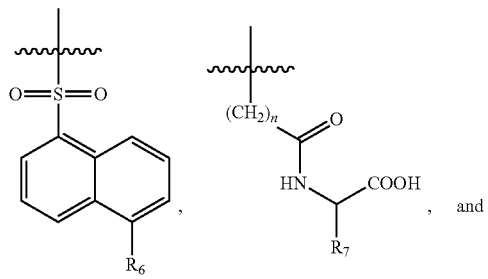

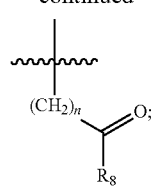

$R_6$ is $C_{1-6}$ dialkyl amine; $R_7$ is selected from the group consisting of hydrogen and $C_{1-6}$ alkyl; $R_8$ is $C_{1-6}$ alkyl; $R_3$, $R_4$, $R_5$, $R_9$, $R_{10}$, $R_{11}$, $R_{12}$, and $R_{13}$ are independently selected from the group consisting of hydrogen, halogen, $C_{1-6}$ alkyl, $C_{1-6}$ alkoxy, —C(=O)NH$_2$, —NO$_2$, —NH$_2$, and —OH; and n is an integer from 0 to 4.

In an embodiment of the eleventh aspect, $R_1$ is hydrogen.

In an embodiment of the eleventh aspect, $R_1$ is selected from the group consisting of Leu, Leu-Asp, Leu-Asp-Ala, —CH$_2$—C(=O)—NHCH$_2$COOH, —CH$_2$—C(=O)—(CH$_2$)C(CH$_3$)$_2$,

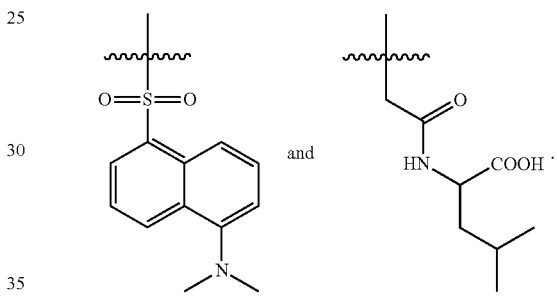

In an embodiment of the eleventh aspect, $R_3$, $R_4$, $R_5$, $R_9$, $R_{10}$, $R_{11}$, $R_{12}$, $R_{13}$, and $R_{14}$ are independently selected from the group consisting of hydrogen, chlorine, and fluorine.

In a twelfth aspect, the compound of the eleventh aspect is provided in combination with at least one pharmaceutically acceptable carrier or diluent.

In a thirteenth aspect, a method for treating cancer in a mammal is provided, comprising administering to the mammal an effective amount of a compound selected from the group consisting of:

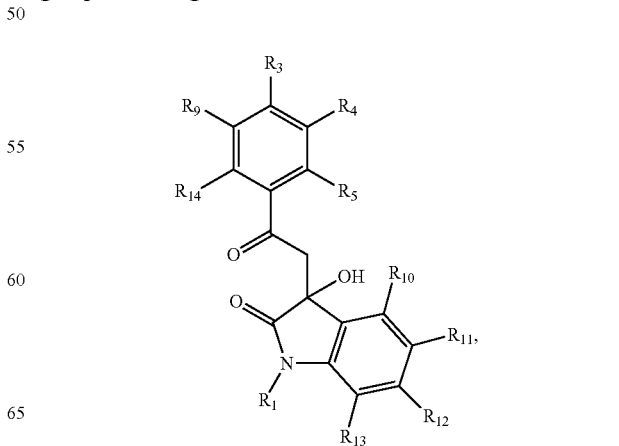

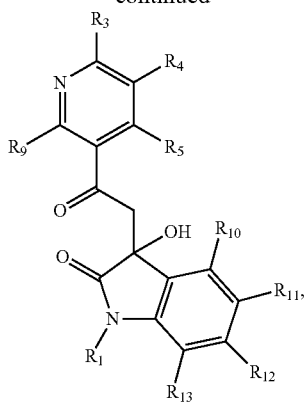
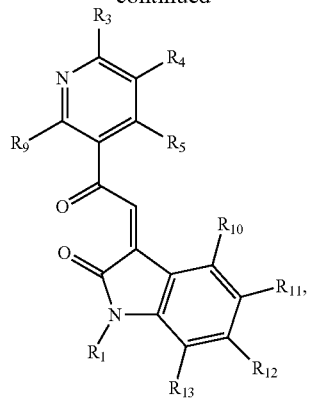
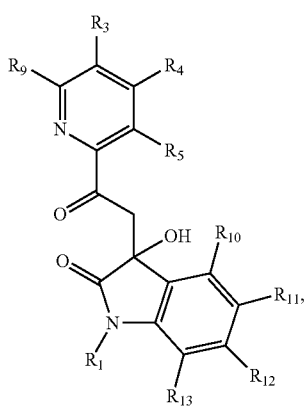
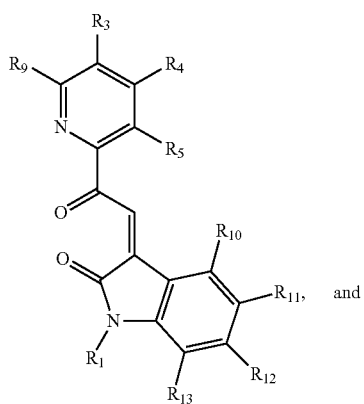
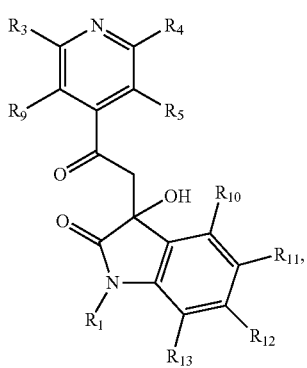
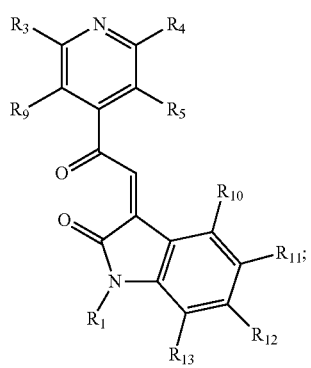
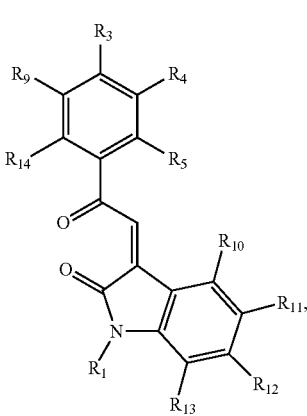
wherein $R_1$ is selected from the group consisting of hydrogen, one amino acid, two amino acids linked together, three amino acids linked together,
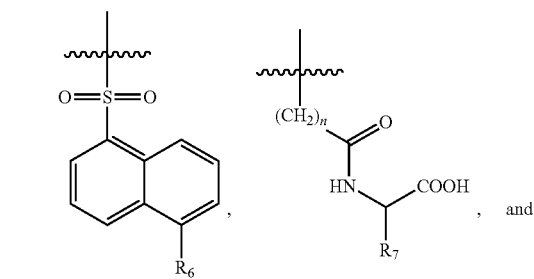
and -continued

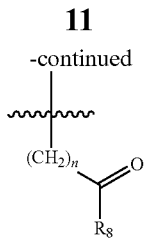

$R_6$ is $C_{1-6}$ dialkyl amine; $R_7$ is selected from the group consisting of hydrogen and $C_{1-6}$ alkyl; $R_8$ is $C_{1-6}$ alkyl; $R_3$, $R_4$, $R_5$, $R_9$, $R_{10}$, $R_{11}$, $R_{12}$, $R_{13}$, and $R_{14}$ are independently selected from the group consisting of hydrogen, halogen, $C_{1-6}$ alkyl, $C_{1-6}$ alkoxy, —C(=O)NH$_2$, —NO$_2$, —NH$_2$, and —OH; and n is an integer from 0 to 4.

In an embodiment of the thirteenth aspect, $R_3$, $R_4$, $R_5$, $R_9$, $R_{10}$, $R_{11}$, $R_{12}$, $R_{13}$, and $R_{14}$ are independently selected from the group consisting of hydrogen, chlorine, and fluorine.

In an embodiment of the thirteenth aspect, a compound is provided with the formula:

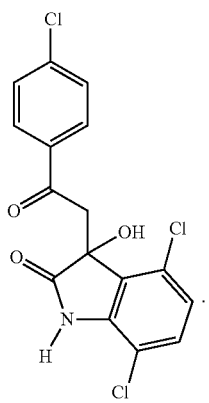 [SMILES: O=C(CC1(O)C(=O)Nc2c(Cl)ccc(Cl)c21)c1ccc(Cl)cc1]

In an embodiment of the thirteenth aspect, the cancer comprises a translocation gene fusion.

In an embodiment of the thirteenth aspect, the cancer is selected from the group consisting of Ewing's sarcoma, clear-cell sarcoma, myxoid liposarcoma, desmoplastic small round-cell tumor, myxoid chondrosarcoma, acute myeloid leukemia, congenital fibrosarcoma, prostate cancer and pancreatic cancer.

In an embodiment of the thirteenth aspect, the cancer is Ewing's sarcoma.

In a fourteenth aspect, the compound of the thirteenth aspect is administered in combination with another pharmaceutically active agent, either simultaneously, or in sequence.

In a fifteenth aspect, a use of a compound of the thirteenth aspect is provided for the manufacture of a medicament for the treatment of cancer.

Methods are also provided for screening agents that disrupt protein-protein interactions. Such methods include performing fluorescence polarization, and surface Plasmon resonance to detect such agents. In some embodiments, the protein-protein interaction comprises EWS-FLI1. In some embodiments, the EWS-FLI1 comprises a recombinant protein. In other embodiments of methods for screening, the protein-protein interaction can comprise a peptide.

BRIEF DESCRIPTION OF THE DRAWINGS

In FIG. 1A, standard 96 well ELISA plates were coated with 500 ng EWS-FLI1 or BSA. Wells were incubated with 250 ng RHA and bound RHA was detected with a polyclonal anti-RHA antibody. RHA bound specifically to EWS-FLI1 coated wells. When the experiment was done in the reciprocal order, RHA immobilized to surface, EWS-FLI1 bound specifically to RHA. In FIG. 1B, wells were coated with 500 ng EWS-FLI1. Increasing concentrations of RHA (0.0133 nM to 13.3 nM) were incubated in wells and detected by anti-RHA antibody.

In FIG. 2A, recombinant EWS-FLI1 specifically binds to fragment RHA (630-1020) compared to albumin (BSA) using an ELISA assay. The RHA(630-1020) fragment is the one that contains the homology to the peptide found to bind EWS-FLI1 by phage display library screening. In FIG. 2B, a diagram is provided showing the binding sites of proteins that bind to RHA. In FIG. 2C, GST-RHA fragments were used to coimmunoprecipitate EWS-FLI1 from ESFT lysate (TC32 cells). GST proteins were equalized using Coomassie staining. Glutathione conjugated beads were mixed with GST-RHA fragments and TC32 cell lysate. Following PAGE resolution, EWS-FLI1 was detected with anti-FLI1 antibody.

In FIG. 5A, E9RP was used in a competition experiment for blocking binding of RHA to EWS-FLI1. Wells were coated with 500 ng EWS-FLI1. RHA (4 nM) was added on to wells in the presence of E9RP (0.01-30 μM). In FIG. 5B, wells were coated with 500 ng/well recombinant CBP. RHA (4 nM) was added to wells with E9RP (0.01-30 μM).

FIG. 7A shows amino-acid positions 1, 2, 3, 5, and 9 of the E9R sequence (PPPLDAVIEA; SEQ ID NO: 29) mutated to alanine in the GST-RHA(630-1020) and used in solution immunoprecipitation experiments similar to FIGS. 2 and 6. FIG. 7B shows the results of densitometry of three immunoprecipitation experiments. Wild-type and mutations at position 1, 3, and 9 showed the expected complex formation while mutations at positions 2 (P824A) and 5 (D827A) showed reduced complex formation. The graph shows a summary of three experiments using densitometry to quantify the amount of complex formation. *Student two-tailed t-test comparison of each mutant to wild-type P824A p=0.0129 and D827A p=0.0344, others were not significant.

In FIGS. 8A and 8B, E9RP is the peptide region of RHA (SEQ ID NO:29) fused to the Penetratin peptide (from the Antennapedia homeodomain; SEQ ID NO:34) and contains amino-terminal fluorescein (FITC). ESFT cell lines TC32, (ESFT 1), and 5838 (ESFT 2) and a neuroblastoma cell line (SKNAS, NB, that lacks EWS-FLI1) demonstrated uptake of peptide at 24 hours following addition of peptide to culture media. Neither lipids nor electricity were used for transduction of peptides into cells. Confocal microscopy identified peptide (green) throughout cells with nuclear uptake. Nuclear uptake was confirmed by DAPI staining. In FIG. 8C, two ESFT cell lines, 1 and 2, demonstrate reduced growth after seven days in culture, while the growth of the NB cells (lacking EWS-FLI1) is not affected (Row C). Cell lines were placed in 96-well plates with either vehicle alone (λ, blue), or E9RP (10 µM) on days 0, 3 and 5 (σ, green). No lipid or other transfection method was utilized. This represents two experiments with similar results. FIG. 8D depicts dose response of ESFT 1 to either wild-type or single amino-acid mutant peptides. (■) wild-type E9RP, (E9R (SEQ ID NO:29) fused to the Penetratin peptide (SEQ ID NO:34)), ( )(E9RP (P2A peptide (SEQ ID NO:30) fused to the Penetratin peptide (SEQ ID NO:34)), ( )E9RP (D5A peptide (SEQ ID NO:31) fused to the Penetratin peptide (SEQ ID NO:34)). Growth normalized to treating cells with the 16 aa Antp sequence alone (SEQ ID NO:34). FIG. 8E is a comparison of wild-type versus mutant peptides in ESFT and NB cells.

FIGS. 10A-C show expression of E9R (SEQ ID NO:29) peptide reduces ESFT xenografts growth. ESFT cells TC71 were transfected with pGE9R (wild-type sequence peptide (SEQ ID NO: 29)) or pGE9R-D5A (control, mutated peptide; D5A (SEQ ID NO: 31)). In FIG. 10A, fluorescent micrographs of transfected cells after 4 days in culture are presented. The first panel shows brightfield cells, the second with green filter, and the third, magnification of a representative area. Bar equals 300 microns. In FIG. 10B, each group contains six mice. Mice legs were measured every 2-3 days. Tumors appeared in 2 weeks. The experiment was terminated after 26 days when the largest tumor caused the mouse to limp. Tumor volumes were calculated according to (D×d2/6)×π formula, where large diameter of tumor mass is D and small diameter is d. 2-way ANOVA analysis, followed by Bonferroni correction for multiple variables, the difference in the two growth curves was highly significant, p=0.016. FIG. 10C is a demonstration of orthotopic site of representative mice after 26 days.

NSC: 635437

The red lines are the actual binding curves while the thin black lines are the curve fit overlays.

Figure 13A:
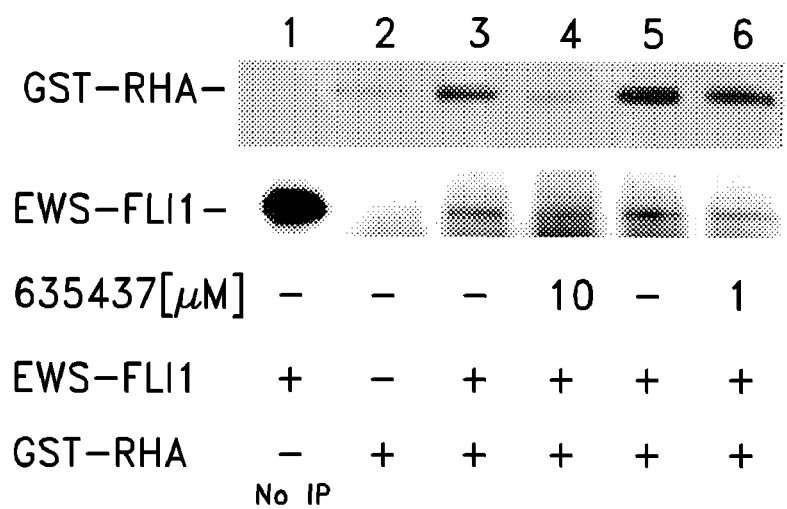
Figure 13B:
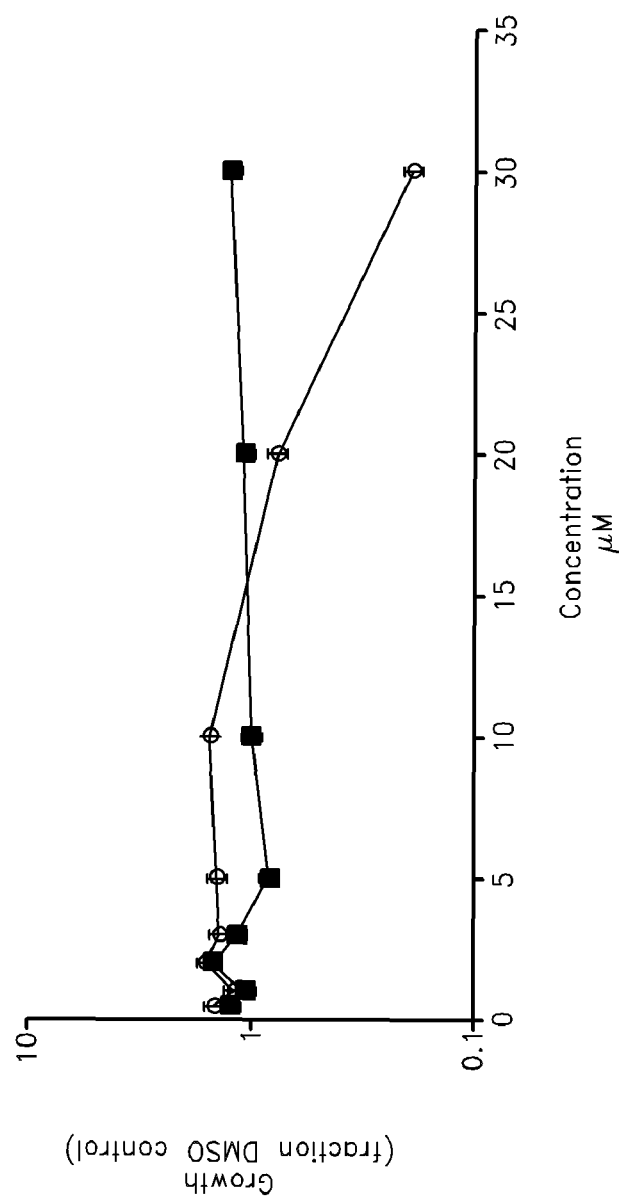

FIGS. 13A and 13B show that NSC635437 decreases RHA binding to EWS-FLI1 and demonstrates specific toxicity. In FIG. 13A, recombinant EWS-FLI1 was treated with NSC635437 for 30 minutes. GST-RHA(630-1020) was added and the complexes were then precipitated with antibody to EWS-FLI1 and Protein G beads. Resolved complexes showing the immunoprecipitated complex control without compound are in lanes 3 (0.1% DMSO) and 5 (0.01% DMSO). Addition of NSC635437, shown in lanes 4 (10 µM) and 6 (1 µM), decreased complex formation compared to DMSO matched controls in lanes 3 and 5, respectively. FIG. 13B shows NSC635437 reduces ESFT but not neuroblastoma cell growth. ESFT TC32 (○) and neuroblastoma SK-N-AS (■) were grown for 72 hours in the continuous presence of NSC635437. Cells were incubated in MTT reagent for 4 hours and the dried precipitate was dissolved isopropanol and the absorbance read at 570 nm. Each cell line was standardized to the growth of the DMSO control.

FIG. 14A shows the BLAST Alignment for peptide motif E9R PPPLDAVIEA (E9R; SEQ ID NO: 29) with the peptide PPDLDTTIEA (SEQ ID NO: 39). The best sequence alignment was extracted and the structure was predicted using homology modeling with a SQUALENE-HOPENE-CYCLASE (PDB: 1SQC) x-ray structure as a template. The input alignment for the Modeler was obtained with BLAST. FIG. 14B shows the BLAST Alignment for peptide sequence motif 'PPPLD' (SEQ ID NO: 32) with root mean square deviation (RMSD, black) of their structure in comparison to query. In the ligand overlap strategy, the Brookhaven database for x-ray structures that contained the PPPLDAVIEA (E9R; SEQ ID NO: 29) motif was sampled, a BLAST alignment was made for the 10-mer PPPLDAVIEA sequence (E9R; SEQ ID NO: 29) to predict the structure.

Figure 15C:
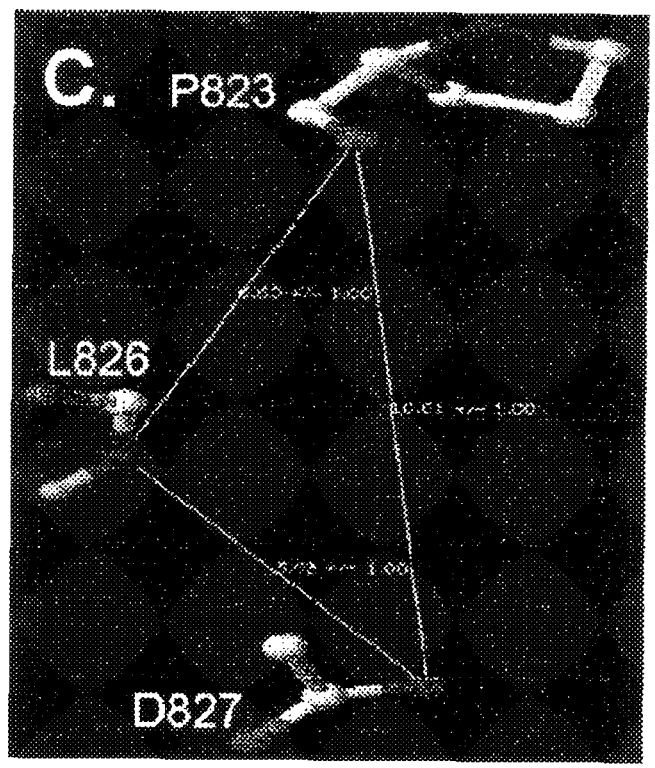

FIGS. 15A-15C show modeling of E9R with existing proteins and NSC635437. FIG. 15A shows the PPPLDAVIEA (E9R; SEQ ID NO: 29) motif (in green) superimposed with the structures of 'PPPLD'(SEQ ID NO: 32) sequence finger print retrieved from the Protein database. FIG. 15B shows PPPLDAVIEA (E9R; SEQ ID NO: 29) peptide RMS fit with NSC635437. Ligand carbon atoms are colored green. FIG. 15C shows a pharmacophore model for library screening using the PPPLD motif.

Figure 16:
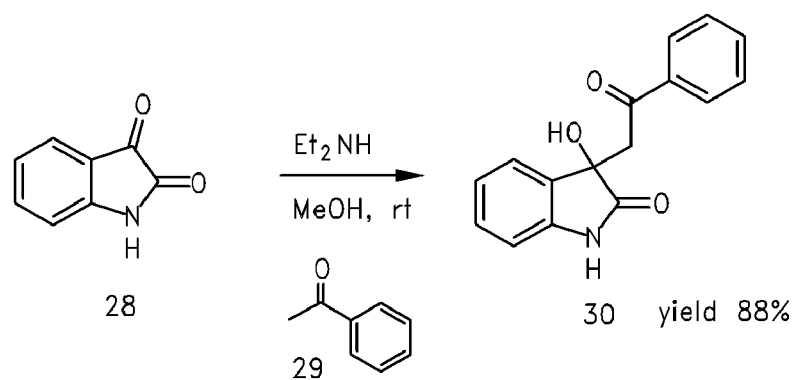

FIG. 16 shows synthesis of 3-hydroxy-3-(2-oxo-2-phenyl-ethyl)-1,3-dihydro-indol-2-one (30).

Figure 17:
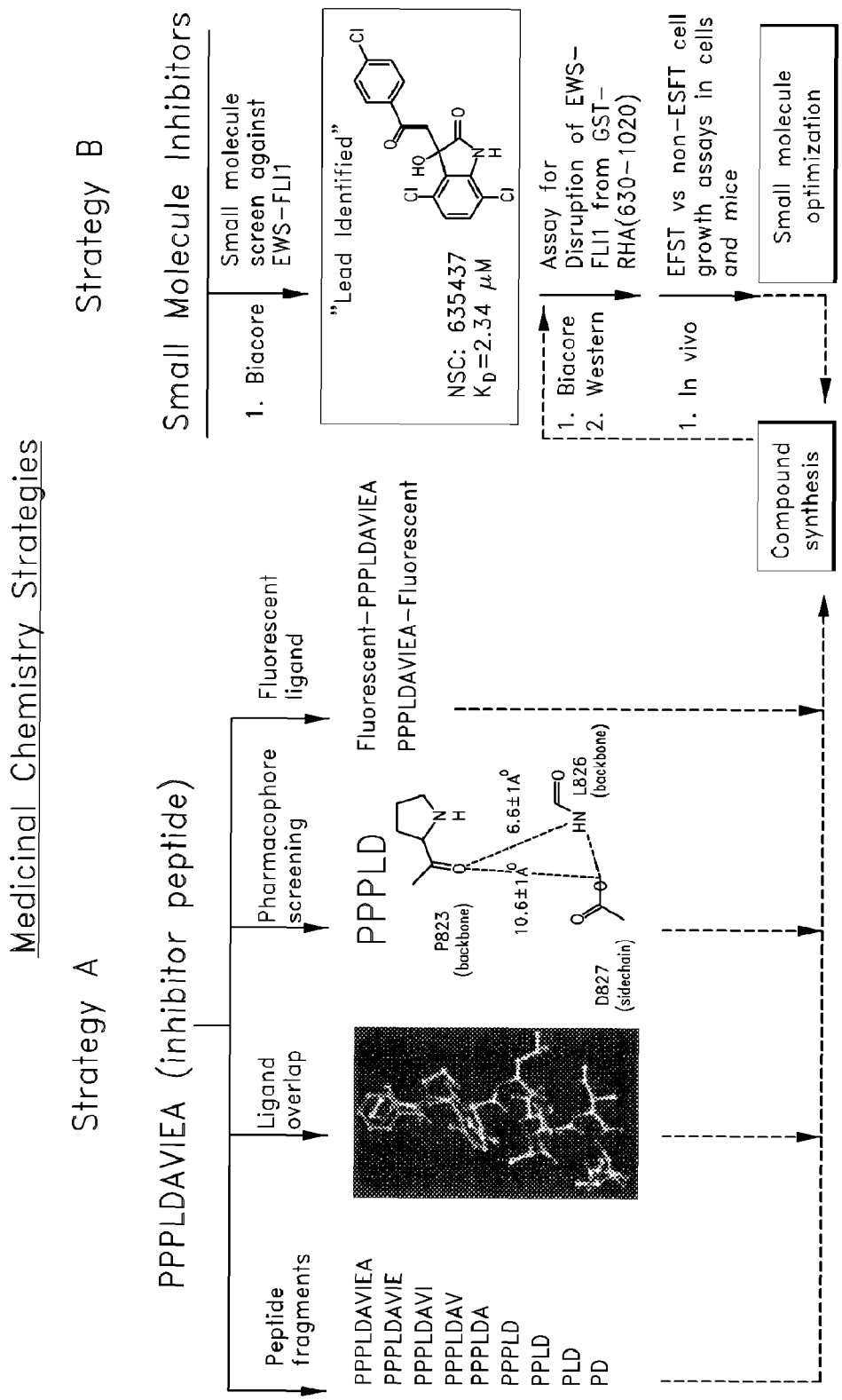

FIG. 17 shows schema for EWS-FLI1 small molecule and peptide development and includes inhibitor peptide "PPPLDAVIEA" (SEQ ID NO: 29), peptide fragments thereof (SEQ ID NOs.: 40-45), and fluorescent ligand associated with the inhibitor peptide.

Figure 18:
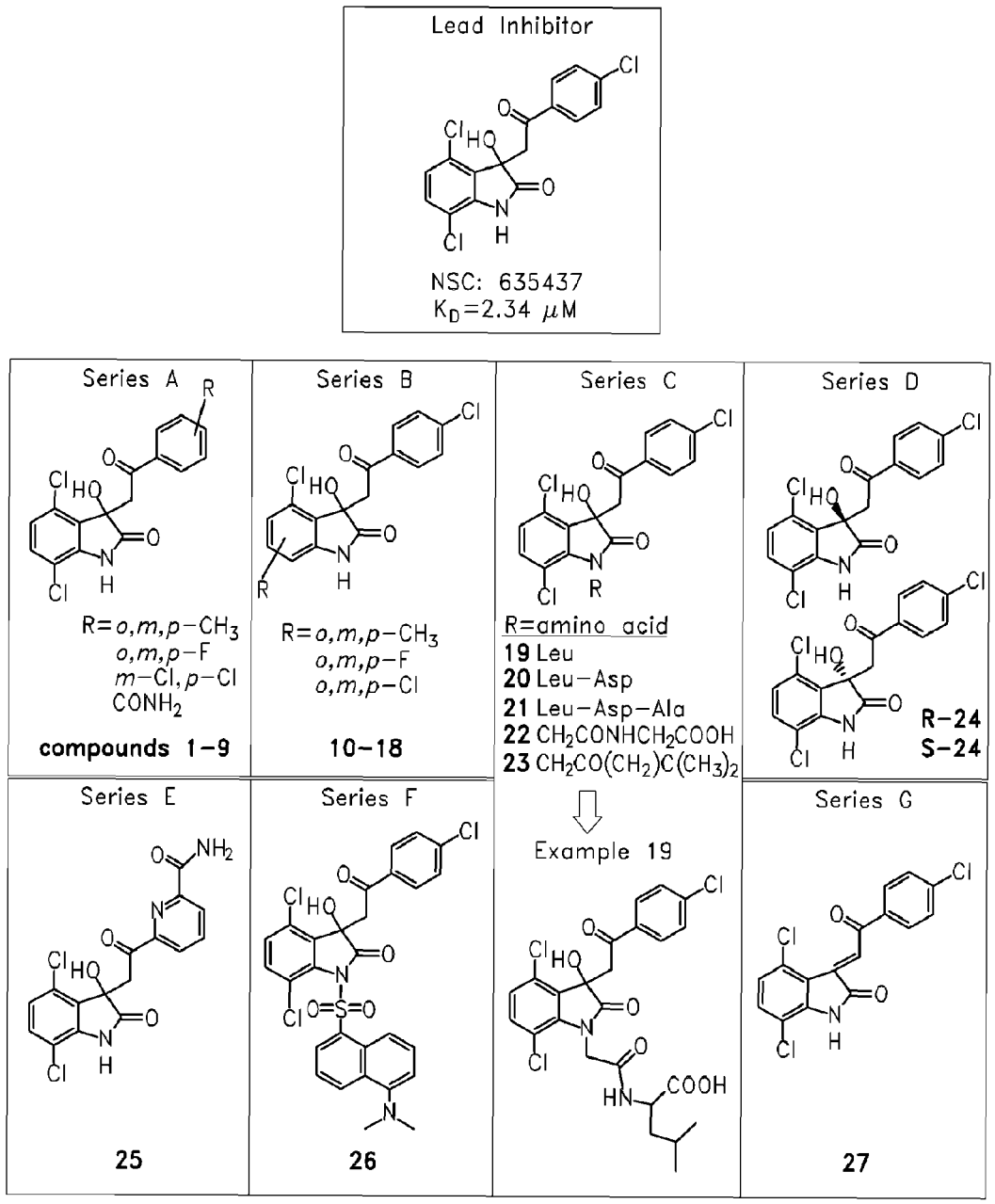

FIG. 18 shows planned modifications of compound NSC635437.

Figure 19:
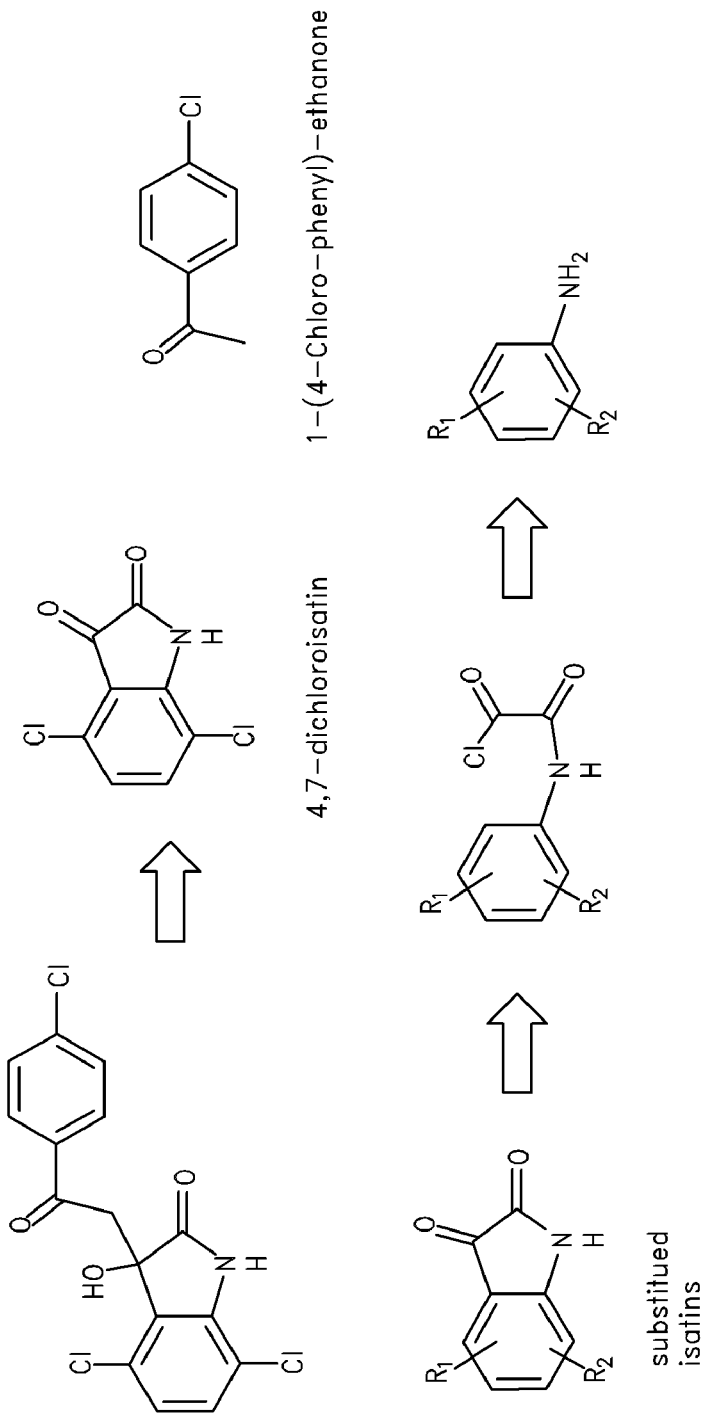

FIG. 19 shows retrosynthesis of the key isatin core.

Figures 20A, 20B:
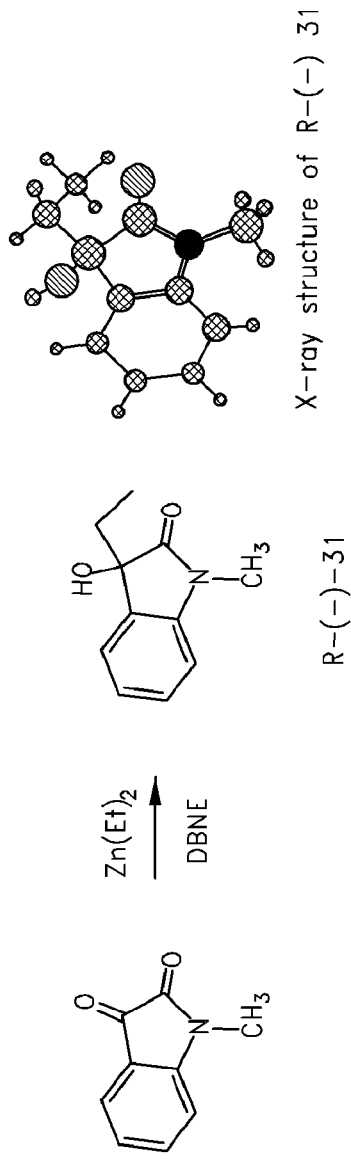

FIG. 20A shows a model synthesis for enantiomers R-(−)-31 and S-(+)-31, and an x-ray structure of R-(−)-31. FIG. 20B shows NMR spectroscopy of the R-(−)-31 enantiomer.

Figure 21:
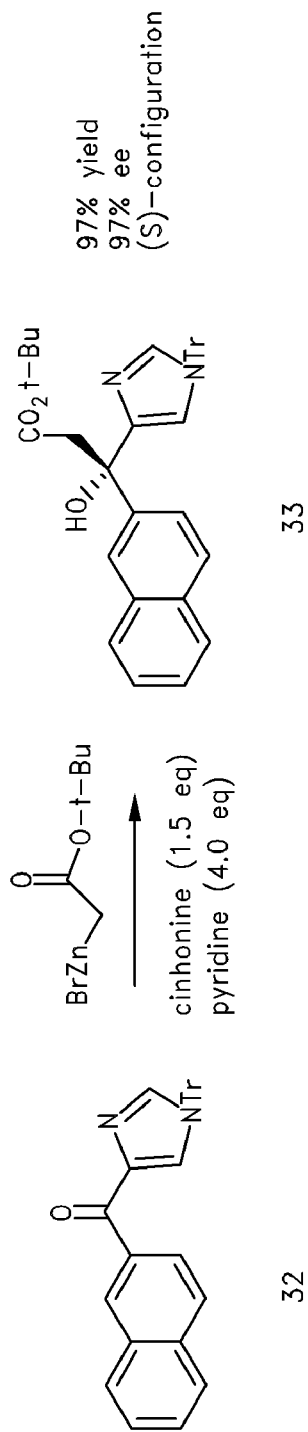

FIG. 21 shows the addition of the Reformasky reagent in the presence of 1.5 equivalents of cinchonine and 4.0 equivalents of pyridine to aromatic ketone to yield a tertiary alcohol in 97% yield and 97% ee.

Figure 22:
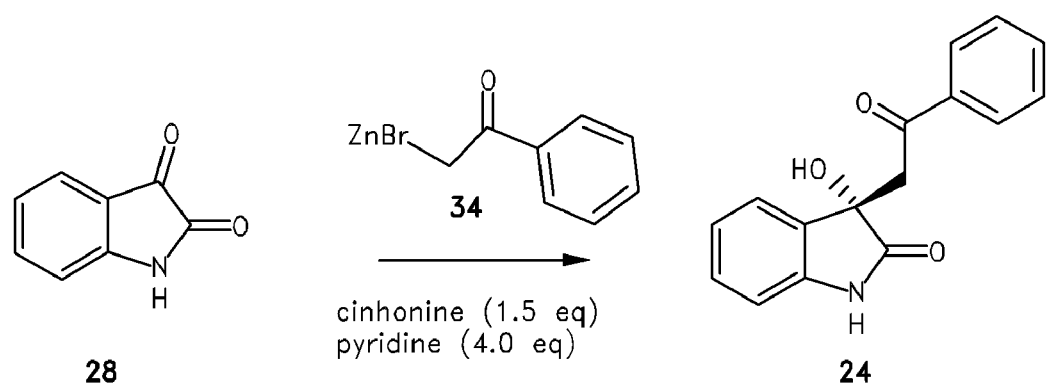

FIG. 22 shows the synthesis of non-racemic isatin derivatives by enantioselective Reformatsky-like reaction.

Figure 23A:
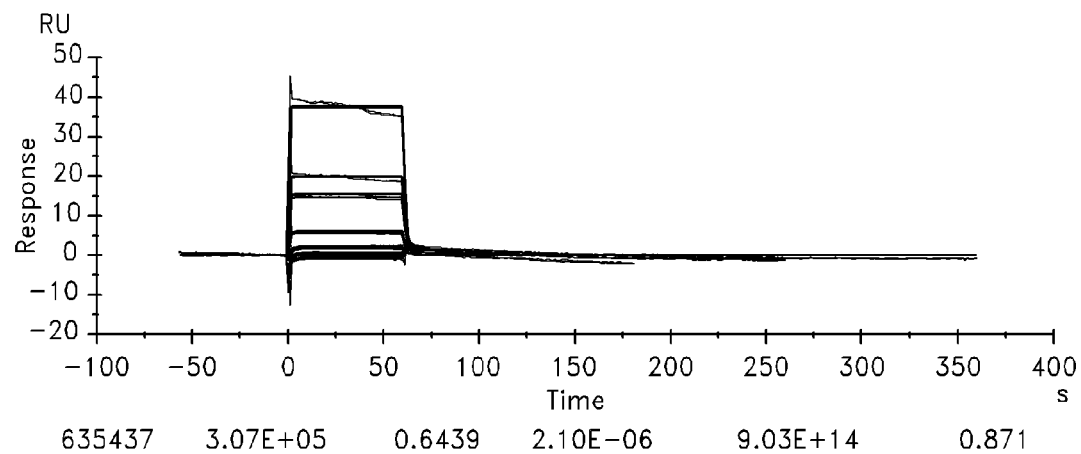
Figure 23A:
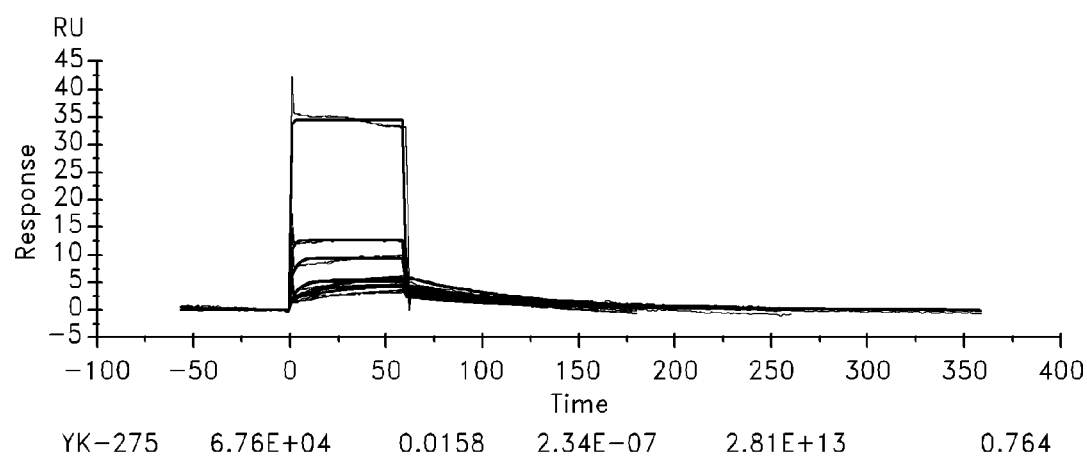
Figure 23B:
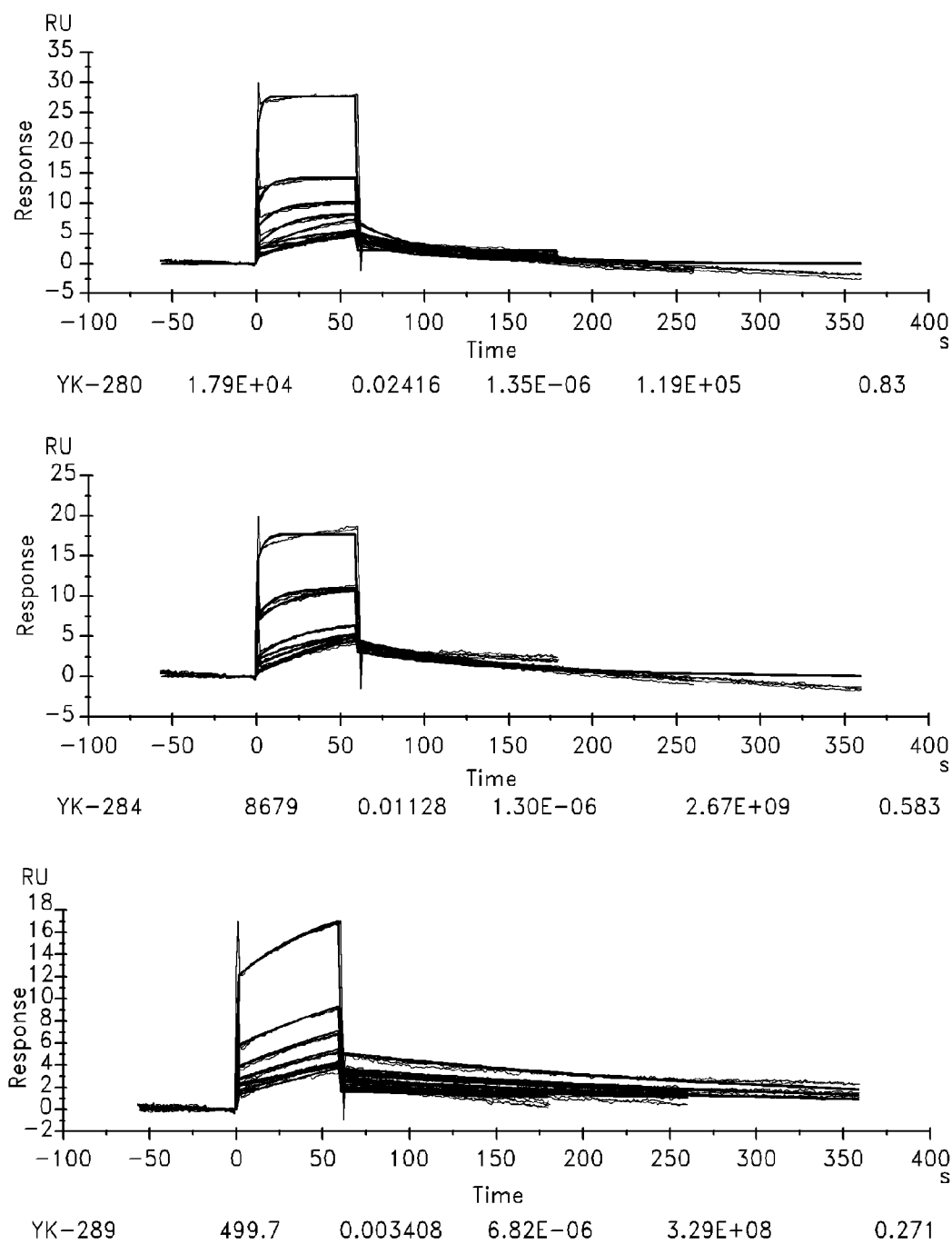

FIG. 23A and FIG. 23B show results of surface plasmon resonance for various compounds binding to EWS-FLI1. Each trace represents a different concentration of the tested compound. For the control NSC635437 compound, a KD of 2.10E-06 M was measured. For the YK-4-275 compound, a KD of 2.34E-07 M was measured. For the YK-4-280 compound, a KD of 1.35E-06 M was measured. For the YK-4-284 compound, a KD 1.30E-06 M was measured. For the YK-4-289 compound, a KD of 6.82E-06 M was measured.

Figure 24A:
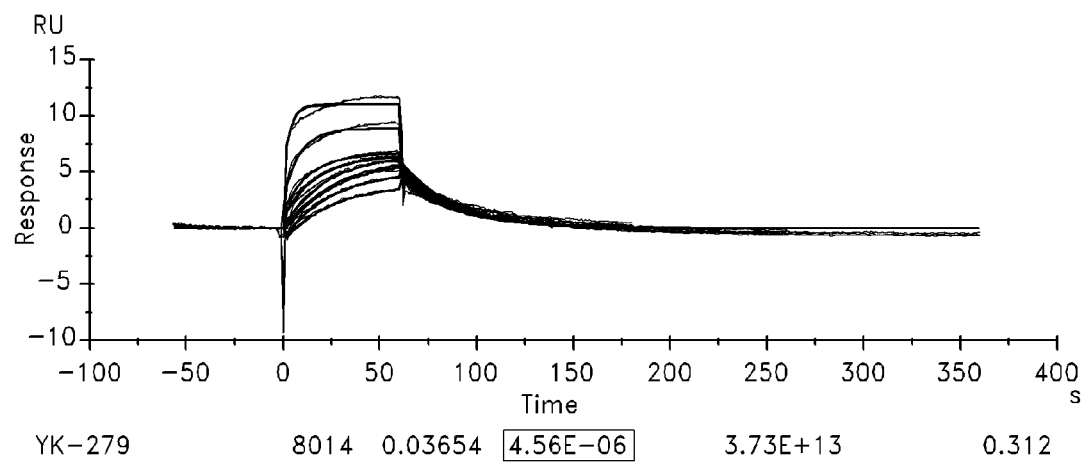
Figure 24A:
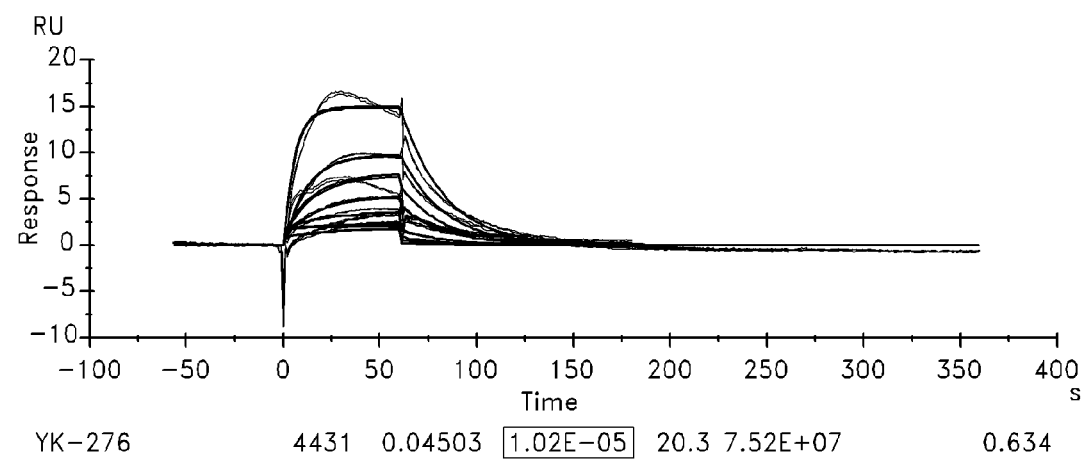
Figure 24B:
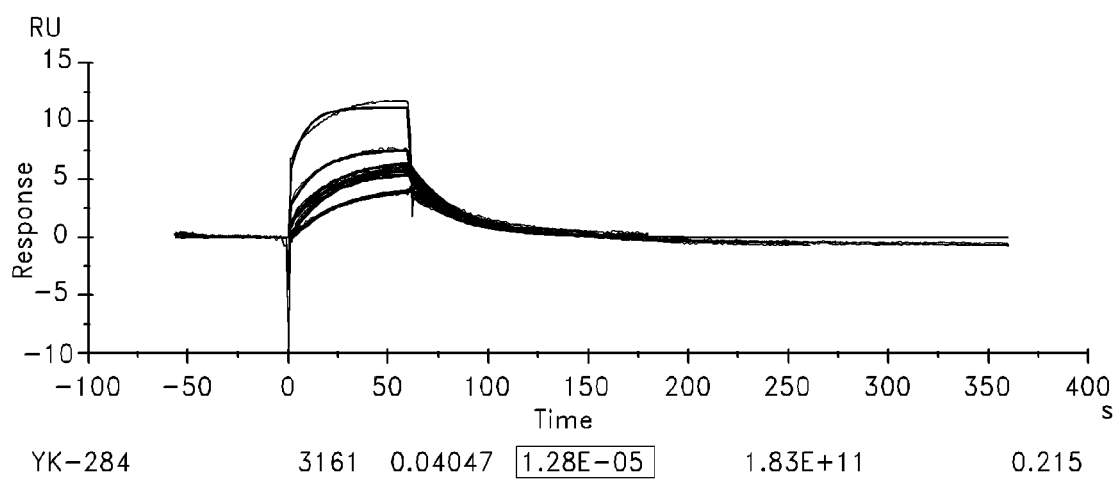
Figure 24B:
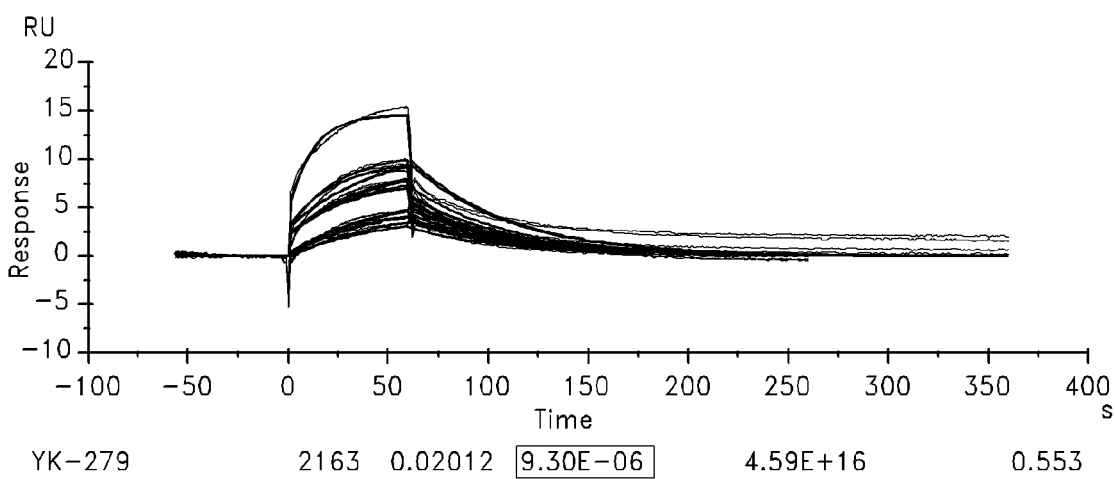
Figure 24C:
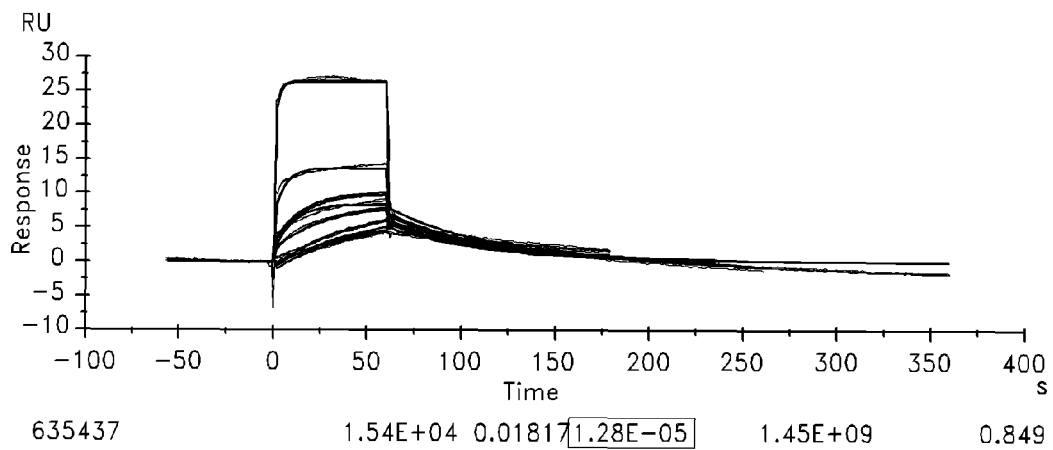
Figure 24C:
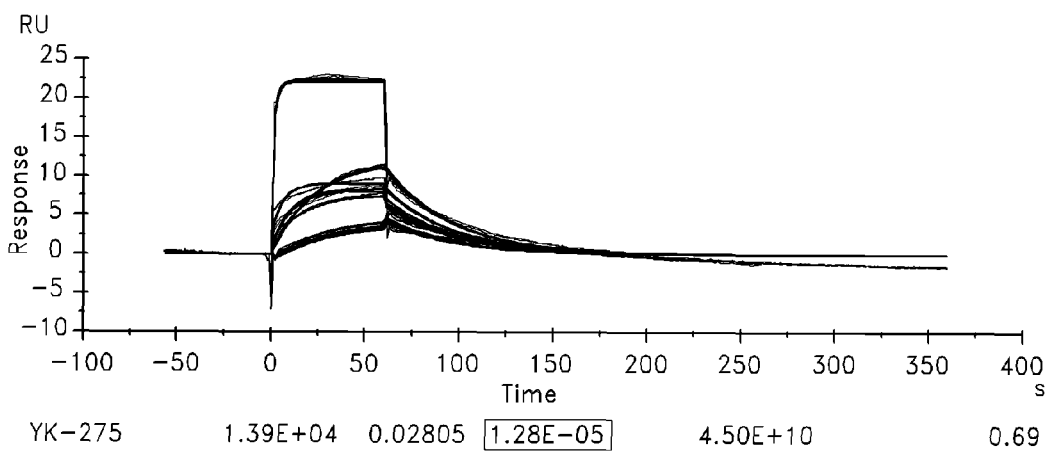
Figure 24C:
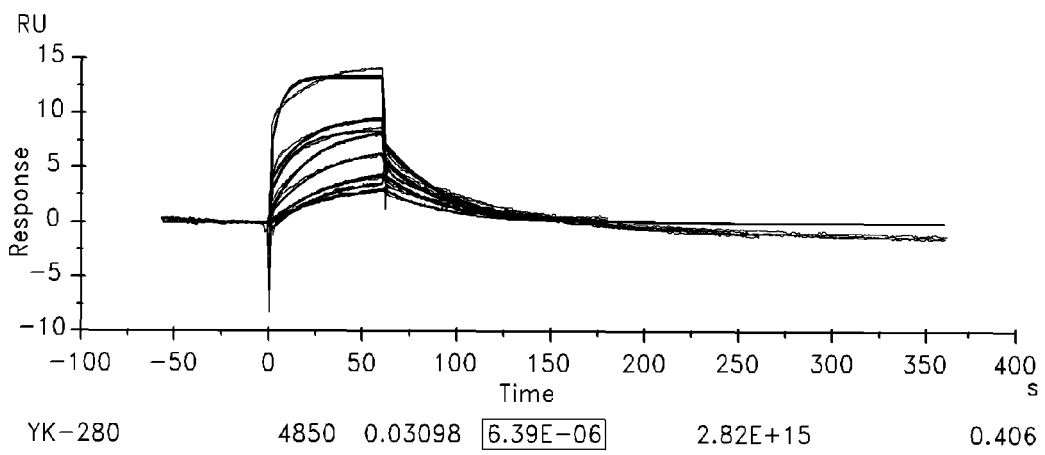

FIG. 24A, FIG. 24B, and FIG. 24C show results of surface plasmon resonance for various compounds binding to EWS-FLI1. Each trace represents a different concentration of the tested compound. For the control NSC635437 compound, a KD of 1.21E-06 M was measured. For the YK-4-279 compound, a KD of 4.56E-06 M was measured. For the YK-4-276 compound, a KD of 1.02E-05 M was measured. For the YK-4-284 compound, a KD of 1.28E-05 M was measured. For the YK-4-289 compound, a KD of 9.30E-06 M was measured. For the compound YK-4-275, a KD of 2.02E-06 M was measured. For the YK-4-280 compound a KD of 6.39E-06 M was measured.

Figure 25:
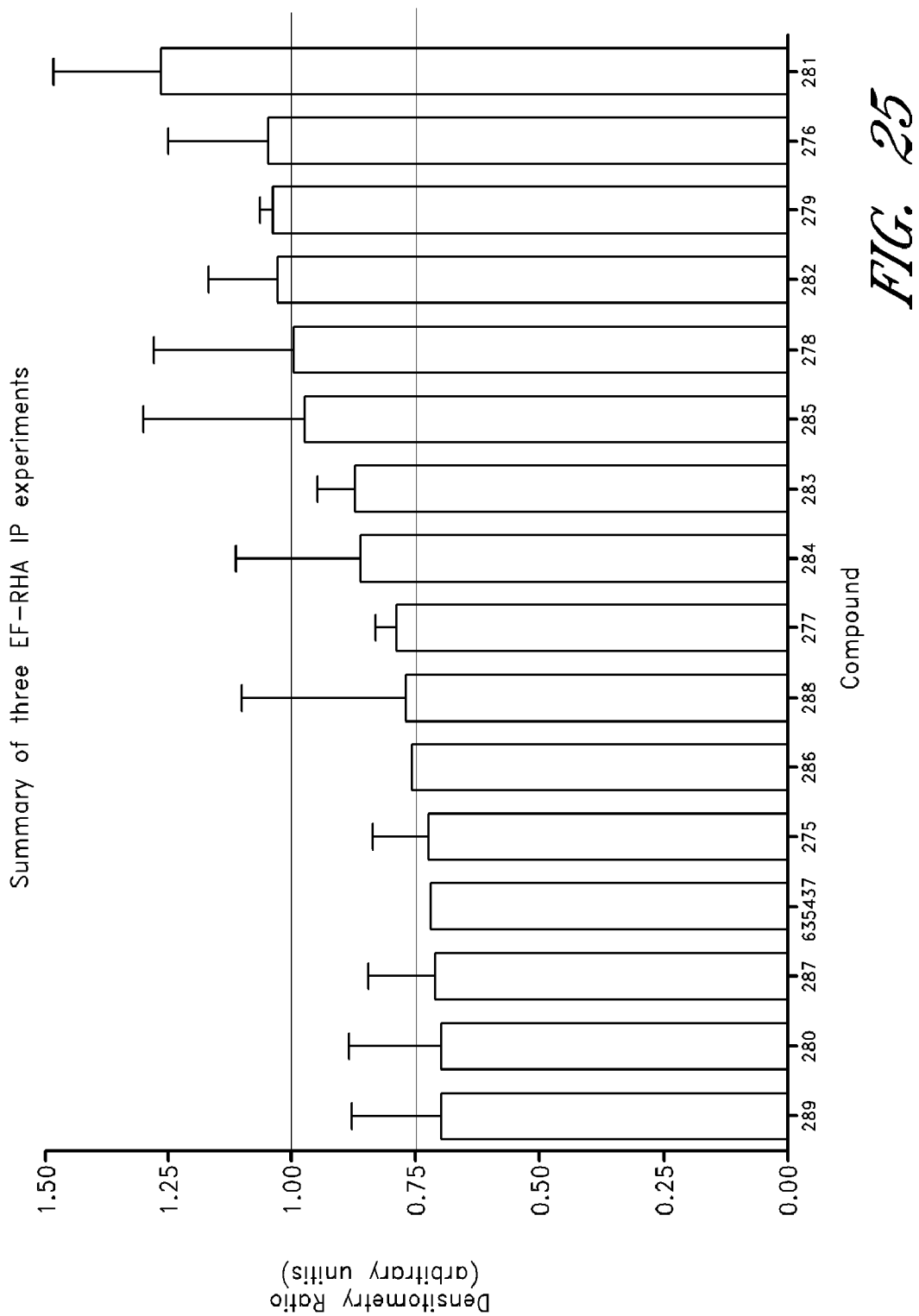
Figure 26A:
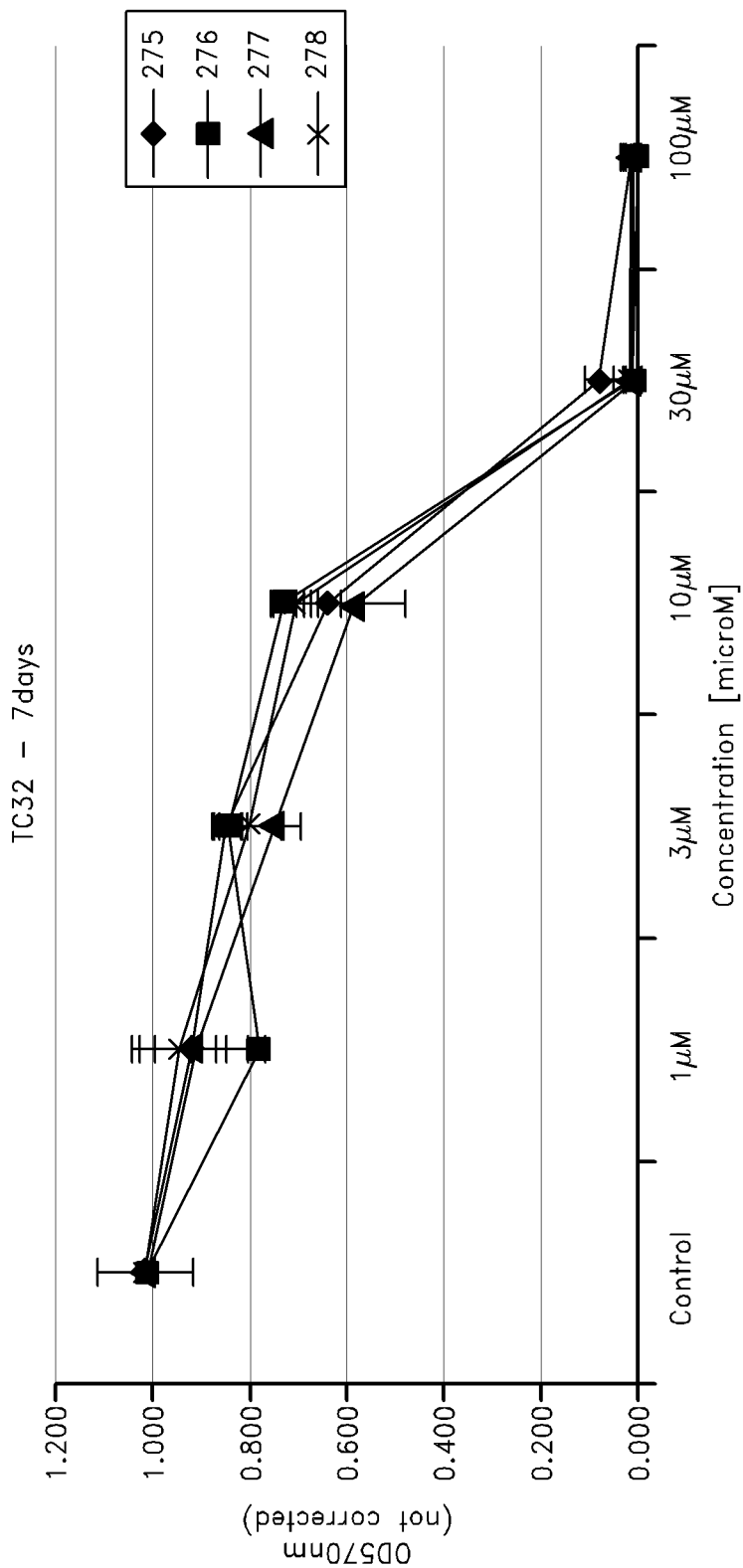
Figure 26B:
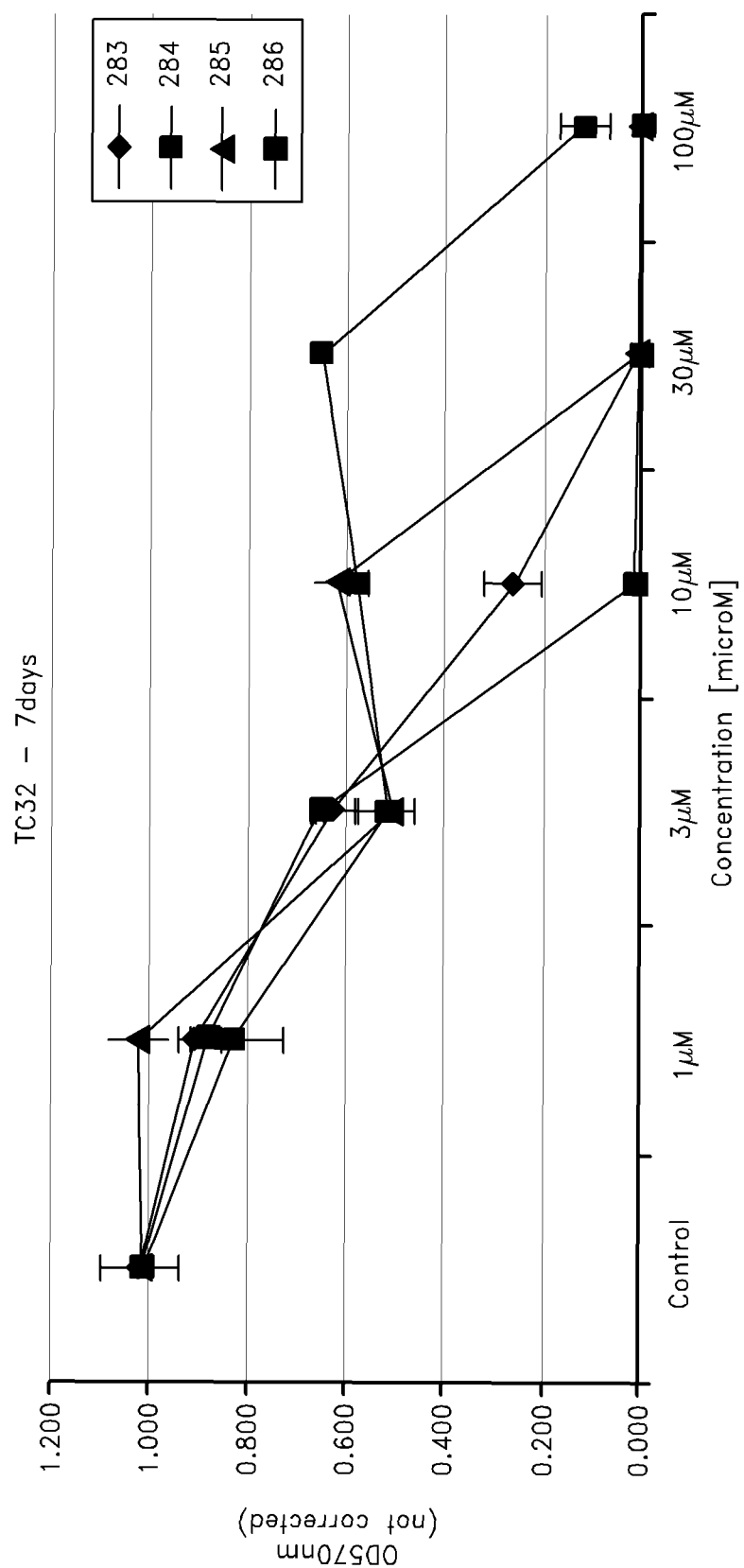
Figure 26C:
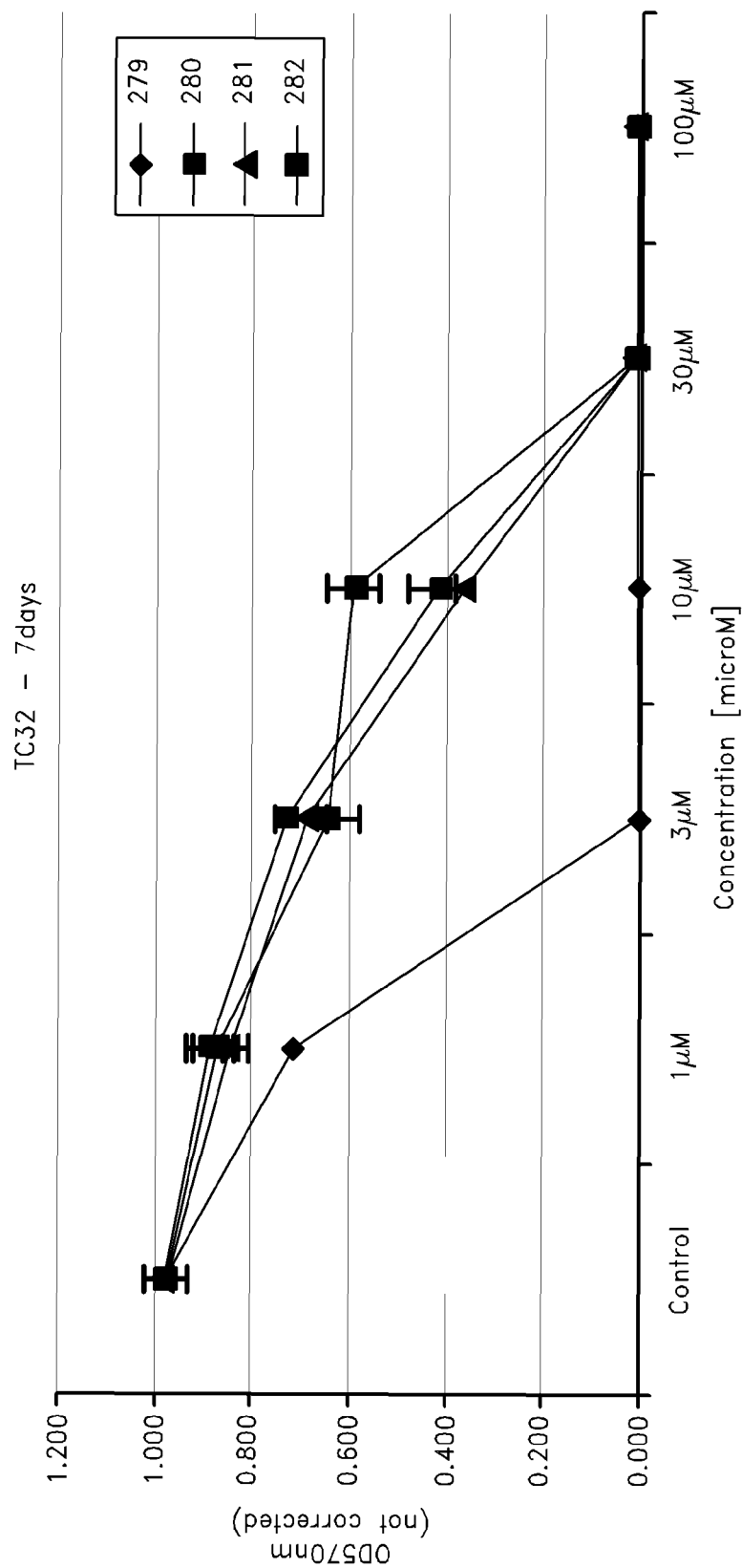
Figure 26D:
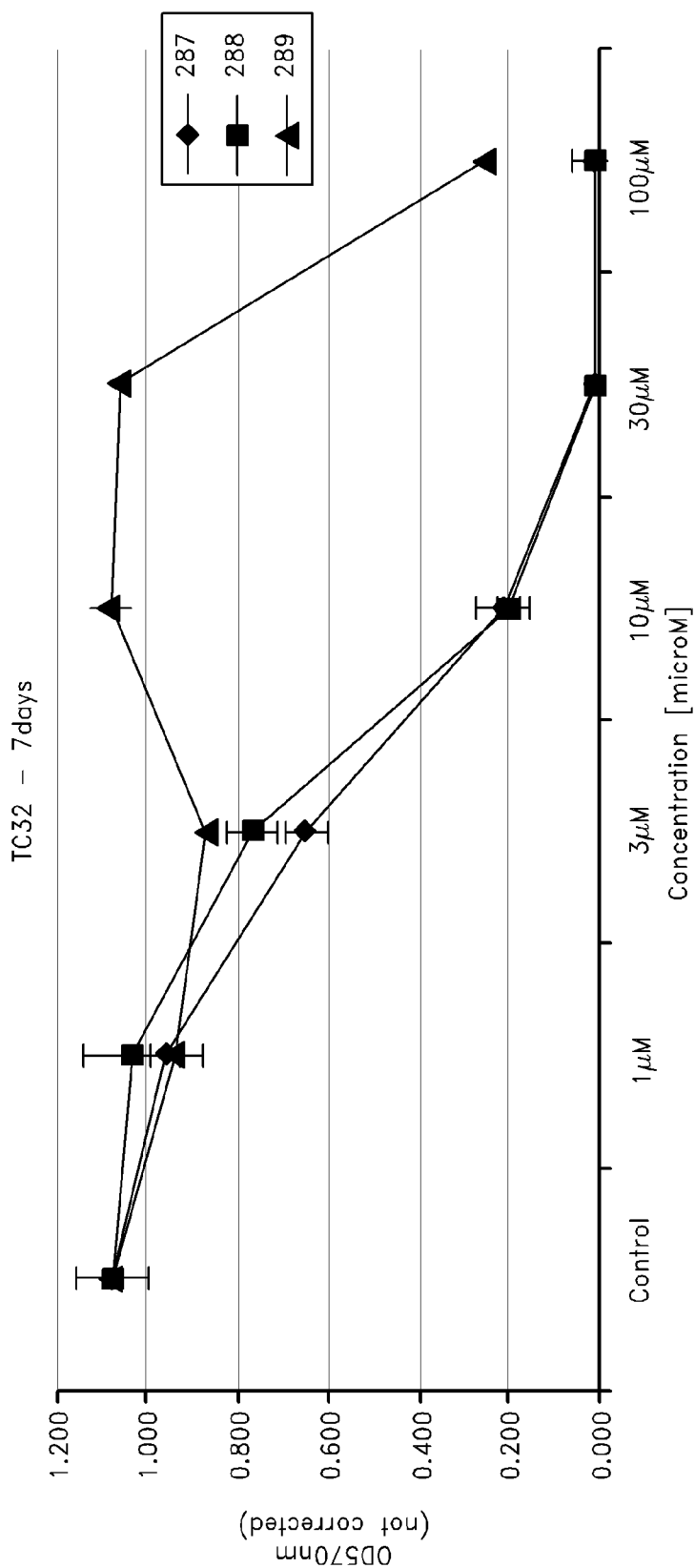

FIG. 25 shows the summary of three EF-RHA IP experiments. FIG. 25 demonstrates the effect of each of the YK-4-XXX and NSC635437 compounds (where XXX is the compound number labeled on the x-axis) upon RHA binding to EWS-FLI1. Each of the YK-4-XXX compounds was added to recombinant EWS-FLI1 at a final concentration of 10 microM. GST-RHA(630-1020) was added and the complex was immunoprecipitated with rabbit antiserum against FLI1. Complexes were resolved used PAGE and the amount of GST-RHA(630-1020) that co-precipitated was quantified using densitometry. Three experiments were averaged to obtain the data presented in the figure. The lower the value, the more effective the small molecule at disrupting EWS-FLI1 binding to RHA.

FIG. 26A, FIG. 26B, FIG. 26C, and FIG. 26D show 1050 on Ewing's sarcoma cells and demonstrate the effects of each of the YK-4-XXX compounds (where XXX is the compound number labeled on the x-axis) upon the growth of ESFT cell line TC-32. Cells were added to triplicate wells of a 96-well plate. Twenty-four hours after adding cells, compounds were added to the wells in at the doses indicated. Seven days after plating the cells, the dye WST was added to cells and following a 3-hour incubation, the absorbance indicated the relative cell number.

Figure 27:
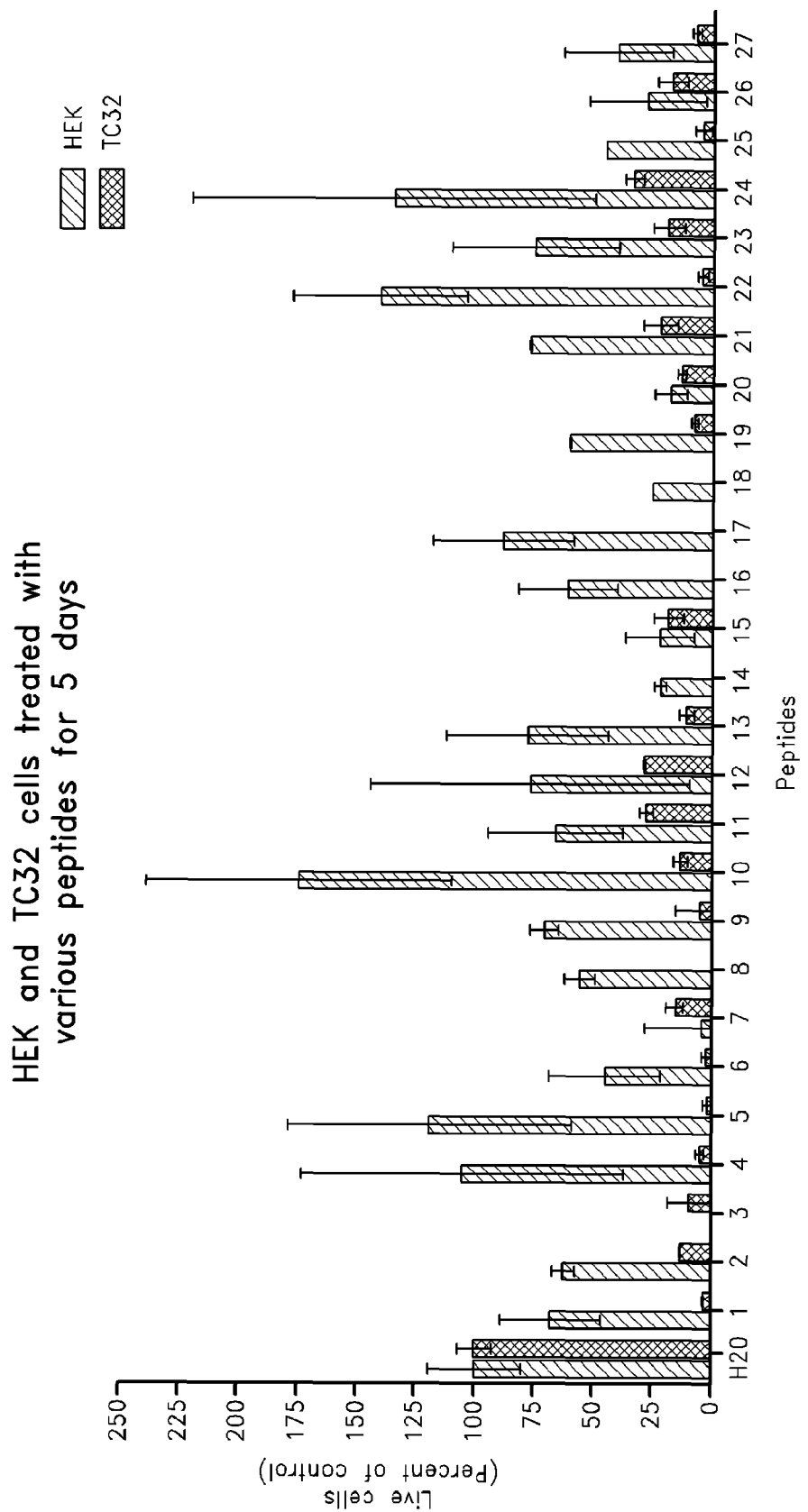

FIG. 27 shows toxicity of peptides on the TC32 (ESFT) and HEK (control) cell lines. Both cell lines were treated at 0, 3 and 5 days, with 30 μM peptides corresponding to SEQ ID NO.s: 1-27 (See Table 1). Cell viability was measured by MTT on day 7. Water was used as a control.

Figure 28:
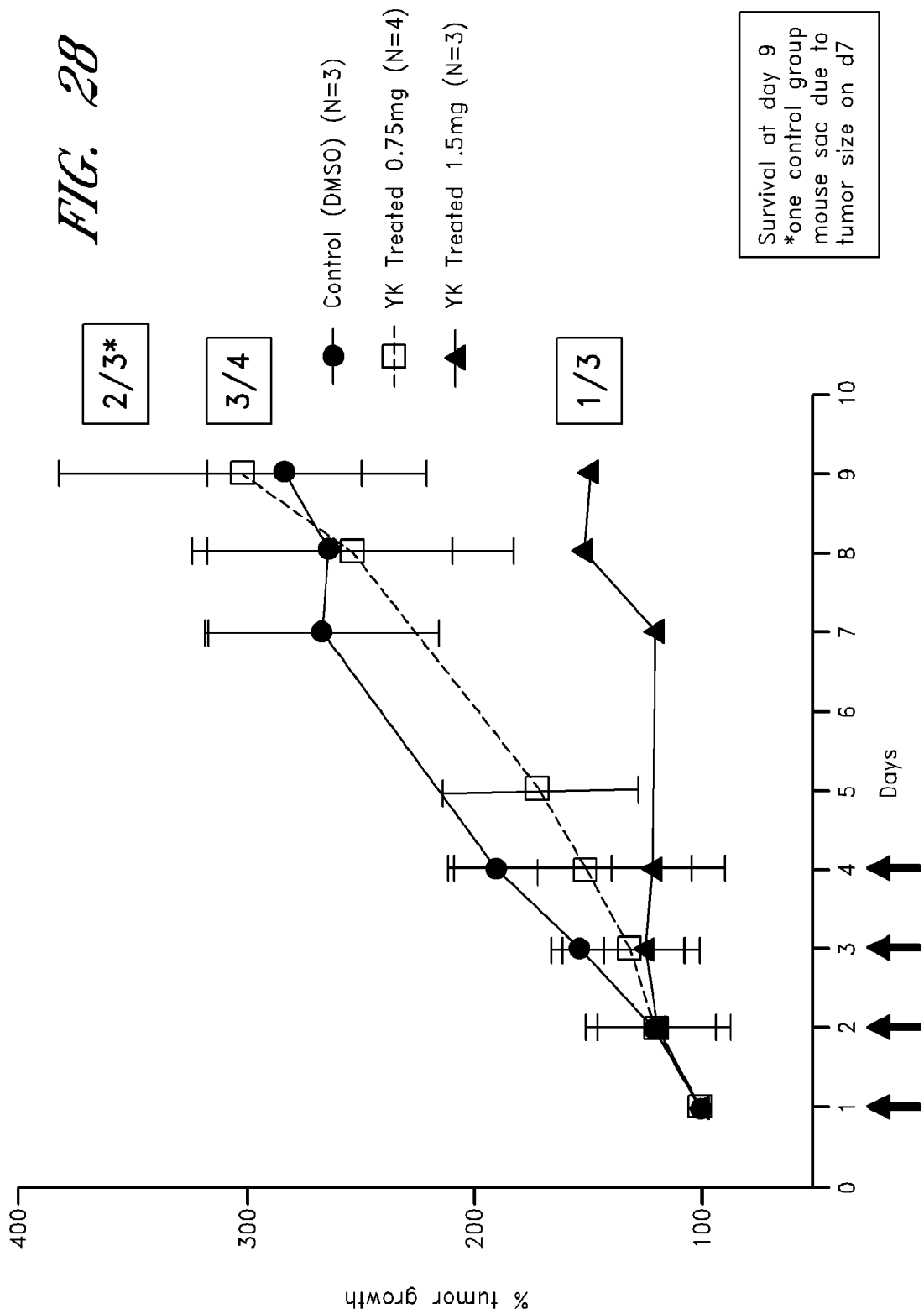

FIG. 28 shows inhibition of tumor growth in mice. Nude mice were inoculated with ESFT cell line CHP-100. When tumors were palpable, animals were treated with YK-4-275 (NSC635437) for 4 days. Curves show tumor volumes over time.

Figure 29A:
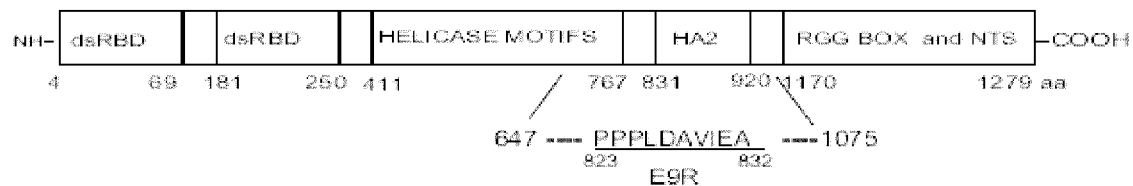
Figure 29B:
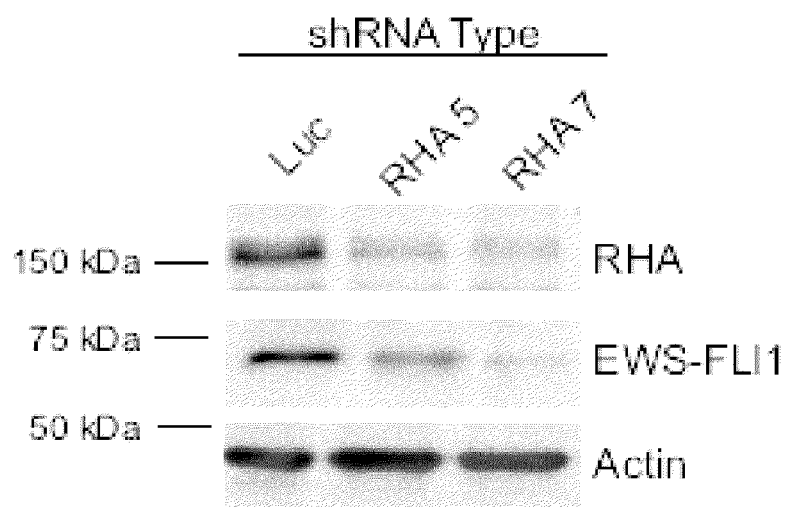
Figure 29C:
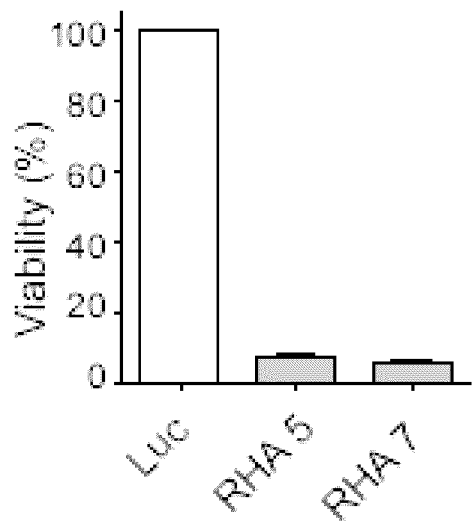
Figure 29D:
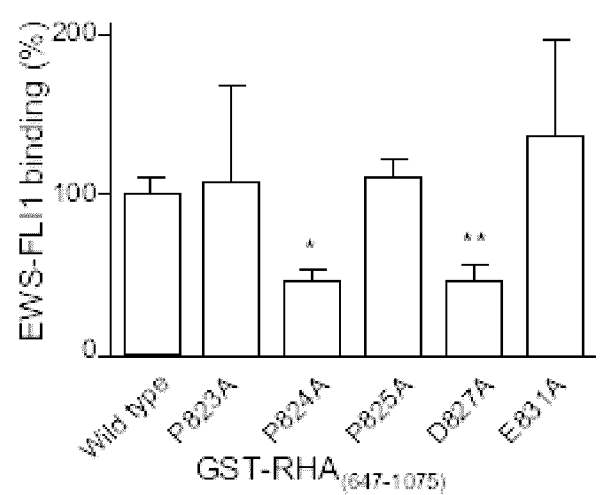
Figure 29E:
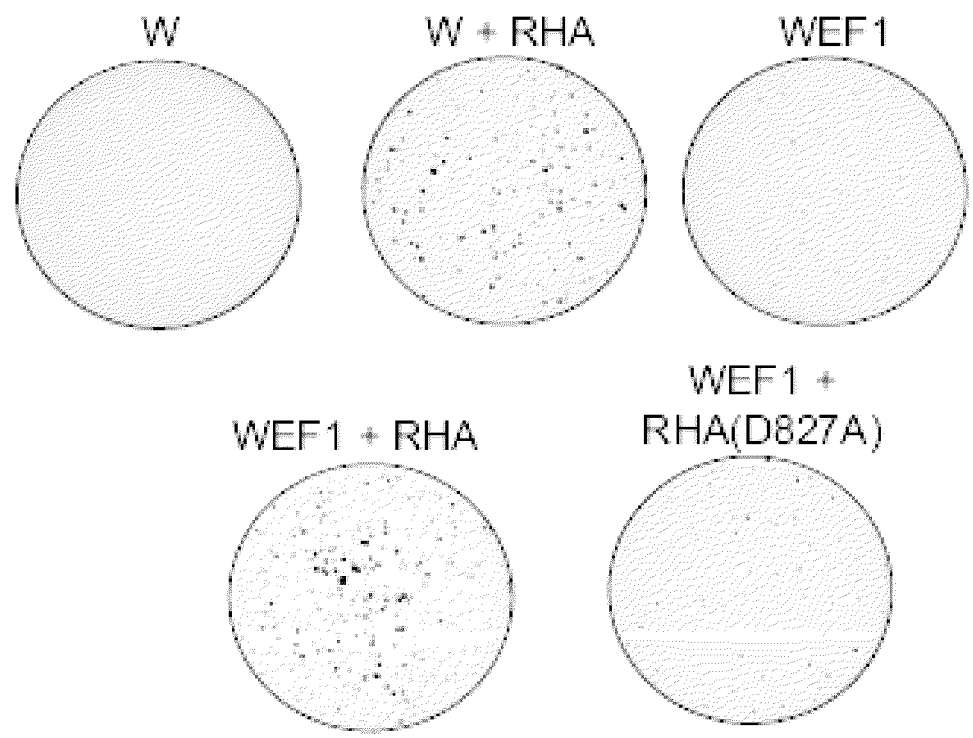
Figure 29F:
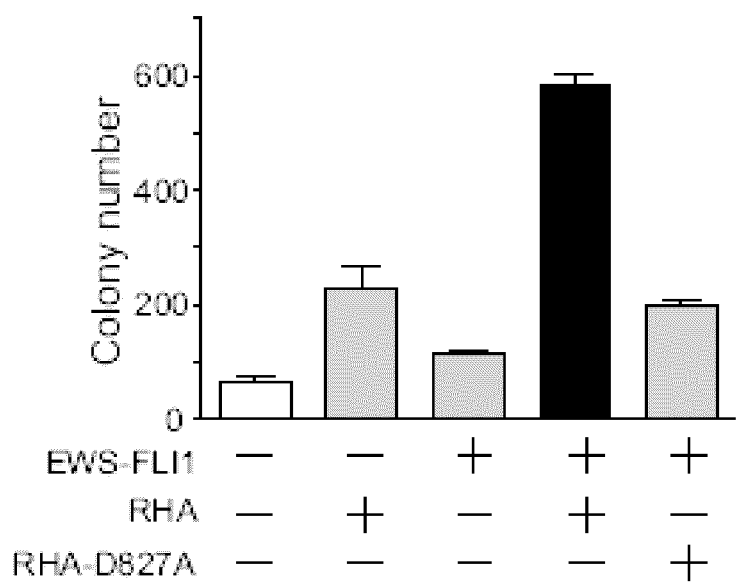
Figure 29G:
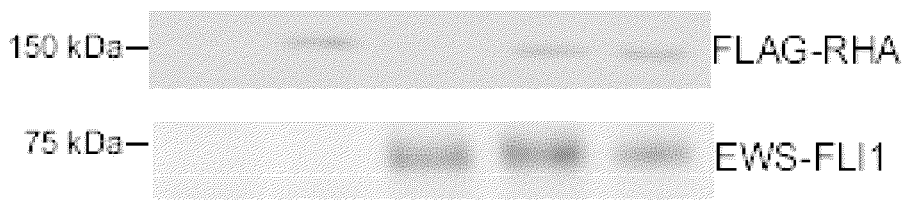
Figure 29H:
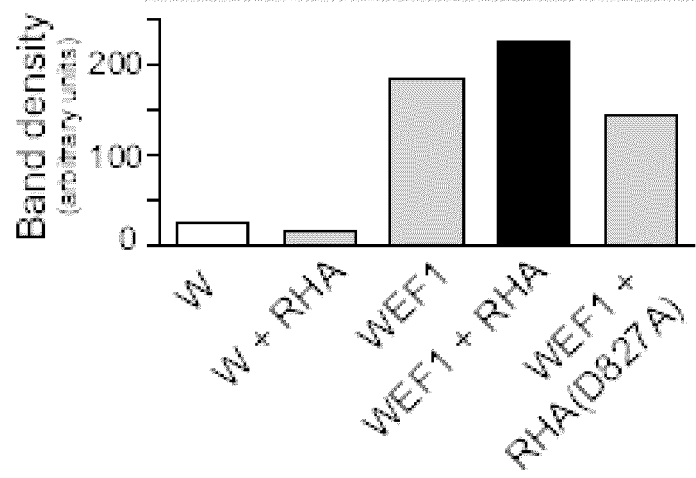

FIG. 29A shows a schematic representation of RHA including the region that binds to EWS-FLI1. The E9R peptide ("PPPLDAVIEA" SEQ ID NO: 29) corresponds to amino acids 823 to 832, located in the proximal of HA2 region of RHA. FIG. 29B shows a Northern blot for an shRNA expression vector transfected into TC71 (ESFT) cells to reduce RHA levels. FIG. 29C shows TC71 viability was reduced, as measured by WST reduction, following RHA shRNA expression. FIG. 29D shows a graph of alanine mutagenesis within E9R sequence followed by in vitro immunoprecipitation with EWS-FLI1. The density of the GST-RHA band was measured and this graph is the average of three experiments. RHA P824A and D827A mutants have significantly lower binding to EWSFLI1 (*p=0.0129 and **p=0.0034 respectively). FIG. 29E shows the results of murine fibroblasts placed in soft-agar for anchorage-independent growth assays (empty vector (W), EWS-FLI1 alone (WEF1)). FIG. 29F shows a graph that enumerates the colonies counted in three separate experiments; the difference between wild-type and mutant RHA was significant (*p=0.0028). FIG. 29G shows protein expression for the fibroblasts, detected with anti-FLAG (top) or anti-FLI1 (bottom). FIG. 29H shows a graph of densitometry of the EWSFLI1 blot performed using MultiGauge software.

Figure 30A:
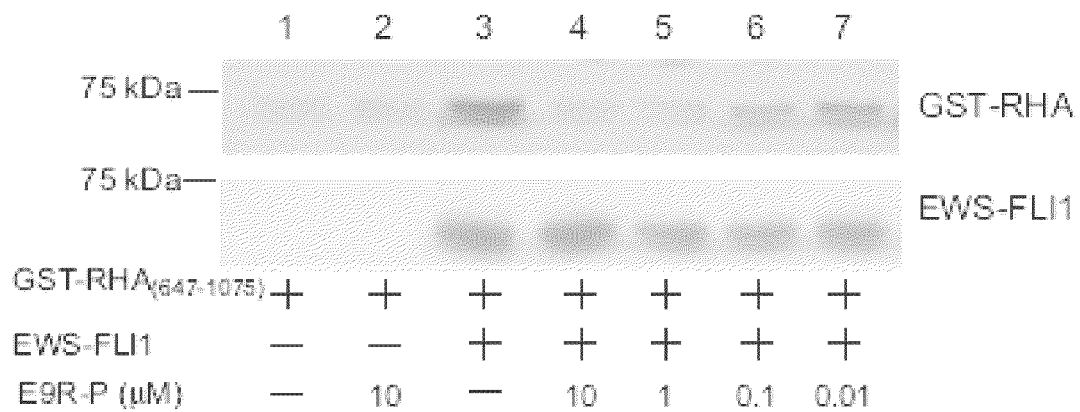
Figure 30B:
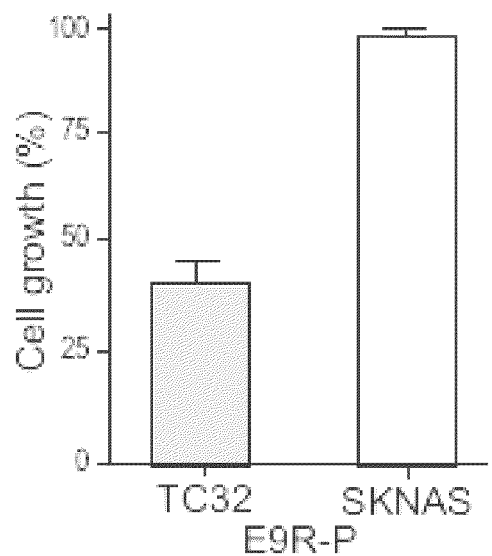
Figure 30C:
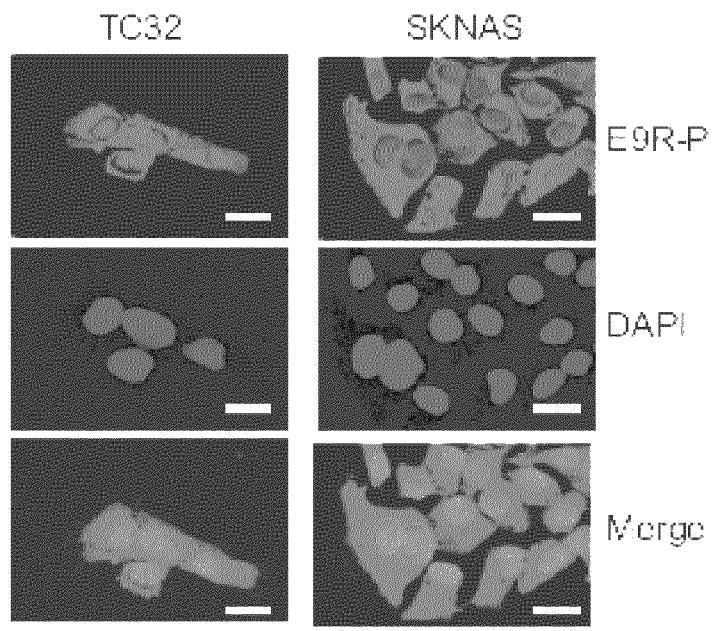
Figure 30D:
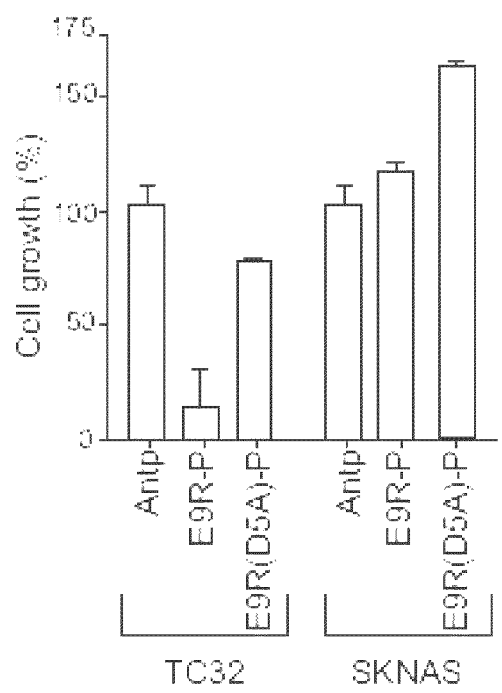
Figures 30E, 30F:
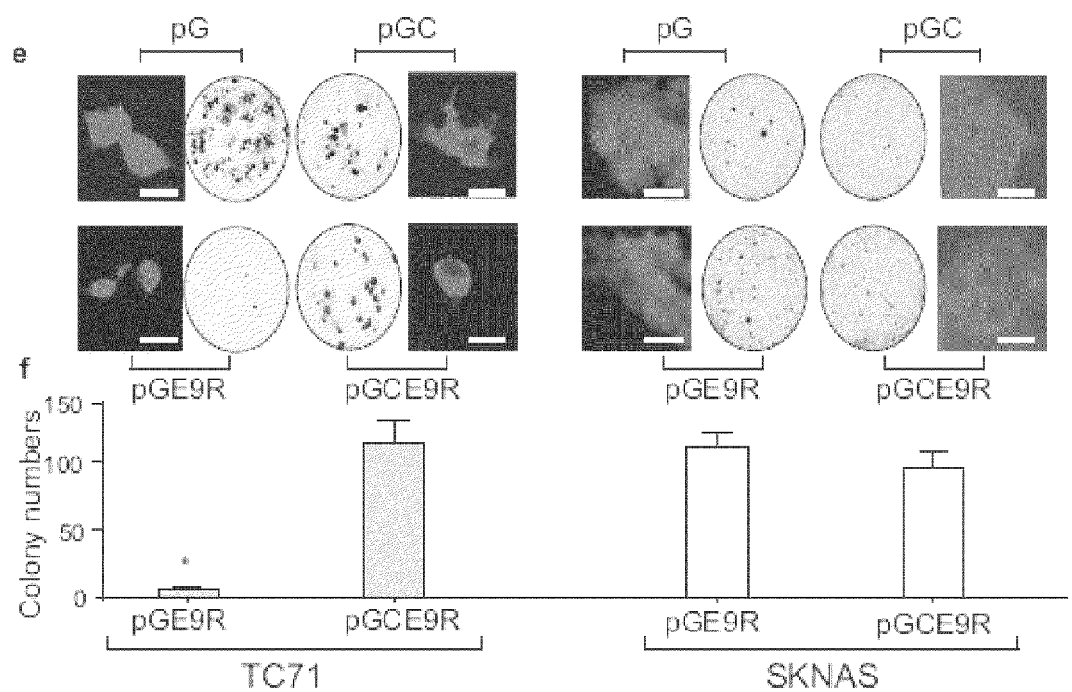

FIGS. 30A-30F provide data to show E9R peptide prevents EWS-FLI1 binding to RHA with specific detrimental effects upon ESFT growth and transformation. FIG. 30A shows a Western blot for immunoprecipitation of GST-RHA (647-1075) using recombinant full-length EWS-FLI1 bound to a FLI1 antibody. FIG. 30B shows a graph for growth reduction upon E9R-P (Antennapedia-E9R) treatment (10 μM) was observed in TC32 cells but not SKNAS cells. FIG. 30C shows photomicrographs for E9R-P peptide uptake tracked with FITC label (upper panels). Merged images of DAPI nuclear counter-stain (middle panels) and FITC-Ant-E9R (lower panels) showed peptide was distributed throughout the cytoplasm and nucleus of both TC32 and SKNAS cells. Scale bar equals 20 μm. FIG. 30D shows a graph where neither Antennapedia alone (Antp), nor a mutant of an aspartic acid residue important for RHA binding to EWS-FLI1 (E9R-D5A-P) reduced growth of TC32 cells while E9R-P reduced cell growth. FIG. 30E shows photomicrographs for TC71 and SKNAS cells expressed EGFP empty vector (pG), EGFP-E9R (pGE9R), EGFP with nuclear export sequence (pGC) or EGFP-E9R with nuclear export sequence (pGCE9R). Only expression of EGFP-E9R in TC71 reduced anchorage independent growth. FIG. 30F shows a graph for colony numbers of three experiments averaged with a significant reduction in only TC71 cells when expressing E9R throughout the cell (*p=0.0012). Scale bar equals 20 μm.

Figure 31A:
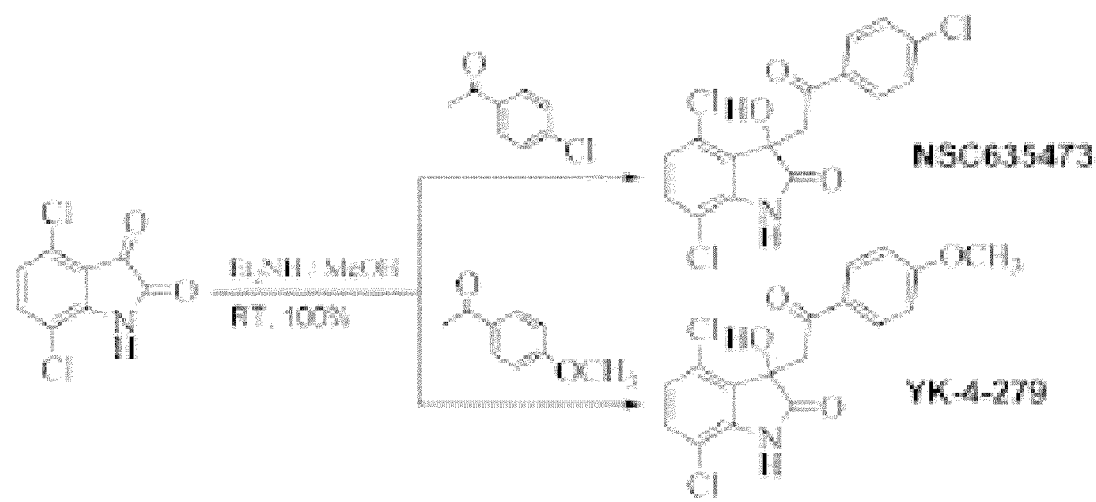
Figure 31B:
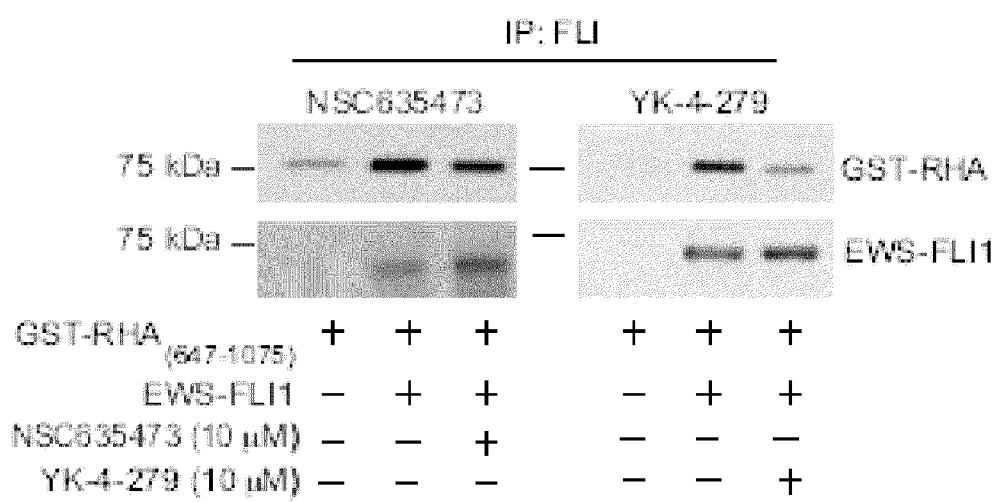
Figure 31C:
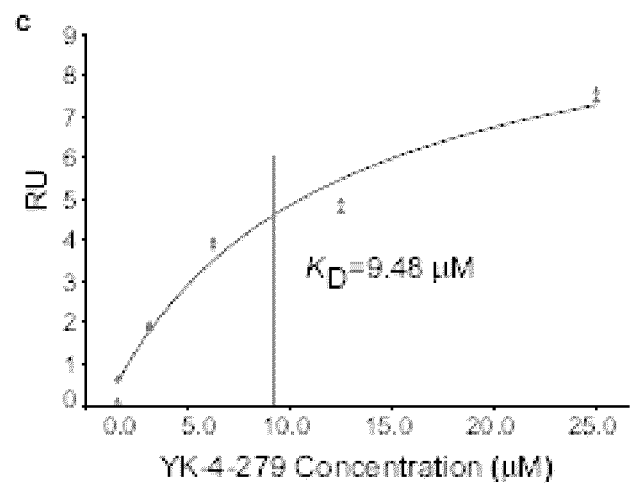
Figure 31D:
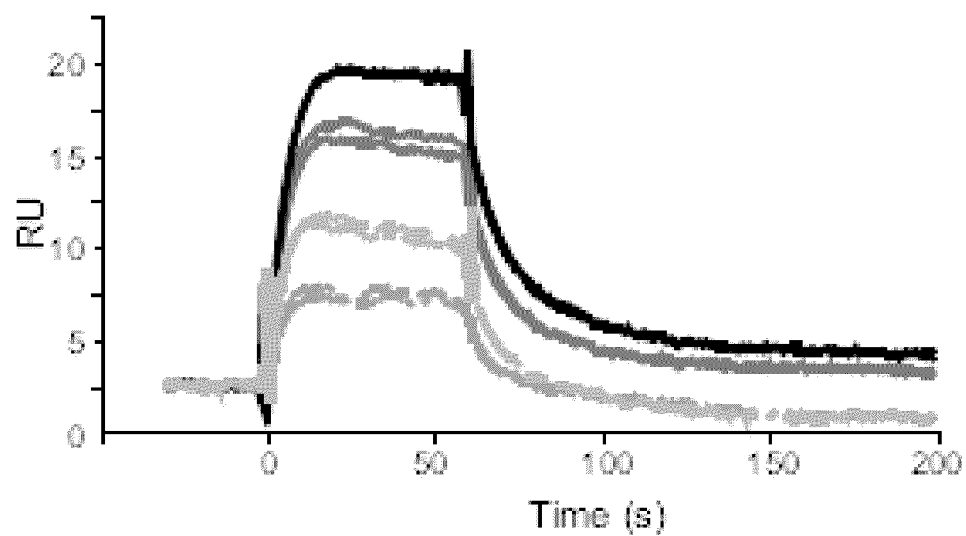
Figure 31E:
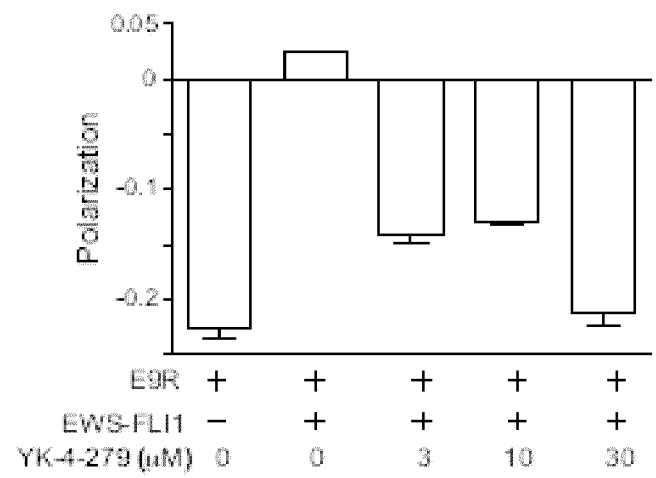

FIGS. 31A-31E provide data showing a small molecule binding to EWS-FLI1 and displaces E9R from EWS-FLI1. FIG. 31A shows NSC635437, 3-hydroxy-3-(2-oxo-2-phenyl-ethyl)-1,3-dihydro-indol-2-one synthesized with 100% yield. Aromatic functionalization produced YK-4-279 a para-methoxy derivative of NSC635437. FIG. 31B shows a Western blot for EWS-FLI1 incubated with NSC635437 (three left-most lanes/columns) or YK-4-279 (three right-most lanes/columns) followed by the addition of GST-RHA (647-1075). A FLI1 antibody complexed EWS-FLI1 and precipitated it from the solution. FIG. 31C shows a graph for YK-4-279 steady state kinetics for binding to recombinant EWS-FLI1 that was immobilized on a CM5 Biacore chip. FIG. 31D shows a graph for SPR displacement assay of 64 μM E9R alone (Black solid line) and with addition of YK-4-279 (Grey dashed line); 32 μM E9R alone (Dark blue solid line) and with addition of YK-4-279 (Light blue dashed line). FIG. 31E shows a graph for fluorescent polarization indicated the binding of 3.2 μM of FITC-E9R to EWS-FLI1, which was competitively inhibited by increasing concentrations of YK-4-279.

Figure 32A:
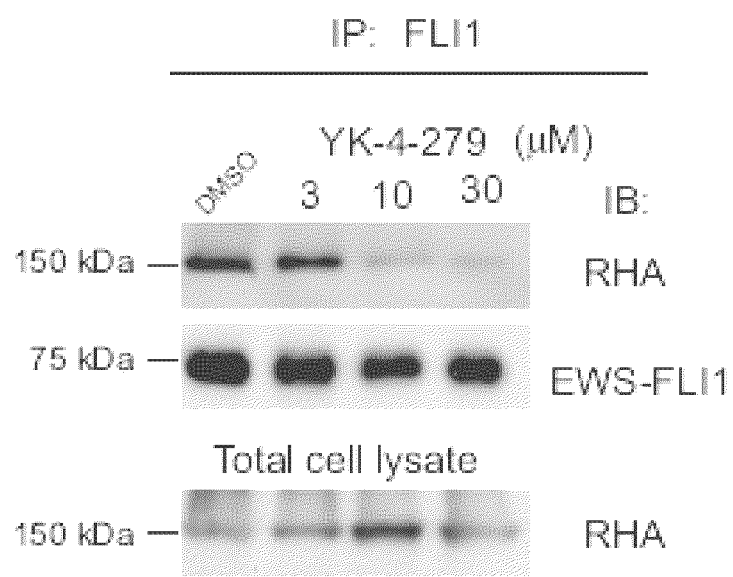
Figures 32B, 32C:
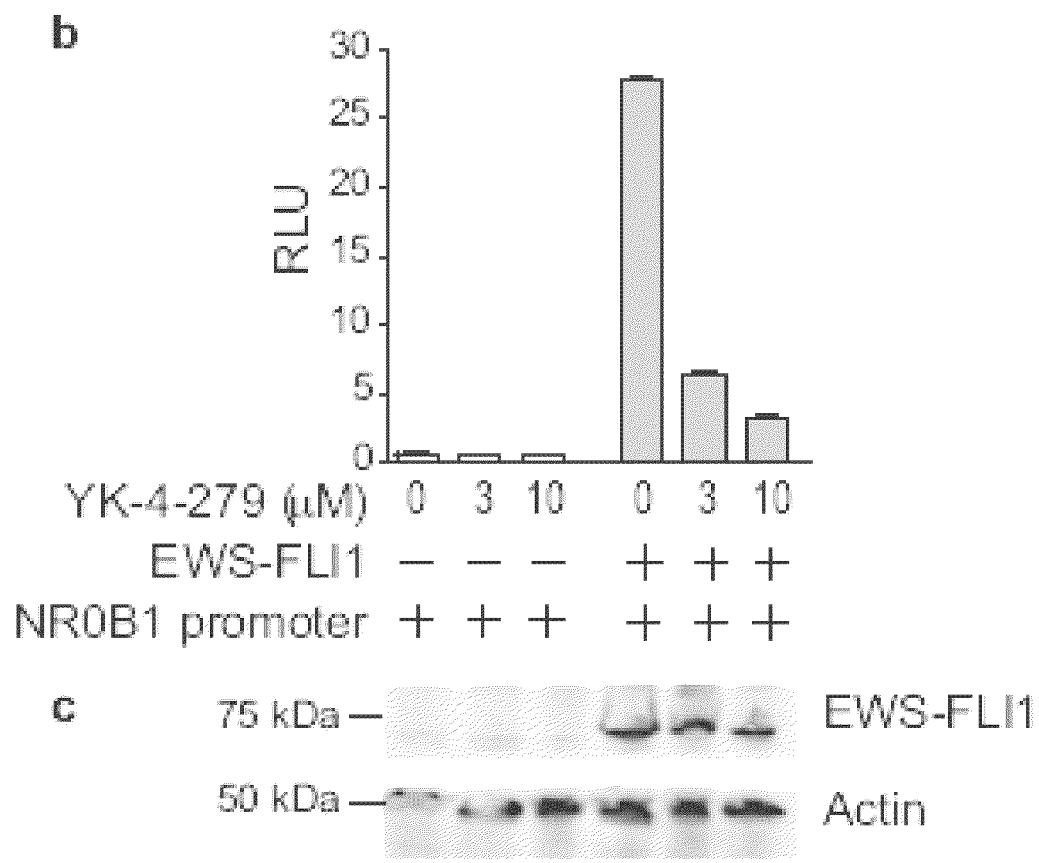
Figure 32D:
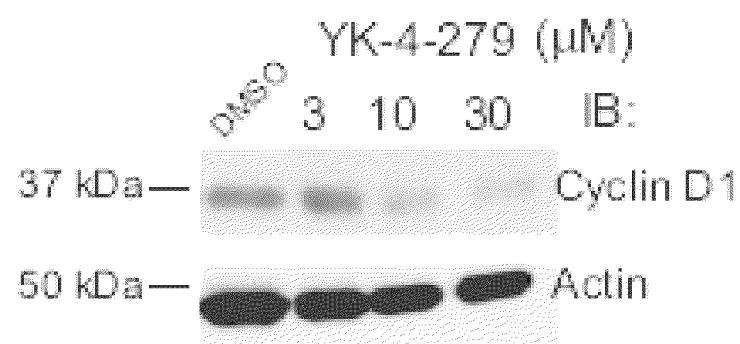

FIGS. 32A-32D provide data showing YK-4-279 reduces EWS-FLI1 functional activity. FIG. 32A concerns TC32 cells that were treated with YK-4-279 and resolved protein lysates and that were immunoblotted for co-precipitated RHA (top), EWS-FLI1 (middle), or total RHA (bottom). FIG. 32B shows a graph for a luciferase reporter assay of EWS-FLI1 responsive NR0B1 promoter showed YK-4-279 dose-dependent (18-hour treatment) reduction in the promoter activity in COS7 cells. FIG. 32C shows a Northern blot for protein lysates from transfected cells showed expression of EWS-FLI1. FIG. 32D shows a Northern blot for YK-4-279 treated TC32 cell lysates (treated for 14 hours) were blotted for cyclin D1 and actin.

Figures 33A, 33B, 33C:
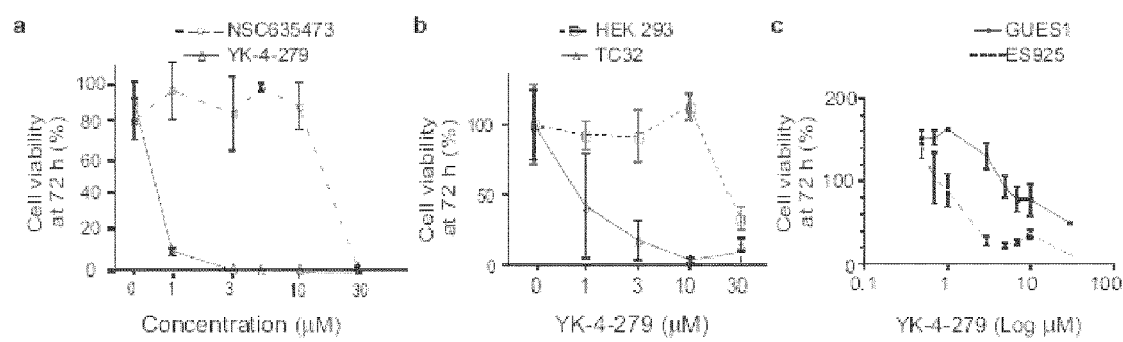
Figure 33D:
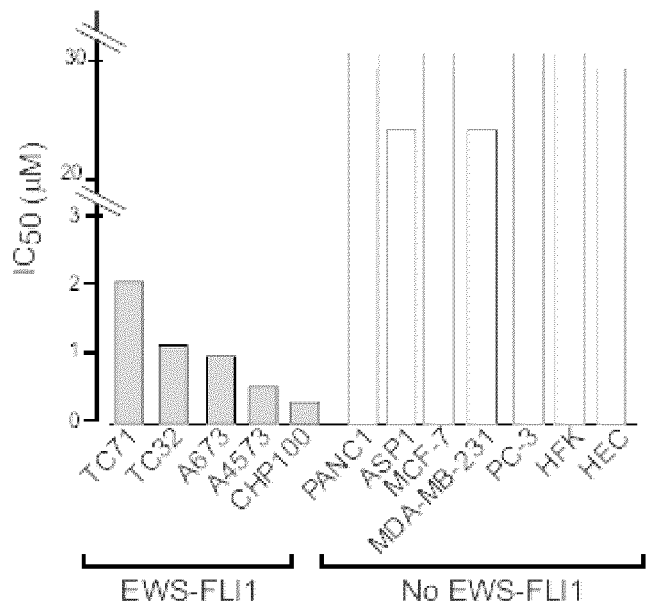
Figure 33E:
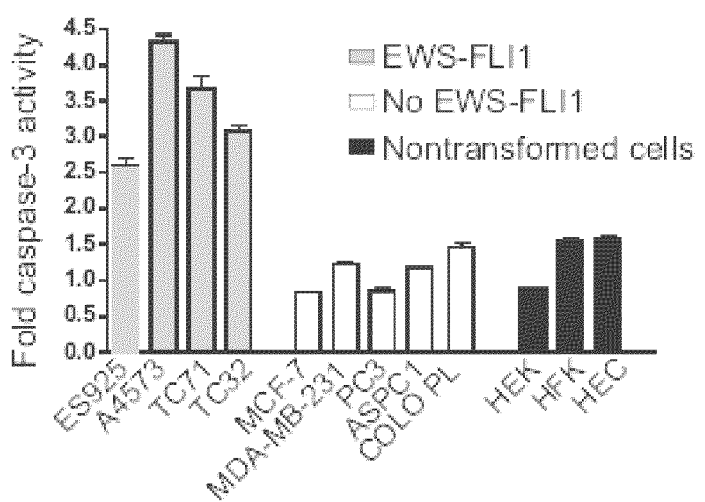
Figure 33F:
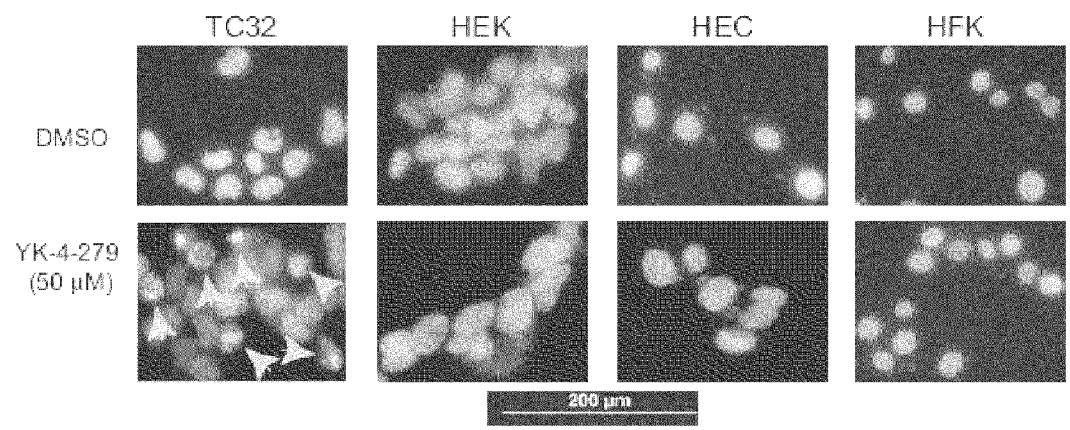

FIGS. 33A-33F provide data showing YK-4-279 is potent and specific inhibitor of ESFT. FIG. 33A shows a graph for TC32 cells treated with a dose range of YK-4-279 and NSC635437. Cell number was measured by MTT or WST reduction after seven days in culture. FIG. 33B shows a graph for TC32 and HEK-293 (non-transformed, lacking EWS-FLI1) treated similarly to (A). FIG. 33C shows a graph for primary ESFT explant cell lines GUES1 and ES925 treated for 3 days with YK-4-279. FIG. 33D cell lines expressing EWS-FLI1 compared to non-EWS-FLI1 malignant cell lines following 3 days in culture to establish the IC50 using WST assay. FIG. 33E shows a graph for caspase 3 activity of a panel of ESFT (TC32, TC71, A4573, and ES925), malignant non-EWS-FLI1 expressing (MCF-7, MDA-MB-231, PC3, ASPC1, COLO-PL), and non-transformed cells (HEK-293, HFK, and HEC). Graph plots level of fluorescence in treated divided by untreated lysate. FIG. 33F shows photomicrographs where arrows indicated apoptotic nuclear fragmentation after 50 μM YK-4-279 treated ESFT (TC32) and non-transformed cells (HEK-293, HFK, and HEC). Scale bar equals 200 μm.

Figures 34A, 34B:
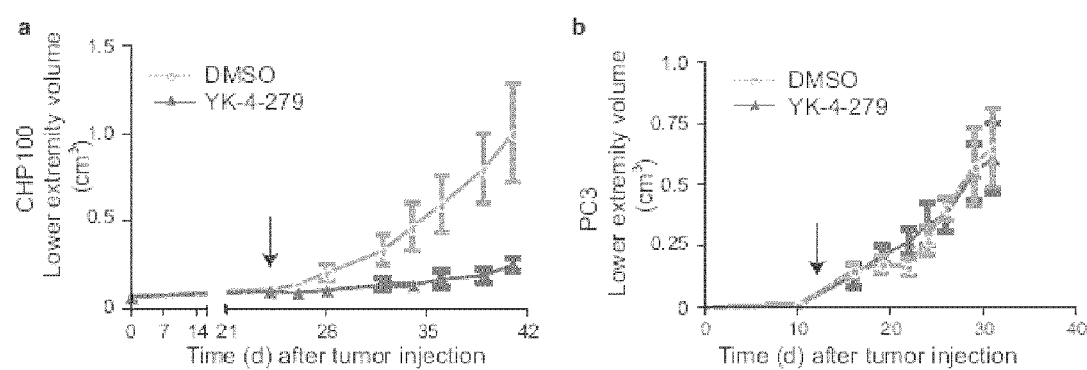
Figure 34C:
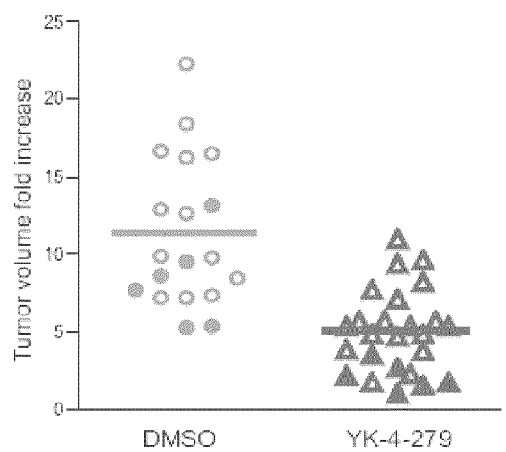
Figure 34D:
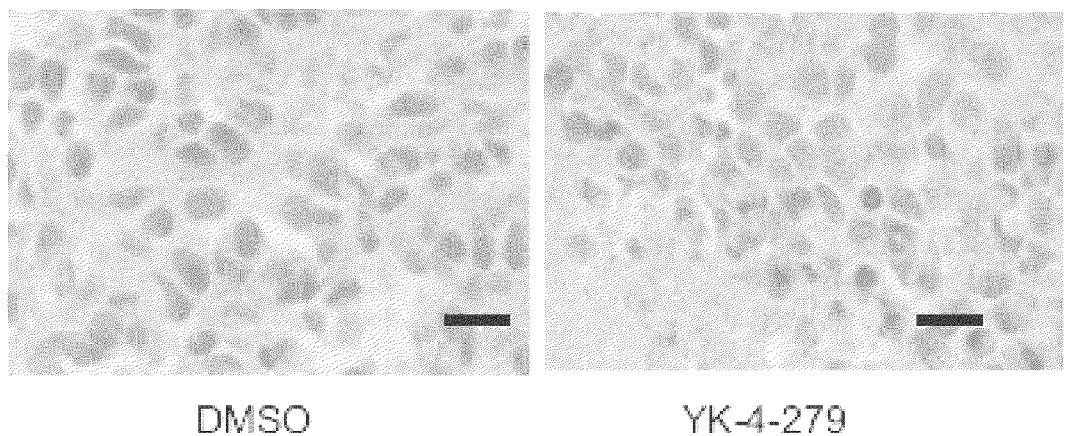
Figure 34E:
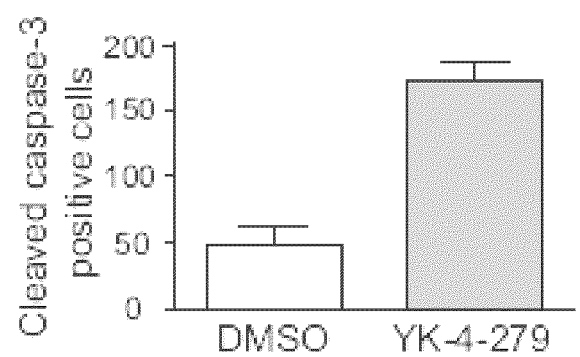

FIGS. 34A-34E provide data showing YK-4-279 inhibited the growth of ESFT xenograft tumors. Xenografts were established with injection of either ESFT (CHP-100 or TC71) or Prostate cancer (PC3) cells. FIG. 34A shows a graph for CHP-100 intramuscular xenografts (arrow indicates when tumors were palpable) receiving DMSO (n=4; open circles) or 1.5 mg YK-4-279 (n=5; triangles) (p=0.016, by t Test comparison). Single experiment growth curves depicted are representative of five independent experiments. FIG. 34B shows a graph for PC3 subcutaneous xenografts (arrow indicates when tumors were palpable) treated as CHP-100 cells (a) (n=5 per group, representative of 3 independent experiments). FIG. 34C shows a graph for overall response of ESFT xenografts (TC71, open symbols, and CHP-100, closed symbols) to YK-4-279 (1.5 mg/dose). Tumor volumes at day 14 after treatment initiation compared across 5 experiments (DMSO n=19, YK-4-279 n=25, p<0.0001, by Mann-Whitney test). FIG. 34D shows a photomicrograph for tumors from the mice in (A) analyzed for activation of caspase-3 activity using immunohistochemistry. FIG. 34E shows a graph for caspase-3 positive cells counted (n>500 in 3 high-power-fields) in 4 separately stained slides for each group (p=0.041).

Figure 35A:
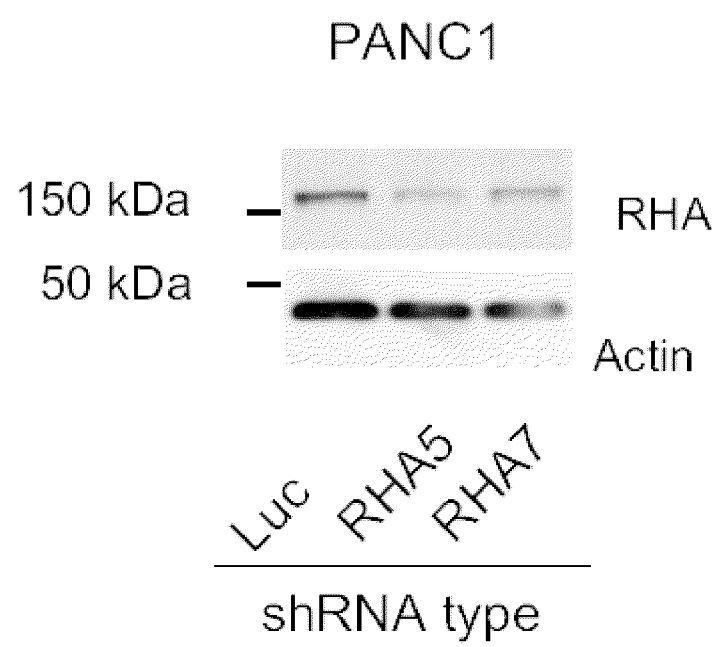
Figure 35B:
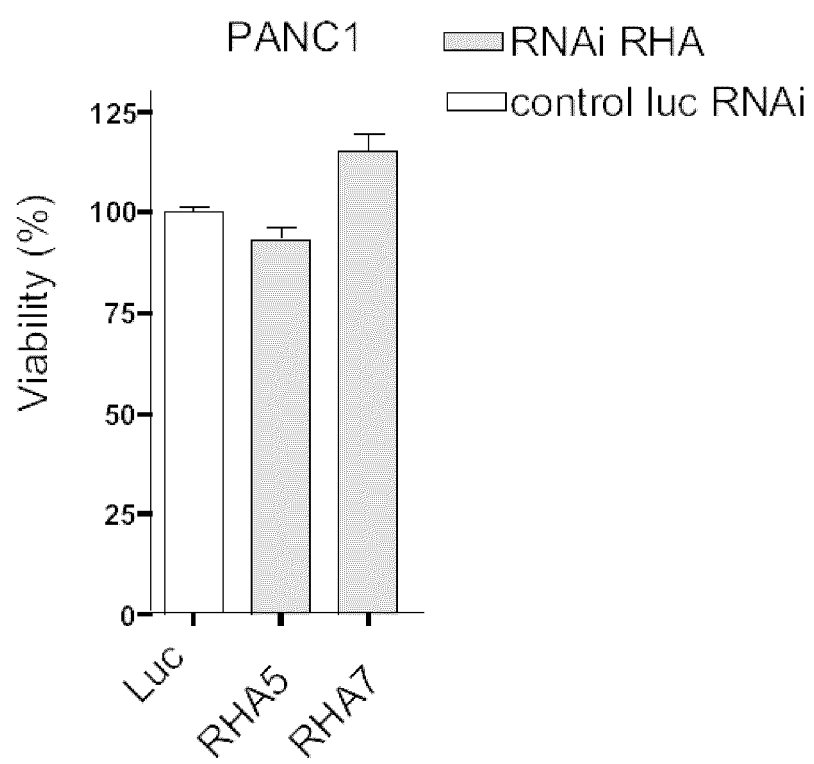

FIGS. 35A and 35B provide data showing PANC1 cells infected with virus containing either siRNA for RHA or control luciferase. FIG. 35A shows an immunoblot showing protein levels following 6 days of selection. FIG. 35B shows viability of cells using WST reduction 6 days after selection and RHA reduction.

Figure 36:
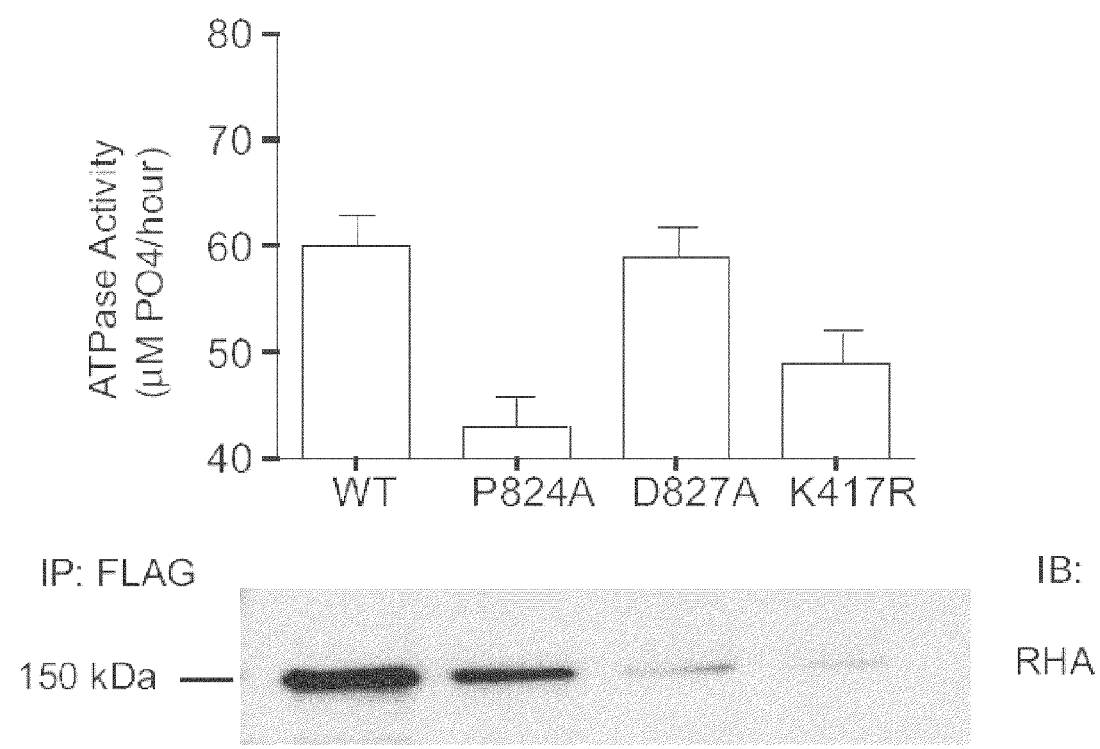

FIG. 36 shows a graph for ATPase assay where Biomol Green was used to detect free phosphate. While the P824A mutant did show reduced ATPase activity, the D827A mutation did not affect RHA function. Phosphate standards were used to calibrate the assay and determine the rate of ATP hydrolysis. RHA(K417R) is a known NTPase-null mutant of RHA. Immunoglobulin control immunoprecipitations did not demonstrate ATPase activity.

Figure 37:
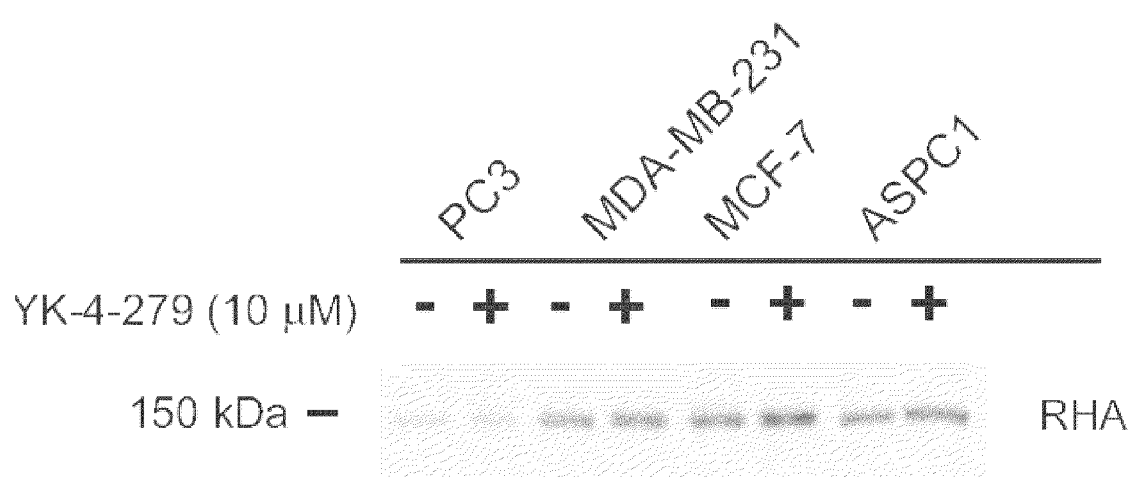

FIG. 37 shows an immunoblot from log-phase cell lysates that were either treated with DMSO control or 10 μM YK-4-279 overnight.

Figure 38A:
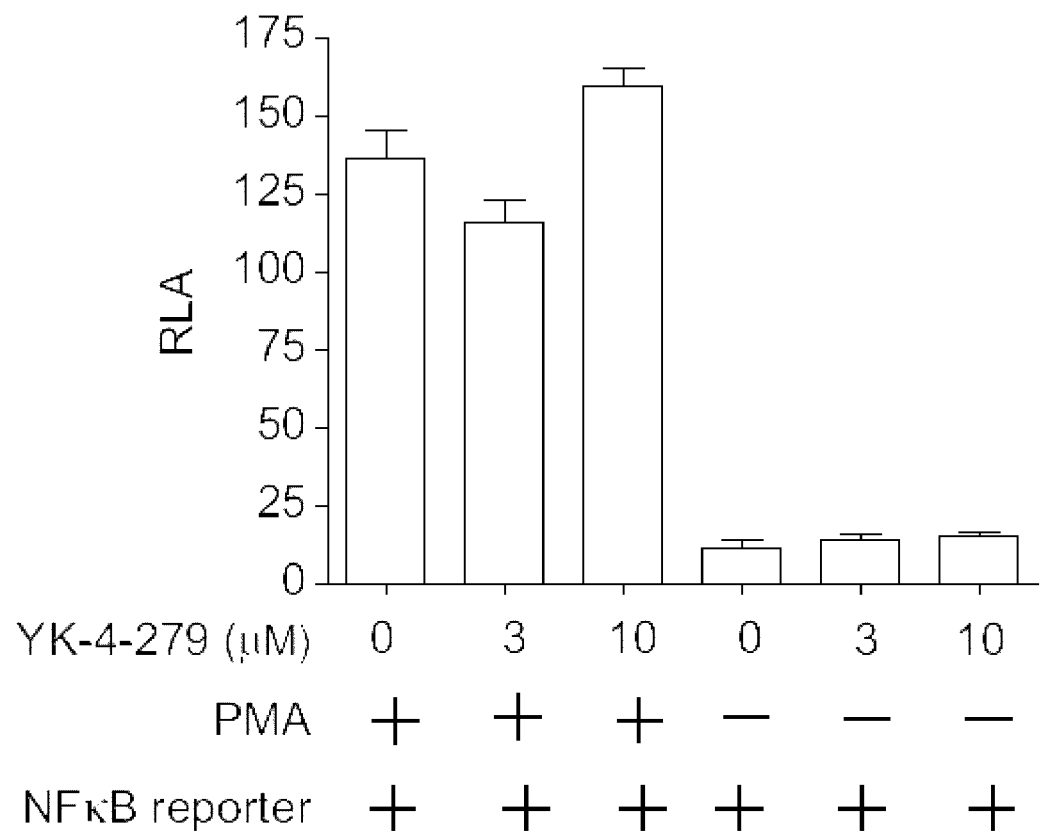
Figure 38B:
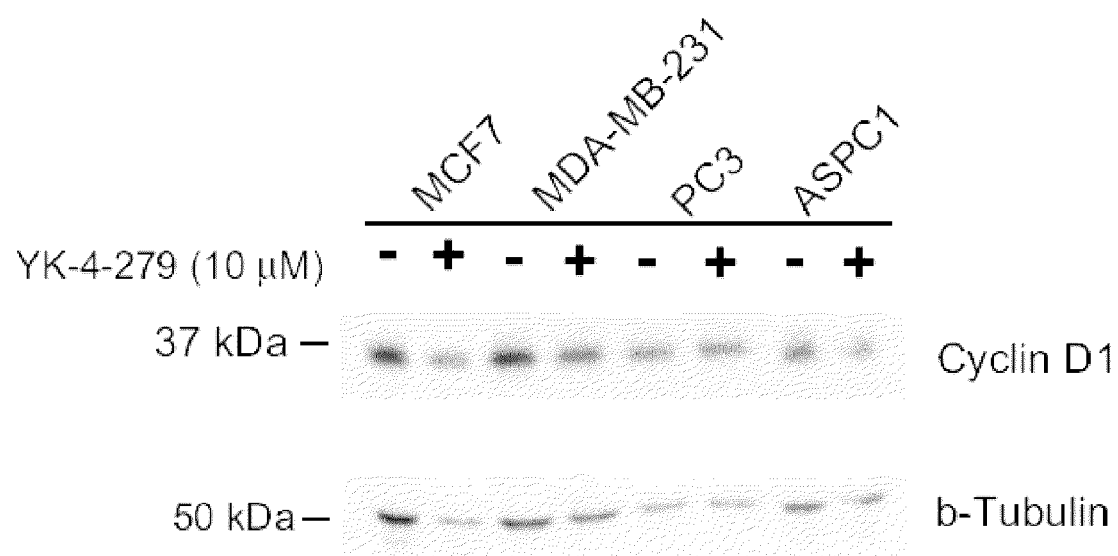
Figure 38C:
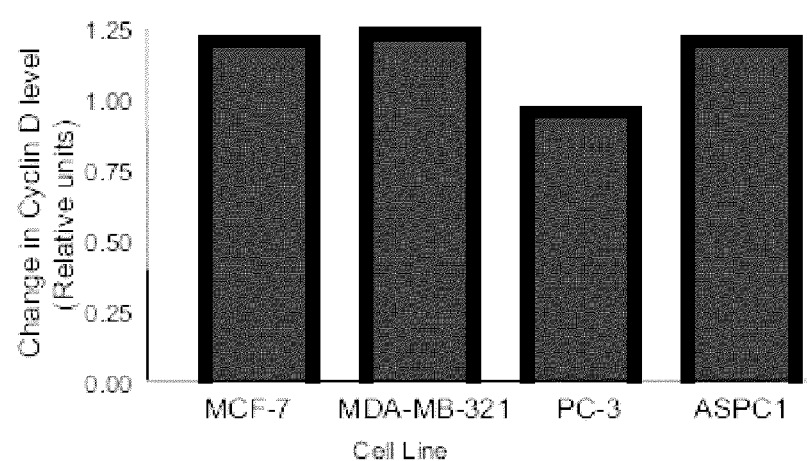

FIG. 38A provides data showing COST cells transfected with an NFκB reporter construct followed by stimulation with PMA. Cells were treated with YK-4-279 following PMA treatment. Cell lysates were analyzed for NFκB induced luciferase activity as standardized to LTR activated renilla luciferase. FIG. 38B shows an immunoblot from log-phase cell lysates that were either treated with DMSO control or 10 μM YK-4-279 overnight. FIG. 38C shows a graph of densitometry of treated/untreated with both standardized for β-tubulin expression.

Figure 39A:
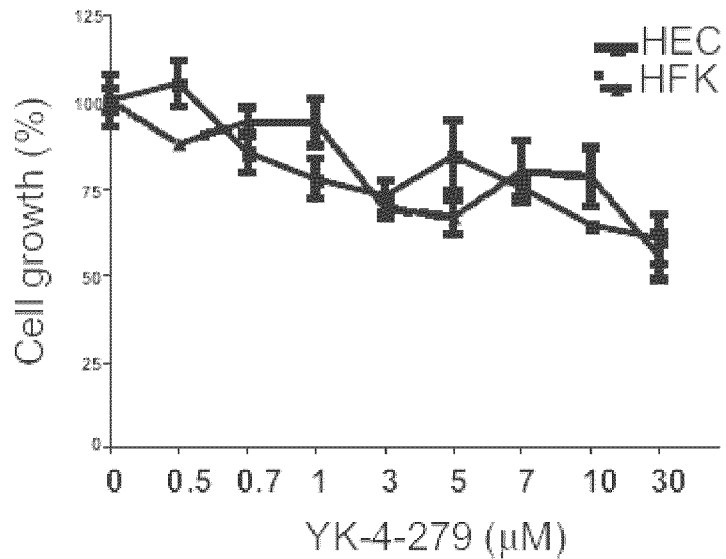
Figure 39B:
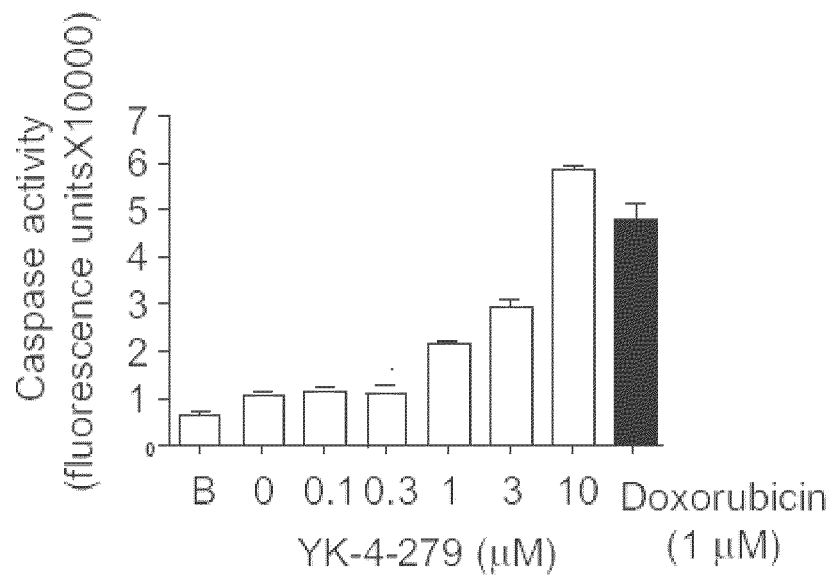
Figure 39C:
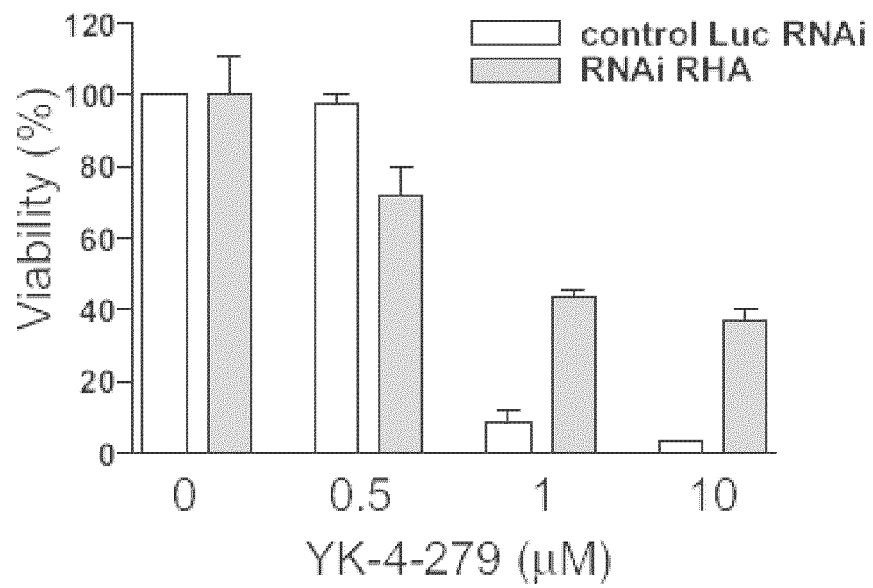
Figure 39D:
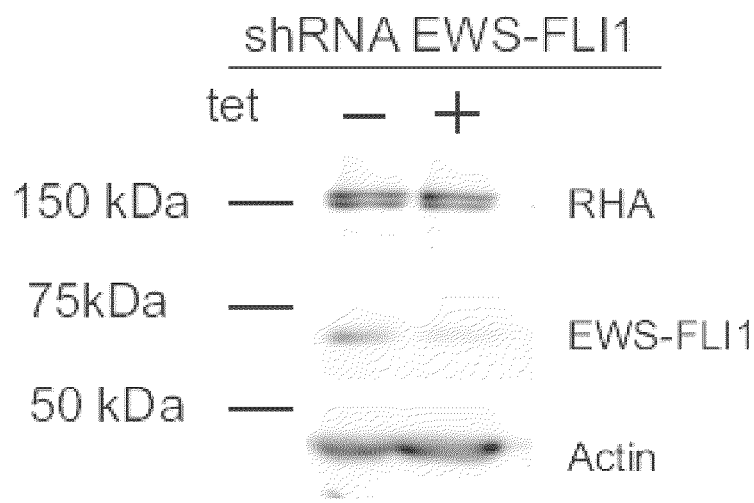
Figure 39E:
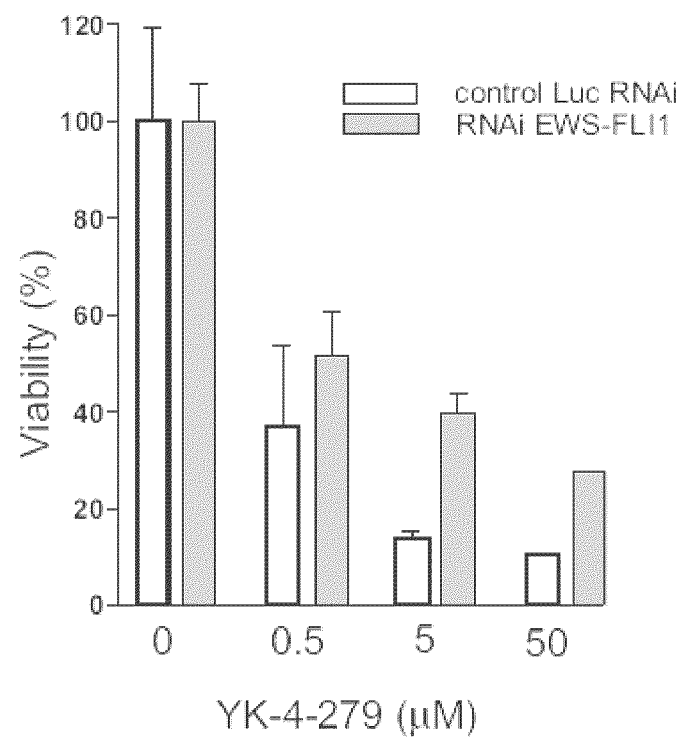

FIG. 39A provides data showing HEC and HFK, non-transformed endocervical cells and keritinocytes, treated with YK-4-279 for 72 hours and assayed for viability using WST reduction. FIG. 39B provides data showing TC71 cells treated for 16 hours with YK-4-279 or doxorubicin. Lysates were assayed for cleavage of AMC-DEVD by induced caspase-3 and fluorescence was measured. FIG. 39C provides data showing that RHA reduced TC71 cells were more resistant to YK-4-279 treatment than wild-type cells. FIG. 39D provides data showing an shRNA tet-inducible expression vector stably transfected into A673 (ESFT) cells to reduce EWS-FLI1 levels. FIG. 39E provides data showing that EWS-FLI1 reduced A673 cells were more resistant to YK-4-279 treatment than wild-type cells.

DETAILED DESCRIPTION OF THE PREFERRED EMBODIMENTS

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Overview

The greater the tumor target specificity the more likely that successful agents will be effective and lack non-specific toxicity. Many tumors, particularly chemotherapy-resistant leukemias and sarcomas, contain tumor-specific chromosomal translocations that encode fusion proteins that are present only in the tumor. The Ewing's Sarcoma Family of Tumors (ESFT) contains a characteristic translocation, t(11:22), which leads to the oncogenic transcription factor EWS-FLI1 (synonyms include: EWS/FLI-1; EWS-FLI-1). EWS-FLI1 is a critical tumor-specific oncogene in patients with ESFT because it is derived from a chromosomal translocation and is necessary to maintain tumor growth.

RNA helicase A (RHA), a member of the DEXH box helicase family of proteins, is an integral component of protein complexes that regulate transcription, splicing and mRNA translation in a distinct class of proteins. A novel direct protein-protein interaction between RHA and EWS-FLI1 by phage display library screening has been demonstrated. EWS-FLI1 oncoprotein is expressed as a result of a chromosomal translocation that occurs in patients with Ewing's Sarcoma Family of Tumors (ESFT). Although more than 95% of the tumors carry EWS-FLI1, therapeutic applications using this target have not been developed. EWS-FLI1 and RHA interact to promote and maintain the oncogenic phenotype of ESFT. Endogenous and direct interaction of RHA and EWS-FLI1 both in ESFT cell lines and with recombinant proteins has been observed. Chromatin immunoprecipitation experiments demonstrated both proteins bound to EWS-FLI1 target gene promoters. RHA stimulated the transcriptional activity of EWS-FLI1 regulated promoters, including Id2, in ESFT cells. In vitro mutagenesis of each aa 823-832 of RHA into alanine prevented EWS-FLI1 binding only with mutations of amino acids P824A and D827 A. Wild-type RHA expression in MEF cells stably transfected with EWS-FLI1 enhanced the anchorage-independent phenotype compared to EWS-FLI1 alone. When MEF cells are transfected with RHA(K417R), abolishing ATPase activity, diminished anchorage-independent growth is observed. When RHA(P824A) or RHA (D827A) are transfected into EWS-FLI1 expressing MEFs, there was no increase in anchorage independent growth over empty vector transfected cells. The E9R peptide was also evaluated for the ability to disrupt EWS-FLI1 from RHA. The peptide caused dissociation of EWS-FLI1 from GST-RHA(630-1020). The E9R of RHA was cloned into a vector expressing the peptide as a fusion protein with EGFP. The peptide-EGFP chimera significantly reduced anchorage-independent growth when present in the nucleus, but not when present exclusively in the cytoplasm. When the peptide was expressed in rhabdomyosarcoma cells, colony formation was not affected. Reduction of RHA protein levels by siRNA in ESFT cell lines also decreased their growth rate. These results indicate that the EWS-FLI1 interaction with RHA is important for the oncogenic function of EWS-FLI1.

Since EWS-FLI1 lacks intrinsic enzymatic activity, one approach to pharmacologic inhibition is through inhibition of protein-protein interaction. RNA Helicase A (RHA, p150), a DEAD/H family member that modulates gene expression, has been identified as a critical partner of EWS-FLI1. EWS-FLI1 binds to a unique region of RHA that is not involved in non-malignant RHA transcriptional modulation. A compound has been identified that blocks EWS-FLI1 interaction with RHA. The interaction that is targeted is that of RHA with EWS-FLI1, which results in a potent transcriptional activator/coactivator complex, which amplifies the functions of both proteins and drives the malignant phenotype of ESFT.

EWS-FLI1 is a very promising ESFT molecular target since it is relevant in patients, required for growth, and specific to tumors. Therapies directed towards the inactivation of EWS-FLI1 can address the significant problem of recurrent disease for patients. Reagents have been developed that disrupt the interaction of EWS-FLI1 with RHA and thus provide new therapeutic agents. Also provided are additional small molecules that bind and inhibit EWS-FLI1, and thus have utility in therapeutic agents.

The molecular signature, cellular biology, and anti-tumor effect of blocking EWS-FLI1 from binding to RNA Helicase A (RHA) has been determined, and peptides have been developed that bind to EWS-FLI1, block RHA from interacting with EWS-FLI1, and lead to ESFT-specific cell toxicity. Small molecules that exert a similar function have also been identified by screening the NCI DTP library of compounds for molecules that bind to EWS-FLI1. The small molecules have significant 3-dimensional homology to the first 3 amino acids of the functional peptide, E9R.

The therapeutic agents of preferred embodiments have broad applicability to a larger group of tumors, and are useful as therapeutics for other translocation fusion-protein defined malignancies such as chemotherapy-resistant sarcomas and leukemias, and other difficult to treat tumors, including ESFT. These therapeutic agents offer enhanced specificity of treatment leading to reduced mortality and morbidity.

Small Molecule EWS-FLI1-Protein Inhibitors

Small molecule EWS-FLI1 protein inhibitors include compounds of the following structure:

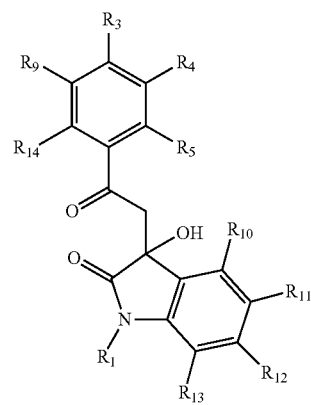

In the above structure, $R_1$ is a substituent selected from the group consisting of hydrogen, from one to three amino acids (e.g. Leu, Leu-Asp, Leu-Asp-Ala),

21

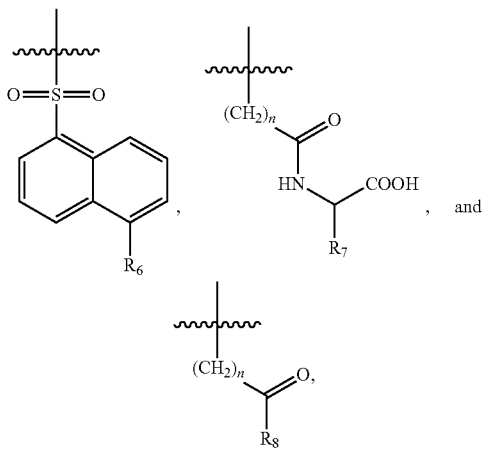

wherein R6 is C1-6 dialkyl amine; R7 is selected from the group consisting of hydrogen and C1-6 alkyl; R8 is C1-6 alkyl; R3, R4, R5, R9, R10, R11, R12, R13, and R14 are independently selected from the group consisting of hydrogen, halogen (e.g., F, Cl, Br, I), C1-6 alkyl (e.g., —CH3), C1-6 alkoxy (e.g. —OCH3), —C(=O)NH2, —NO2, —NH2, and —OH; and n is an integer from 0 to 4 (e.g., 0, 1, 2, 3, 4); with the proviso that R3 is not chlorine or fluorine when R1, R4, R5, R11, and R12 are hydrogen and R10 and R13 are chlorine.

Small molecule EWS-FLI1 protein inhibitors also include compounds of the following structure:

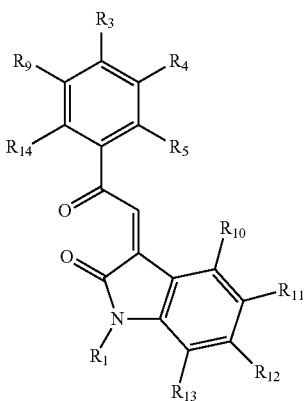

In the above structure, $R_1$ is selected from the group consisting of hydrogen, from one to three amino acids (e.g. Leu, Leu-Asp, Leu-Asp-Ala),

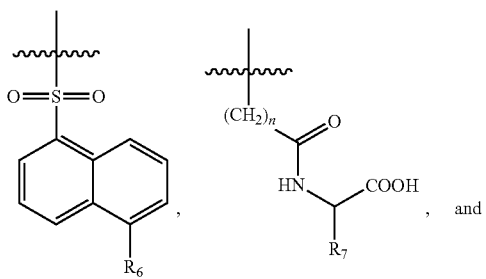

22

-continued

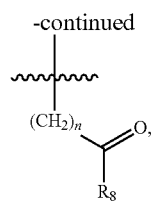

wherein R6 is C1-6 dialkyl amine; R7 is selected from the group consisting of hydrogen and C1-6 alkyl; R8 is C1-6 alkyl; R3, R4, R5, R9, R10, R11, R12, R13, and R14 are independently selected from the group consisting of hydrogen, halogen (e.g., F, Cl, Br, I), C1-6 alkyl (e.g. —CH3), C1-6 alkoxy (e.g., —CH3), —C(=O)NH2, —NO2, —NH2, and —OH; and n is an integer from 0 to 4 (e.g., 0, 1, 2, 3, 4).

One subset of preferred compounds includes compounds with the formula:

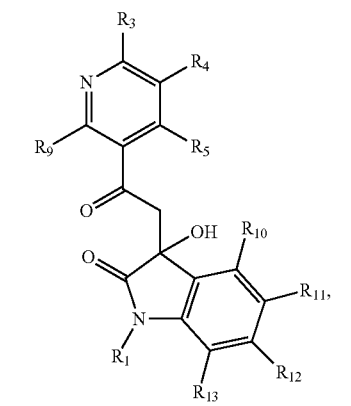

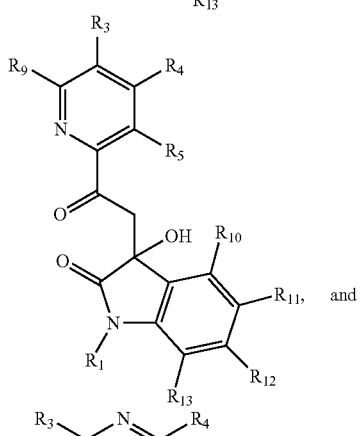

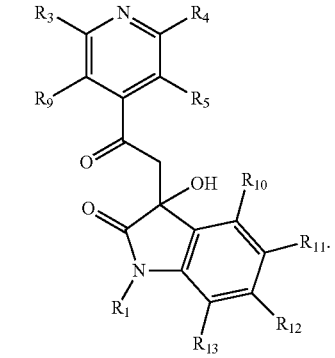

In the above structures, $R_1$ is selected from the group consisting of hydrogen, from one to three amino acids (e.g. Leu, Leu-Asp, Leu-Asp-Ala),

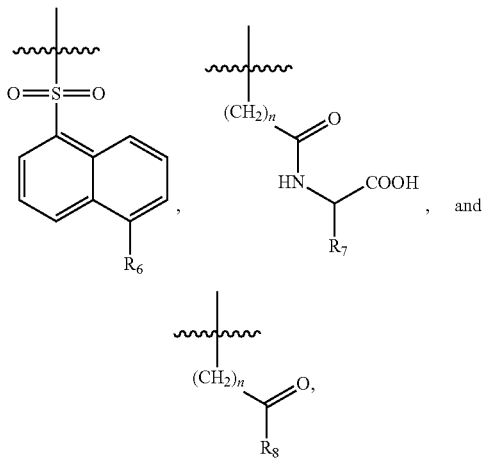

wherein, R6 is C1-6 dialkyl amine; R7 is selected from the group consisting of hydrogen and C1-6 alkyl; R8 is C1-6 alkyl; R3, R4, R5, R9, R10, R11, R12, and R13 are independently selected from the group consisting of hydrogen, halogen (e.g., F, Cl, Br, I), C1-6 alkyl (e.g., —CH3), C1-6 alkoxy (e.g. —OCH3), —C(=O)NH2, —NO2, —NH2, and —OH; and n is an integer from 0 to 4 (e.g., 0, 1, 2, 3, 4).

Yet another subset of preferred compounds includes compounds of the following formula:

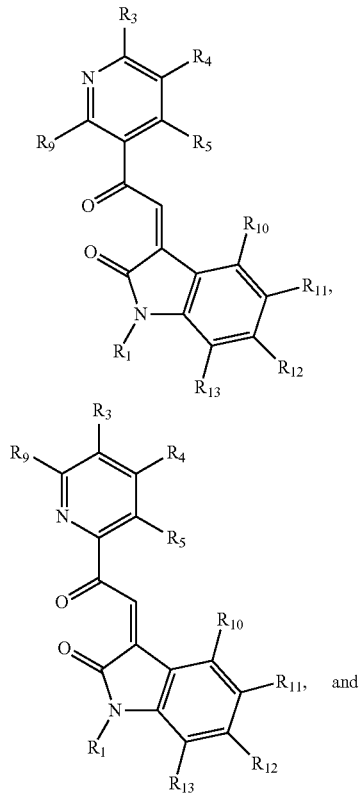

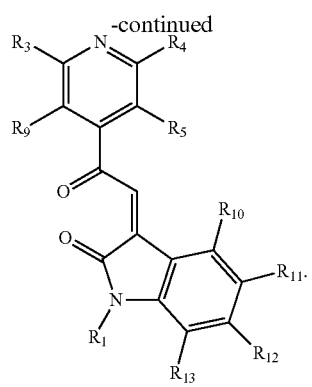

In the above structures, $R_1$ is selected from the group consisting of hydrogen, from one to three amino acids (e.g. Leu, Leu-Asp, Leu-Asp-Ala),

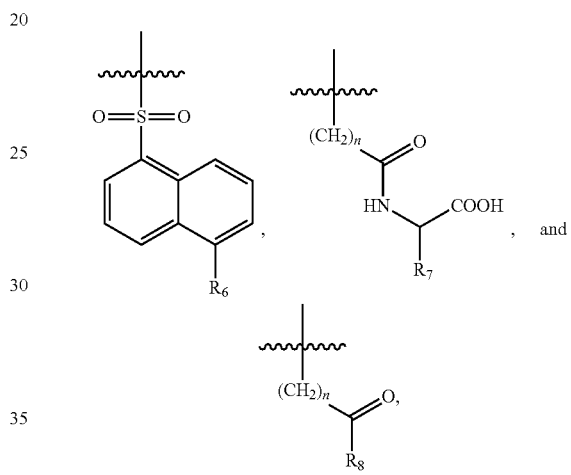

wherein $R_6$ is $C_{1-6}$ dialkyl amine; $R_7$ is selected from the group consisting of hydrogen and $C_{1-6}$ alkyl; $R_8$ is $C_{1-6}$ alkyl; $R_3$, $R_4$, $R_5$, $R_9$, $R_{10}$, $R_{11}$, $R_{12}$, and $R_{13}$ are independently selected from the group consisting of hydrogen, halogen (e.g., F, Cl, Br, I), $C_{1-6}$ alkyl (e.g., —$CH_3$), $C_{1-6}$ alkoxy (e.g. —$OCH_3$), —$C(=O)NH_2$, —$NO_2$, —$NH_2$, and —OH; and n is an integer from 0 to 4 (e.g., 0, 1, 2, 3, 4).

A particularly preferred compound for use in treating cancers including the Ewing's sarcoma family of tumors, pancreatic cancer, prostate cancer, and other cancers comprising translocation gene fusions has the formula:

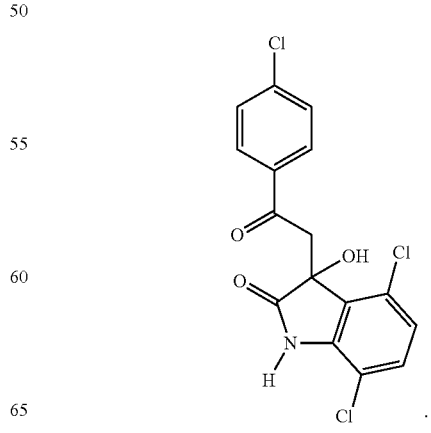

A preferred subset of small molecule EWS-FLI1 protein inhibitors include compounds of the following structures:

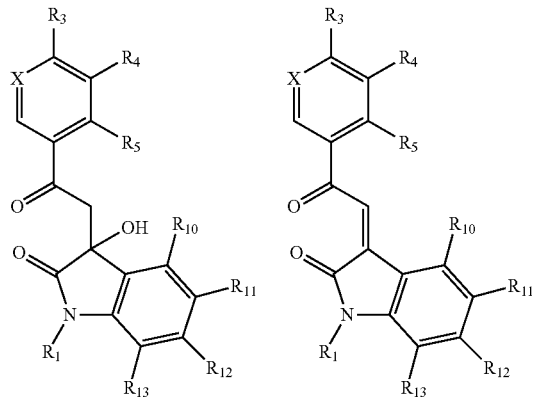
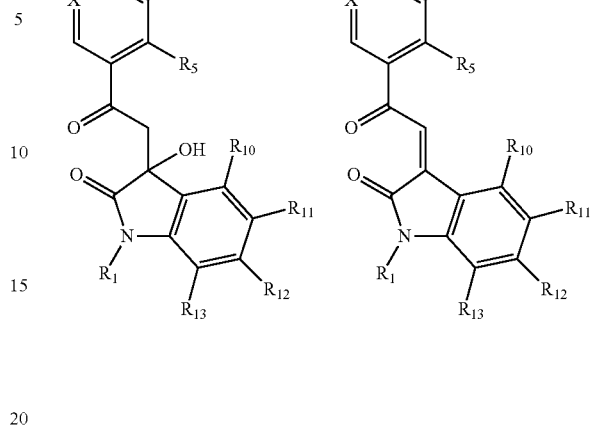

In the above structures, X is carbon or nitrogen; $R_1$ is a substituent selected from the group consisting of hydrogen, from one to three amino acids (e.g., Leu, Leu-Asp, Leu-Asp-Ala), In the above structures, X is carbon or nitrogen; $R_1$ is a substituent selected from the group consisting of hydrogen, from one to three amino acids (e.g., Leu, Leu-Asp, Leu-Asp-Ala),

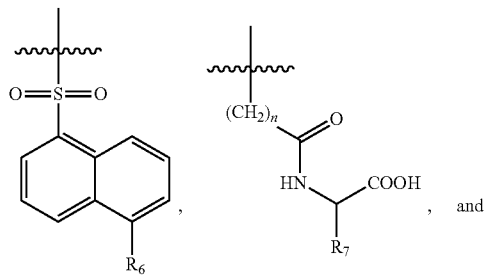
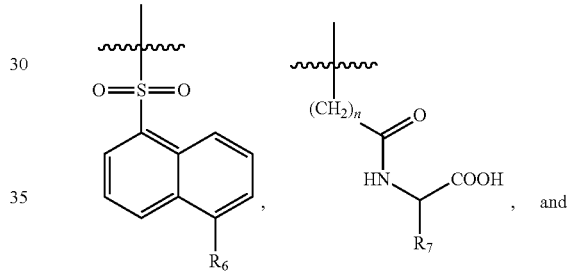

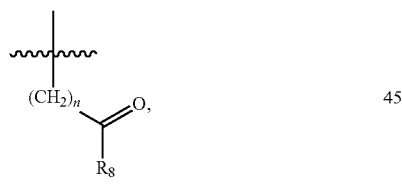
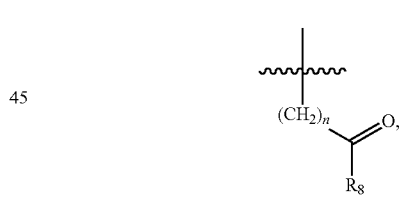

wherein $R_6$ is a $C_{1-6}$ dialkyl amine, $R_7$ is hydrogen or $C_{1-6}$ alkyl, and $R_8$ is $C_{1-6}$ alkyl; $R_3$, $R_4$, $R_5$, $R_{10}$, $R_{11}$, $R_{12}$, and $R_{13}$ are independently selected from the group consisting of hydrogen, halogen (e.g., F, Cl, Br, I), $C_{1-6}$ alkyl (e.g., —CH$_3$), $C_{1-6}$ alkoxy (e.g., —OCH$_3$), —C(=O)NH$_2$, —NO$_2$, —NH$_2$, and —OH; and n is an integer from 0 to 4 (e.g., 0, 1, 2, 3, 4); with the proviso that $R_3$ is not chlorine or fluorine when the compound includes a hydroxy group on the carbon atom of the bicyclic ring system that links the bicyclic ring system to the monocyclic ring via the linking group, X is carbon, $R_1$, $R_4$, $R_5$, $R_{11}$, and $R_{12}$ are hydrogen and $R_{10}$ and $R_{13}$ are chlorine.

Another subset of preferred compounds includes those of the formulas:

wherein $R_6$ is a $C_{1-6}$ dialkyl amine, $R_7$ is hydrogen or $C_{1-6}$ alkyl, and $R_8$ is $C_{1-6}$ alkyl; $R_3$ is selected from the group consisting of hydrogen, bromine, iodine, $C_{1-6}$ alkyl (e.g., —CH$_3$), $C_{1-6}$ alkoxy (e.g., —OCH$_3$), —C(=O)NH$_2$, —NO$_2$, —NH$_2$, and —OH; $R_4$, $R_5$, $R_{10}$, $R_{11}$, $R_{12}$, and $R_{13}$ are independently selected from the group consisting of hydrogen, halogen (e.g., F, Cl, Br, I), $C_{1-6}$ alkyl (e.g., —CH$_3$), $C_{1-6}$ alkoxy (e.g., —OCH$_3$), —C(=O)NH$_2$, —NO$_2$, —NH$_2$, and —OH; and n is an integer from 0 to 4 (e.g., 0, 1, 2, 3, 4).

Another subset of preferred compounds includes those of the formulas:

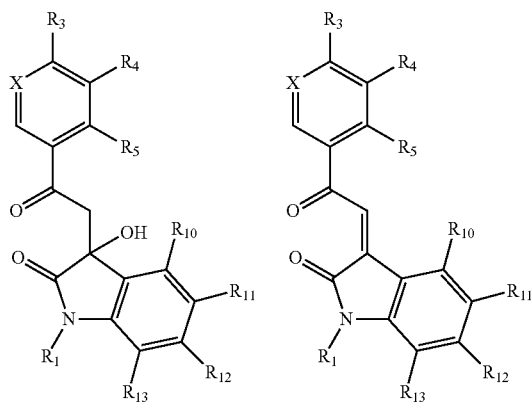

In the above structures, X is carbon or nitrogen; $R_1$ is a substituent selected from the group consisting of hydrogen, from one to three amino acids (e.g., Leu, Leu-Asp, Leu-Asp-Ala),

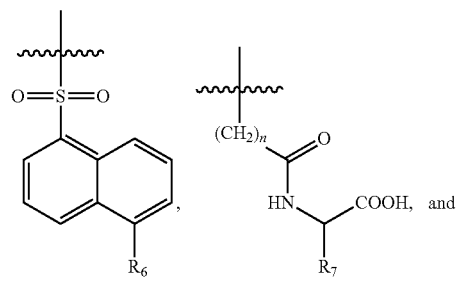
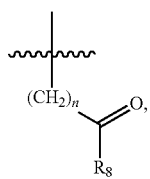

wherein $R_6$ is a $C_{1-6}$ dialkyl amine, $R_7$ is hydrogen or $C_{1-6}$ alkyl, and $R_8$ is $C_{1-6}$ alkyl; $R_3$, $R_4$, $R_5$, $R_{11}$, and $R_{12}$ are independently selected from the group consisting of hydrogen, halogen (e.g., F, Cl, Br, I), $C_{1-6}$ alkyl (e.g., —CH$_3$), $C_{1-6}$ alkoxy (e.g., —OCH$_3$), —C(=O)NH$_2$, —NO$_2$, —NH$_2$, and —OH; $R_{10}$ and $R_{13}$ are independently selected from the group consisting of hydrogen, bromine, iodine, $C_{1-6}$ alkyl (e.g., —CH$_3$), $C_{1-6}$ alkoxy (e.g., —OCH$_3$), —C(=O)NH$_2$, —NO$_2$, —NH$_2$, and —OH; and n is an integer from 0 to 4 (e.g., 0, 1, 2, 3, 4).

Yet another subset of preferred compounds includes those of the following formula:

wherein $R_1$ is a substituent selected from the group consisting of hydrogen, from one to three amino acids (e.g., Leu, Leu-Asp, Leu-Asp-Ala),

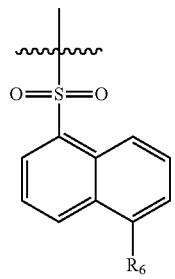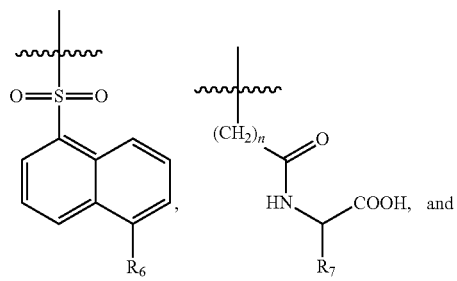
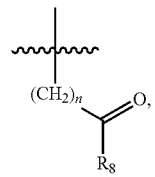

wherein $R_6$ is a $C_{1-6}$ dialkyl amine, $R_7$ is hydrogen or $C_{1-6}$ alkyl, and $R_8$ is $C_{1-6}$ alkyl; $R_3$, $R_4$, $R_5$, $R_{11}$, and $R_{12}$ are independently selected from the group consisting of hydrogen, halogen (e.g., F, Cl, Br, I), $C_{1-6}$ alkyl (e.g., —CH$_3$), $C_{1-6}$ alkoxy (e.g., —OCH$_3$), —C(=O)NH$_2$, —NO$_2$, —NH$_2$, and —OH; $R_{10}$ and $R_{13}$ are independently selected from the group consisting of hydrogen, bromine, iodine, $C_{1-6}$ alkyl (e.g., —CH$_3$), $C_{1-6}$ alkoxy (e.g., —OCH$_3$), —C(=O)NH$_2$, —NO$_2$, —NH$_2$, and —OH; and n is an integer from 0 to 4 (e.g., 0, 1, 2, 3, 4).

Another subset of preferred compounds includes those of the following formulas.

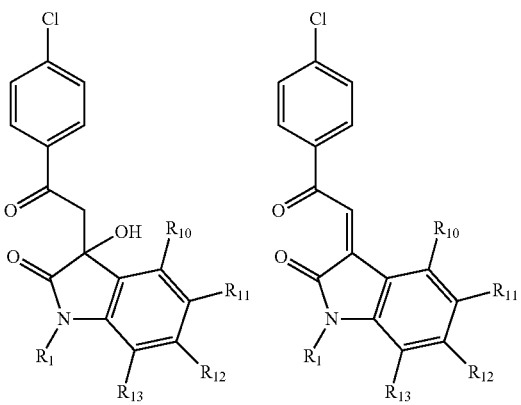

wherein $R_1$ is a substituent selected from the group consisting of hydrogen, from one to three amino acids (e.g., Leu, Leu-Asp, Leu-Asp-Ala),

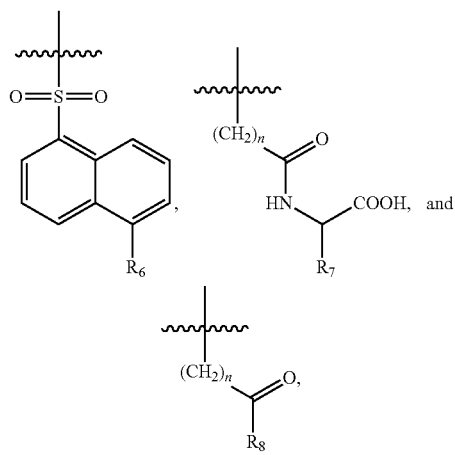

wherein $R_6$ is a $C_{1-6}$ dialkyl amine, $R_7$ is hydrogen or $C_{1-6}$ alkyl, and $R_8$ is $C_{1-6}$ alkyl; $R_{11}$, and $R_{12}$ are independently selected from the group consisting of hydrogen, halogen (e.g., F, Cl, Br, I), $C_{1-6}$ alkyl (e.g., —$CH_3$), $C_{1-6}$ alkoxy (e.g., —$OCH_3$), —C(=O)$NH_2$, —$NO_2$, —$NH_2$, and —OH; $R_{10}$ and $R_{13}$ are independently selected from the group consisting of hydrogen, bromine, iodine, $C_{1-6}$ alkyl (e.g., —$CH_3$), $C_{1-6}$ alkoxy (e.g., —$OCH_3$), —C(=O)$NH_2$, —$NO_2$, —$NH_2$, and —OH; and n is an integer from 0 to 4 (e.g., 0, 1, 2, 3, 4).

Another subset of preferred compounds includes those of the following formulas.

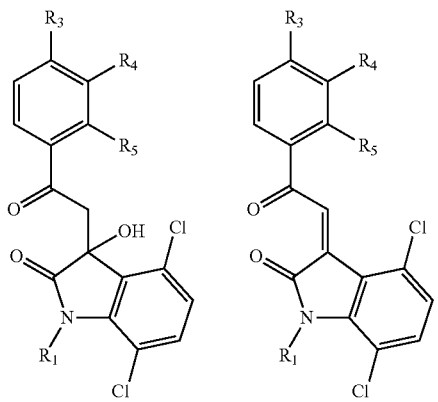

wherein $R_1$ is a substituent selected from the group consisting of hydrogen, from one to three amino acids (e.g., Leu, Leu-Asp, Leu-Asp-Ala),

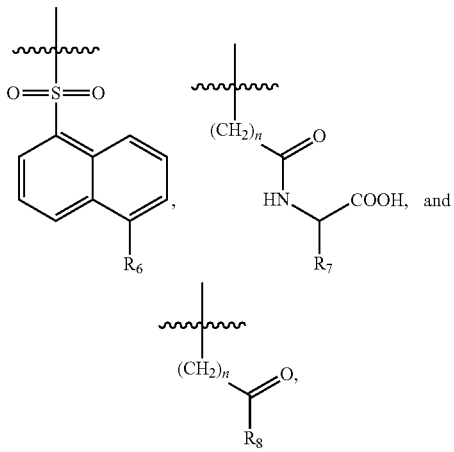

wherein $R_6$ is a $C_{1-6}$ dialkyl amine, $R_7$ is hydrogen or $C_{1-6}$ alkyl, and $R_8$ is $C_{1-6}$ alkyl; $R_3$, $R_4$, and $R_5$, are independently selected from the group consisting of hydrogen, halogen (e.g., F, Cl, Br, I), $C_{1-6}$ alkyl (e.g., —$CH_3$), $C_{1-6}$ alkoxy (e.g., —$OCH_3$), —C(=O)$NH_2$, —$NO_2$, —$NH_2$, and —OH; and n is an integer from 0 to 4 (e.g., 0, 1, 2, 3, 4).

Particularly preferred compounds also include those of the following formulas.

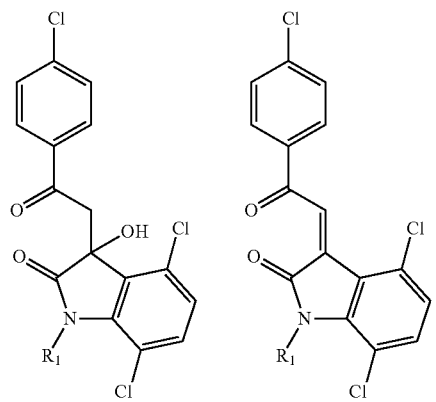

wherein $R_1$ is a substituent selected from the group consisting of hydrogen, from one to three amino acids (e.g., Leu, Leu-Asp, Leu-Asp-Ala),

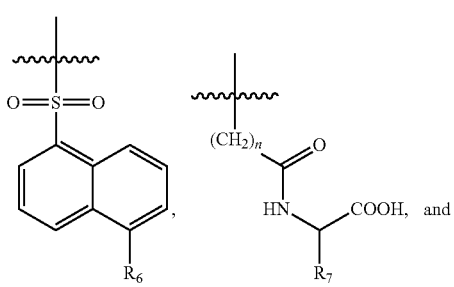

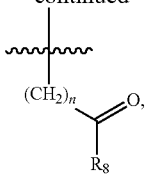

wherein $R_6$ is a $C_{1-6}$ dialkyl amine, $R_7$ is hydrogen or $C_{1-6}$ alkyl, and $R_8$ is $C_{1-6}$ alkyl; and n is an integer from 0 to 4 (e.g., 0, 1, 2, 3, 4).

In preferred embodiments of the above subsets, $R_1$ is hydrogen. Other preferred substituents for $R_1$ include —$CH_2$—C(=O)—$NHCH_2COOH$, $CH_2$—C(=O)—($CH_2$) $C(CH_3)_2$, Leu-Asp, Leu-Asp-Ala, Leu,

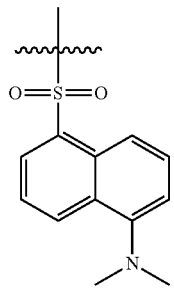
and
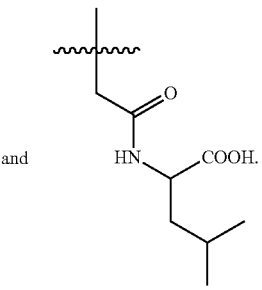

Other preferred substituents include $R_3$ as halogen (e.g., F, Cl, Br, I), $C_{1-6}$ alkyl (e.g., —$CH_3$), $C_{1-6}$ alkoxy (e.g., —$OCH_3$), —$NO_2$, $NH_2$, or —OH, and $R_4$ and $R_5$ as hydrogen. Alternatively, other preferred substituent combinations include $R_4$ as chloro and $R_3$ and $R_5$ as hydrogen; or $R_5$ as chloro and $R_3$ and $R_4$ as hydrogen; or $R_4$ and $R_3$ as chloro and $R_5$ as hydrogen; or $R_3$, $R_4$ and $R_5$ as chloro. It is particularly preferred to have $R_4$ and $R_5$ as hydrogen, with a non-hydrogen substituent as $R_3$ (para substitution), although ortho and meta substitution are also acceptable. Particularly preferred compounds are disubstituted (two non-hydrogen substituents amongst $R_3$, $R_4$ and $R_5$) and trisubstituted ($R_3$, $R_4$ and $R_5$ are each non-hydrogen substituents).

Certain compounds of preferred embodiments include a chiral center at the point of attachment of the hydroxy substituent. Both the R and the S enantiomers can be prepared. A method of preparing the enantiomeric forms for the core ring structure is provided in FIG. 20, and can be adapted to prepare desired enantiomers preferentially.

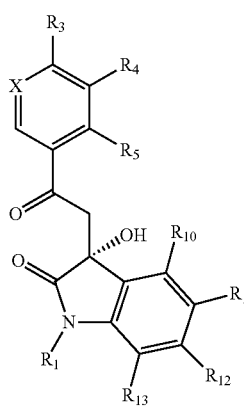
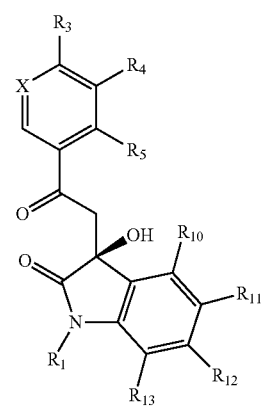

Compounds of the above structures can be prepared according to the following synthesis schemes.

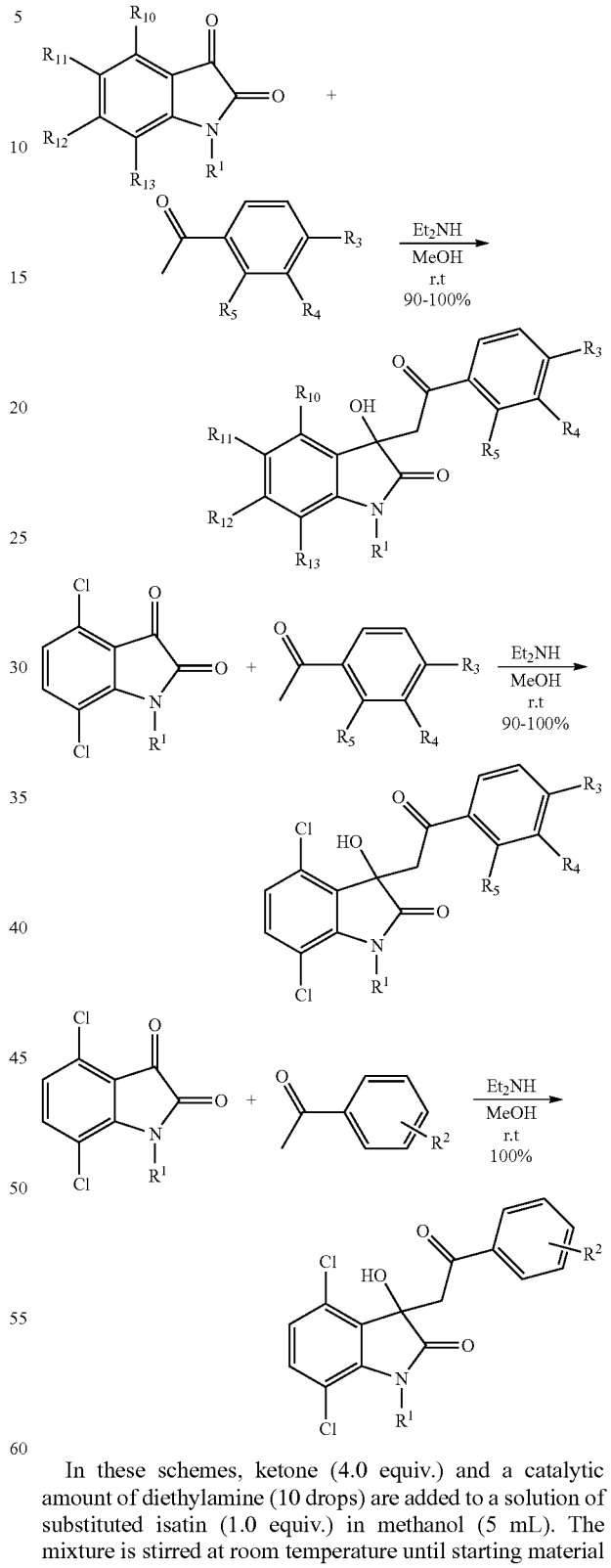

In these schemes, ketone (4.0 equiv.) and a catalytic amount of diethylamine (10 drops) are added to a solution of substituted isatin (1.0 equiv.) in methanol (5 mL). The mixture is stirred at room temperature until starting material (substituted isatin) disappears completely. The resulting solution is concentrated and applied to flash chromatography eluting with hexane/ethyl acetate to afford pure product in quantitative yield. Further purification is done by recrystallization with hexane/ethyl acetate.

The inhibitors incorporating a carbon-carbon double bond in the group linking the two ring systems can be prepared from the corresponding saturated inhibitor by reducing the compound using synthetic techniques known in the art.

Compounds of the following structures were prepared according to the above-references synthesis scheme.

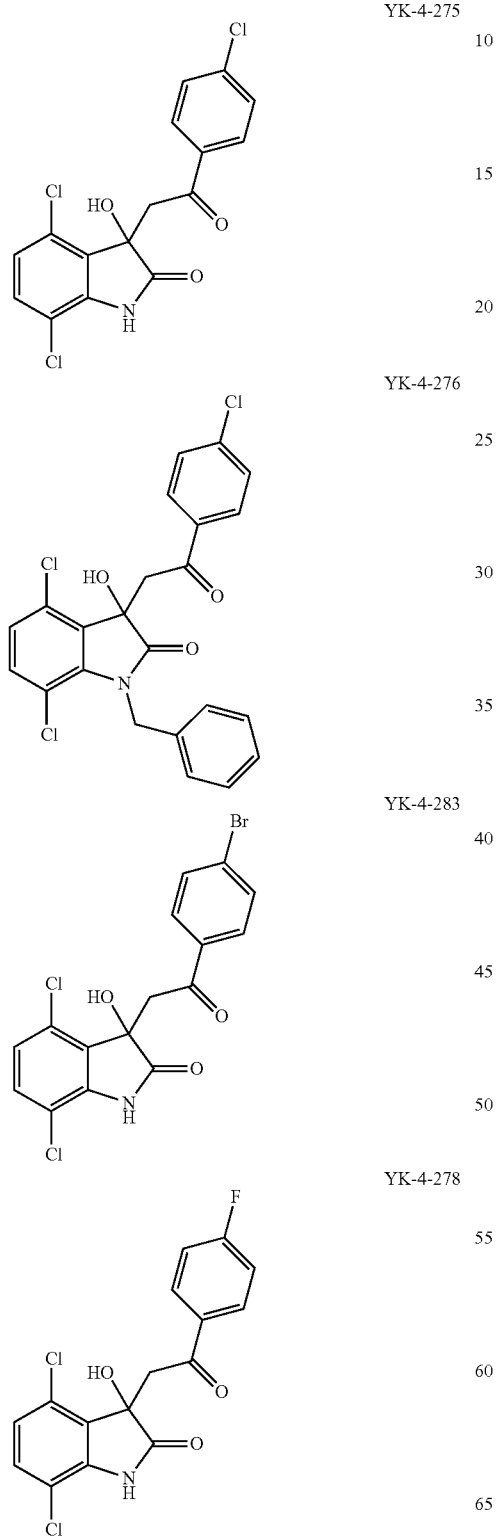

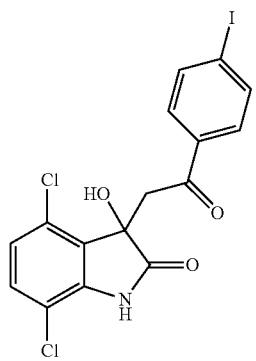

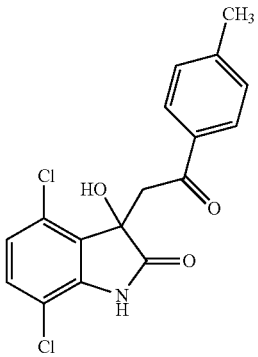

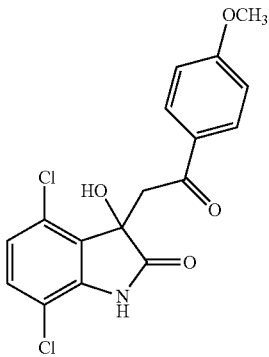

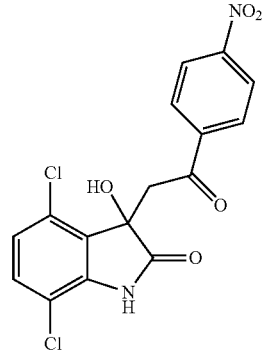

YK-4-285
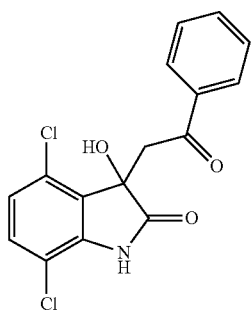

YK-4-281
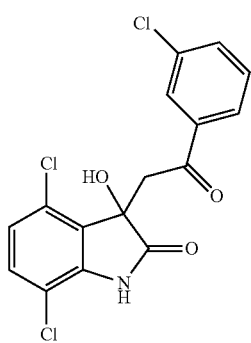

YK-4-282
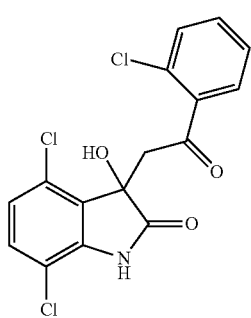

YK-4-287
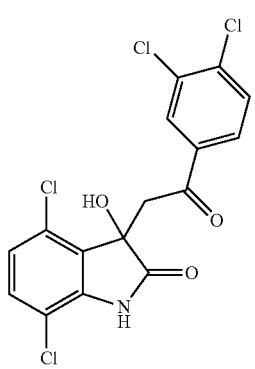

YK-4-288
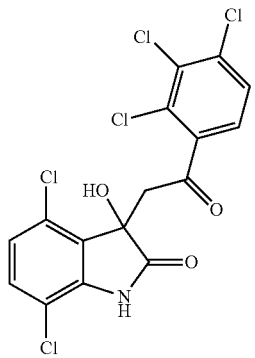

YK-4-289
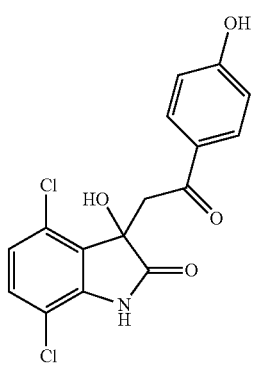

YK-4-284
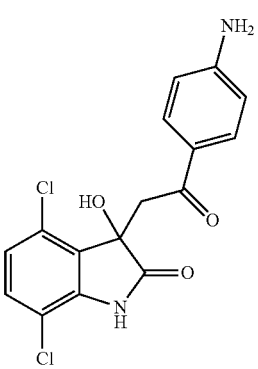

NMR spectra were recorded for the compounds using a Varian-400 spectrometer for $^1$H (400 MHz). Chemical shifts (δ) are given in ppm downfield from tetramethylsilane as internal standard, and coupling constants (J-values) are in hertz (Hz). Purifications by flash chromatography were performed. The results were as follows.

4,7-Dichloro-3-[2-(4-chlorophenyl-2-oxoethyl)]-3-hydroxyl-1,3-dihydroindol-2-one (YK-4-275): white solid; mp 194-196° C.; $^1$H NMR (DMSO, 400 MHz) δ 10.96 (s, 1H), 7.93 (d, 2H, J=8.8 Hz), 7.57 (d, 2H, J=8.8 Hz), 7.30 (d, 1H, J=8.8 Hz), 6.90 (d, 1H, J=8.8 Hz), 6.47 (s, 1H), 4.36 (d, 1H, J=18.4 Hz), 3.71 (d, 1H, J=18.0 Hz).

1-Benzyl-4,7-dichloro-3-[2-(4-chlorophenyl-2-oxoethyl)]-3-hydroxyl-1,3-dihydroindol-2-one (YK-4-276): white solid; mp 154-156° C.; $^1$H NMR (DMSO, 400 MHz) δ 7.94 (d, 2H, J=8.8 Hz), 7.56 (d, 2H, J=8.8 Hz), 7.30 (m, 4H), 7.25 (d, 2H, J=8.8 Hz), 6.98 (d, 1H, J=8.8 Hz), 6.68 (s, 1H), 5.22 (s, 2H), 4.49 (d, 1H, J=18.4 Hz), 3.84 (d, 1H, J=18.4 Hz).

3-[2-(4-Bromophenyl-2-oxoethyl)]-4,7-dichloro-3-hydroxyl-1,3-dihydroindol-2-one (YK-4-283): light yellow solid; mp 200-202° C.; $^1$H NMR (DMSO, 400 MHz) δ 10.98

(s, 1H), 7.82 (d, 2H, J=8.8 Hz), 7.69 (d, 2H, J=8.8 Hz), 7.27 (d, 1H, J=8.8 Hz), 6.87 (d, 1H, J=8.8 Hz), 6.45 (s, 1H), 4.32 (d, 1H, J=18.4 Hz), 3.67 (d, 1H, J=18.0 Hz).

4,7-Dichloro-3-[2-(4-fluorophenyl-2-oxoethyl)]-3-hydroxyl-1,3-dihydroindol-2-one (YK-4-278): light yellow solid; mp 176-178° C.; $^1$H NMR (DMSO, 400 MHz) δ 10.98 (s, 1H), 7.98 (m, 2H), 7.29 (m, 3H), 6.87 (d, 1H, J=8.4 Hz), 6.43 (s, 1H), 4.34 (d, 1H, J=18.4 Hz), 3.68 (d, 1H, J=18.4 Hz).

4,7-Dichloro-3-hydroxyl-3-[2-(4-iodophenyl-2-oxoethyl)]-1,3-dihydroindol-2-one (YK-4-277): white solid; mp 190-192° C.; $^1$H NMR (DMSO, 400 MHz) δ 10.98 (s, 1H), 7.87 (d, 2H, J=8.8 Hz), 7.64 (d, 2H, J=8.8 Hz), 7.27 (d, 1H, J=8.8 Hz), 6.87 (d, 1H, J=8.8 Hz), 6.44 (s, 1H), 4.30 (d, 1H, J=18.4 Hz), 3.65 (d, 1H, J=18.4 Hz).

4,7-Dichloro-3-hydroxyl-3-(2-oxo-2-p-tolylethyl)-1,3-dihydroindol-2-one (YK-4-280): white solid; mp 189-192° C.; $^1$H NMR (DMSO, 400 MHz) δ 10.95 (s, 1H), 7.78 (d, 2H, J=8.4 Hz), 7.27 (m, 3H), 6.86 (d, 1H, J=8.8 Hz), 6.41 (s, 1H), 4.33 (d, 1H, J=18.4 Hz), 3.64 (d, 1H, J=18.4 Hz), 2.33 (s, 3H).

4,7-Dichloro-3-hydroxy-3-[2-(4-methoxyphenyl-2-oxoethyl)]-1,3-dihydroindol-2-one (YK-4-279): white solid; mp 149-151° C.; $^1$H NMR (DMSO, 400 MH 1 z) δ 10.93 (s, 1H), 7.86 (d, 2H, J=9.2 Hz), 7.26 (d, 1H, J=8.8 Hz), 6.98 (d, 2H, J=8.8 Hz), 6.86 (d, 1H, J=8.4 Hz), 6.39 (s, 1H), 4.31 (d, 1H, J=18.0 Hz), 3.80 (s, 3H), 3.61 (d, 1H, J=18.0 Hz).

4,7-Dichloro-3-hydroxyl-3-[2-(4-nitrohenyl-2-oxoethyl)]-1,3-dihydroindol-2-one (YK-4-286): yellow solid; mp 209-211° C.; $^1$H NMR (DMSO, 400 MHz) δ 11.03 (s, 1H), 8.27 (d, 2H, J=9.2 Hz), 8.13 (d, 2H, J=9.2 Hz), 7.28 (d, 1H, J=8.8 Hz), 6.88 (d, 1H, J=8.4 Hz), 6.51 (s, 1H), 4.38 (d, 1H, J=18.4 Hz), 3.79 (d, 1H, J=18.0 Hz).

4,7-Dichloro-3-hydroxyl-3-(2-oxo2-phenylethyl)-1,3-dihydroindol-2-one (YK-4-285): white solid; mp 198-200° C.; $^1$H NMR (DMSO, 400 MHz) δ 10.97 (s, 1H), 7.88 (dd, 2H, J=0.8, 1.6 Hz), 7.62 (m, 1H), 7.48 (t, 2H, J=8.4, 7.2 Hz), 7.27 (d, 1H, J=8.8 Hz), 6.87 (d, 1H, J=8.8 Hz), 6.43 (s, 1H), 4.36 (d, 1H, J=18.4 Hz), 3.68 (d, 1H, J=18.4 Hz).

4,7-Dichloro-3-[2-(3-chlorophenyl-2-oxoethyl)]-3-hydroxyl-1,3-dihydroindol-2-one (YK-4-281): white solid; mp 201-203° C.; $^1$H NMR (DMSO, 400 MHz) δ 11.01 (s, 1H), 7.49 (m, 3H), 7.39 (m, 1H), 7.29 (d, 1H, J=8.4 Hz), 6.89 (d, 1H, J=8.8 Hz), 6.49 (s, 1H), 4.17 (d, 1H, J=17.6 Hz), 3.64 (d, 1H, J=17.6 Hz).

4,7-Dichloro-3-[2-(2-chlorophenyl-2-oxoethyl)]-3-hydroxyl-1,3-dihydroindol-2-one (YK-4-282): light yellow solid; mp 164-166° C.; $^1$H NMR (DMSO, 400 MHz) δ 11.00 (s, 1H), 7.87 (m, 2H), 7.69 (m, 1H), 7.52 (m, 1H), 7.28 (d, 1H, J=8.8 Hz), 6.87 (d, 1H, J=8.8 Hz), 6.45 (s, 1H), 4.33 (d, 1H, J=18.4 Hz), 3.71 (d, 1H, J=18.4 Hz).

4,7-Dichloro-3-[2-(3,4-dichlorophenyl-2-oxoethyl)]-3-hydroxyl-1,3-dihydroindol-2-one (YK-4-287): white solid; mp 193-196° C.; $^1$H NMR (DMSO, 400 MHz) δ 11.00 (s, 1H), 8.09 (d, 1H, J=1.6 Hz), 7.86 (dd, 1H, J=1.6, 2.0 Hz), 7.75 (d, 1H, J=8.4 Hz), 7.28 (d, 1H, J=8.8 Hz), 6.87 (d, 1H, J=8.4 Hz), 6.46 (s, 1H), 4.32 (d, 1H, J=18.4 Hz), 3.72 (d, 1H, J=18.0 Hz).

4,7-Dichloro-3-hydroxyl-3-[2-oxo-2-(2,3,4-trichlorophenylethyl)]-1,3-dihydroindol-2-one (YK-4-288): light yellow solid; mp 172-174° C.; $^1$H NMR (DMSO, 400 MHz) δ 11.03 (s, 1H), 7.71 (d, 1H, J=9.2 Hz), 7.48 (d, 1H, J=8.4 Hz), 7.29 (d, 1H, J=8.8 Hz), 6.90 (d, 1H, J=8.8 Hz), 6.53 (s, 1H), 4.09 (d, 1H, J=16.4 Hz), 3.66 (d, 1H, J=17.2 Hz).

4,7-Dichloro-3-hydroxyl-3-[2-(4-hydroxyphenyl-2-oxoethyl)]-1,3-dihydroindol-2-one (YK-4-289): white solid; mp 240-242° C.; $^1$H NMR (DMSO, 400 MHz) δ 10.91 (s, 1H), 10.43 (br, 1H), 7.75 (d, 2H, J=8.8 Hz), 7.25 (d, 2H, J=8.8 Hz), 6.85 (d, 1H, J=8.8 Hz), 6.78 (d, 1H, J=8.8 Hz), 6.36 (s, 1H), 4.27 (d, 1H, J=18.0 Hz), 3.56 (d, 1H, J=17.6 Hz).

3-[2-(4-Aminophenyl-2-oxoethyl)]-4,7-dichloro-3-hydroxyl 1,3-dihydroindol-2-one (YK-4-284): white solid; mp 240-243° C.; $^1$H NMR (DMSO, 400 MHz) δ 10.85 (s, 1H), 7.56 (d, 2H, J=8.8 Hz), 7.24 (d, 1H, J=8.8 Hz), 6.84 (d, 1H, J=8.8 Hz), 6.49 (d, 2H, J=8.8 Hz), 6.28 (s, 1H), 6.10 (s, 2H), 4.20 (d, 1H, J=18.0 Hz), 3.45 (d, 1H, J=17.6 Hz).

Depending upon the substituents present, the small molecule inhibitors can be in a form of a pharmaceutically acceptable salt. The terms "pharmaceutically acceptable salt" as used herein are broad terms, and is to be given its ordinary and customary meaning to a person of ordinary skill in the art (and is not to be limited to a special or customized meaning), and refers without limitation to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as, for example, The Merck Index. Any suitable constituent can be selected to make a salt of the therapeutic agents discussed herein, provided that it is non-toxic and does not substantially interfere with the desired activity.

The compounds of preferred embodiments can include isomers, racemates, optical isomers, enantiomers, diastereomers, tautomers, and cis/trans conformers. All such isomeric forms are included within preferred embodiments, including mixtures thereof. As discussed above, the compounds of preferred embodiments may have chiral centers, for example, they may contain asymmetric carbon atoms and may thus exist in the form of enantiomers or diastereoisomers and mixtures thereof, e.g., racemates. Asymmetric carbon atom(s) can be present in the (R)-, (S)-, or (R,S)-configuration, preferably in the (R)- or (S)-configuration, or can be present as mixtures. Isomeric mixtures can be separated, as desired, according to conventional methods to obtain pure isomers.

The compounds can be in amorphous form, or in crystalline forms. The crystalline forms of the compounds of preferred embodiments can exist as polymorphs, which are included in preferred embodiments. In addition, some of the compounds of preferred embodiments may also form solvates with water or other organic solvents. Such solvates are similarly included within the scope of the preferred embodiments.

Peptide EWS-FLI1-Protein Inhibitors

Peptide EWS-FLI1-protein inhibitors preferably comprise the peptide sequence comprises SEQ ID NO: 29.

In some embodiments the peptide sequence comprises SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 and 31.

In some embodiments the peptide sequence comprises an N-terminal tag containing the cell-permeable Antennapedia peptide sequence (SEQ ID NO: 34) linked to SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, and 31.

In certain embodiments the peptide sequence comprises an N-terminal tag containing a cell-penetrating cationic peptide sequence linked to SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, and 31.

In certain embodiments the peptide comprises the sequence of a peptide isolated from a phage display library by the peptide's ability to bind a EWS-FLI1 protein. In some embodiments the peptide comprises the sequence of a peptide isolated from a phage display library by the peptide's ability to bind a EWS-FLI1 protein homologue. In some embodiments the peptide comprises the sequence of a peptide isolated from a phage display library by the peptide's ability to bind a translocation fusion protein. Preferred amino acid sequences for the peptides of preferred embodiments are provided in Table 1.

TABLE 1

| SEQ ID NO: | Alternative peptide IDs | AMINO ACID SEQUENCE |
|---|---|---|
| 1 | A1 | TMRGKKKRTRAN |
| 2 | B12 | QHRMASMSPTLP |
| 3 | D6 | GLLPYRPREANF |
| 4 | D10 | AMIPYTWFSPSP |
| 5 | D11 | KQPKKAPRRIPQ |
| 6 | E5 | SIPTTWFHPPPS |
| 7 | E6 | GVSLHNTNWNIY |
| 8 | E7 | SDTSVNWLTLWY |
| 9 | E8 | NTPQRPPYKRSP |
| 28 | E9 | YTPPPLIEAFAT |
| 10 | F4 | LAKSPSNSAREW |
| 11 | F6 | AKCHSDVPSPAC |
| 12 | F7 | VHFKPTHLPSPP |
| 13 | F8 | STSQALSRFPSF |
| 14 | F10 | GMMRALSHPSAS |
| 15 | F11 | GTLTTPRLDLIM |
| 16 | G2 | MKISAPALAFGL |
| 17 | G3 | MFAKSPPYPSLM |
| 18 | G4 | FNWHWLSRPYFP |
| 19 | G5 | FANHLTNAVHAL |
| 20 | G7 | SQPWTNALVVSS |
| 21 | G8 | TAFWPLYPLSDW |
| 22 | G10 | KLWNVPWPPHMR |
| 23 | G11 | FTPPPAYGRNEG |
| 24 | H1 | HWIPQTLPASFI |
| 25 | H3 | HEPFVTNTPSLI |
| 26 | H5 | PNRLGRRPVRWE |
| 27 | H11 | HWWYPLLPVRQM |

TABLE 1-continued

| SEQ ID NO: | Alternative peptide IDs | AMINO ACID SEQUENCE |
|---|---|---|
| 29 | E9R | PPPLDAVIEA |
| 30 | P2A | PAPLDAVIEA |
| 31 | D5A | PPPLAAVIEA |

Pharmaceutical Compositions

It is generally preferred to administer the inhibitors of preferred embodiments in an intravenous or subcutaneous unit dosage form; however, other routes of administration are also contemplated. Contemplated routes of administration include but are not limited to oral, parenteral, intravenous, and subcutaneous. The inhibitors of preferred embodiments can be formulated into liquid preparations for, e.g., oral administration. Suitable forms include suspensions, syrups, elixirs, and the like. Particularly preferred unit dosage forms for oral administration include tablets and capsules. Unit dosage forms configured for administration once a day are particularly preferred; however, in certain embodiments it can be desirable to configure the unit dosage form for administration twice a day, or more.

The pharmaceutical compositions of preferred embodiments are preferably isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Viscosity of the pharmaceutical compositions can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the thickening agent selected. An amount is preferably used that will achieve the selected viscosity. Viscous compositions are normally prepared from solutions by the addition of such thickening agents.

A pharmaceutically acceptable preservative can be employed to increase the shelf life of the pharmaceutical compositions. Benzyl alcohol can be suitable, although a variety of preservatives including, for example, parabens, thimerosal, chlorobutanol, or benzalkonium chloride can also be employed. A suitable concentration of the preservative is typically from about 0.02% to about 2% based on the total weight of the composition, although larger or smaller amounts can be desirable depending upon the agent selected. Reducing agents, as described above, can be advantageously used to maintain good shelf life of the formulation.

The inhibitors of preferred embodiments can be in admixture with a suitable carrier, diluent, or excipient such as sterile water, physiological saline, glucose, or the like, and can contain auxiliary substances such as wetting or emulsifying agents, pH buffering agents, gelling or viscosity enhancing additives, preservatives, flavoring agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; $18^{th}$ and $19^{th}$ editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components can influence the physical state, solubility, stability, rate of in vivo release, and rate of in vivo clearance, and are thus chosen according to the intended application, such that the characteristics of the carrier are tailored to the selected route of administration.

For oral administration, the pharmaceutical compositions can be provided as a tablet, aqueous or oil suspension, dispersible powder or granule, emulsion, hard or soft capsule, syrup or elixir. Compositions intended for oral use can be prepared according to any method known in the art for the manufacture of pharmaceutical compositions and can include one or more of the following agents: sweeteners, flavoring agents, coloring agents and preservatives. Aqueous suspensions can contain the active ingredient in admixture with excipients suitable for the manufacture of aqueous suspensions.

Formulations for oral use can also be provided as hard gelatin capsules, wherein the active ingredient(s) are mixed with an inert solid diluent, such as calcium carbonate, calcium phosphate, or kaolin, or as soft gelatin capsules. In soft capsules, the inhibitors can be dissolved or suspended in suitable liquids, such as water or an oil medium, such as peanut oil, olive oil, fatty oils, liquid paraffin, or liquid polyethylene glycols. Stabilizers and microspheres formulated for oral administration can also be used. Capsules can include push-fit capsules made of gelatin, as well as soft, sealed capsules made of gelatin and a plasticizer, such as glycerol or sorbitol. The push-fit capsules can contain the active ingredient in admixture with fillers such as lactose, binders such as starches, and/or lubricants such as talc or magnesium stearate and, optionally, stabilizers.

Tablets can be uncoated or coated by known methods to delay disintegration and absorption in the gastrointestinal tract and thereby provide a sustained action over a longer period of time. For example, a time delay material such as glyceryl monostearate can be used. When administered in solid form, such as tablet form, the solid form typically comprises from about 0.001 wt. % or less to about 50 wt. % or more of active ingredient(s), preferably from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, or 45 wt. %.

Tablets can contain the active ingredients in admixture with non-toxic pharmaceutically acceptable excipients including inert materials. For example, a tablet can be prepared by compression or molding, optionally, with one or more additional ingredients. Compressed tablets can be prepared by compressing in a suitable machine the active ingredients in a free-flowing form such as powder or granules, optionally mixed with a binder, lubricant, inert diluent, surface active or dispersing agent. Molded tablets can be made by molding, in a suitable machine, a mixture of the powdered inhibitor moistened with an inert liquid diluent.

Preferably, each tablet or capsule contains from about 1 mg or less to about 1,000 mg or more of an inhibitor of the preferred embodiments, more preferably from about 10, 20, 30, 40, 50, 60, 70, 80, 90, or 100 mg to about 150, 200, 250, 300, 350, 400, 450, 500, 550, 600, 650, 700, 750, 800, or 900 mg. Most preferably, tablets or capsules are provided in a range of dosages to permit divided dosages to be administered. A dosage appropriate to the patient and the number of doses to be administered daily can thus be conveniently selected. In certain embodiments it can be preferred to incorporate two or more of the therapeutic agents to be administered into a single tablet or other dosage form (e.g., in a combination therapy); however, in other embodiments it can be preferred to provide the therapeutic agents in separate dosage forms.

Suitable inert materials include diluents, such as carbohydrates, mannitol, lactose, anhydrous lactose, cellulose, sucrose, modified dextrans, starch, and the like, or inorganic salts such as calcium triphosphate, calcium phosphate, sodium phosphate, calcium carbonate, sodium carbonate, magnesium carbonate, and sodium chloride. Disintegrants or granulating agents can be included in the formulation, for example, starches such as corn starch, alginic acid, sodium starch glycolate, Amberlite, sodium carboxymethylcellulose, ultramylopectin, sodium alginate, gelatin, orange peel, acid carboxymethyl cellulose, natural sponge and bentonite, insoluble cationic exchange resins, powdered gums such as agar, karaya or tragacanth, or alginic acid or salts thereof.

Binders can be used to form a hard tablet. Binders include materials from natural products such as acacia, tragacanth, starch and gelatin, methyl cellulose, ethyl cellulose, carboxymethyl cellulose, polyvinyl pyrrolidone, hydroxypropylmethyl cellulose, and the like.

Lubricants, such as stearic acid or magnesium or calcium salts thereof, polytetrafluoroethylene, liquid paraffin, vegetable oils and waxes, sodium lauryl sulfate, magnesium lauryl sulfate, polyethylene glycol, starch, talc, pyrogenic silica, hydrated silicoaluminate, and the like, can be included in tablet formulations.

Surfactants can also be employed, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

Controlled release formulations can be employed wherein the amifostine or analog(s) thereof is incorporated into an inert matrix that permits release by either diffusion or leaching mechanisms. Slowly degenerating matrices can also be incorporated into the formulation. Other delivery systems can include timed release, delayed release, or sustained release delivery systems.

Coatings can be used, for example, nonenteric materials such as methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols, or enteric materials such as phthalic acid esters. Dyestuffs or pigments can be added for identification or to characterize different combinations of inhibitor doses.

When administered orally in liquid form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain sweetening and flavoring agents.

Pulmonary delivery of the inhibitor can also be employed. The inhibitor is delivered to the lungs while inhaling and traverses across the lung epithelial lining to the blood stream. A wide range of mechanical devices designed for pulmonary delivery of therapeutic products can be employed, including but not limited to nebulizers, metered dose inhalers, and powder inhalers, all of which are familiar to those skilled in the art. These devices employ formulations suitable for the dispensing of inhibitor. Typically, each formulation is specific to the type of device employed and can involve the use of an appropriate propellant material, in addition to diluents, adjuvants, and/or carriers useful in therapy.

The inhibitor and/or other optional active ingredients are advantageously prepared for pulmonary delivery in particulate form with an average particle size of from 0.1 μm or less to 10 μm or more, more preferably from about 0.2, 0.3, 0.4, 0.5, 0.6, 0.7, 0.8, or 0.9 μm to about 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5 Pharmaceutically acceptable carriers for pulmonary delivery of inhibitor include carbohydrates such as trehalose, mannitol, xylitol, sucrose, lactose, and sorbitol. Other ingredients for use in formulations can include DPPC, DOPE, DSPC, and DOPC. Natural or synthetic surfactants can be used, including polyethylene glycol and dextrans, such as cyclodextran. Bile salts and other related enhancers, as well as cellulose and cellulose derivatives, and amino acids can also be used. Liposomes, microcapsules, microspheres, inclusion complexes, and other types of carriers can also be employed.

Pharmaceutical formulations suitable for use with a nebulizer, either jet or ultrasonic, typically comprise the inhibitor dissolved or suspended in water at a concentration of about 0.01 or less to 100 mg or more of inhibitor per mL of solution, preferably from about 0.1, 1, 2, 3, 4, 5, 6, 7, 8, 9, or 10 mg to about 15, 20, 25, 30, 35, 40, 45, 50, 55, 60, 65, 70, 75, 80, 85, or 90 mg per mL of solution. The formulation can also include a buffer and a simple sugar (e.g., for protein stabilization and regulation of osmotic pressure). The nebulizer formulation can also contain a surfactant, to reduce or prevent surface induced aggregation of the inhibitor caused by atomization of the solution in forming the aerosol.

Formulations for use with a metered-dose inhaler device generally comprise a finely divided powder containing the active ingredients suspended in a propellant with the aid of a surfactant. The propellant can include conventional propellants, such as chlorofluorocarbons, hydrochlorofluorocarbons, hydrofluorocarbons, and hydrocarbons. Preferred propellants include trichlorofluoromethane, dichlorodifluoromethane, dichlorotetrafluoroethanol, 1,1,1,2-tetrafluoroethane, and combinations thereof. Suitable surfactants include sorbitan trioleate, soya lecithin, and oleic acid.

Formulations for dispensing from a powder inhaler device typically comprise a finely divided dry powder containing inhibitor, optionally including a bulking agent, such as lactose, sorbitol, sucrose, mannitol, trehalose, or xylitol in an amount that facilitates dispersal of the powder from the device, typically from about 1 wt. % or less to 99 wt. % or more of the formulation, preferably from about 5, 10, 15, 20, 25, 30, 35, 40, 45, or 50 wt. % to about 55, 60, 65, 70, 75, 80, 85, or 90 wt. % of the formulation.

When an inhibitor of the preferred embodiments is administered by intravenous, parenteral, or other injection, it is preferably in the form of a pyrogen-free, parenterally acceptable aqueous solution or oleaginous suspension. Suspensions can be formulated according to methods well known in the art using suitable dispersing or wetting agents and suspending agents. The preparation of acceptable aqueous solutions with suitable pH, isotonicity, stability, and the like, is within the skill in the art. A preferred pharmaceutical composition for injection preferably contains an isotonic vehicle such as 1,3-butanediol, water, isotonic sodium chloride solution, Ringer's solution, dextrose solution, dextrose and sodium chloride solution, lactated Ringer's solution, or other vehicles as are known in the art. In addition, sterile fixed oils can be employed conventionally as a solvent or suspending medium. For this purpose, any bland fixed oil can be employed including synthetic mono or diglycerides. In addition, fatty acids such as oleic acid can likewise be used in the formation of injectable preparations. The pharmaceutical compositions can also contain stabilizers, preservatives, buffers, antioxidants, or other additives known to those of skill in the art.

The duration of the injection can be adjusted depending upon various factors, and can comprise a single injection administered over the course of a few seconds or less, to 0.5, 0.1, 0.25, 0.5, 0.75, 1, 2, 3, 4, 5, 6, 7, 8, 9, 10, 11, 12, 13, 14, 15, 16, 17, 18, 19, 20, 21, 22, 23, or 24 hours or more of continuous intravenous administration.

The inhibitors of the preferred embodiments can additionally employ adjunct components conventionally found in pharmaceutical compositions in their art-established fashion and at their art-established levels. Thus, for example, the compositions can contain additional compatible pharmaceutically active materials for combination therapy (such as supplementary antimicrobials, antipruritics, astringents, local anesthetics, anti-inflammatory agents, reducing agents, chemotherapeutics and the like), or can contain materials useful in physically formulating various dosage forms of the preferred embodiments, such as excipients, dyes, thickening agents, stabilizers, preservatives or antioxidants. Anti-cancer agents that can be used in combination with the inhibitors of preferred embodiments include, but are not limited to, vinca alkaloids such as vinblastine and vincristine; anthracyclines such as doxorubicin, daunorubicin, epirubicin; anthracenes such as bisantrene and mitoxantrone; epipodophyllo-toxins such as etoposide and teniposide; and other anticancer drugs such as actinomyocin D, mithomycin C, mitramycin, methotrexate, docetaxel, etoposide (VP-16), paclitaxel, docetaxel, and adriamycin); and immunosuppressants (e.g., cyclosporine A, tacrolimus).

The inhibitors of the preferred embodiments can be provided to an administering physician or other health care professional in the form of a kit. The kit is a package which houses a container which contains the inhibitor(s) in a suitable pharmaceutical composition, and instructions for administering the pharmaceutical composition to a subject. The kit can optionally also contain one or more additional therapeutic agents, e.g., chemotherapeutics currently employed for treating the sarcomas described herein. For example, a kit containing one or more compositions comprising inhibitor(s) of the preferred embodiments in combination with one or more additional chemotherapeutic agents can be provided, or separate pharmaceutical compositions containing an inhibitor of the preferred embodiments and additional therapeutic agents can be provided. The kit can also contain separate doses of an inhibitor of the preferred embodiments for serial or sequential administration. The kit can optionally contain one or more diagnostic tools and instructions for use. The kit can contain suitable delivery devices, e.g., syringes, and the like, along with instructions for administering the inhibitor(s) and any other therapeutic agent. The kit can optionally contain instructions for storage, reconstitution (if applicable), and administration of any or all therapeutic agents included. The kits can include a plurality of containers reflecting the number of administrations to be given to a subject.

Mechanism of Action

Ewing's sarcoma family of tumors (ESFT) contains the unique Fusion Protein EWS-FLI1. ESFT affects patients between the ages of 3 and 40 years, with most cases occurring in the second decade. Although the embryologic cell type from which ESFT are derived is unknown, the tumor often grows in close proximity to bone, but can occur as a soft-tissue mass. Over 40% of patients who present with localized tumors will develop recurrent disease and the majority of these will die from ESFT, while 75-80% of patients who present with metastatic ESFT will die within 5 years despite high-dose chemotherapy (Grier H E, Krailo M D, Tarbell N J, et al. Addition of ifosfamide and etoposide to standard chemotherapy for Ewing's sarcoma and primitive neuroectodermal tumor of bone. N Engl J Med 2003; 348(8):694-701). These survival rates have not improved for the past 20 years, even after dose-intensifying chemotherapy. To improve survival and reduce therapy-related morbidity, novel targeted strategies for treating ESFT patients, as provided in the preferred embodiments, can be employed.

ESFT are characterized by a translocation, occurring in 95% of tumors, between the central exons of the EWS gene (Ewing Sarcoma) located on chromosome 22 to the central exons of an ets family gene; either FLI1 (Friend Leukemia Insertion) located on chromosome 11, t(11;22), or ERG located on chromosome 21, t(21;22). The EWS-FLI1 fusion transcript encodes a 55 kDa protein (electrophoretic motility of approximately 68 kD) with two primary domains. The EWS domain is a potent transcriptional activator, while the FLI1 domain contains a highly conserved ets DNA binding domain (May W A, Lessnick S L, Braun B S, et al. The Ewing's sarcoma EWS/FLI-1 fusion gene encodes a more potent transcriptional activator and is a more powerful transforming gene than FLI-1. Mol Cell Biol 1993; 13(12): 7393-8); the resulting EWS-FLI1 fusion protein acts as an aberrant transcription factor. EWS-FLI1 transformation of mouse fibroblasts requires both the EWS and FLI1 functional domains to be intact (May W A, Gishizky M L, Lessnick S L, et al. Ewing sarcoma 11;22 translocation produces a chimeric transcription factor that requires the DNA-binding domain encoded by FLI1 for transformation. Proc Natl Acad Sci USA 1993; 90(12):5752-6).

EWS-FLI1 is an outstanding therapeutic target, in that it is expressed only in tumor cells and is required to maintain the growth of ESFT cell lines. Reduced expression levels of EWS-FLI1 using either antisense oligodeoxynucleotides (ODN) (Toretsky J A, Connell Y, Neckers L, Bhat N K. Inhibition of EWS-FLI-1 fusion protein with antisense oligodeoxynucleotides. J Neurooncol 1997; 31(1-2):9-16; Tanaka K, Iwakuma T, Harimaya K, Sato H, Iwamoto Y. EWS-Fli1 antisense oligodeoxynucleotide inhibits proliferation of human Ewing's sarcoma and primitive neuroectodermal tumor cells. J Clin Invest 1997; 99(2):239-47) or small interfering RNAs (siRNA) (Ouchida M, Ohno T, Fujimura Y, Rao V N, Reddy E S. Loss of tumorigenicity of Ewing's sarcoma cells expressing antisense RNA to EWS-fusion transcripts. Oncogene 1995; 11(6):1049-54; Maksimenko A, Malvy C, Lambert G, et al. Oligonucleotides targeted against a junction oncogene are made efficient by nanotechnologies. Pharm Res 2003; 20(10):1565-7; Kovar H, Aryee D N, Jug G, et al. EWS/FLI-1 antagonists induce growth inhibition of Ewing tumor cells in vitro. Cell Growth Differ 1996; 7(4):429-37) cause decreased proliferation of ESFT cell lines and regression of tumors in nude mice. Recent advances in nanotechnology have improved the delivery and controlled release of siRNA, yet neither antisense ODN nor siRNA reduction of EWS-FLI1 in humans is possible with current technologies (Maksimenko A, Malvy C, Lambert G, et al. Oligonucleotides targeted against a junction oncogene are made efficient by nanotechnologies. Pharm Res 2003; 20(10):1565-7; Lambert G, Bertrand J R, Fattal E, et al. EWS fli-1 antisense nanocapsules inhibits Ewing sarcoma-related tumor in mice. Biochem Biophys Res Commun 2000; 279(2):401-6). One interesting approach to EWS-FLI1 targeting used comparative expression between siRNA reduced EWS-FLI1 and a library of small molecules, which led to a current clinical trial with Ara-C (Stegmaier K, Wong J S, Ross K N, et al. Signature-based small molecule screening identifies cytosine arabinoside as an EWS/FLI modulator in Ewing sarcoma. PLoS medicine 2007; 4(4):e122). This method of identifying Ara-C also indicated doxorubicin and puromycin would reduce EWS-FLI1 levels. Doxorubicin is currently used as standard therapy for ESFT patients and yet, survival is far from acceptable (Grier H E, Krailo M D, Tarbell N J, et al. Addition of ifosfamide and etoposide to standard chemotherapy for Ewing's sarcoma and primitive neuroectodermal tumor of bone. N Engl J Med 2003; 348(8):694-701). The use of Ara-C in ESFT patients is currently being evaluated in a Phase II trial. While it is hoped that this represents a needed clinical breakthrough, it certainly demonstrates the importance of small molecule targeting of EWS-FLI1. The preferred embodiments provide small molecule protein-protein interaction inhibitors (SMPPII) that disrupt EWS-FLI1 from critical protein partners, thereby achieving tumor specificity and more precise targeting of EWS-FLI1.

There is sufficient evidence to conclude that EWS-FLI1 fusion protein functions differently than either untranslocated EWS or FLI1 (May W A, Gishizky M L, Lessnick S L, et al. Ewing sarcoma 11;22 translocation produces a chimeric transcription factor that requires the DNA-binding domain encoded by FLI1 for transformation. Proc Natl Acad Sci USA 1993; 90(12):5752-6). Changes in gene expression profiles of EWS-FLI1-expressing cell lines (Braun B S, Frieden R, Lessnick S L, May W A, Denny C T. Identification of target genes for the Ewing's sarcoma EWS/FLI fusion protein by representational difference analysis. Mol Cell Biol 1995; 15(8):4623-30) or tumor cells taken from ESFT patients, compared to tumors lacking EWS-FLI1 expression, indicate that EWS-FLI1 may play a role in transcriptional regulation (Khan J, Wei J S, Ringner M, et al. Classification and diagnostic prediction of cancers using gene expression profiling and artificial neural networks. Nat Med 2001; 7(6):673-9; Baer C, Nees M, Breit S, et al. Profiling and functional annotation of mRNA gene expression in pediatric rhabdomyosarcoma and Ewing's sarcoma. Int J Cancer 2004; 110(5):687-94). While a clear picture of the mechanism of EWS-FLI1-regulated gene expression has yet to emerge, this activity is likely the result of direct or secondary interactions between EWS-FLI1 and regulators of RNA synthesis and splicing (Uren A, Toretsky J A. Ewing's Sarcoma Oncoprotein EWS-FLI1: the Perfect Target without a Therapeutic Agent. Future Onc 2005; 1(4):521-8).

EWS-FLI1 is a great therapeutic target since it is only expressed in tumor cells; however, the ability to target this tumor-specific oncogene has previously not been successful. One of the challenges towards small molecule development is that EWS-FLI1 lacks any know enzymatic domains, and enzyme domains have been thought to be critical for targeted therapeutics. In addition, EWS-FLI1 is a disordered protein, indicating that it does not exhibit a rigid structure that can be used for structure based drug design (Uren A, Tcherkasskaya O, Toretsky J A. Recombinant EWS-FLI1 oncoprotein activates transcription. Biochemistry 2004; 43(42):13579-89). In fact, the disordered nature of EWS-FLI1 is critical for its transcriptional regulation (Ng K P, Potikyan G, Savene R O, Denny C T, Uversky V N, Lee K A. Multiple aromatic side chains within a disordered structure are critical for transcription and transforming activity of EWS family oncoproteins. Proc Natl Acad Sci USA 2007; 104(2):479-84). Disordered proteins are considered as more attractive targets for small molecule protein-protein interaction inhibitors specifically because of their biochemical disordered properties (Cheng Y, LeGall T, Oldfield C J, et al. Rational drug design via intrinsically disordered protein. Trends Biotechnol 2006; 24(10):435-42).

EWS-FLI1 binds RNA helicase A in vitro and in vivo. It is believed that protein-protein interactions of EWS-FLI1 may contribute to its oncogenic potential; therefore, novel proteins have been sought that directly interact with and functionally modulate EWS-FLI1. Recombinant EWS-FLI1 that is transcriptionally active (Uren A, Tcherkasskaya O, Toretsky J A. Recombinant EWS-FLI1 oncoprotein activates transcription. Biochemistry 2004; 43(42):13579-89) was used as a target for screening a commercial peptide phage display library. Twenty-eight novel peptides that differentially bind to EWS-FLI1 were identified from phage sequencing. A National Center for Biotechnology Information database search for human proteins homologous to these peptides identified a peptide that was homologous to aa 823-832 of the human RNA helicase A, (RHA, gene bank accession number A47363) (Toretsky J A, Erkizan V, Levenson A, et al. Oncoprotein EWS-FLI1 activity is enhanced by RNA helicase A. Cancer Res 2006; 66(11):5574-81).

RHA, a member of the highly conserved DEXD/H box helicase family of proteins, is an integral, multifunctional member of the human transcriptome (Zhang S, Grosse F. Multiple functions of nuclear DNA helicase II (RNA helicase A) in nucleic acid metabolism. Acta Biochim Biophys Sin (Shanghai) 2004; 36(3):177-83; von Hippel P H, Delagoutte E. A general model for nucleic acid helicases and their "coupling" within macromolecular machines. Cell 2001; 104(2):177-90). These proteins are involved in diverse functions in a variety of organisms, from archaea, eubacteria, lower and higher eukaryotes and a number of viruses, including the positive-sense RNA viruses of the Flavivirus family. RHA is a transcriptional coactivator for NF-κB, and has been shown to form complexes with Creb-binding protein (CBP) (Nakajima T, Uchida C, Anderson S F, et al. RNA helicase A mediates association of CBP with RNA polymerase II. Cell 1997; 90(6):1107-12), RNA Polymerase II (Nakajima T, Uchida C, Anderson S F, et al. RNA helicase A mediates association of CBP with RNA polymerase II. Cell 1997; 90(6):1107-12), the breast cancer tumor suppressor BRCA1 (Anderson S F, Schlegel B P, Nakajima T, Wolpin E S, Parvin J D. BRCA1 protein is linked to the RNA polymerase II holoenzyme complex via RNA helicase A. Nat Genet 1998; 19(3):254-6), and, most recently, EWS-FLI1 (Toretsky J A, Erkizan V, Levenson A, et al. Oncoprotein EWS-FLI1 activity is enhanced by RNA helicase A. Cancer Res 2006; 66(11):5574-81). EWS-FLI1 binds to a region of RHA that is unique and not known as a binding site for any of the other RHA binding partners (Toretsky J A, Erkizan V, Levenson A, et al. Oncoprotein EWS-FLI1 activity is enhanced by RNA helicase A. Cancer Res 2006; 66(11):5574-81). RHA expression enhanced EWS-FLI1 mediated anchorage-independent colony formation, while an inactivating mutation of RHA prevented colony formation (Toretsky J A, Erkizan V, Levenson A, et al. Oncoprotein EWS-FLI1 activity is enhanced by RNA helicase A. Cancer Res 2006; 66(11):5574-81). This structural and function interaction is the basis for the therapeutic agents of preferred embodiments.

Despite the importance of transcription in tumorigenesis, the role of helicases in this process has not been well-studied. RHA is an integral member of the human transcriptome with diverse functions (Zhang S, Grosse F. Multiple functions of nuclear DNA helicase II (RNA helicase A) in nucleic acid metabolism. Acta Biochim Biophys Sin (Shanghai) 2004; 36(3):177-83; von Hippel P H, Delagoutte E. A general model for nucleic acid helicases and their "coupling" within macromolecular machines. Cell 2001; 104(2):177-90). Our recently published data show that RHA interacts with the multifunctional EWS-FLI1 oncoprotein (Toretsky J A, Erkizan V, Levenson A, et al. Oncoprotein EWS-FLI1 activity is enhanced by RNA helicase A. Cancer Res 2006; 66(11):5574-81). This interaction could account for the observed ability of EWS-FLI1 to function in both transcription initiation and post-transcriptional RNA modification. RNA helicases are also known to bind and act as a bridge for some of the same factors that have been identified as binding partners for EWS-FLI1, including the splicing factor U1C (Chen J Y, Stands L, Staley J P, Jackups R R, Jr., Latus L J, Chang T H. Specific alterations of U1-C protein or U1 small nuclear RNA can eliminate the requirement of Prp28p, an essential DEAD box splicing factor. Mol Cell 2001; 7(1):227-32; Knoop L L, Baker S J. The splicing factor U1C represses EWS/FLI-mediated transactivation. J Biol Chem 2000; 275(32):24865-71), Creb-binding protein (CBP) (Nakajima T, Uchida C, Anderson S F, et al. RNA helicase A mediates association of CBP with RNA polymerase II. Cell 1997; 90(6):1107-12) and RNA Polymerase II (Nakajima T, Uchida C, Anderson S F, et al. RNA helicase A mediates association of CBP with RNA polymerase II. Cell 1997; 90(6):1107-12). RHA may perform a similar function for EWS-FLI1 and RNA Pol II, acting in the recruitment of key processing proteins. RHA may also contribute to ESFT oncogenesis by maintaining EWS-FLI1 as part of a large transcriptional complex whose function relies on the ATPase activity of RHA as an energy source. Finally, helicases, like RHA, can stabilize mRNA species (Iost I, Dreyfus M. mRNAs can be stabilized by DEAD-box proteins. Nature 1994; 372(6502):193-6). The stabilization and metabolism of EWS-FLI1 transcribed mRNA by RHA may augment the oncogenic nature of EWS-FLI1.

While EWS-FLI1 is quite specific to ESFT cells, EWS and RHA are ubiquitously expressed. The region between EWS-FLI1 and RHA are targeted by molecular therapeutics that may have specificity; since EWS-FLI1 is expressed only in tumors and the interaction points with RHA may be unique. Two different types of therapeutic agents are provided to inhibit EWS-FLI1 function, peptide inhibitors and small molecules protein-protein interaction inhibitors (SMP-PII).

Peptides that inhibit protein-protein interactions have been developed as molecular therapeutics because of their specificity of interaction. While there are challenges in the delivery of these peptides, their specificity allows for their development in laboratory models and proof-of-principle experiments. The AF4-MLL fusion protein in acute leukemia has been targeted by peptides and leads to cell death (Palermo C M, Bennett C A, Winters A C, Hemenway C S. The AF4-mimetic peptide, PFWT, induces necrotic cell death in MV4-11 leukemia cells. Leuk Res 2007; Srinivasan R S, Nesbit J B, Marrero L, Erfurth F, LaRussa V F, Hemenway C S. The synthetic peptide PFWT disrupts AF4-AF9 protein complexes and induces apoptosis in t(4; 11) leukemia cells. Leukemia 2004; 18(8):1364-72). Another peptide prevents Hsp90 from stabilizing chaperone partners and reduces mouse model xenografts of multiple tumors (Gyurkocza B, Plescia J, Raskett C M, et al. Anti-leukemic activity of shepherdin and molecular diversity of hsp90 inhibitors. J Natl Cancer Inst 2006; 98(15):1068-77; Plescia J, Salz W, Xia F, et al. Rational design of shepherdin, a novel anticancer agent. Cancer Cell 2005; 7(5):457-68). Activation of p53 enhanced the survival in mice with peritoneal carcinomatosis (Snyder E L, Meade B R, Saenz C C, Dowdy S F. Treatment of terminal peritoneal carcinomatosis by a transducible p53-activating peptide. PLoS Biol 2004; 2(2):E36). Naturally occurring and synthetic defensin peptides are important as antimicrobial and immune modulation agents (Bowdish D M, Davidson D J, Hancock R E. Immunomodulatory properties of defensins and cathelicidins. Curr Top Microbiol Immunol 2006; 306:27-66). Peptides are now being evaluated for reducing organ graft rejection by immune modulation (Lang J, Zhan J, Xu L, Yan Z. Identification of peptide mimetics of xenoreactive alpha-Gal antigenic epitope by phage display. Biochem Biophys Res Commun 2006; 344(1):214-20). A biologically active inhibitory peptide sequence (E9RP) with 4 µM binding affinity to EWS-FLI1 that inhibits ESFT cell growth and can be delivered to cell culture, expressed in cells, or injected into animals has been developed.

Disruption of protein-protein interactions is thought to be a very challenging, albeit surmountable, target for small molecules therapeutics (Sillerud L O, Larson R S. Design and structure of peptide and peptidomimetic antagonists of protein-protein interaction. Curr Protein Pept Sci 2005; 6(2):151-69; Pagliaro L, Felding J, Audouze K, et al. Emerging classes of protein-protein interaction inhibitors and new tools for their development. Curr Opin Chem Biol 2004; 8(4):442-9). Recently, more investigators are both exploring the methodology of identifying small molecule protein-protein interaction inhibitors (SMPPII) (Murray J K, Gellman S H. Targeting protein-protein interactions: Lessons from p53/MDM2. Biopolymers 2007; 88(5):657-86). In addition, some early results supports the feasibility of inhibiting the frizzled receptor from downstream modulator disheveled (Fujii N, You L, Xu Z, et al. An antagonist of disheveled protein-protein interaction suppresses beta-catenin-dependent tumor cell growth. Cancer Res 2007; 67(2):573-9). The vinca alkaloids represent a class of small molecule containing extremely effective anti-cancer agents that exert their effects by binding to β-tubulin and inhibiting its polymerization (Gadek T R, Nicholas J B. Small molecule antagonists of proteins. Biochem Pharmacol 2003; 65(1):1-8). Given the significant challenges of systemic oligonucleotide delivery in patients, and the very successful transport of small molecule pharmacologic agents, drug discovery efforts have been directed towards identification of SMPPII. Two independent groups have developed SMPPII of the myc:max heterodimer based upon library screening (Berg T, Cohen S B, Desharnais J, et al. Small-molecule antagonists of Myc/Max dimerization inhibit Myc-induced transformation of chicken embryo fibroblasts. Proc Natl Acad Sci USA 2002; 99(6):3830-5; Yin X, Giap C, Lazo J S, Prochownik E V. Low molecular weight inhibitors of Myc-Max interaction and function. Oncogene 2003; 22(40): 6151-9).

Most translocation-fusion protein sarcomas portend a poor prognosis, including ESFT. The chromosomal translocation t(11;22), leading to the unique and critical fusion protein EWS-FLI1, is a perfect cancer target. Many other sarcomas share similar translocation variants (Table 2. from Helman L J, Meltzer P. Mechanisms of sarcoma development. Nat Rev Cancer 2003; 3(9):685-94).

EWS-FLI1 translocations have been reported in solid pseudopapillaryneoplasms of the pancreas (Maitra A., et al., Detection of t(11;22)(q24;q12) translocation and EWS-FLI-1 fusion transcript in a case of solid pseudopapillary tumor of the pancreas. Pediatr Dev Pathol 2000; 3:603-605), however the role of EWS-FLI1 in all solid pseudopaillary neoplasms remains to be resolved (Katharina Tiemann et al., Solid pseudopapillary neoplasms of the pancreas are associated with FLI-1 expression, but not with EWS/FLI-1 translocation).

EWS or FLI1 homologues are partners in translocations that occur in a wide range of sarcomas and leukemias. EWS, or its homologue TLS or FUS, is involved in chromosomal translocations of clear cell sarcoma, myxoid liposarcoma, desmoplastic small round cell tumor, chondrosarcoma and acute myeloid leukemia. FLI1 belongs to the ets family of genes. The FLI1 homologue ERG is translocated in approximately 10% of Ewing's sarcomas and 20% of acute myeloid leukemias. This suggests that EWS-FLI1 can serve as model system that might impact upon a family of diseases (related by translocation partners) that affect a large number of patients (Uren A., Tcherkasskaya O. and Toretsky J. A. Recombinant EWS-FLI1 oncoprotein activates transcription. Biochemistry 43(42) 13579-89 (2004)).

ERG is also translocated in prostate cancer, where the TMPRSS2:ERG fusion suggests a distinct molecular subtype that may define risk for disease progression (F. Demichelis et al., TMPRSS2:ERG gene fusion associated with lethal cancer in a watchful waiting cohort. Oncogene (2007) 26, 4596-4599). Other diseases where translocations of EWS or FLI1 family members have been observed include congenital fibrosarcoma and cellular mesobalstic nephroma where the ets family member ETV6 is juxtaposed with NTRK3. Other translocation gene fusions include chronic myeloid leukemia that leads to expression of the BCR-ABL fusion protein, and synovial sarcoma where the SYT gene from chromosome 18 is juxtaposed with either SSX1 or SSX2 from the X chromosome (Aykut Uren and Jeffrey A. Toretsky, Pediatric malignancies provide unique cancer therapy targets. Curr Opin Pediatr 17:14-19 (2005)).

Therefore, the therapeutic agents of the preferred embodiments have potential for application in many other tumors. More broadly, some of the most difficult leukemias also have translocation-generated fusion proteins involving the mixed-lineage leukemia gene (MLL,11q23), and our work could serve as a paradigm for a very treatment-resistant group of cancers (Pui C H, Chessells J M, Camitta B, et al. Clinical heterogeneity in childhood acute lymphoblastic leukemia with 11 q23 rearrangements. Leukemia 2003; 17(4):700-6). Thus embodiments include cancers where translocations have occurred. Translocation fusion genes are listed in Table 2.

TABLE 2

Translocation Fusion-Genes in Sarcoma

| Translocation | Genes | Type of fusion gene |
|---|---|---|
| Ewing's sarcoma | | |
| t(11; 22)(q24; q12) | EWSR1-FLI1 | Transcription factor |
| t(21; 22)(q22; q12) | EWSR1-ERG | Transcription factor |
| t(7; 22)(p22; q12) | EWSR1-ETV1 | Transcription factor |
| t(17; 22)(q21; q12) | EWSR1-ETV4 | Transcription factor |
| t(2; 22)(q33; q12) | EWSR1-FEV | Transcription factor |
| Clear-cell sarcoma | | |
| t(12; 22)(q13; q12) | EWSR1-ATF1 | Transcription factor |
| Desmoplastic small round-cell tumor | | |
| t(11; 22)(p13: q12) | EWSR1-WT1 | Transcription factor |
| Myxoid chondrosarcoma | | |
| t(9; 22)(q22-31; q11-12) | EWSR1-NR4A3 | Transcription factor |
| Myxoid liposarcoma | | |
| t(12; 16)(q13; p11) | FUS-DDIT3 | Transcription factor |
| t(12; 22)(q13; q12) | EWSR1-DDIT3 | Transcription factor |
| Alveolar rhabdomyosarcoma | | |
| t(2; 13)(q35; q14) | PAX3-FOXO1A | Transcription factor |
| t(1; 13)(p36; q14) | PAX7-FOXO1A | Transcription factor |
| Synovial sarcoma | | |
| t(X; 18)(p11; q11) | SYT-SSX | Transcription factor |
| Dermatofibrosarcoma protuberans | | |
| t(17; 22)(q22; q13) | COL1A1-PDGFB | Growth factor |
| Congenital fibrosarcoma | | |
| t(12; 15)(p13; q25) | ETV6-NTRK3 | Transcription-factor receptor |
| Inflammatory myofibroblastic tumor | | |
| 2p23 rearrangements | TMP3-ALK; TMP4-ALK | Growth-factor receptor |
| Alveolar soft-part sarcoma | | |
| t(X; 17)(p11.2; q25) | ASPL-TFE3 | Transcription factor |

Experimental

Experiments have been conducted validating the functional importance of the interaction and demonstrating how SPR can identify small molecules that bind to EWS-FLI 1. These experiments include a demonstration of direct RHA binding to EWS-FLI1, RHA required for optimal EWS-FLI1 function, a peptide that binds to EWS-FLI1, blocks RHA binding and reduces tumorigenesis, small molecule screening and compound identification, and optimization and synthetic strategies for developing therapeutic compounds.

EWS-FLI1 Binds to a Unique Region of RHA

Figure 1A:
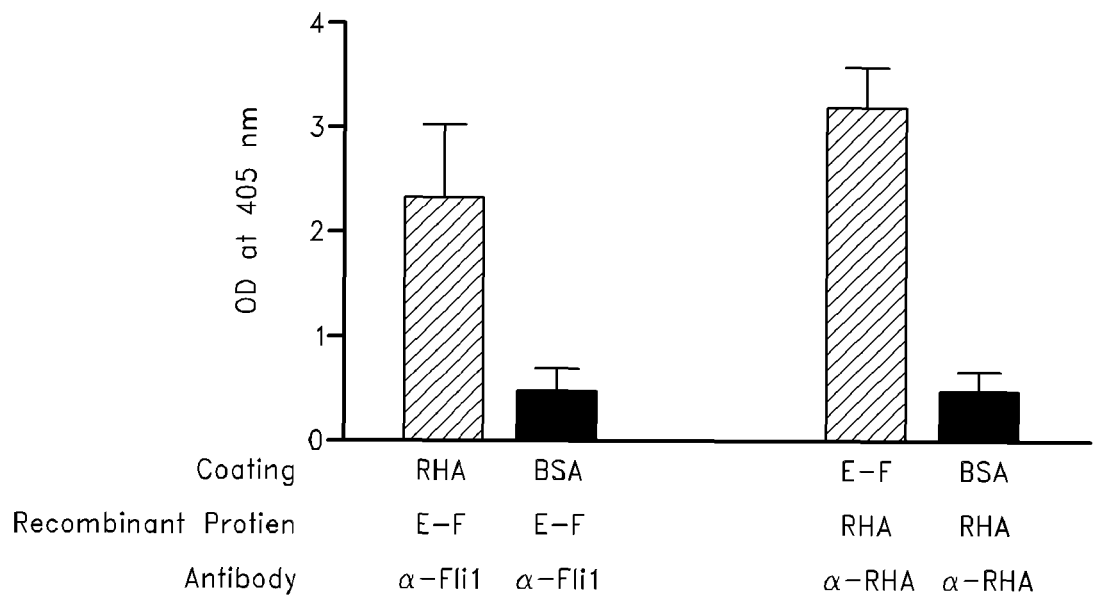
FIGS. 1A-B provides data demonstrating the binding of recombinant RHA to recombinant EWS-FLI1 in ELISA.
Figure 1B:
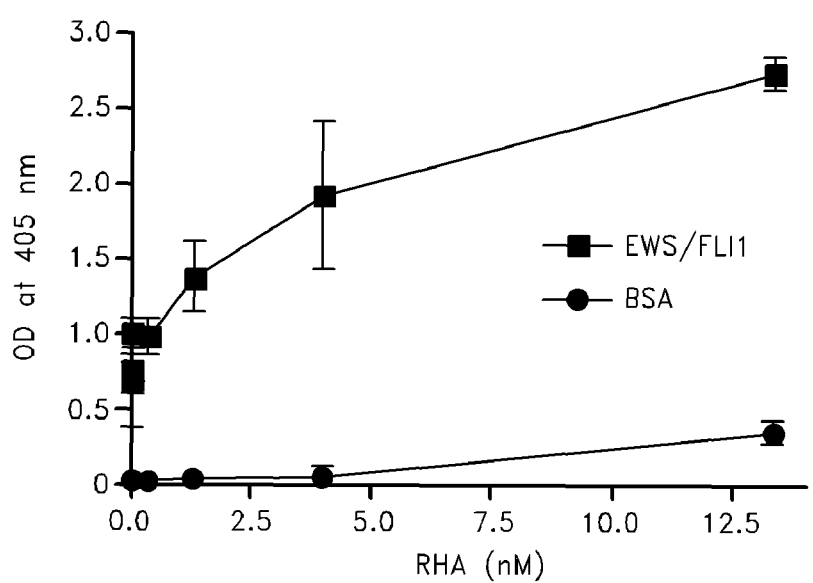

RNA Helicase A (RHA) has been established as a partner of EWS-FLI1 (Toretsky J A, Erkizan V, Levenson A, et al. Oncoprotein EWS-FLI1 activity is enhanced by RNA helicase A. Cancer Res 2006; 66(11):5574-81). In order to show that RHA was directly binding to EWS-FLI1, ELISA and solution immunoprecipitation assays were developed. ELISA assay suggested the direct binding of EWS-FLI1 to RHA (FIG. 1A). RHA protein specifically bound EWS-FLI1 compared with bovine serum albumin (BSA) in a dose-dependent manner (FIG. 1B).

Figure 2A:
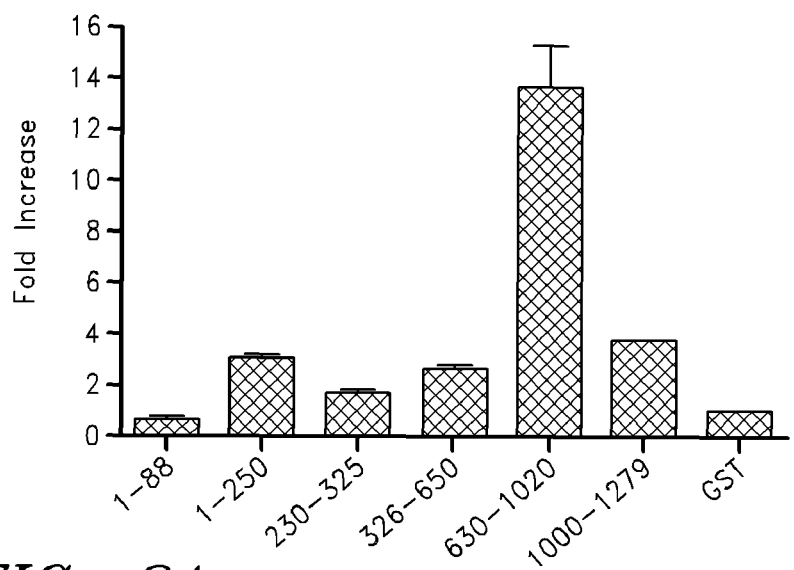
FIGS. 2A-C provide data regarding identification of the region of RHA that binds to EWS-FLI1.
Figure 2B:
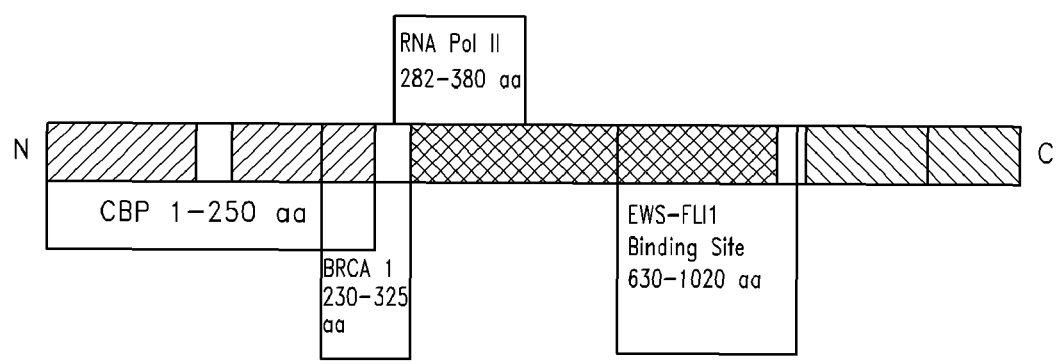
Figure 2C:
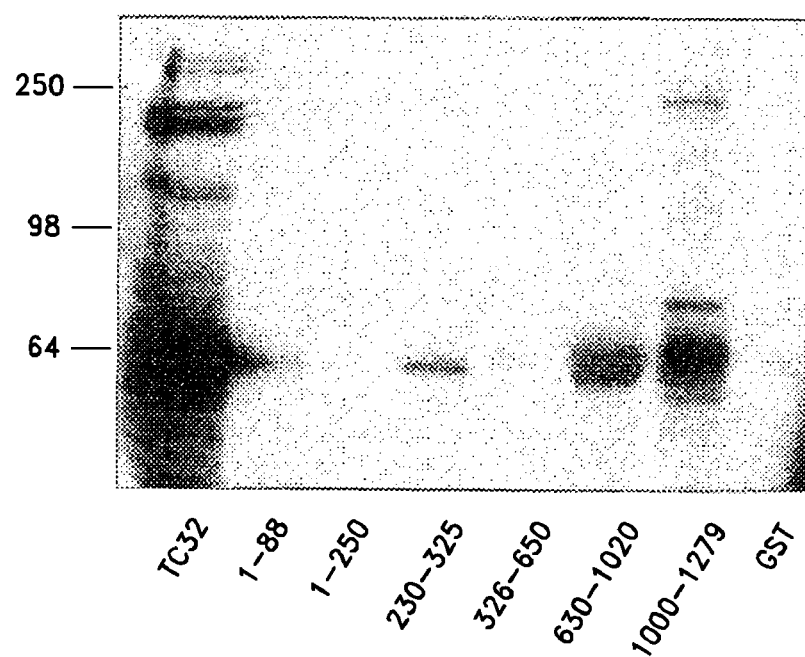

ELISA was used to identify the region of RHA that binds to EWS-FLI1. GST-tagged human RHA fragments aa 1-88, 1-250, 230-325, 326-650, 630-1020 and 1000-1279 (Anderson S F, Schlegel B P, Nakajima T, Wolpin E S, Parvin J D. BRCA1 protein is linked to the RNA polymerase II holoenzyme complex via RNA helicase A. Nat Genet 1998; 19(3): 254-6) were analyzed for EWS-FLI1 binding in an ELISA assay normalized using bovine serum albumin (BSA) (FIG. 2A). Results showed that GST-RHA(630-1020) bound to EWS-FLI1 14-fold greater than it bound to BSA. GST-RHA (630-1020) contains homology (aa 823-832) to the E9R peptide sequence (later used to develop inhibitory peptides). Fragment GST-RHA(630-1020) also bound to endogenous EWS-FLI1, in a GST pull-down immunoprecipitation assay using endogenous ESFT cell lysate followed by FLI1 antibody western blot (FIG. 2C). The immunoprecipitation study identified a potential second site of interaction in the C-terminal RHA(1000-1279). This potential second site of interaction will be evaluated in other proposals. This data enabled a robust, reproducible assay to evaluate RHA binding to EWS-FLI1 to be created.

RHA Binding to EWS-FLI1 is Required for Optimal Soft-Agar Colony Growth

GST-RHA(630-1020) had the strongest evidence for containing a significant binding site to EWS-FLI1 including containing the phage display peptide that identified RHA as a putative EWS-FLI1 partner as well as immunoprecipitation and ELISA assays. The amino-acids from the region of GST-RHA(630-1020) were independently mutated and mutants that did not bind to EWS-FLI1 were identified. These EWS-FLI1 "non-binding" mutants were prepared in the full length RHA expression plasmid.

Figure 3A:
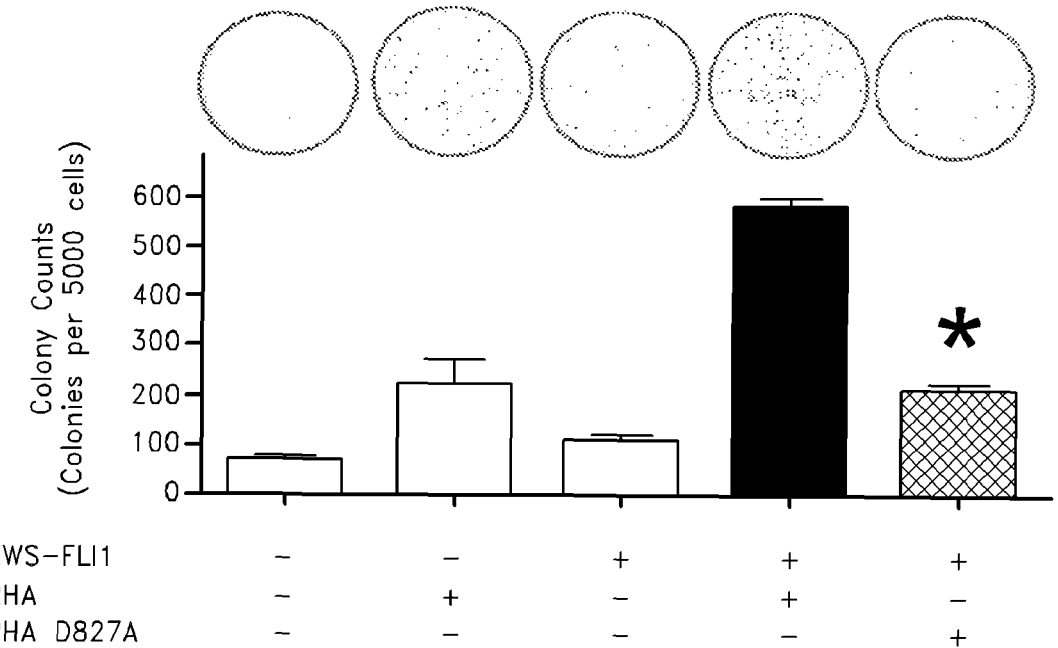
FIG. 3A shows wild-type RHA augments EWS-FLI1 induced colony formation, while RHA mutant defective for EWS-FLI1 binding does NOT enhance colony growth. Murine embryonic fibroblasts were transfected with EWS-FLI1 and/or RHA. EWS-FLI1 was expressed from the pBABE retroviral vector. RHA or mutants were expressed from pCMV-FLAG. The bars under the colonies are the counts of triplicate soft-agar assays. Statistical analysis of triplicate assays: EF+RHA versus EF+D827A p<0.001, EF+e.v. versus EF+either mutant, n.s. This experiment has been performed three times with independent transfections of plasmids.
Figure 3B:
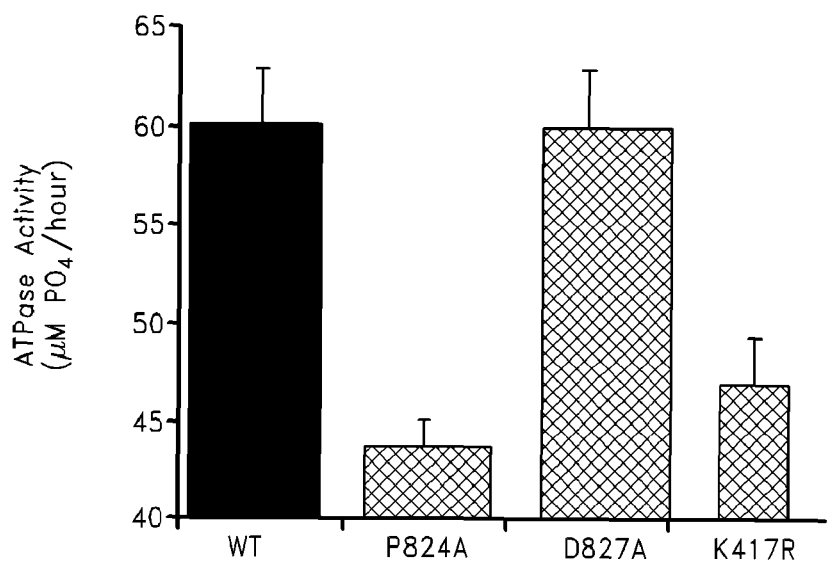
FIG. 3B shows that the D827A mutation did not affect RHA function. Blue bar represents a known RHA mutant, K417R. Immunoglobulin control immunoprecipitates did not demonstrate ATPase activity. Phosphate standards were used to calibrate the assay and determine the rate of ATP hydrolysis. RHA(K417R) is a known NTPase-null mutant of RHA.

Using the standard anchorage-independent growth assay with primary murine embryonic fibroblasts (containing a small amount of endogenous RHA), expression of EWS-FLI1 induced colony formation as did over-expression of the wild-type RHA (FIG. 3, open bars). When the two proteins were co-expressed there was a synergistic increase in colony formation (FIG. 3, orange bar). However, when RHA D827A, a mutant that does not bind to EWS-FLI1 was expressed, no increase in colony formation was seen (FIG. 3, yellow bar). In order to determine if this lack of colony growth was only due to the inability to bind to EWS-FLI1 or secondary to RHA structural changes, ATPase activity was measured from the FLAG immunoprecipitated protein. The D827A mutation did not affect RHA function (FIG. 3B).

Peptide Binds to EWS-FLI1 and Blocks RHA from Binding to EWS-FLI1

An assay that will identify whether a peptide can disrupt RHA from interacting with EWS-FLI1 was developed. The Biacore device is a biosensor that utilizes surface plasmon resonance (SPR) to measure the strength of molecular interactions. SPR is the sensitive measurement of diffracted light based upon alterations of surface characteristics that change with molecules binding to a surface. The Biacore device combines SPR with a microfluidic system. The y-axis demonstrates resonance units (RU), which is the position of a reflected beam of light at any given time. The x-axis shows time in seconds.

Figure 4:
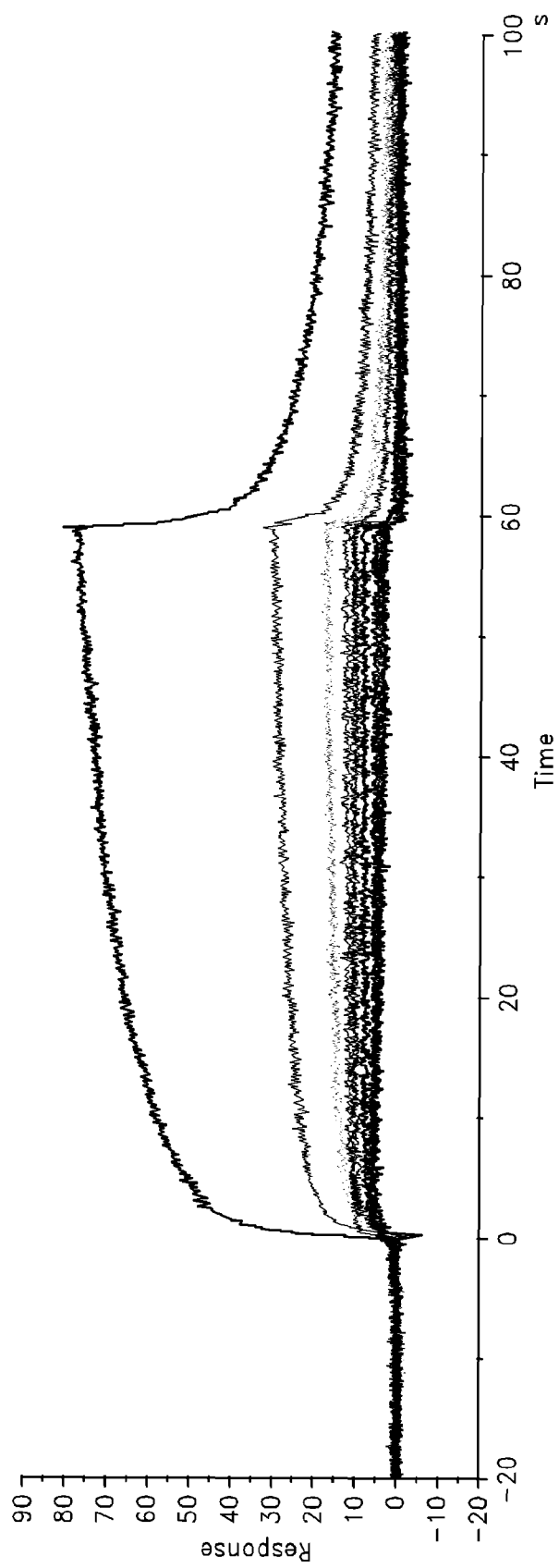
FIG. 4 shows surface plasmon binding of the E9RP peptide to EWS-FLI1, where E9RP is the peptide region of RHA (E9R; SEQ ID NO: 29) fused to the Penetratin peptide (a 16 aa long peptide from *Drosophila* Antennapedia homeodomain protein (Antp) (SEQ ID NO: 34)) to achieve intracellular delivery of our peptides. Antp is conjugated to the amino terminal of all peptides used in these studies. Recombinant EWS-FLI1 (MW 55 kDa) was covalently linked to a CM5 chip at a density of 1200 RU, and E9RP (MW 4 kDa) was evaluated for binding. The E9RP analyte concentrations ranged from 0.03-30 μM, and all are shown in duplicate. E9RP bound to EWS-FLI1 with a KD of 4.0 μM.

Surface plasmon resonance (SPR) was used to demonstrate an interaction between EWS-FLI1 and a peptide containing the 10 amino-acids of RHA (E9R; SEQ ID NO: 29), identified from the phage experiment fused to the cell-penetrating peptide antennapedia (SEQ ID NO: 34), Antp-PPPLDAVIEA (E9RP, FIG. 4). The $K_D$ of E9RP binding to EWS-FLI1 was calculated to be 4.0 µM (FIG. 4).

E9RP was evaluated for the ability to block RHA from binding to EWS-FLI1 using both competitive ELISA assay and solution immunoprecipitation assays. In addition, specificity of interaction was evaluated by disrupting EWS-FLI1 binding from RHA without interfering with other RHA binding proteins. Creb-binding protein (CBP, p300) is critical to cellular basal transcription, so it was determined if a peptide that would disrupt EWS-FLI1 binding from RHA could also disrupt CBP binding.

Figure 5A:
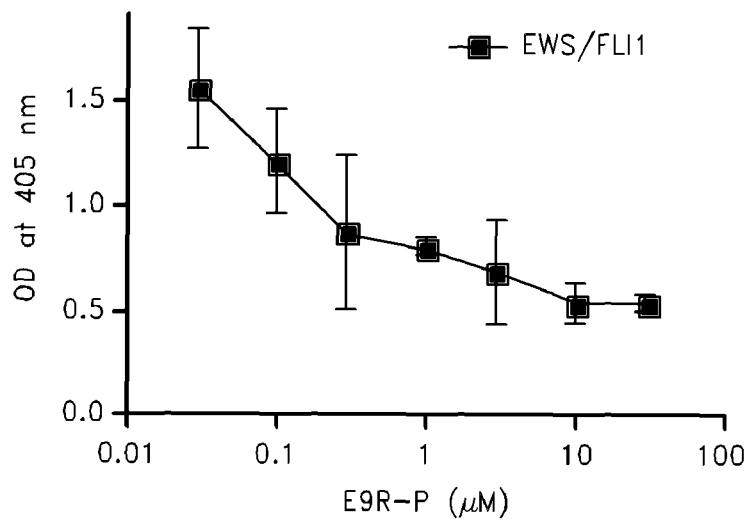
FIGS. 5A-B demonstrate that E9RP competes for RHA binding to EWS-FLI1 in ELISA. E9RP is the peptide region of RHA (E9R; SEQ ID NO: 29) fused to the Penetratin peptide (from the Antennapedia homeodomain; SEQ ID NO: 34).
Figure 5B:
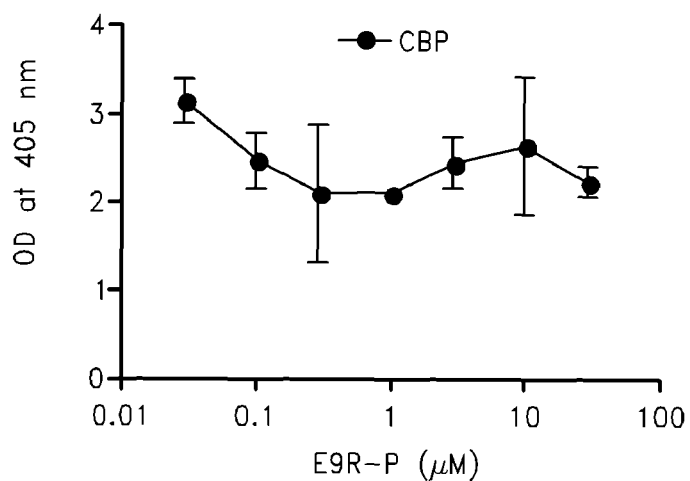

The EWS-FLI1 binding peptide, E9RP (SEQ ID NO: 29), was able to prevent the binding of RHA to EWS-FLI1 in a dose-dependent manner in this ELISA assay, with an IC50 of approximately 0.2 µM (FIG. 5, Panel A), while lacking a dose-dependent effect upon the binding of CBP (aa 1680-1890) (FIG. 5, Panel B).

Figure 6:
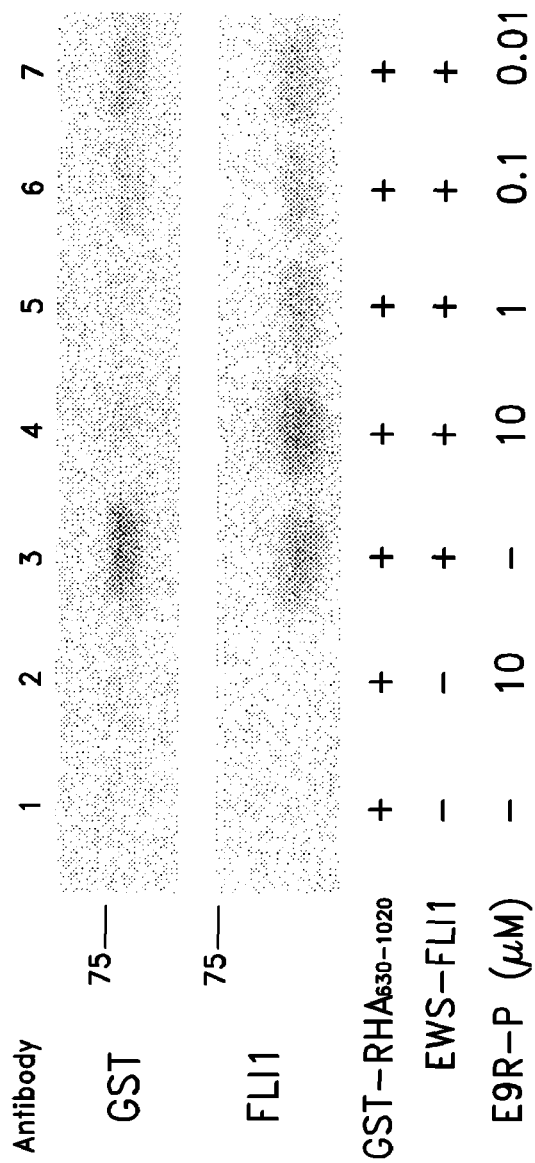
FIG. 6 shows that E9RP disrupts RHA from binding to EWS-FLI1. E9RP is the peptide region of RHA (E9R; SEQ ID NO: 29) fused to the Penetratin peptide (from the Antennapedia homeodomain; SEQ ID NO: 34). Immunoprecipitation of GST-RHA using recombinant EWS-FLI1 bound to a FLI1 antibody. Lane 3 demonstrates the full complex while lanes 4 through 7 show a dissociation of the complex using a 10 amino-acid peptide, E9RP. E9RP is the sequence of aa 823-832 of human RHA that were synthesized. Previous data show that this peptide binds to EWS-FLI1.

The data suggest that E9RP can prevent the interaction of EWS-FLI1 and RHA, both by ELISA (FIG. 5) and in solution by showing that their complex is disrupted by the peptide, E9RP (FIG. 6). The $IC_{50}$ to prevent complex formation is approximately 0.1 µM, very similar to results from the ELISA assay (FIG. 5).

Single Amino Acid Substitutions in GST-RHA(630-1020) Reduce EWS-FLI1 Binding.

Figures 7A, 7B:
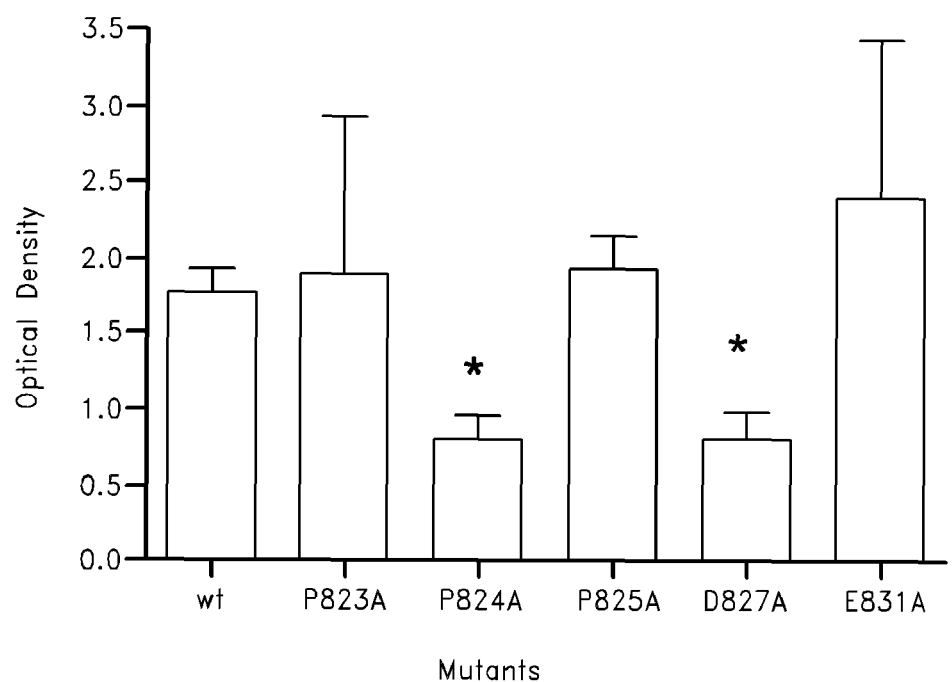
FIGS. 7A-B show that amino acids in positions 824 and 827 are important for EWS-FLI1 binding.

Amino-acids in positions 824 and 827 appear to be the important for EWS-FLI1 binding. The region of RHA identified by the E9RP peptide was mutated in the GST-RHA(630-1020) fusion. Five amino acids were independently mutated to alanine for immunoprecipitation studies (FIG. 7A). Wild-type GST RHA(630-1020) showed a 2-fold increase over background, whereas P824A and D827A did not show increased binding over background (FIG. 7B). Thus amino-acids in positions 824 and 827 appear to be important for EWS-FLI1 binding, as their mutation results in a reduction of complex formation (FIG. 7B). These mutations have allowed the creation of a definitive RHA mutant that does not bind to EWS-FLI1 as well as prepare control peptides for cell growth experiments.

RHA Peptide Inhibits Monolayer ESFT Cell Growth but not Neuroblastoma Growth.

Figure 8A:
FIGS. 8A-E show E9RP inhibits ESFT cell growth.
Figure 8B:
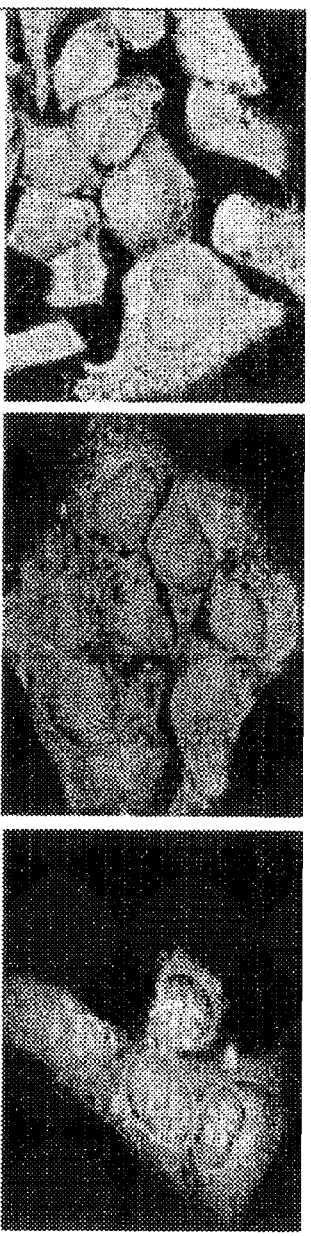

Disrupting the RHA:EWS-FLI1 complex is believed to inhibit growth in an ESFT cell line specific fashion. For these experiments, the RHA peptide identified from the original phage display experiments was synthesized with an N-terminal tag containing the cell-permeable peptide (CPP) Penetratin (a.k.a. Antennapedia), a sequence used for transport into cells as well as N-ter fluorescein (E9RP) (Terrone D, Sang S L, Roudaia L, Silvius J R. Penetratin and related cell-penetrating cationic peptides can translocate across lipid bilayers in the presence of a transbilayer potential. Biochemistry 2003; 42(47):13787-99; Lindgren M, Gallet X, Soomets U, et al. Translocation properties of novel cell penetrating transportan and penetratin analogues. Bioconjug Chem 2000; 11(5):619-26; and Thoren P E, Persson D, Karlsson M, Norden B. The antennapedia peptide penetratin translocates across lipid bilayers—the first direct observation. FEBS Lett 2000; 482(3):265-8). The 16 aa Penetratin peptide was derived from the Drosophila Antennapedia homeodomain that enhances uptake of peptides by cells (Derossi D, Joliot A H, Chassaing G, Prochiantz A. The third helix of the Antennapedia homeodomain translocates through biological membranes. J Biol Chem 1994; 269(14): 10444-50, Perez F, Joliot A, Bloch-Gallego E, Zahraoui A, Triller A, Prochiantz A. Antennapedia homeobox as a signal for the cellular internalization and nuclear addressing of a small exogenous peptide. J Cell Sci 1992; 102 (Pt 4):717-22). Confocal imaging demonstrated the E9RP peptide entering nearly 100% of the cells as well as entering the nucleus of ESFT cell lines 1 and 2 as well as control neuroblastoma cells (FIGS. 8A and 8B).

Figure 8C:
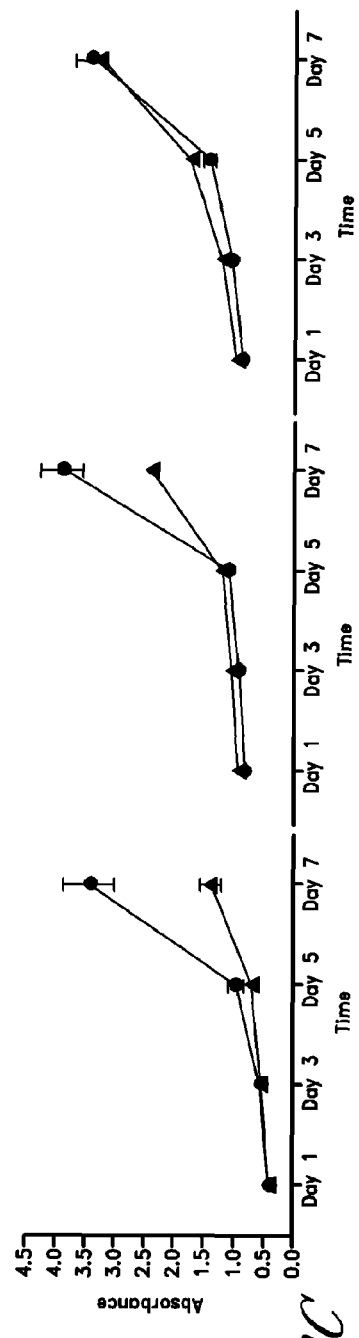
Figure 8D:
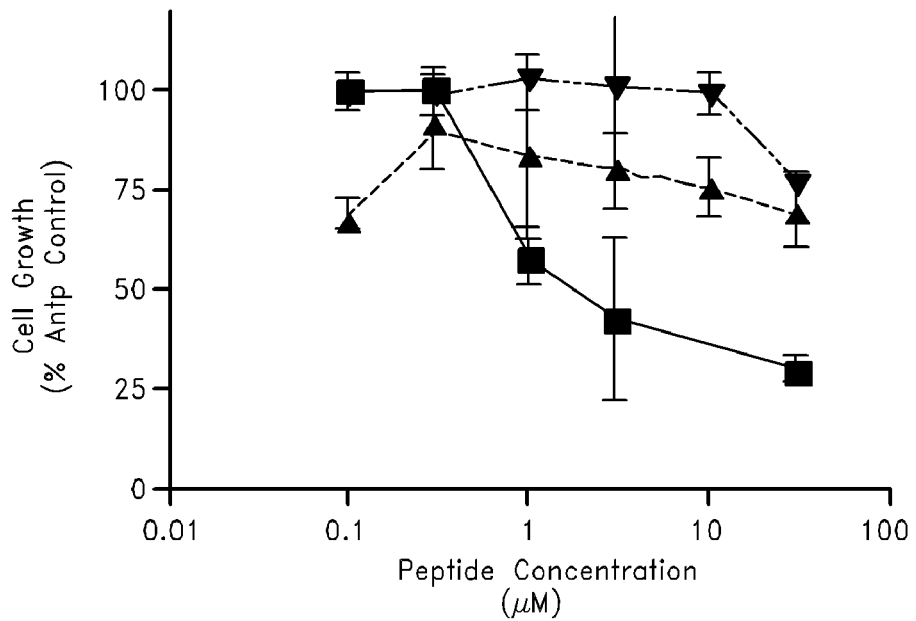
Figure 8E:
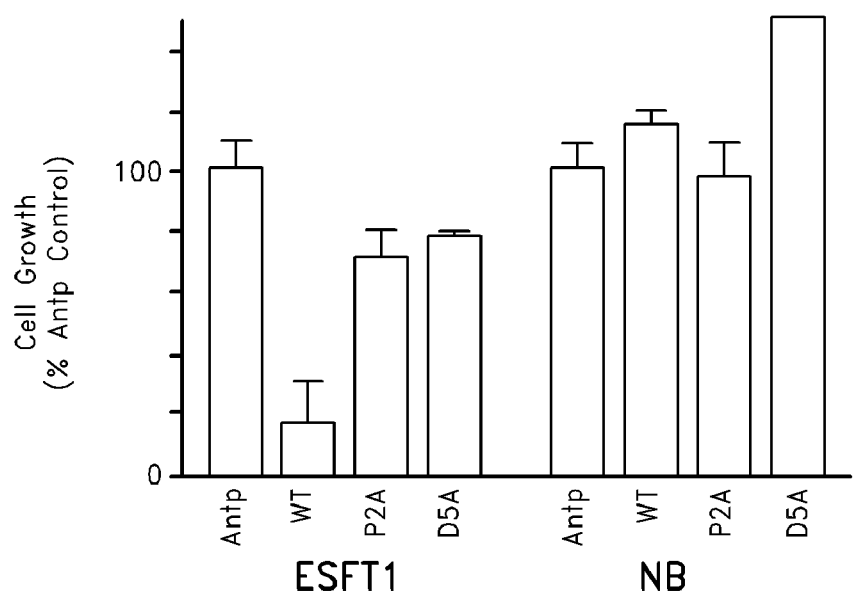

E9RP (10 µM) inhibited the growth of two ESFT cell lines 1 and 2, but did not affect the growth of a neuroblastoma cell line that lacks EWS-FLI1 but expresses wild-type EWS (FIG. 8C). Two additional sarcoma cell lines, lacking EWS-FLI1, were not growth inhibited by E9RP, yet both exhibited significant nuclear uptake of the peptide (data not shown). Control peptides with the single amino acid substitutions shown above demonstrated no effect on cell growth (FIGS. 8D, 8E). These results support the concept of the specific inhibition of ESFT cell growth using a peptide directed at EWS-FLI1.

Figure 9:
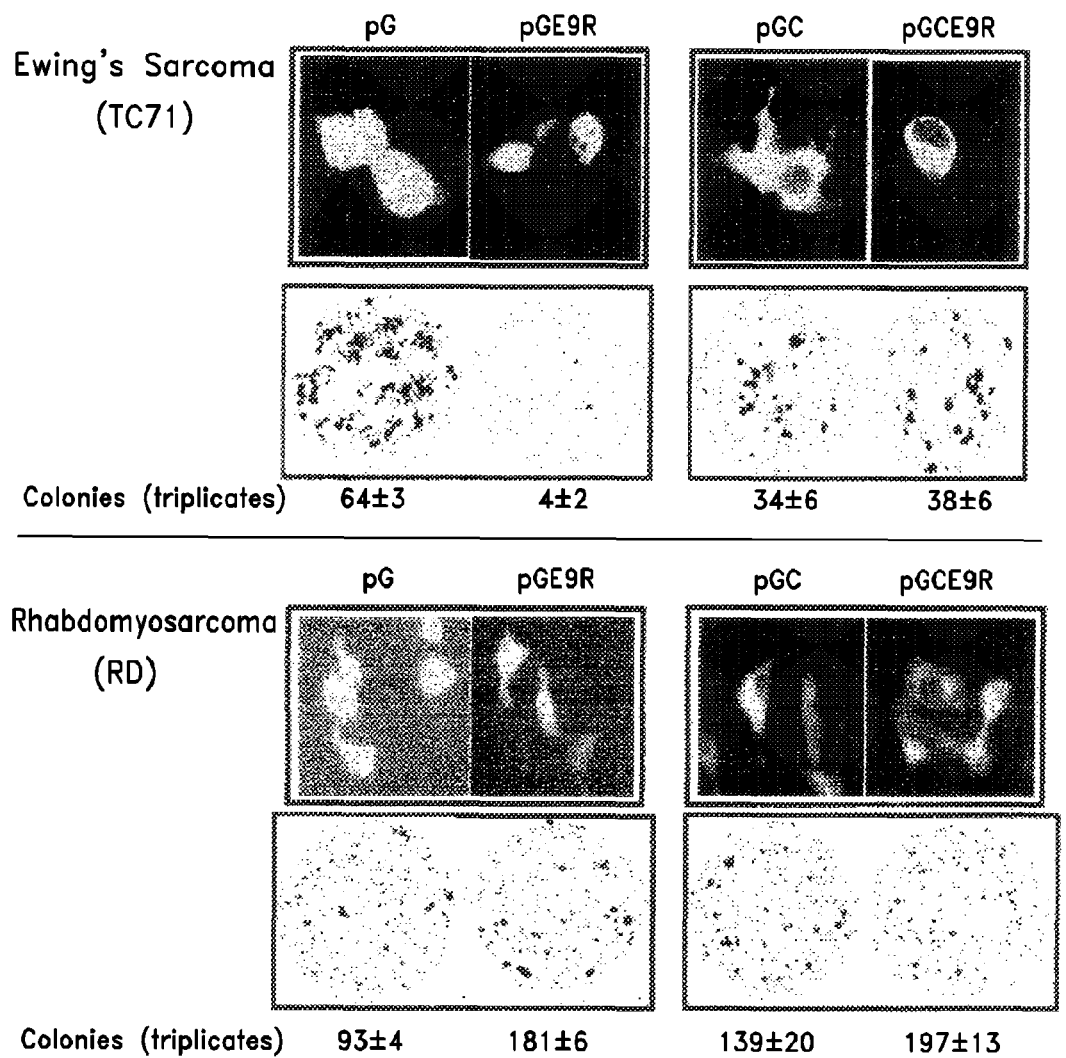
FIG. 9 shows expressed E9R reduced ESFT soft-agar growth, but not rhabdomyosarcoma growth. Plasmids that express E9R fused to enhanced green fluorescent protein (EGFP) were transfected into either Ewing's Sarcoma (TC71) or rhabdomyosarcoma (RD) cells and placed in soft-agar for anchorage-independent growth. The pGE9R plasmid diffusely expressed E9R while the pGCE9R plasmid contained a nuclear export sequence to prevent expressed peptide from entering the nucleus. The transfected cells were placed in soft agar culture for 2 weeks and stained with MTT. When E9R was diffusely expressed, including the nucleus, ESFT (containing EWS-FLI1) soft-agar colony growth was suppressed. Expressed E9R did not affect the growth of rhabdomyosarcoma cells, which lack EWS-FLI1. Nuclear exclusion of expressed peptide did not decrease the growth of either cell line.

RHA Peptide Expressed in ESFT Cells Reduces Soft-Agar Colonies, but does not Reduce Rhabdomyosarcoma Colony Growth Since the Antp peptides added to media would not remain in the cells for 2 weeks during soft-agar colony growth, expression peptides were used to provide continuous exposure to peptide. A pair of expression plasmids with cloning sites downstream of the enhanced green fluorescent protein (EGFP) was obtained; the pG plasmid contained no localizing sequence and was expressed throughout the cells (FIG. 9, left panels). The pGC plasmids contained a nuclear export sequence that blocked peptide transport into the nucleus (FIG. 9, right panels). The E9R DNA sequence was synthesized and the hybridized oligodeoxynucleotides were inserted into the cloning site downstream of either EGFP or EGFP and nuclear export sequence.

When E9R was expressed throughout ESFT (TC71) cells, soft agar colony growth was suppressed (FIG. 9, left upper). However, rhabdomyosarcoma cells were not reduced by the E9R expression (FIG. 9, left lower). When the E9R was excluded from the nucleus (pGCE9R), no growth reduction was seen for either cell line (FIG. 9, right panels). Expressed E9R also did not affect soft agar growth of neuroblastoma cells, also lacking EWS-FLI1 (not shown). This supports our conclusion about the specific effects of E9R inhibition of ESFT cells and suggests that nuclear peptide is required for an effect. Unfortunately, the empty vector plasmid with the nuclear import signal was toxic to all cells, potentially from high levels of EGFP in the nucleus (not shown).

E9R Peptide Expression Reduces ESFT Murine Xenograft Growth

Figure 10A:
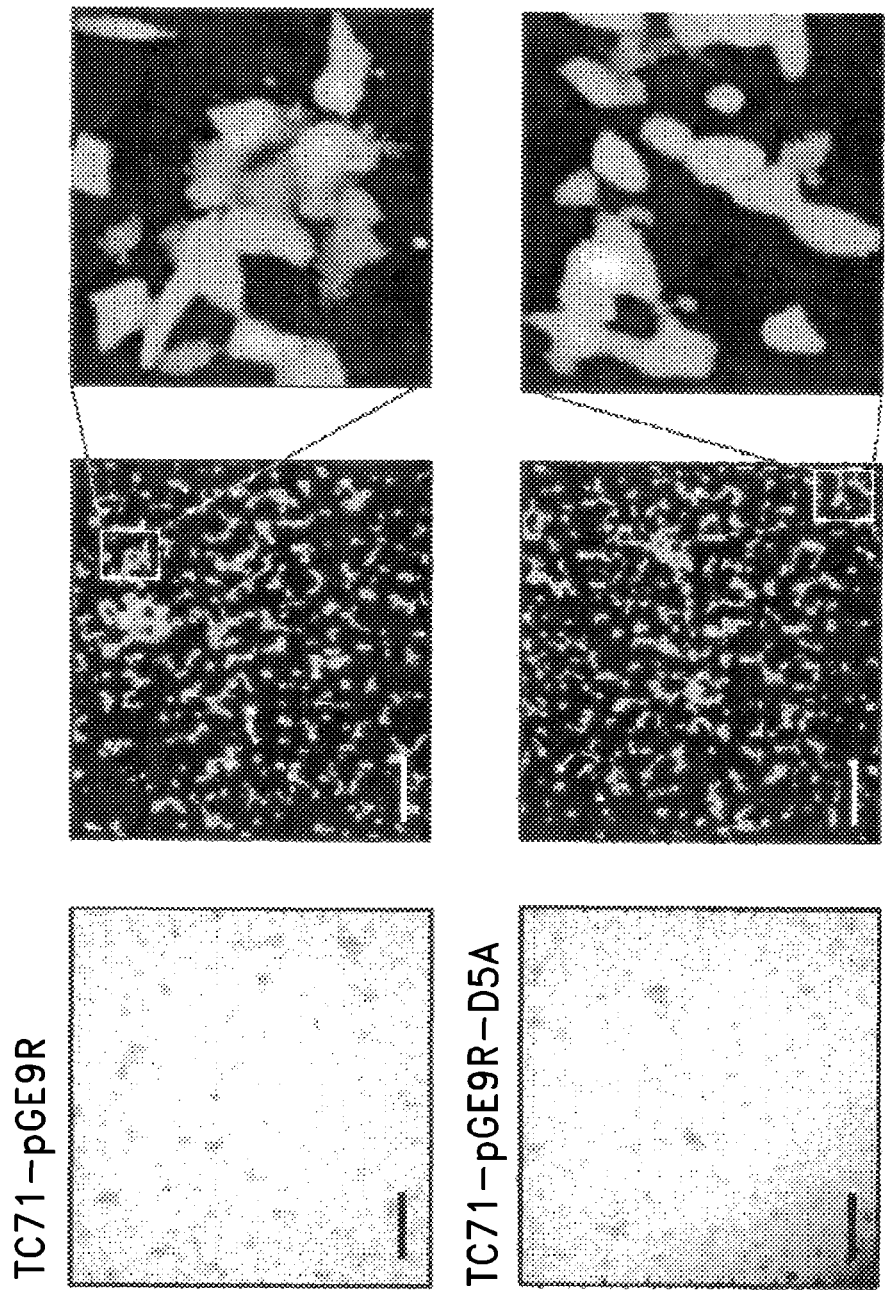

The ability of the E9R peptide sequence to prevent ESFT tumorigenesis in a pilot murine xenograft experiment was determined. As a control peptide, the same mutation that prevented wild-type RHA from binding to EWS-FLI1 (D827A, noted in the 10-mer peptide as E9R-D5A) was created. ESFT cells were transfected with either pGE9R or pGE9R-D5A by electroporation. A transfection efficiency of greater than 80% using fluorescent microscopy (FIG. 10A) was observed. Transfected cells, 500,000 cells per mouse, were implanted into the gastrocnemius muscle of 6 mice per group by syringe injection. Animals were observed for tumor growth, and were measured as soon as palpable tumors appeared after 14 days. Every two to three days, each animal's thigh was measured in three dimensions, and tumor volumes were calculated. The tumor take-rate and rate of growth was greater in the animals whose tumors contained the mutated peptide (E9R-D5A) (FIG. 10B). After 26 days, the animals with the largest tumors began to limp and the experiment was ended (FIG. 10C). Using a 2-way ANOVA analysis, followed by Bonferroni correction for multiple variables, the difference in the two growth curves was highly significant, p=0.016.

Small Molecule Screening Identifies a Lead Compound with High Affinity for EWS-FLI1

Figure 11:
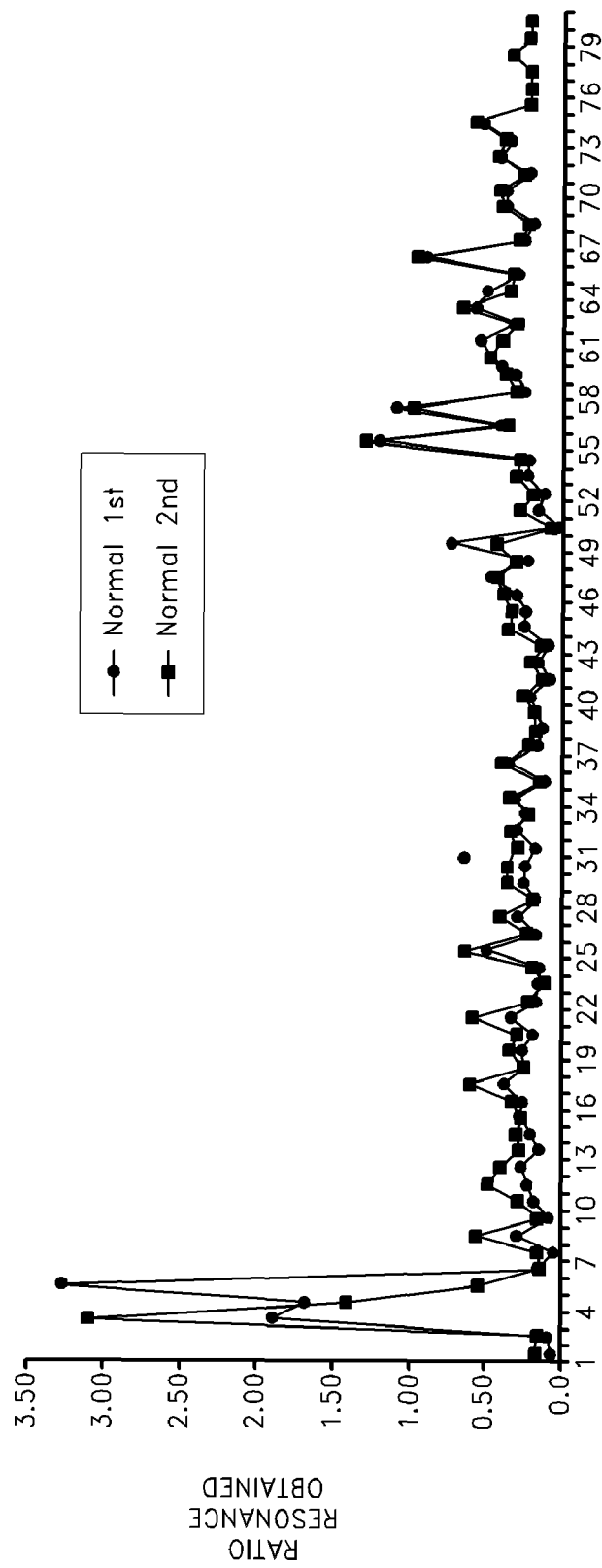
FIG. 11 relates to small molecule libraries that contain EWS-FLI1 binding molecules and shows the results of two SPR screens using Biacore T100. This demonstrates the type of results obtained from screening 80 compounds from the NCI DTP. The values are the ratio of the resonance units obtained divided by the expected resonance maximum. The consistency of two independent experiments is shown by the overlap in red and blue. Each number on the x-axis represents one tested compound.

Using the validated interaction between EWS-FLI1 and RHA as a therapeutic target, one logical progression is to identify small molecules in silico that could be predicted to prevent the interaction. Unfortunately, since EWS-FLI1 is a disordered protein (Ng K P, Potikyan G, Savene R O, Denny C T, Uversky V N, Lee K A. Multiple aromatic side chains within a disordered structure are critical for transcription and transforming activity of EWS family oncoproteins. Proc Natl Acad Sci USA 2007; 104(2):479-84) and significantly hydrophobic (Uren A, Tcherkasskaya O, Toretsky J A. Recombinant EWS-FLI1 oncoprotein activates transcription. Biochemistry 2004; 43 (42): 13579-89), 3-dimensional structural information of the chimera is not available. An approach was chosen to screen small molecule libraries for compounds that bind to EWS-FLI1. Recombinant EWS-FLI1 was bound to a CM5 sensor chip. 1000 compounds from the NIH, NCI, DTP library of compounds were screened using a single concentration injection of each compound. An example of the screening from a portion of one plate containing 80 compounds is shown (squares, FIG. 11). The data shown include the position on a 96-well plate, the NSC compound number, the molecular weight and Rm normalization. An initial selection of promising compounds was based on the Rm normalization. The Rm normalization is a ratio of the actual resonance unit binding measurement divided by the theoretical maximal binding. Ratios that exceed 2.0 likely indicate issues of compound solubility or polymerization. Ratios less than 0.7 suggest poor binding with affinity that would not be adequate for blocking a protein-protein interaction. The compounds that were selected as potentially binding to EWS-FLI1 were further evaluated over a range of concentrations in order to identify a binding affinity (not shown).

Figure 15C:
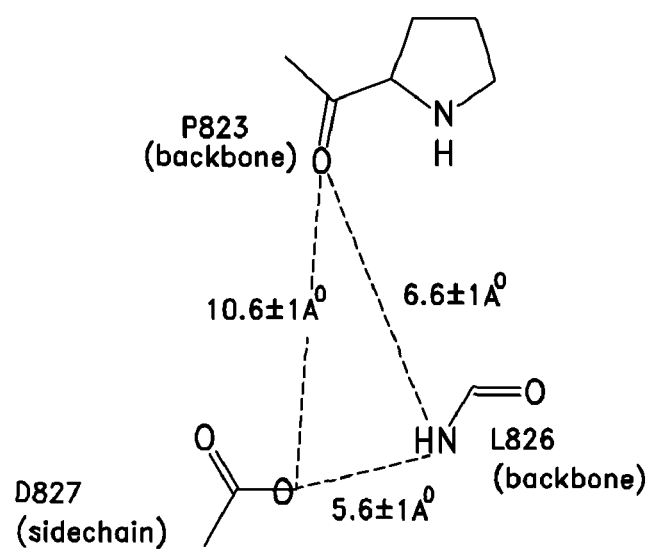

Following Biacore T100 screening of 1000 compounds, one of the compounds with outstanding binding kinetics (FIG. 12), both qualitatively and quantitatively demonstrated a unique 3-dimensional structure (FIG. 15). In a comparative modeling experiment, this compound, NSC635437, had surprisingly similar structure to our well-studied peptide sequence E9R (SEQ ID NO: 29). NSC635437 also has significant structural homology to the first three prolines in our peptide using a ligand overlap strategy (FIG. 15). The combination of a significant binding affinity and a surprising structure will lead us to pursue a series of structural modifications to optimize binding and functional inhibition in future proposals.

Figure 12:
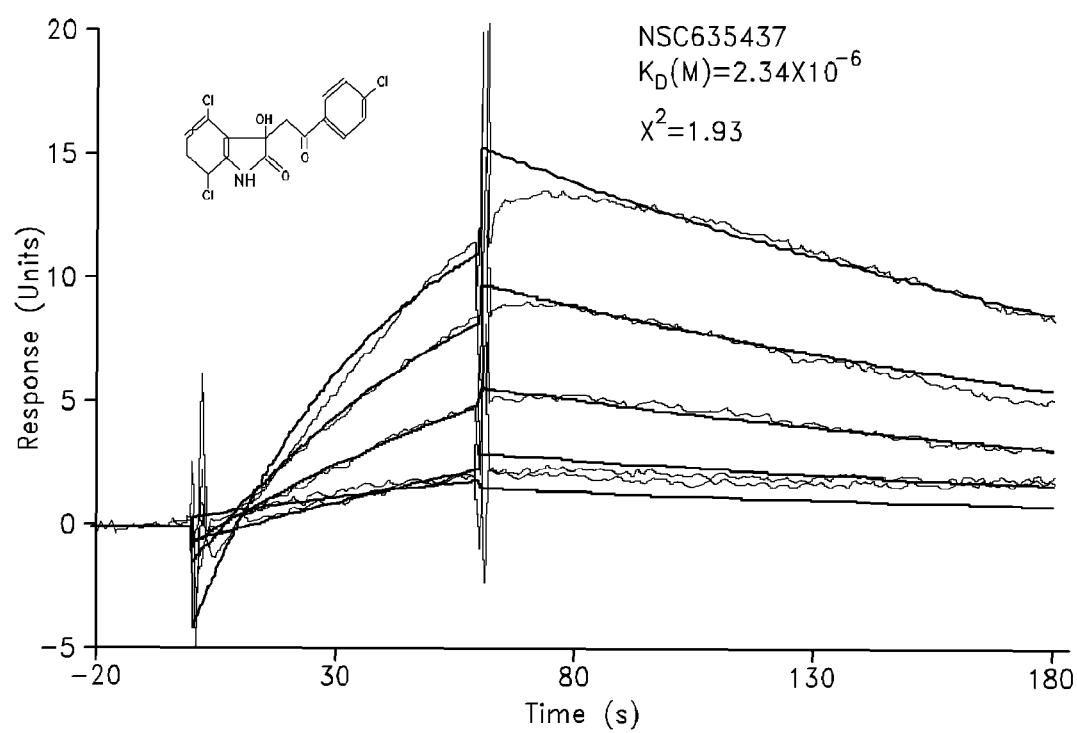
FIG. 12 shows surface plasmon binding of NSC635437 to EWS-FLI1 with a KD of 2.34 µM.

The small molecule lead compound was tested for the ability to block RHA from binding to EWS-FLI1 using a solution immunoprecipitation assay. NSC635437 not only has good binding to EWS-FLI1, but can block the binding of RHA to EWS-FLI1 in solution binding assay at 10 µM (FIG. 13A), consistent with the SPR measured binding affinity (FIG. 12). In addition, the lead compound was specifically cytotoxic to ESFT cells in culture compared with neuroblastoma cells (FIG. 13B).

Compound NSC635437 has Homology to Peptide E9R

A 3-dimensional model of the E9R peptide was developed to determine if any of our lead compounds might have structural similarity. A ligand overlap strategy was used by first sampling the Brookhaven database for x-ray structures that contained the PPPLDAVIEA (SEQ ID NO; 29) motif and BLAST alignment was made for the 10-mer PPPLDA-VIEA (SEQ ID NO; 29) sequence to predict the structure. The best sequence alignment (FIG. 14) was extracted and predicted the structure using homology modeling (1) with a SQUALENE-HOPENE-CYCLASE (PDB: 1SQC) x-ray structure as a template. The input alignment for the Modeler (1) was obtained with BLAST (2).

Subsequently, to confirm the correct orientation of the mutated residues, BLAST was counter searched for the sequence motif 'PPPLD' (SEQ ID NO: 32). Several hits were obtained and five structures were superimposed together with the 10-mer peptide (FIG. 15). The predicted orientation matches well with the x-ray orientation obtained for the 'PPPLD' sequence (SEQ ID NO: 32) with a minimum root mean square deviation (RMSD) of 0.62 Å and maximum RMSD of 1.69 Å. Using a multi-fit procedure, a fit of the atom coordinates of the lead NSC635437 onto atom coordinates of the inhibitory peptide motif (FIG. 15) was searched for. NSC635437 (identified from the Biacore screening, FIG. 11 to have a $K_D$ of 2.34 µM) provided an excellent mimic of the PPP portion of the E9R motif (see FIG. 15B). Based on this fit, decoration of NH of the lactam ring of NCS635437 with peptide motifs to mimic the LDAVIEA (SEQ ID NO: 33) portion of PPPLDAVIEA (SEQ ID NO; 29) can be performed, and pharmacophores within PPPLDAVIEA (SEQ ID NO; 29) defined by physico-chemical descriptors (i.e., distance, H-bond donor acceptors) can be generated. A preliminary 3-D pharmacophore model (FIG. 15C) was generated using the UNITY module of Sybyl 7.0 (Tripos Inc., St. Louis, USA) by assigning hydrogen bond donors and acceptors. Screening of a virtual database of 55 million compounds has begun, and the basic core of NSC635437 (FIG. 16) has been synthesized.

Results

Data show that RHA binds directly to EWS-FLI1 (FIGS. 1 and 2), and that this interaction leads to functional modulation (FIG. 3). Based upon this discovery, the E9R peptide is a useful tool to probe the binding of EWS-FLI1 to RHA. The E9RP binds to EWS-FLI1 (FIG. 4) and can disrupt RHA from binding to EWS-FLI1 (FIGS. 5 and 6). The growth of ESFT cells, but not other embryologic tumors, is reduced by the E9RP (FIG. 8) and the expressed E9R reduces soft-agar colony and xenograft tumor formation in ESFT but not other tumors (FIGS. 9 and 10).

Enhanced binding studies have been demonstrated with small molecules using a Biacore T100 (FIGS. 11, 12, 23, 24). This identified small molecule lead compound, identified from SPR analysis of a library of compounds is proof-of-principle of the general approach (FIGS. 13-15). The effect of peptide E9R blocking RHA from binding to EWS-FLI1 is established as a comparative signature and 'gold-standard' for small molecules. A lead compound has been developed and a series of active small molecules that specifically disrupt EWS-FLI1 regulated transcription have been discovered.

Additional Experiments Involving the Peptide

E9R can be used as a tool to disrupt EWS-FLI1 from interacting with RHA and measure the consequences of that disruption. The effects of disrupting EWS-FLI1 from RHA on the full ESFT transcriptome can be evaluated. A cDNA signature of the E9R peptide treated ESFT cells can be established and compared to the small molecule lead compounds.

The growth effects of the E9R peptide upon ESFT cells can be determined in comparison with a panel of non-transformed cell lines. The peptide can be tested in animal models of ESFT to validate whether disruption of EWS-FLI1 from RHA will result in decreased ESFT tumor growth, reduction of established tumors, and the cellular biochemical effects of this disruption. NSC635437 can be tested to compare the effectiveness of the small molecule with the peptide 'gold standard'.

Modifications of NSC635437 can be made and the resulting compounds tested using surface plasmon resonance for EWS-FLI1 binding kinetics and in solution RHA binding experiments. Compounds that have improved parameters compared to the lead compound can be tested in cDNA array, cell based assays, and animal tumorigenesis.

EGFP-peptide expression vectors can be transfected into ESFT A673 cells. To directly examine genes regulated by EWS-FLI1, the first step is to grow a population of EWS-FLI1 bearing A673 Ewing's sarcoma cells. The experiment can be done with A673 cells. The signature for these cells both expressing EWS-FLI1 and an inducible siRNA that eliminates EWS-FLI1 expression have been validated in multiple U133 Affymetrix oligonucleotide arrays. After sufficient numbers are grown, this cell line can then be transfected with EWS-FLI1 interacting peptide constructs (FIG. 9) as well as the mutant controls.

A population of EGFP positive cells can be selected and RNA harvested. After a recovery period following transfection, flow sorting can be used to select for successfully transfected cells. These cells can be grown in a "carry plate." When a sufficient number of cells has been grown, the flow sorted cells can then be plated out at ~9×10$^6$ cells per 15 cm plate. RNA can then be harvested approximately one day after uniform plating. This can be repeated a total of three times for each transfected line, resulting in nine total cell pellets. Harvested cell pellets can be processed with RNeasy Mini Kit (Qiagen). RNA can then be quantified and frozen for transport and further processing.

Once received, the RNA samples can be analyzed for quality via the BioAnalyzer, and then processed with the Affymetrix probe preparation kits. These samples can then be hybridized to Affymetrix U133Plus GeneChips. "Signatures" from peptide-treated cells can be obtained using the an approach to derive the EWS-FLI1 signatures (Smith R, Owen L A, Trem D J, et al. Expression profiling of EWS/FLI identifies NKX2.2 as a critical target gene in Ewing's sarcoma. Cancer Cell 2006; 9(5):405-16). Thus, genes can be sorted using the signal-to-noise metric followed by permutation testing. Both up- and down-regulated gene sets can be identified in this manner. Comparisons between the peptide-induced signatures and the EWS-FLI1 transcriptional profile can be performed using two complementary approaches. In the simplest approach, Chi square analysis can be used to determine whether the overlaps in each gene set are greater than expected by chance alone. In the second approach, Gene Set Enrichment Analysis (GSEA; (Smith R, Owen L A, Trem D J, et al. Expression profiling of EWS/FLI identifies NKX2.2 as a critical target gene in Ewing's sarcoma. Cancer Cell 2006; 9(5):405-16)) can be used to compare datasets. GSEA measures the enrichment of one gene set near the top of a second rank-ordered gene list, and quantifies this enrichment using a running sum statistic called the enrichment score (Smith R, Owen L A, Trem D J, et al. Expression profiling of EWS/FLI identifies NKX2.2 as a critical target gene in Ewing's sarcoma. Cancer Cell 2006; 9(5):405-16). The EWS-FLI1-regulated gene list will be order ranked, and whether the peptide-derived signature is enriched near the top of this rank-ordered list will be determined. This second approach is useful as it tends to identify correlations that are more subtle, or difficult to identify due to noise in the system (Smith R, Owen L A, Trem D J, et al. Expression profiling of EWS/FLI identifies NKX2.2 as a critical target gene in Ewing's sarcoma. Cancer Cell 2006; 9(5):405-16). The Lessnick lab has used both of these approaches to compare distinct microarray experiments (Lessnick S L, Dacwag C S, Golub T R. The Ewing's sarcoma oncoprotein EWS/FLI induces a p53-dependent growth arrest in primary human fibroblasts. Cancer Cell 2002; 1(4):393-401; Smith R, Owen L A, Trem D J, et al. Expression profiling of EWS/FLI identifies NKX2.2 as a critical target gene in Ewing's sarcoma. Cancer Cell 2006; 9(5):405-16; Kinsey M, Smith R, Lessnick S L. NR0B1 is required for the oncogenic phenotype mediated by EWS/FLI in Ewing's sarcoma. Mol Cancer Res 2006; 4(11):851-9). Furthermore, by obtaining the "leading edge" gene lists from the GSEA analysis (that is, the genes that are most correlated between the two experiments; (Subramanian A, Tamayo P, Mootha V K, et al. Gene set enrichment analysis: a knowledge-based approach for interpreting genome-wide expression profiles. Proceedings of the National Academy of Sciences of the United States of America 2005; 102(43): 15545-50)), genes can be identified that are most likely to be regulated by the RHA-EWS-FLI1 interaction. The net result is that it can be determined how much, and which portion, of both the EWS-FLI1 and RHA signatures are due to the interaction between the two proteins.

Signatures can be used for small molecule development. Once the signature of peptide E9R that prevents RHA from binding to EWS-FLI1 is identified, the small molecules can be tested to see if they have similar signatures to peptide E9R and siRNA reduction of EWS-FLI1. This comparison can be used as additional lead compounds are identified, and those molecules that most closely resemble the EWS-FLI1 reduction or peptide treated signatures can be considered as mechanistic probes. The cDNA comparison signatures can be used in the prioritization of compounds. For example if a derivative of NSC635437 or a new compound has a signature that is markedly different from the E9R peptide, it can suggest a broader, and likely, less specific mechanism. If a signature is qualitatively different, it will suggest alternate mechanisms. This data can be used in both compound modification and later for toxicity evaluation.

The E9R peptide can be validated for specificity in additional ESFT and non-ESFT cell lines. E9R can be synthesized with the Antennapedia sequence (E9RP). These peptides can be tested against a panel of ESFT cell lines (TC32, TC71, SK-ES1, A4573, RD-ES, and ES0925) for growth inhibition and soft-agar colony formation as previously published (Abaan O D, Levenson A, Khan O, Furth P A, Uren A, Toretsky J A. PTPL1 is a direct transcriptional target of EWS-FLI1 and modulates Ewing's Sarcoma tumorigenesis. Oncogene 2005; 24(16):2715-22). Testing can also occur in cancer cell lines that lack EWS-FLI1 including neuroblastoma and leiomyosarcoma. NON-TRANSFORMED control cell lines will be used for testing specificity including primary fibroblasts, MCF-10A epithelial cells, and HEK293 kidney cells. Since the ESFT cell of origin is suggested as a mesenchymal stem cell (MSC), these MSC can be prepared from murine bone marrow as a final control of normal cells (Castillero-Trejo Y, Eliazer S, Xiang L, Richardson J A, Ilaria R L, Jr. Expression of the EWS/FLI-1 oncogene in murine primary bone-derived cells Results in EWS/FLI-1-dependent, Ewing sarcoma-like tumors. Cancer Res 2005; 65(19):8698-705; Riggi N, Suva M L, Stamenkovic I. Ewing's Sarcoma-Like Tumors Originate from EWS-FLI-1-Expressing Mesenchymal Progenitor Cells. Cancer Res 2006; 66(19):9786). Given the challenge of preparing these MSC, they are only used for specificity studies of the most promising compounds. Control peptides can be those with single amino acid substitutions. Compounds can be tested for effects in standard 96-well growth assays (FIG. 8) and for their ability to initiate apoptosis using caspase-3 cleavage, as previously published (Toretsky J A, Thakar M, Eskenazi A E, Frantz C N. Phosphoinositide 3-hydroxide kinase blockade enhances apoptosis in the Ewing's sarcoma family of tumors. Cancer Res 1999; 59(22):5745-50).

The in vivo anti-tumor effect of peptides and small molecules that prevent EWS-FLI1 and RHA interaction can be tested. It is believed that demonstrating efficacy of hitting the molecular target can lead to reduced tumor growth in an animal model. Data was obtained with cell lines constitutively expressing the peptides. While this is useful as proof-of-concept, these derived cell lines may ultimately undergo mutation to allow their optimal growth, and therefore, native ESFT cells that are grown as xenografts can be useful. Xenografts can then be treated with injected peptides. There is a significant amount of literature suggesting that modified peptides can be injected intraperitoneally or intravenously in mice with resultant uptake in tumors (Toretsky J A, Thakar M, Eskenazi A E, Frantz C N. Phosphoinositide 3-hydroxide kinase blockade enhances apoptosis in the Ewing's sarcoma family of tumors. Cancer Res 1999; 59(22):5745-50; Walensky L D, Kung A L, Escher I, et al. Activation of apoptosis in vivo by a hydrocarbon-stapled BH3 helix. Science 2004; 305(5689):1466-70). This aim will test the optimized peptides for their distribution in murine tissue, ability to disrupt EWS-FLI1 from RHA in growing tumors, and ability to prevent or reduce tumor growth.

Tissue distribution and dose finding experiments can be conducted. SCID/bg can be injected with fluorescein and Antennapedia labeled peptides. A dose escalation of 3, 10, 30, and 100 mg/kg based upon similar peptide dosing in the literature (Walensky L D, Kung A L, Escher I, et al. Activation of apoptosis in vivo by a hydrocarbon-stapled BH3 helix. Science 2004; 305(5689):1466-70) can be employed. Six mice can be injected by tail vein injection at each dose. Two mice from each group can be euthanized at 8 and 24 hours and can undergo full necropsy to identify the distribution of peptide. Tissue sections from major organs can be analyzed for distribution of fluorescent peptide. If significant peptide is found at 24 hours, then a follow-up experiment can use the highest concentration of peptide that achieves good tissue levels without toxicity to the mouse (loss of 10% body weight or neurologic dysfunction). In this follow-up experiment, six mice per time point can determine the kinetics of tissue distribution. Time points can include 24, 48, and 72 hours. Dose finding experiments can require 24 mice and time course experiments can require 18 mice. Tissues can be analyzed for toxic effects of peptide using standard histological analysis. This experiment can be repeated once, for a total of 84 mice.

Pharmacodynamic effect of E9RP on in vivo disruption of EWS-FLI1 and RHA can be investigated using a model of ESFT in a nude mouse that consists of orthotopic placement (gastrocnemius) of tumor, as described in detail below (Merchant M S, Woo C W, Mackall C L, Thiele C J. Potential use of imatinib in Ewing's Sarcoma: evidence for in vitro and in vivo activity. J Natl Cancer Inst 2002; 94(22):1673-9). Seven days following tumor cell injection, animals can be treated with daily i.v. injections of E9RP. Eight hours following the third injection, a subgroup of animals can be euthanized and undergo necropsy. Eight hours following an injection can be used to maximize the potential of high peptide concentration and dissociated EWS-FLI1 and RHA. Gross specimen tumors can be measured for size and mass; however, the primary endpoint is biochemical dissociation of EWS-FLI1 and RHA. Tumors can then be split, with approximately ⅔ snap-frozen in liquid nitrogen and ⅓ preserved in formalin for paraffin embedding. Other organs with fluorescent peptide distribution, as determined above, can be preserved for toxicologic and immunologic evaluation.

Tumors can be analyzed for signature effects of peptide. Paraffin embedded tissue can undergo sectioning followed by routine hematoxylin and eosin staining as well as TUNEL (for apoptosis), and immunohistochemistry for expression of EWS-FLI1, RHA, PTPL1, TGFβRII, and markers of ESFT such as CD99. Additional immunohistochemistry can evaluate tumor and organ vascularization, techniques recently published (Torchia E C, Boyd K, Rehg J E, Qu C, Baker S J. EWS/FLI-1 Induces Rapid Onset of Myeloid/Erythroid Leukemia in Mice. Mol Cell Biol 2007; 27(22):7918-34). These studies can allow determination of whether the protein levels of EWS-FLI1 targets are affected by the peptides. The apoptosis index can provide information about the tumor toxicity of the peptides and potential toxicity to non-tumor tissues. Snap-frozen tissue can be pulverized under liquid nitrogen and divided for extraction of RNA or protein, as previously published (Toretsky J A, Zitomersky N L, Eskenazi A E, et al. Glypican-3 expression in Wilms tumor and hepatoblastoma. J Pediatr Hematol Oncol 2001; 23(8):496-9). RNA can be evaluated by quantitative RT-PCR for expression of ESFT target mRNA such as ID2, PTPL1, TGFβRII, and $p21^{Waf/CIP}$. Protein can be immunoprecipitated with EWS and FLI1 antibodies as demonstrated (FIG. 6) to determine if the peptide has prevented the association of EWS-FLI1 from RHA in vivo.

Primary tumor growth effects can be investigated using a model of ESFT in a SCID/bg mouse that consists of orthotopic placement of tumor as described in detail below and has been recently published (Merchant M S, Yang X, Melchionda F, et al. Interferon gamma enhances the effectiveness of tumor necrosis factor-related apoptosis-inducing ligand receptor agonists in a xenograft model of Ewing's sarcoma. Cancer Res 2004; 64(22):8349-56). A luciferase gene can be transfected under a constitutive promoter into an ES0925 ESFT cell line. Peptides can be administered as determined above every other day. The top two peptides and a control based on their in vitro activity can be administered seven days after injection of the tumor cells. ESFT injected mice develop tumors with approximately 90% efficiency following tumor injection (data not shown). The diameter of the tumors can be measured at 3 day intervals, beginning at on day 5 post-inoculation with $1 \times 10^6$ Ewing's Sarcoma tumor cells injected into the gastrocnemeous. After beginning treatment the tumor size can be measured daily until the completion of the study. Intraperitoneal luciferase can be injected followed by Xenogen imaging every 4-5 days to both monitor primary tumor volume and assess for metastatic lesions. Mice can be treated until the tumor reaches a volume of 1.0 cm³. The majority of untreated mice can be expected to reach this volume in two to three weeks. The tumor can be resected during a survival surgery that has been IACUC approved and previously published (Merchant M S, Woo C W, Mackall C L, Thiele C J. Potential use of imatinib in Ewing's Sarcoma: evidence for in vitro and in vivo activity. J Natl Cancer Inst 2002; 94(22):1673-9). The size of the tumor can be measured and weighed upon removal and then subdivided for preservation as both snap frozen tissue and formalin-fixed tissue. Histopathologic evaluation of hematoxylin and eosin stained sections can be conducted on the tumor, or on serial sections at the site of inoculation, as appropriate based on observations at the gross dissection examination. The tumor can be examined for histological features of neoplasia and pleomorphism, invasion and evidence of apoptosis.

Sample size for localized tumor growth effects of peptide can be investigated. Mice can be randomized into two groups 7 days after the injection, and receive either a control or an active peptide. Mice can be observed 3 times per week, and the tumor incidence between the two groups can be compared using a Chi-square test or Fisher's exact test. The tumor incidence of the control and the active-peptide groups are expected to be 90-100% and 30%, respectively. Table 3 gives the number of samples per group needed to detect a statistically significant difference in tumor incidence between the two groups at the 5% level. For example, if one assumes that the tumor incidence of the two groups are 95% and 30% respectively, 8 mice per group will provide 86% power to detect a statistically significant difference in tumor incidences between the two groups at the 5% level. A first experiment can use 10 mice per group, with adjustment in the follow-up experiment based upon results.

TABLE 3

| Incidence for controls (%) | 90 | 90 | 90 | 90 | 95 |
| Incidence for active-peptide group (%) | 50 | 40 | 30 | 30 | 30 |
| Power (%) | 79 | 82 | 81 | 85 | 86 |
| N per group | 18 | 13 | 9 | 10 | 8 |

Anti-metastatic activity of the peptide can be investigated. Following resection of primary tumors as detailed above, mice are rendered free of gross disease. Within 6-9 weeks, greater than 90% of untreated mice can develop metastastic Ewing's tumors in the lungs, bones, subcutaneous tissues, and abdomen. These tumors are first detectable on clinical exam of the mice with palpation and assessment of inducible dyspnea. Mice can be assessed a minimum of 3 times per week after resection of the primary tumor for signs and symptoms of recurrent disease. Mice determined to be hindered by metastatic disease can be sacrificed and tissues examined for histologic evidence of Ewing's sarcoma. As above with primary tumors, gross tumor can be snap frozen and formalin fixed for further analysis of EWS-FLI1 expression. Mice can be followed for metastatic disease following treatment during primary tumor growth. In addition, a second grouping of mice can receive no treatment during primary growth, but can be treated with 3 weeks of peptide administration starting 7 days after primary resection. This treatment during a stage of minimal residual disease can mimic the opportunity in the clinical to treat high risk patients following standard of care therapies. Ten mice per group can be followed for subsequent development of metastatic disease. Determination of power is equivalent to the calculations for primary disease as above. Intraperitoneal luciferase can be injected followed by Xenogen imaging every 4-5 days to both monitor metastatic lesions.

The ability of peptide to shrink existing tumors can be investigated. SCID/bg mice can be injected orthotopically with ESFT tumor cells. When the tumors reach 0.125 cm$^3$, the mice can be randomized into the following two treatment groups: control peptide, active peptide. The mice can be observed 3 times per week, and tumor volumes 1 week after the treatment are expected to be 0.5 cm$^3$ and 0.25 cm$^3$ for the control and treated groups, respectively. It can be assumed that the two groups have equal standard deviations. Table 4 gives the number of mice per group needed to detect a statistically significant difference in tumor volumes at 1 week after the treatment at the 5% level. Tumor growth rates can be estimated by a linear mixed regression model with repeated measures for each mouse, and the difference in slopes can be tested using the p-value for the coefficient associated with the treatment group. Appropriate transformations can be applied (log or arcsine-square-root) as needed to ensure normality. Sample size can be selected with Ying Zhang (statistician) after the above experiments. Animals can be euthanized and necropsy procedure as described above.

TABLE 4

| Mean volume for controls (cm$^3$) | 0.5 | 0.5 | 0.5 |
| Mean volume for treatment groups (cm$^3$) | 0.25 | 0.25 | 0.25 |
| Standard deviation for both groups | 0.15 | 0.15 | 0.2 |
| Power (%) | 82 | 91 | 75 |
| N per group | 7 | 9 | 10 |

Additional Experiments Involving Small Molecules

A small molecule has been identified by screening the NCI DTP library of compounds for molecules that bind to EWS-FLI1. The small molecule has significant 3-dimensional homology to the first 3 amino acids of the functional peptide, E9R. This small molecule has been used to design for testing a series of small molecules for the ability to bind to EWS-FLI1 and prevent or displace RHA. Derivatives can be evaluated for effectiveness in cDNA array, cell growth and motility, and tumorigenesis assays.

Derivatives can be synthesized as outlined herein (FIG. 18). As compounds are prepared, they can be evaluated for EWS-FLI1 binding and the ability to prevent RHA binding. Based upon these binding studies, chemical modifications can be designed and synthesized. As the compounds develop stronger affinities for EWS-FLI1 and prevent RHA binding at lower concentrations, compounds can be advanced to cell based assays. Those compounds with reasonable drug-like properties (i.e. soluble, log P<5, structurally stable) and an IC$_{50}$ less than 2 μM can be evaluated against ESFT cell lines. Compounds that demonstrate an enhanced activity profile against transformed cells as compared with non-transformed cells can be advanced to xenograft studies.

Superimposing structures between NSC635437 and peptide E9R (FIG. 15C) have been identified. In the strategy depicted in FIG. 17, four medicinal chemistry directions are implemented to find inhibitors based on the inhibitory peptide sequence PPPLDAVIEA and to develop biochemical tools to study EWS-FLI1 interactions. Eight peptides fragments (9-mers to 2-mers) are synthesized to investigate the importance of the P and D amino acid arrangement in the active site. Overlap can be modeled between peptides and synthesized compounds. This overlap strategy can allow prediction of enantiomers that might lack effectiveness, test those compounds, and further support our modeling. Non-effective enantiomers can act as outstanding control small molecules for cellular toxicity studies. The preparation of fluorescent peptide ligands can be useful for in vitro studies that can measure displacement upon small molecule binding. This can provide alternative and potentially effective means of screening for small molecule binding to EWS-FLI1 by causing peptide displacement. This can allow confirmation that the actual location of small molecule binding was the site of peptide binding as well as cellular localization and peptide penetration into the cells.

A lead compound that binds to EWS-FLI1 with a K$_D$ of 2 μM has been identified. Based on the lead NCS635437, seven series of analogues have been designed in order to optimize this scaffold (FIG. 18). Series A, B and E represents optimization of the aromatic rings. Series C attempts to elongate the lead NCS635437 to approximate the LDA-VIEA portion of the peptide (see FIG. 15C for overlap). An example of the conjugated ligand is shown in FIG. 21. Series D represents enantiomers of NCS635437. Series F provides for a dansylated derivative of the lead for use as a biochemical tool. These dansylated small molecules can be used to evaluate compound uptake, intracellular kinetics, and localization in cells. Finally, series G represents a dehydrated NCS635437 to evaluate the importance of the hydrogen bonding component.

The synthesis of the basic core of NSC635437 is shown in FIG. 16. The synthetic strategy can be easily adapted using known synthesis techniques to functionalize all key analogues proposed (FIG. 18), as will be appreciated by one of skill in the art.

Because NSC635437 is a chiral compound, a synthetic strategy to make each enantiomer (FIG. 21) has been developed. High enantioselectivity was achieved by addition of diethylzinc to N-methylisatin in the presence of the DBNE catalyst (FIG. 20). A high resolution x-ray crystal structure is provided assigning the R-configuration to the (−) enantiomer of 31 (FIG. 20). Recently, Ojida (Ojida A, Yamano T, Taya N, Tasaka A. Highly enantioselective reformatsky reaction of ketones: chelation-assisted enantioface discrimination. Org Lett 2002; 4(18):3051-4) and coworkers showed that a high enantioselective Reformatsky reaction with ketones could be achieved using cinchonine as a chiral additive. As shown in FIG. 21, addition of the Reformasky reagent 32 in the presence of 1.5 equivalents of cinchonine and 4.0 equivalents of pyridine to aromatic ketone 32, gave the tertiary alcohol 33 in 97% yield and 97% ee.

Enantioselective organozinc addition to isatin (FIG. 20) has been successfully performed, and results of enantioselective Reformatsky addition into ketones (FIG. 21), has been published, indicating that synthesis of non-racemic isatin derivatives by enantioselective Reformatsky-like reaction (FIG. 22) can be achieved. The Reformatsky reagent 34 derived from the aryl bromomethyl ketone in the presence of cinchonine and pyridine is expected to give non-racemic isatin derivative 24 in high ee. Protection of 28 may be required and chemistry can be adapted based on initial results.

Small molecules can be evaluated for the ability to bind to EWS-FLI1 and prevent its binding to RHA. The Biacore T100 can be used to establish the binding kinetics of small molecules to EWS-FLI1 (FIGS. 4, 12, 23 and 24). Each of the small molecules generated can undergo kinetic evaluation for binding to EWS-FLI1. In addition, all synthesized molecules can be tested for the ability to disrupt EWS-FLI1 from RHA using solution immunoprecipitation (FIGS. 6 and 13) and ELISA (FIGS. 1 and 5). Control proteins can include other RHA binding proteins such as CBP (FIG. 5).

Additional iterative cycles of modeling, chemistry, bioassay, and rational modifications can be done to the lead structures in order to optimize binding and develop molecules that reasonably fit criteria for pharmaceutical agents, namely, that they exhibit a drug-like profile and fulfill standard guidelines such as Lipinski's rule of 5. Compounds can initially be prioritized based on the following sequence: (1) strength of binding to EWS-FLI1 with dissociation of RHA, (2) specificity of toxicity to ESFT cell lines, and (3) drug-like properties. When the compounds bind EWS-FLI1 with low nanomolar affinity and exhibit specific cytotoxicity, then drug-like properties for optimized delivery and minimized toxicity will be pursued.

Small molecules can be tested in ESFT cell lines for toxicity in monolayer and soft-agar growth. A panel of ESFT and non-transformed cell lines is described herein that can be used to determine the cellular toxicity of developed small molecules. These can be applied to advance agents into small molecule animal testing to identify one or more new chemical entities capable of inhibiting ESFT oncogenesis in vivo while exhibiting appropriate pharmacokinetic parameters and limited toxicity to normal cells. The toxicity to cells can be correlated with the ability to disrupt EWS-FLI1 from RHA in order to advance to new iterations of small molecules. Control molecules can include inactive enantiomers identified herein. Control cell lines can include non-transformed epithelial and mesodermal cultures as well as non-ESFT tumor cell lines.

Small molecule testing in ESFT xenograft models can be conducted. These molecules can be tested in animal studies. Dosage can be based upon determining the MTD using toxicity criteria (10% weight loss or neurologic dysfunction) and then dose reductions from 67% of the MTD in tumor xenograft studies to find the minimal useful dose. Serum, tumor and non-tumor tissues can be analyzed for compound levels at timepoints 0, 1, 2, 4, 6, 12, and 24 following a single injection of compound using HPLC. Additional pharmacokinetic/pharmacodynamic studies can be performed.

Recombinant EWS-FLI1, EWS, and FLI1 can be produced. Recombinant His(6×)-EWS-FLI1 can be prepared using an expression system in BL21 E. coli and purification of His-tagged protein using a Ni-charged column followed by an on-column re-folding protocol. This is both a time and labor intensive component of purification. Since the protein is only useful for two weeks, a constant supply is required and thus a reliable protein purification apparatus is required. This strategy provides the best quality, transcriptionally active EWS-FLI1 (Uren A, Tcherkasskaya O, Toretsky J A. Recombinant EWS-FLI1 oncoprotein activates transcription. Biochemistry 2004; 43(42):13579-89). Experience with recombinant EWS-FLI1 indicates that protein is optimal for use for 3-4 weeks. Similar vectors have been prepared and transformed into BL21 cells with full length EWS and FLI1. Both recombinant proteins have successfully been prepared.

Bioinformatics of small molecule array can be investigated. Each protein is screened against three replicate microarrays and fluorescence intensities are calculated for each printed feature. Composite Z-scores are computed for the replicate datasets and used to rank compounds for further characterization. Promiscuous binders are filtered from the data set and each compound is ranked for specificity of binding against a panel of nearly 250 proteins unrelated to EWS-FLI1. Compounds that reproducibly bind to the protein in a specific manner are considered for analysis in SPR assays.

Small molecule activity can be confirmed using a secondary screen for ESFT cytotoxicity and measurements of surface plasmon resonance (SPR) assay for direct EWS-FLI1 binding. The secondary screen for small molecules that bind to EWS-FLI1 on the glass slide array can be ESFT cellular cytotoxicity assays. SPR allows for a tertiary screen to identify the highest-affinity compounds for EWS-FLI1. It is expected that if 1% of screened small molecules show EWS-FLI1 binding, further evaluation of up to 1000 compounds will be required, which is feasible in multiwell cytotoxicity assays. SPR can evaluate 1000 compounds from the NIH DTP library diversity and natural product sets.

Thus, as compounds are identified from the glass-slide array screen, they can be advanced to cytotoxicity testing followed by SPR analysis. Those compounds that have relatively specific ESFT cytotoxicity and strong binding kinetics to EWS-FLI1 ($K_D$ of less than 10 microM) can be advanced for further characterization. The additional evaluation of compounds that bind to EWS-FLI1 can include (i) EWS-FLI1 functional inactivation and (ii) screening for the ability to inhibit protein-protein interactions with RHA.

Assays for cell growth can be employed. Parallel plates of TC32 (ESFT) and NON-tumorigenic mouse embryonic fibroblasts (MEF), kidney (HEK293), and breast epithelial (MCF-10A) cells can be prepared with triplicate concentrations of compounds. If four concentrations of compound (30, 3, 0.3, 0.03 µM) are used, then six compounds are tested per plate per assay. In a semi-automated assay, if 16 plates (4 plates for each of 4 cell lines) are set up per day, then 24 compounds could be tested per day (6 compounds per plate×4 plates per cell line=24 compounds per cell line). Cells are grown for 72 hours and viable cell number is estimated following incubation with MTT reagent. Solubilized dye will be measured spectrophotometrically. Cell number is estimated from standard curves established for each cell line. Some compounds may react chemically with the dye and this would be apparent from the absorbance readings. Those compounds can be retested using alternate cell viability methods, such as BrdU uptake.

A biochemical screen for target specificity can be conducted. Small molecules that demonstrate ESFT cytotoxicity and a $K_D$ of binding to EWS-FLI1 in the nanomolar range can be tested for the ability to block RHA from binding to EWS-FLI1. These experiments can be performed for both peptide (FIG. 6) and small molecule (FIG. 13). The biochemistry experiments can help to establish mechanism for novel compounds.

A general screen of EWS-FLI1 function can be performed. An ESFT cell-based assay for testing the transcriptional activity of EWS-FLI1 oncoprotein can be developed. An EWS-FLI1 responsive promoter sequence upstream of a short half-life green fluorescent protein coding sequence and a nonspecific promoter that does not respond to EWS-FLI1 upstream of a short half-life red fluorescent protein coding sequence cab be stably present in ESFT cells. Cells with both functioning promoters would be identified as yellow in a fluorescent assay. This assay can be validated with the E9R peptide and siRNA against EWS-FLI1, such that successful reduction of EWS-FLI1 function causes cells to turn red, indicating a specific effect on EWS-FLI1 transcriptional activity but no effect on CMV viral promoter activity. Compounds with non-specific activity diminish both red and green signals.

Example

Many sarcomas and leukemias carry non-random chromosomal translocations encoding mutant fusion transcription factors that are essential to their molecular pathogenesis. These tumor-specific proteins can be employed in the development of highly selective anticancer drugs. A particularly clear example is provided by Ewing's Sarcoma Family Tumors (ESFT) which contain a characteristic t(11;22) translocation leading to expression of the oncogenic fusion protein EWS-FLI1. EWS-FLI1 is a disordered protein that precluded standard structure-based small molecule inhibitor design. Using surface Plasmon resonance screening, a lead compound, NSC635437, was identified.

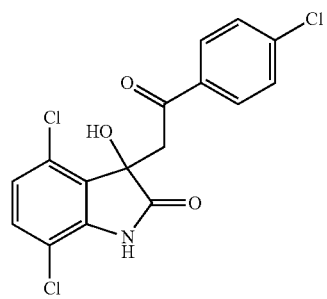

NSC: 635437

YK-4-279, a para-methoxy derivative of NSC635437, blocks RHA binding to EWS-FLI1, induces apoptosis in ESFT cells, and reduces the growth of ESFT orthotopic xenografts. These findings demonstrate inhibition of the interaction of mutant cancer-specific transcription factors with the normal cellular binding partners required for their oncogenic activity and suitability for use as uniquely effective, tumor-specific anticancer agents.

Methods

E9R peptide was obtained from Bio-synthesis Inc, Lewisville, Tex. Protein G beads (Invitrogen, Carlsbad, Calif.), anti-GST, anti-FLI1, anti-Cyclin D1 antibodies (Santa Cruz, Calif.), Ac-DEVDAMC, caspase-3 fluorogenic substrate (BD Biosciences Pharmingen), and anti-Cleaved Caspase 3(Asp175) (Cell Signaling) were commercially obtained.

Site Directed Mutagenesis

Every non-alanine amino acid in aa 823-832 region of RHA changed to alanine by site directed mutagenesis by using QuickChange II XL Site-Directed Mutagenesis Kit (Stratagene, Cedar Creek, Tex.) according to manufacturer's protocol.

Cell Cultures

Established TC32, TC71, A4573, CHP-100 and primary ES925 and GUES1 ESFT cell lines were maintained in RPMI (Invitrogen) media supplemented with 10% FBS (Gemini Bioproducts). HEC and HFK cell lines, previously described (Uren, A., et al. Activation of the Canonical Wnt Pathway during Genital Keratinocyte Transformation: A Model for Cervical Cancer Progression. Cancer Res 65, 6199-6206 (2005)). Stably EWS-FLI1 expressing subclones of these cells were tested in anchorage independent growth assay as described previously (Toretsky, J. A., et al. Oncoprotein EWS-FLI1 activity is enhanced by RNA helicase A. Cancer Res 66, 5574-5581 (2006)).

Protein Immunoprecipitation Assays

Protein lysates and immunoprecipitations were performed as previously published (Uren et al (2005)). Recombinant GST-RHA(647-1075) was prepared from crude bacterial extracts without further purification.

Small Molecule Library Screening and Selection of Lead Compound

A surface plasmon resonance assay using the Biacore T100 was established with EWS-FLI1, prepared in our laboratory as previously published (Uren, A., Tcherkasskaya, O. & Toretsky, J. A. Recombinant EWS-FLI1 oncoprotein activates transcription. *Biochemistry* 43, 13579-13589 (2004)). DNA oligonucleotides were used to quality control the proper conformation of EWS-FLI1 on the surface of a CM5 chip. Small molecules obtained from the Developmental Therapeutics Program of the National Cancer Institute, NIH (http://dtp.nci.nih.gov/branches/dscb/repo_open.html) were prioritized based upon their molecular weight and solubility. An initial screening of molecules was performed at 1 or 10 µM compound, based on solubility. We used a model that compares the actual binding maximum (actual RU) with the theoretical binding maximum (RU-theor). If the RUactual to RUtheor is 0.9-1.0, this suggests a binding, and a compound was considered a 'hit'. Hits (RUactual to RUtheor of 0.7-2.0) were then reviewed by a team of medicinal chemists and those with structural potentials were selected for further study. Selected molecules were tested in vitro in a solution coimmunoprecipitation assay using recombinant EWS-FLI1 and GST-RHA(647-1075).

General Method for the Synthesis and Analysis of Small Molecule Compounds

Appropriated acetophenone (4.0 equv.) and catalytic amount of diethylamine (10 drops) were added to a solution of 4,7-dichloroisatin (1.0 equv.) in methanol (5 mL). The mixture was stirred at room temperature until starting material (4,7-dichloroisatin) disappeared completely. The resulted solution was concentrated and applied to flash chromatography eluting with Hexane/Ethyl acetate to afford pure product in quantitative yield. Further purification was done by recrystallization with Hexane/Ethyl acetate. NMR spectra were recorded using a Varian-400 spectrometer for $^1$H (400 MHz), chemical shifts ($\delta$) are given in ppm downfield from tetramethylsilane as internal standard, and coupling constants (J-values) are in hertz (Hz). Elemental analyses were performed by Atlantic Microlabs.

4,7-Dichloro-3-[2-(4-chlorophenyl)-2-oxoethyl]-3-hydroxyl-1,3-dihydro-2H-indol-2-one (NSC635437): white solid; mp 194-196° C.; $^1$H NMR (DMSO, 400 MHz) $\delta$ 10.96 (s, 1H), 7.93 (d, 2H, J=8.8 Hz), 7.57 (d, 2H, J=8.8 Hz), 7.30 (d, 1H, J=8.8 Hz), 6.90 (d, 1H, J=8.8 Hz), 6.47 (s, 1H), 4.36 (d, 1H, J=18.4 Hz), 3.71 (d, 1H, J=18.0 Hz). Anal. Calcd for $C_{16}H_{10}Cl_3NO_3$. ½ EtOAc: C, 52.09; H, 3.38; N, 3.38. Found: C, 52.53; H, 3.17; N, 3.55.

4,7-Dichloro-3-hydroxy-3-[2-(4-methoxyphenyl)-2-oxoethyl]-1,3-dihydro-2H-indol-2-one (YK-4-279): white solid; mp 149-151° C.; $^1$H NMR (DMSO, 400 MH 1 z) $\delta$ 10.93 (s, 1H), 7.86 (d, 2H, J=9.2 Hz), 7.26 (d, 1H, J=8.8 Hz), 6.98 (d, 2H, J=8.8 Hz), 6.86 (d, 1H, J=8.4 Hz), 6.39 (s, 1H), 4.31 (d, 1H, J=18.0 Hz), 3.80 (s, 3H), 3.61 (d, 1H, J=18.0 Hz). Anal. Calcd for $C_{17}H_{13}Cl_2NO_4$: C, 55.76; H, 3.58; N, 3.82. Found: C, 55.82; H, 3.98; N, 3.51.

Fluorescence Polarization Assay

Increasing concentrations of FITC-E9R were added to a fixed concentration of EWS-FLI1 (4.8 µM) to obtain a saturated binding curve. The assay was performed in 20 mM Tris, 500 mM NaCl, 0.67 M imidazole, pH 7.4. The fluorescence polarization was analyzed in a QuantaMaster fluorimeter (Photon Technology International, Ford, West Sussex, UK) equipped with polymer sheet polarizers at an excitation wavelength of 495 nm and emission wavelength of 517 nm. Increasing concentrations of YK-4-279 were added to a fixed concentration of EWS-FLI1 and FITC-E9R (3.2 µM, as determined from saturated binding curve) with the same buffer and instrumental settings as described above.

Plasmids and Reporter Assay

EGFP-E9R fusion constructs prepared as published (Frangioni, J. V. & Neel, B. G. Use of a general purpose mammalian expression vector for studying intracellular protein targeting: identification of critical residues in the nuclear lamin A/C nuclear localization signal. J Cell Sci 105 (Pt 2), 481-488 (1993)). We transiently transfect the NR0B131 luciferase reporter and full-length EWS-FLI1 into COS-7 cells with Fugene-6 (Roche) and luciferase assay performed per manufacturer's protocol (Dual Luciferase Kit, Promega). Six hours following transfection, cells were treated with either 3 or 10 µM YK-4-279. Cell lysates luciferase activity levels were standardized to renilla activity from a non-affected promoter and plotted as relative luciferase activity (RLA).

Caspase-3 Activity Measurement and Nuclear Fragmentation

Cells were treated for 24 hours with 10 µM YK-4-279. The Caspase-3 substrate DEVD-AMC was incubated with equal amounts of protein lysate and fluorescence from cleaved substrate measured in a fluorimeter. TC32 and non-transformed cells HEK-293, HFK, and HEC were treated for 6 hours with high dose (50 µM) YK-4-279. DAPI stained cells were photographed at 600× using inverted fluorescence microscope.

Mouse Strains and In Vivo Small Molecule Testing

One million TC71 or CHP-100 cells in 100 µL HBSS were injected orthotopically into the gastrocnemius muscle of 4-8 week old SCID/bg mice (Taconic, Germantown, N.Y.). Prostate cancer xenografts were established by subcutaneous injection of 5 million PC3 cells into the flanks of 4-8 week old nude mice (Taconic). Mice were randomized to receive three times per week intraperitoneal injections of DMSO, YK-4-279 at 1.5 mg/dose when tumors were palpable. Each of the animal experiments was begun with 10 mice that were randomized into treatment and control groups when the tumors reached palpable size. In the control groups some tumors exceeded the IACUC maximal size (2 cm in any dimension) and were euthanized prior to day 14 and thus not included in the day 14 analysis (FIG. 6c). Tumor length and width were measured every 2-4 days and volume was calculated using the formula v=D×d2×π/6 where D is the longest diameter and d is the shorter diameter. Xenograft studies were approved by the Memorial Sloan-Kettering Cancer Center Institutional Animal Care and Use Committee.

RNAi for RHA and EWS-FLI1 shRNA (short hairpin RNA) against RHA was purchased from Open Biosystems (Huntsville, Ala.) Both virus production and purification were done according to Open Biosystems protocols. (For designing shRNA see McIntyre G. J. et al. "Design and cloning strategies for constructing shRNA expression vectors." BMC Biotechnol. (2006) 6:1)

shRNA RHA (nucleotides 598-618) #5 sequence (SEQ ID NO: 37): CCGGGAAGGATTACTACTCAAGAAACTC-GAGTTTCTTGAGTAGTAATCCTTCTTTTT shRNA RHA (nucleotides 1689-1669) #7 sequence (SEQ ID NO: 38): CCGGTCGAGGAATCAGTCATGTAATCTC-GAGATTACATGACTGATTCCTCGATTTTT Lentivirus infected cells were lysed after 6 days of selection with puromycin.

Statistical Analysis

Statistical analyses were performed using GraphPad Prism, available from GraphPad Software Inc. of La Jolla, Calif.

Results

RHA is a Validated Target in ESFT

A region of RHA that binds to EWS-FLI1 was identified based upon phage-display epitope screening (Toretsky, J. A., et al. Oncoprotein EWS-FLI1 activity is enhanced by RNA helicase A. Cancer Res 66, 5574-5581 (2006)) (FIG. 29A). To validate RHA as critical in ESFT cells, RHA levels were reduced using shRNA and ESFT cell viability was reduced by 90% (FIG. 29B, 29C). A pancreatic cell line, PANC1 cells that do not express EWS-FLI1, were stably transfected with the same shRNA vectors with similar reduction in RHA levels (FIG. 35), but with no decrease in cell viability (FIG. 35). In order to further validate the protein-protein interaction of RHA with EWS-FLI1 as a therapeutic target for ESFT patients, site-directed mutagenesis was performed on the GST-RHA(647-1075) protein fragment. GST-RHA(647-1075) mutants were expressed and coimmunoprecipitated with full length recombinant EWS-FLI1. Mutants P824A and D827A showed a significant decrease in binding compared to wild-type control (FIG. 29D). The full length RHA mutant D827A maintained wild-type ATPase activity (FIG. 36); therefore, the D827A mutant was chosen to test whether RHA binding to EWS-FLI1 was required for neoplastic transformation.

RHA is Required for EWS-FLI1 Modulated Transformation

Murine embryonic fibroblasts (W) that express low levels of endogenous RHA were stably transfected with EWS-FLI1 (WEF1) and either full-length wild-type RHA or full-length RHA(D827A). A greater than additive effect was observed when comparing the colony numbers from W+RHA (227±66) and WEF1 (115±8) to those of WEF1+RHA (582±30) (FIG. 29E, 29F). The RHA(D827A) expressing cells demonstrated 3-fold lower anchorage-independent growth (p=0.0028) than the wild-type (FIG. 29E, 29F). Similar protein expression levels of EWS-FLI1 and RHA were obtained in the fibroblasts (FIG. 29G). The EWS-FLI1 immunoblot was evaluated by densitometry and demonstrated reasonably similar protein levels amongst derived cell populations (FIG. 29H). The significant reduction of colony formation by the RHA(D827A) expressing cells suggests a critical role in anchorage-independent growth that is abrogated by RHA not binding to EWS-FLI1.

E9R Peptide Blocks RHA Binding to EWS-FLI1

Reagents were developed to block RHA binding to EWS-FLI1 since RHA is necessary for optimal EWS-FLI1 activity. The E9R peptide corresponds to amino acids 823 to 832, located in the proximal HA2 region of RHA (FIG. 29A). A cell-free protein interaction assay was developed to test whether E9R peptide inhibits RHA binding to EWS-FLI1. This immunoprecipitation assay demonstrated binding between bacterially expressed GST-RHA(647-1075) and full-length purified recombinant EWS-FLI1 (FIG. 30A, lane 3). Titration of E9R demonstrated a dose-dependent reduction in the binding of GST-RHA(647-1075) and full-length EWS-FLI1 with a decreased association to 50% with 0.1 μM E9R (FIG. 30A, lane 6). It was determined whether disrupted EWS-FLI1/RHA binding inhibited cell growth.

E9R Peptide Specifically Inhibits ESFT Growth

Peptide delivery to growing cells is greatly facilitated by cell permeable peptides (CPP)27. Antennapedia (Antp) is a CPP that was synthesized on the amino-terminus of E9R with or without the D827A mutation (E9R-P and E9R (D5A)-P, respectively) (Table 5).

TABLE 5

| Name | Amino Acid Sequence | SEQ ID NO |
|---|---|---|
| Antp: Antennapedia- | RQIKIWFQNRRMKWKK | 34 |
| E9R-P: Antennnapedia-E9R | [FITC]-RQIKIWFQ NRRMKWKKPPPLDAVIEA | 35 |
| D5A: Antennapedia- E9R-D5A | [FITC]-RQIKIWFQ NRRMKWKKPPPLAAVIEA | 36 |

[FITC] - conjugated fluorescent dye

Monolayer cultures of the EWS-FLI1-positive ESFT cell line, TC32, or a control EWS-FLI1-negative cell line, SKNAS (neuroblastoma), were treated with fluorescein conjugated peptides. Only the EWS-FLI1 containing cells showed reduced growth (FIG. 30B) and the SKNAS cells showed mild stimulation from the peptide based on an unknown mechanism. Confocal microscopy demonstrated uptake throughout the cell, including nuclei (shown by DAPI overlay, FIG. 30C). E9R-P significantly reduced ESFT cell growth (p=0.048) while neither the D5A mutated control nor antennapedia peptides alone reduced ESFT cell growth (FIG. 30D). Neuroblastoma cells treated with the same peptides did not have a statistically significant alteration in growth, although a slight increase was observed with E9R(D5A) treated cells (p=0.175). To determine the effect of E9R upon anchorage-independent growth, we stably transfected E9R as an EGFP fusion protein into TC71 (ESFT) or SKNAS (neuroblastoma) cells. An in-frame expression of LQLPPLERLTL excluded E9R from the nucleus28. Transfected cells showed E9R peptide expression either throughout the cell or excluded from the nucleus as predicted based on the intended targeting (FIG. 30E). TC71 colony formation was significantly reduced by 95% due to the expression of E9R, except when the peptide was excluded from the nucleus (FIG. 30E, 30F). The anchorage-independent growth of SKNAS was not affected by the E9R peptide (FIG. 30E, 30F). To further support specificity of the E9R peptide, a second small round blue cell tumor, embryonal rhabdomyosarcoma (RD cells), expressing pGE9R did not show reduced anchorage-independent growth.

Small Molecule Binds to EWS-FLI1

A library of 3000 small molecules (NCI, DTP) was screened for EWS-FLI1 binding using surface plasmon resonance (SPR). Compounds were selected that exhibited a binding level (actual resonance units, RUactual) to RUtheor ratio between 0.7 and 2.0 suggesting monomeric binding to EWS-FLI1 and also had favorable drug-like properties (Leeson, P. D. & Springthorpe, B. The influence of drug-like concepts on decision-making in medicinal chemistry. *Nature reviews* 6, 881-890 (2007)). NSC635437 had an RUactual: RUtheor of 0.9 and was chosen for further evaluation based upon potential for chemical derivatization. 1.0 gram of NSC635437 was synthesized to complete the studies and for use as a standard (FIG. 31A).

Methoxy-Derivative is a More Potent Inhibitor of EWS-FLI1 Binding to RHA

In a cell-free assay, NSC635437 reduced the direct binding of GST-RHA(647-1075) to full-length recombinant EWS-FLI1 (FIG. 31B, three left-most lanes/columns). An aromatic optimization strategy was used to design analogs to improve upon the activity of NSC635437. One of these compounds (YK-4-279), substituted with a methoxy group at the para position (p-methoxy) of the aromatic ring (FIG. 31A) significantly reduced the protein-protein interaction of EWS-FLI1 with GST-RHA(647-1075) in vitro (FIG. 31B, three right-most lanes/columns). A KD of 9.48 μM was calculated for the affinity of YK-4-279 with EWS-FLI1 using surface plasmon resonance (FIG. 31C). To support a model of YK-4-279 as having similar interaction qualities to E9R, SPR displacement assay shows 10 μM YK-4-279 reducing the binding of 64 μM E9R from 17 R.U. to 7 R.U. and 32 μM E9R from 13 R.U. to 5 R.U. (FIG. 31D). Fluorescence polarization further demonstrated E9R displacement of E9R when YK-4-279 was titrated into the experiment, showing complete displacement at 30 μM YK-4-279 (FIG. 31E).

YK-4-279 Demonstrates Functional Inhibition of EWS-FLI1

ESFT cells treated with YK-4-279 demonstrated a dissociation of EWS-FLI1 from RHA by 10 µM, consistent with the KD value (FIG. 32A, top panel). YK-4-279 did not directly affect EWSFLI1 nor RHA levels (FIG. 32A, middle and lower panels and FIG. 37). To further support YK-4-279 as a functional inhibitor of EWS-FLI1, COS7 cells were cotransfected with EWS-FLI1 and NR0B1 reporter-luciferase plasmid (containing EWS-FLI1 regulatory GGAA elements (Gangwal, K., et al. Microsatellites as EWS/FLI response elements in Ewing's sarcoma. *Proc Natl Acad Sci USA* 105, 10149-10154 (2008)). The EWS-FLI1 transfected cells demonstrated a dose-dependent decrease in promoter activity when treated for 18 hours with 3 and 10 µM YK-4-279 (FIG. 32B). As an additional control for non-specific promoter effects, an NFκB responsive reporter was transfected into COS7 cells and activated with PMA. YK-4-279 did not affect the NFκB responsive promoter (FIG. 38A). In a recent publication, EWS-FLI1 was shown to modulate cyclin D protein levels by altering a cyclin D splice site (Sanchez, G., et al. Alteration of cyclin D1 transcript elongation by a mutated transcription factor up-regulates the oncogenic D1b splice isoform in cancer. *Proc Natl Acad Sci USA* (2008)). Blocking the interaction of EWS-FLI1 with RHA using YK-4-279 nearly eliminated cyclin D levels in TC32 cells treated for 14 hours (FIG. 32D), but did not affect cyclin D levels in four non-EWS-FLI1 containing cell lines (FIG. 38B, FIG. 38C).

YK-4-279 Specifically Inhibits ESFT Cell Growth and Induces Apoptosis

The compound identified from screening, NSC635437, was found to have an IC50 of 20 µM for TC32 cells growing in monolayer; however, YK-4-279 reduced the IC50 to 900 nM (FIG. 33A).

YK-4-279 was relatively specific for ESFT cells as compared to the non-transformed HEK293 cells, demonstrating a 10-fold difference in IC50 (FIG. 33B). Primary cell lines, ES925 and GUES1, established from ESFT patients with recurrent tumors demonstrated sensitivity to YK-4-279 with anti-proliferative IC50 values of 1 and 8 µM, respectively (FIG. 33C). A panel of ESFT cell lines demonstrated IC50 values between 0.5 to 2 µM for YK-4-279 while cell lines that lack EWSFLI1 have IC50 values in excess of 25 µM (FIG. 33D). An additional panel of non-transformed keratinocytes (HFK) and ectocervical cells (HEC) treated for 3 days with 30 µM YK-4-279 showed an IC50 that exceeded 30 µM (FIG. 39A).

Apoptosis leads to tumor cell death through the activation of sequential caspase enzymes, with caspase-3 demonstrating a commitment to cellular suicide (Li, F., et al. Control of apoptosis and mitotic spindle checkpoint by survivin. *Nature* 396, 580-584 (1998). Caspase-3 activity rose in a dose dependent fashion in TC32 cells treated with YK-4-279 for 24 hours (FIG. 39B).

Caspase activity was similar to 1 µM doxorubicin, a standard agent in the treatment of patients with ESFT6. Additional malignant and non-malignant cell lines were evaluated for caspase-3 activation in response to YK-4-279. While YK-4-279 induced caspase-3 activity in four ESFT cell lines (TC32, A4573, TC71, and ES925), none of the 5 non-EWS-FLI1 cancer cell lines nor 3 non-transformed cell lines (HFK, HEC, HEK293) treated with YK-4-279 resulted in apoptosis (FIG. 33E). Treatment of TC32, HEK293, HFK, and HEC with short-term (6 hours) high dose (50 µM) YK-4-279 resulted in significant apoptosis of the ESFT cells but no cell death in the nontransformed cells (FIG. 33F).

Together, these results support the specific toxicity of YK-4-279 upon cell lines containing EWS-FLI1 compared with other tumor and non-transformed cells.

In order to further support for the target specificity of YK-4-279 toxicity upon ESFT cells, the levels of each of the critical proteins were reduced by using shRNA in A673 cells 42. The RHA reduced cells demonstrated a YK-4-279 IC50 of >10 µM, while control shRNA (targeting luciferase) IC50 was less than 1 µM (FIG. 39C). When EWS-FLI1 was reduced using shRNA, the IC50 increased 10-fold from 0.5 µM to approximately 5 µM (FIG. 39D, FIG. 39E).

ESFT Xenograft Growth is Inhibited by YK-4-279

ESFT (orthotopic) or prostate cancer cell xenograft tumors were established in SCID/bg mice. Tumor growth rate was reduced for CHP-100, ESFT, (FIG. 6A), but not the PC3, prostate tumors (FIG. 34B). Five independent experiments were performed with the ESFT xenografts (TC71 and CHP-100) and the cumulative data for these experiments shows a marked overall tumor reduction (p<0.0001) in the YK-4-279 treated animals (FIG. 34C). Pathological analysis of animals treated with YK-4-279 did not show any signs of toxicity except changes related to IP injection. Tumors from animals treated with YK-4-279 were compared with DMSO treatment using immunohistochemistry to identify caspase-3 activity (FIG. 34D). The CHP-100 xenograft tumors from treated animals had a 3-fold increase in caspase-3 activity compared to control animals (FIG. 34E). These results show inhibition of two ESFT tumor models and concomitant increased apoptosis following YK-4-279 treatment.

There is a significant need for new cancer therapies that enhance efficacy and reduce long-term morbidity. Protein products of tumor-specific chromosomal translocations, which are present only in cancer cells, provide unique targets for anti-tumor therapies1. These translocations span a broad range of malignancies, including carcinomas, hematopoietic malignancies, and sarcomas (French, C. A., et al. Midline carcinoma of children and young adults with NUT rearrangement. *J Clin Oncol* 22, 4135-4139 (2004); Helman, L. J. & Meltzer, P. Mechanisms of sarcoma development. *Nat Rev Cancer* 3, 685-694 (2003); Poppe, B., et al. Expression analyses identify MLL as a prominent target of 11q23 amplification and support an etiologic role for MLL gain of function in myeloid malignancies. *Blood* 103, 229-235 (2004)). In many cancers, these translocations lead to novel fusion proteins that both initiate and maintain oncogenesis. While some of these translocations, such as BCR-ABL5, lead to constitutively activated kinases, the majority lead to fusion proteins that function as transcription factors and lack intrinsic enzymatic activity. These translocation-generated transcription factor fusion proteins are ideal targets of anti-cancer therapies, yet no pharmaceuticals have been developed towards these targets.

The Ewing's sarcoma family of tumors (ESFT) can occur anywhere in the body and most often in the 2nd and 3rd decades. ESFT often respond well to initial chemotherapy, yet 40% of patients will develop recurrent disease. The majority of patients with recurrent disease will die from ESFT, while 75-80% of patients who present with metastatic ESFT will die within 5 years despite high-dose chemotherapy (Grier, H. E., et al. Addition of ifosfamide and etoposide to standard chemotherapy for Ewing's sarcoma and primitive neuroectodermal tumor of bone. *N Engl J Med* 348, 694-701 (2003)). ESFT contain a well-characterized chromosomal translocation that fuses the amino-half of EWS to the carboxy-half of an ets-family DNA binding protein (Delattre, O., et al. The Ewing family of tumors—a subgroup of small-round-cell tumors defined by specific chimeric transcripts. *N Engl J Med* 331, 294-299 (1994)). The most common fusion protein is the oncogenic transcription factor EWS-FLI1. Elimination of EWS-FLI1 using antisense and siRNA approaches results in the prolonged survival of ESFT xenograft-bearing animals (Hu-Lieskovan, S., Heidel, J. D., Bartlett, D. W., Davis, M. E. & Triche, T. J. Sequencespecific knockdown of EWS-FLI1 by targeted, nonviral delivery of small interfering RNA inhibits tumor growth in a murine model of metastatic Ewing's sarcoma. *Cancer Res* 65, 8984-8992 (2005)), but this approach currently lacks translation to clinical therapy (Kovar, H., Ban, J. & Pospisilova, S. Potentials for RNAi in sarcoma research and therapy: Ewing's sarcoma as a model. *Semin Cancer Biol* 13, 275-281 (2003); Tanaka, K., Iwakuma, T., Harimaya, K., Sato, H. & Iwamoto, Y. EWS-Fli1 antisense oligodeoxynucleotide inhibits proliferation of human Ewing's sarcoma and primitive neuroectodermal tumor cells. *J Clin Invest* 99, 239-247 (1997)). Small-molecule targeting would be directed towards the disruption of EWS-FLI1 from established transcriptional complexes, since EWS-FLI1 lacks intrinsic enzymatic activity. The EWS-FLI1 transcriptional complex includes: RNA polymerase II, CREB-binding protein (CBP), and RNA Helicase A (RHA) (Petermann, R., et al. Oncogenic EWS-Fli1 interacts with hsRPB7, a subunit of human RNA polymerase II. *Oncogene* 17, 603-610 (1998); Nakatani, F., et al. Identification of p21WAF1/CIP1 as a direct target of EWS-Fli1 oncogenic fusion protein. *J Biol Chem* 278, 15105-15115 (2003); Toretsky, J. A., et al. Oncoprotein EWS-FLI1 activity is enhanced by RNA helicase A. *Cancer Res* 66, 5574-5581 (2006); Zhong, X. & Safa, A. R. RNA helicase A in the MEF1 transcription factor complex upregulates the MDR1 gene in multidrug-resistant cancer cells. *J Biol Chem* 279, 17134-17141 (2004); Nakajima, T., et al. RNA helicase A mediates association of CBP with RNA polymerase II. *Cell* 90, 1107-1112 (1997)). Previous investigations showed RHA augments EWSFLI1 modulated oncogenesis, suggesting that this protein-protein complex is particularly important for tumor maintenance (Toretsky, J. A., et al. Oncoprotein EWS-FLI1 activity is enhanced by RNA helicase A. *Cancer Res* 66, 5574-5581 (2006)). Small molecule inhibitors that block RHA interaction by targeting the oncogenic fusion protein EWS-FLI1 are the first in a new class of anti-tumor therapy. RHA has a critical role in embryogenesis and thus is a reasonable partner for an oncogene in a highly undifferentiated tumor. RHA is indispensable for ectoderm survival in gastrulation of mammals (Lee, C. G., et al. RNA helicase A is essential for normal gastrulation. *Proc Natl Acad Sci USA* 95, 13709-13713 (1998)) and is required beyond embryogenesis because RHA null mouse fibroblast cells are not viable. However, transient reduction of RHA protein levels in COS cells did not affect the viability (Hartman, T. R., et al. RNA helicase A is necessary for translation of selected messenger RNAs. *Nat Struct Mol Biol* (2006)). RHA provides a transcriptional coactivator role in models of tumorigenesis including NFkappaB and STATE transcriptomes. RHA binds to DNA in a sequence specific manner upon the promoters of $p16^{INK4a}$ and MDR1 (Tetsuka, T., et al. RNA helicase A interacts with nuclear factor kappaB p65 and functions as a transcriptional coactivator. *Eur J Biochem* 271, 3741-3751 (2004); Valineva, T., Yang, J. & Silvennoinen, o. Characterization of RNA helicase A as component of STATE-dependent enhanceosome. *Nucleic Acids Res* 34, 3938-3946 (2006); Myohanen, S. & Baylin, S. B. Sequence-specific DNA binding activity of RNA helicase A to the p16INK4a promoter. *J Biol Chem* 276, 1634-1642 (2001); Zhong, X. & Safa, A. R. RNA helicase A in the MEF1 transcription factor complex upregulates the MDR1 gene in multidrug-resistant cancer cells. *J Biol Chem* 279, 17134-17141 (2004); Nakajima, T., et al. RNA helicase A mediates association of CBP with RNA polymerase II. *Cell* 90, 1107-1112 (1997)). The amino-terminal region of RHA is most often the site for protein-protein interactions. CBP binds aa 1-250 of RHA 20, while additional partners for RHA bind in the amino-terminal region including RNA polymerase II21 and BRCA121. In modulating RNA interference in the RISC complex, RHA and Dicer, TRBP and Ago2 interact in the region of aa 1-272 of RHA22. EWS-FLI1 binds to RHA in a unique region that is not occupied by other transcriptional nor RNA metabolism proteins (Toretsky, J. A., et al. Oncoprotein EWS-FLI1 activity is enhanced by RNA helicase A. *Cancer Res* 66, 5574-5581 (2006)), thus increasing the attractiveness of this protein target.

Disruption of protein-protein interactions by small molecules is a rapidly evolving field. Proteins with more flexible structures, in some cases disordered proteins, have a greater potential for small molecule binding than rigid proteins because of higher induced fit sampling probabilities (Bhalla, J., Storchan, G. B., MacCarthy, C. M., Uversky, V. N. & Tcherkasskaya, O. Local flexibility in molecular function paradigm. *Mol Cell Proteomics* 5, 1212-1223 (2006)). A disordered protein is defined, in part, by increased intrinsic movement and the inability to form rigid 3-dimensional structure (Xie, H., et al. Functional anthology of intrinsic disorder. 1. Biological processes and functions of proteins with long disordered regions. *Journal of proteome research* 6, 1882-1898 (2007)). EWS-FLI1 is a disordered protein and requires the disorder for maximal transactivation of transcription (Ng, K. P., et al. Multiple aromatic side chains within a disordered structure are critical for transcription and transforming activity of EWS family oncoproteins. *Proc Natl Acad Sci USA* 104, 479-484 (2007); Uren, A., Tcherkasskaya, O. & Toretsky, J. A. Recombinant EWS-FLI1 oncoprotein activates transcription. *Biochemistry* 43, 13579-13589 (2004)). Based on these observations, EWS-FLI1, along with its binding to RHA, can provide a unique drug target.

EWS-FLI1 is a unique, cancer specific, molecule that can have utility as a therapeutic target in ESFT cells. RHA is critical to the function of EWS-FLI1. A peptide (E9R) that blocks RHA binding to EWS-FLI1 specifically reduced anchorage-independent growth. Use of the small molecule lead compound, NSC635437, that binds to EWS-FLI1, and the lead compound derivative YK-4-279, along with E9R peptide, demonstrate that the EWS-FLI1/RHA interaction can be blocked with a detrimental effect on ESFT cells both in vitro and in vivo. These findings validate a highly specific cancer target, the interaction of EWS-FLI1 with RHA.

It was demonstrated that the small molecule YK-4-279 binds to EWS-FLI1 and blocks the binding of RHA. A series of xenograft experiments demonstrated that 60-75 mg/kg YK-4-279 significantly reduced tumor growth. The small molecule not only inhibited RHA binding to EWS-FLI1, but also reduced EWS-FLI1 modulated transcription. An additional putative function of EWS-FLI1 is splice-site modification (Knoop, L. L. & Baker, S. J. EWS/FLI alters 5'-splice site selection. *J Biol Chem* 276, 22317-22322. (2001)), which was recently supported by the EWS-FLI1 altered splicing of cyclin D132. Treatment of ESFT cells with YK-4-279 led to decreased cyclin D1 levels. Additional investigations of the splicing complex are necessary to determine if this effect is due to the disruption of an EWS-FLI1/RHA complex or allosteric interference with EWS-FLI1. Small molecule inhibitors have use as therapeutics, and are also useful as functional probes.

EWS-FLI1 was recognized as a potential therapeutic target over 15 years ago, almost immediately after the protein was identified as a product of the breakpoint region t(11;22)35. The disordered biophysical nature of EWS-FLI1 precludes standard structure-based small molecule design (Uren, A., Tcherkasskaya, O. & Toretsky, J. A. Recombinant EWS-FLI1 oncoprotein activates transcription. *Biochemistry* 43, 13579-13589 (2004).). Therefore, development of small molecule protein-protein inhibitors was pursued based upon the assumption that EWS-FLI1 would have a binding partner critical for its oncogenic function, which we previously identified as RHA13, and validated in the current study. The exact nature of the requirement of RHA for EWS-FLI1 is currently under investigation, however it is believed that RHA could be involved in EWS-FLI1 function, synthesis or stability. These data support multiple mechanisms and therefore require further enzymatic and structural studies of EWS-FLI1 bound RHA for resolution. The fact that YK-4-279 is still toxic to A673 cells with reduced EWS-FLI1 could be due to residual EWS-FLI1 or suggest broader action of the compound. In addition, while data suggest that YK-4-279 is specific for ESFT cell toxicity, YK-4-279 may reveal other protein interactions.

Inhibitory peptides offer a greater likelihood of specificity to validate protein-protein interaction targets and to evaluate protein-complex disruption; however, peptides are problematic for clinical development. Peptides were used to compare the effects of disrupting protein-protein interactions with our small molecules. While small peptides are currently being developed as therapeutic agents (Plescia, J., et al. Rational design of shepherdin, a novel anticancer agent. *Cancer Cell* 7, 457-468 (2005); Palermo, C. M., Bennett, C. A., Winters, A. C. & Hemenway, C. S. The AF4-mimetic peptide, PFWT, induces necrotic cell death in MV4-11 leukemia cells. *Leuk Res* (2007)), 10-20 aa peptides present formidable pharmacokinetic stability and delivery challenges. The E9R peptide may compete with full-length RHA binding to EWS-FLI1 and data support a functional displacement of RHA by E9R. Using surface plasmon resonance and fluorescence polarization, it was demonstrated that YK-4-279 can 'displace' E9R from EWS-FLI1. While these results support E9R and YK-4-279 binding to the same site on EWS-FLI1, allosteric interference cannot be excluded. Therefore, a structural model of EWSFLI1 is required to both fully prove this interaction and YK-4-279 binding site, but is yet unavailable due to the challenges of disordered proteins (Bhalla, J., Storchan, G. B., MacCarthy, C. M., Uversky, V. N. & Tcherkasskaya, O. Local flexibility in molecular function paradigm. *Mol Cell Proteomics* 5, 1212-1223 (2006)).

The interaction of RHA with EWS-FLI1 presents an ideal opportunity for the development of small molecule protein-protein interaction inhibitors (SMPPII). Both evidence and prevailing opinion support disordered proteins as potential targets of small molecule therapeutics (Cheng, Y., et al. Rational drug design via intrinsically disordered protein. *Trends Biotechnol* 24, 435-442 (2006).). This data also support EWS-FLI1 protein interaction targeting to modulate oncogene function and potentially lead to novel therapeutics. Small molecules that disable EWS-FLI1 function with minimal toxicity, in particular sparing of hematopoetic stem cells, can potentially provide a valuable adjuvant therapy for patients with ESFT. In addition, this paradigm for drug discovery can be applied to many related sarcomas that share similar oncogenic fusion proteins.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. A compound having a formula:

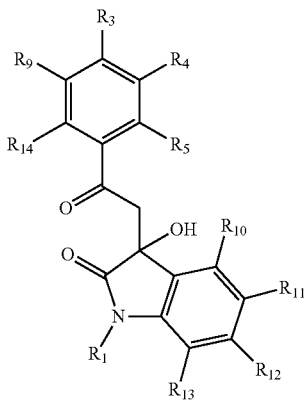

wherein $R_1$ is selected from the group consisting of hydrogen, one amino acid, two amino acids linked together, three amino acids linked together,

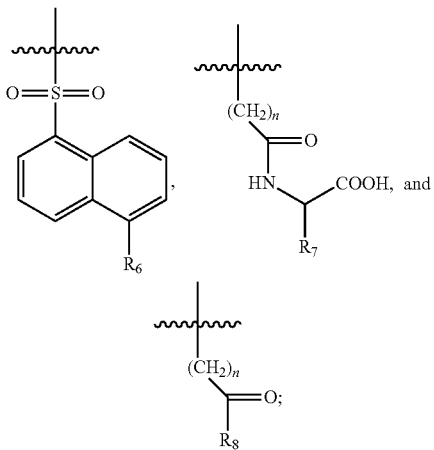

$R_3$ is selected from the group consisting of halogen, $C_{1-6}$ alkoxy, —C(=O)NH$_2$, —NO$_2$, and —OH;
$R_6$ is $C_{1-6}$ dialkyl amine;
$R_7$ is selected from the group consisting of hydrogen and $C_{1-6}$ alkyl;
$R_8$ is $C_{1-6}$ alkyl;
$R_4$, $R_5$, $R_9$, $R_{12}$ and $R_{14}$ are independently selected from the group consisting of hydrogen, halogen, $C_{1-6}$ alkyl, $C_{1-6}$ alkoxy, —C(=O)NH$_2$, —NO$_2$, —NH$_2$, and —OH;
$R_{10}$ is selected from the group consisting of halogen, $C_{1-6}$ alkyl, $C_{1-6}$ alkoxy, —C(=O)NH$_2$, —NO$_2$, —NH$_2$, and —OH;
$R_{11}$ is selected from the group consisting of hydrogen, halogen, $C_{1-6}$ alkoxy, —C(=O)NH$_2$, —NO$_2$, —NH$_2$, and —OH;
$R_{13}$ is halogen; and
n is an integer from 0 to 4,
with the proviso that $R_3$ is not chlorine or fluorine when $R_1$, $R_4$, $R_5$, $R_{11}$, and $R_{12}$ are hydrogen and $R_{10}$ and $R_{13}$ are chlorine.

2. The compound of claim 1, wherein $R_4$, $R_5$, $R_9$, $R_{11}$, $R_{12}$, and $R_{14}$ are independently selected from the group consisting of hydrogen, $C_{1-6}$ alkoxy, chlorine, and fluorine.

3. The compound of claim 1, wherein $R_1$ is selected from the group consisting of hydrogen, Leu, Leu-Asp, Leu-Asp-Ala, —CH$_2$—C(=O)—NHCH$_2$COOH, —CH$_2$—C(=O)—(CH$_2$)C(CH$_3$)$_2$,

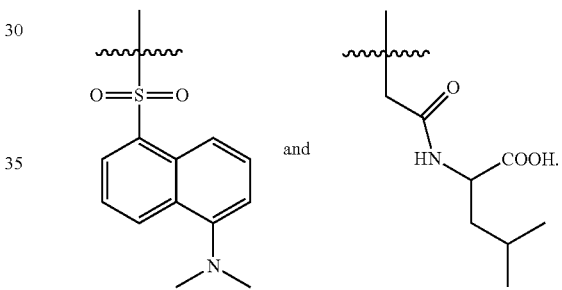

4. A pharmaceutical composition comprising the compound of claim 1 and a pharmaceutically acceptable carrier or diluent.

5. A compound having a formula:

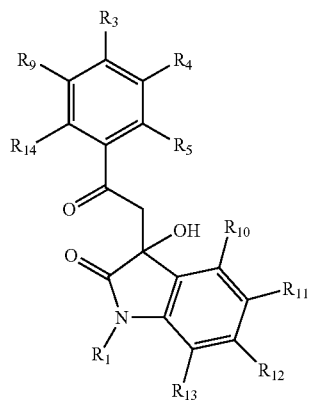

wherein $R_1$ is selected from the group consisting of hydrogen, one amino acid, two amino acids linked together, three amino acids linked together,

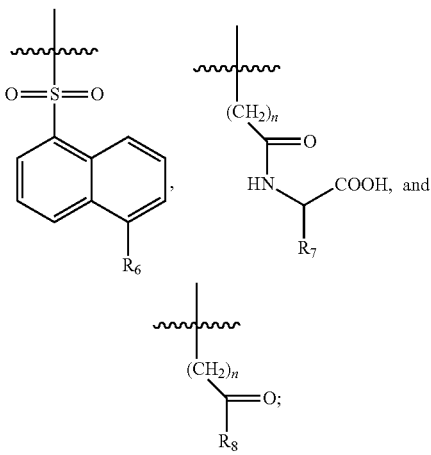

R$_3$ is selected from the group consisting of halogen, C$_{1-6}$ alkyl, C$_{1-6}$ alkoxy, —C(=O)NH$_2$, —NO$_2$, —NH$_2$—, and —OH;

R$_4$ is selected from the group consisting of hydrogen, halogen, C$_{1-6}$ alkyl, C$_{1-6}$ alkoxy, —C(=O)NH$_2$, —NH$_2$, and —OH;

R$_6$ is C$_{1-6}$ dialkyl amine;

R$_7$ is selected from the group consisting of hydrogen and C$_{1-6}$ alkyl;

R$_8$ is C$_{1-6}$ alkyl;

R$_5$, R$_{11}$, R$_{12}$ and R$_{14}$ are independently selected from the group consisting of hydrogen, halogen, C$_{1-6}$ alkyl, C$_{1-6}$ alkoxy, —C(=O)NH$_2$, —NO$_2$, —NH$_2$, and —OH;

R$_9$ is selected from the group consisting of hydrogen, halogen, C$_{1-6}$ alkyl, —C(=O)NH$_2$, —NO$_2$, —NH$_2$, and —OH;

R$_{10}$ is halogen;

R$_{13}$ is selected from the group consisting of halogen, C$_{1-6}$ alkoxy, —C(=O)NH$_2$, —NO$_2$, —NH$_2$, and —OH; and n is an integer from 0 to 4, with the proviso that R$_3$ is not chlorine or fluorine when R$_1$, R$_4$, R$_5$, R$_{11}$, and R$_{12}$ are hydrogen and R$_{10}$ and R$_{13}$ are chlorine.

6. The compound of claim 5, wherein R$_4$, R$_5$, R$_9$, R$_{11}$, R$_{12}$, and R$_{14}$ are independently selected from the group consisting of hydrogen, C$_{1-6}$ alkoxy, chlorine, and fluorine.

7. The compound of claim 5, wherein R$_1$ is selected from the group consisting of hydrogen, Leu, Leu-Asp, Leu-Asp-Ala, —CH$_2$—C(=O)—NHCH$_2$COOH, —CH$_2$—C(=O)—(CH$_2$)C(CH$_3$)$_2$,

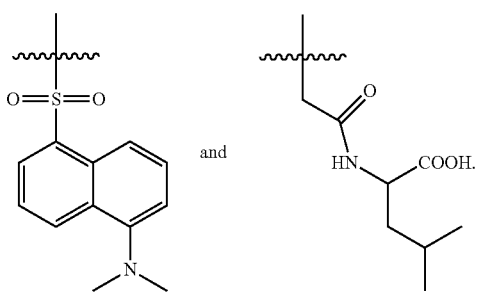 [SMILES: *S(=O)(=O)c1cccc2c(N(C)C)cccc12 ; *CC(=O)NC(CC(C)C)C(=O)O]

8. A pharmaceutical composition comprising the compound of claim 5 and a pharmaceutically acceptable carrier or diluent.

9. A compound having a formula selected from the group consisting of:

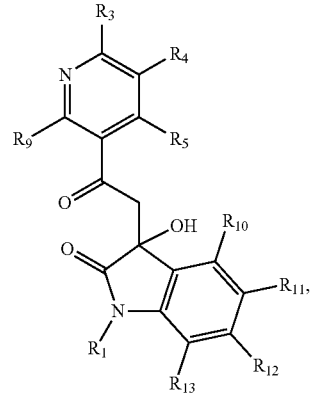

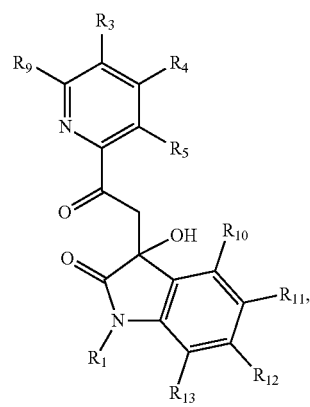

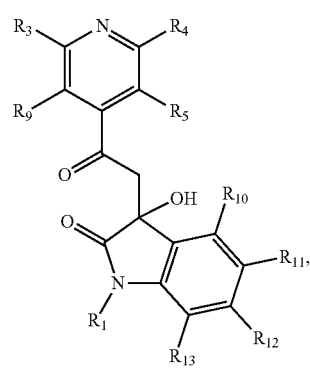

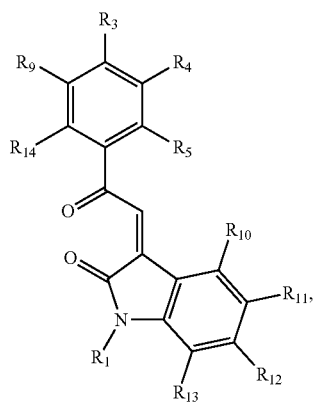

-continued

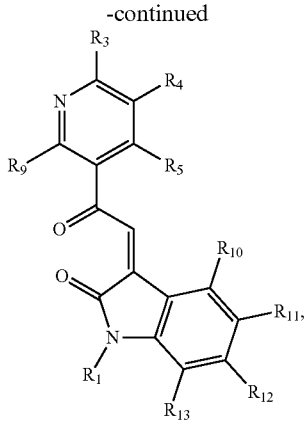

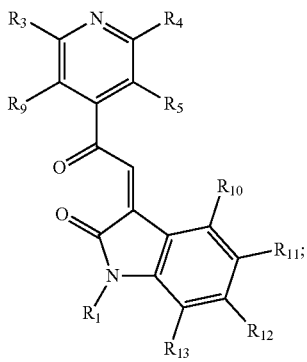
and

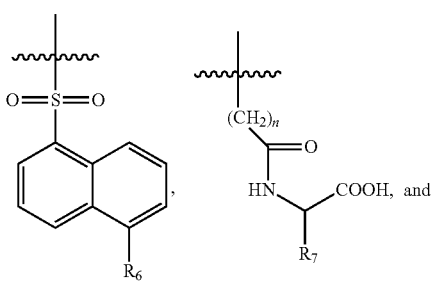

wherein $R_1$ is selected from the group consisting of hydrogen, one amino acid, two amino acids linked together, three amino acids linked together, -continued

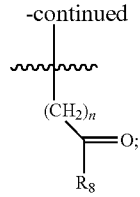

$R_3$ is selected from the group consisting of halogen, $C_{1-6}$ alkoxy, —C(=O)NH$_2$, —NO$_2$, and —OH;

$R_6$ is $C_{1-6}$ dialkyl amine;

$R_7$ is selected from the group consisting of hydrogen and $C_{1-6}$ alkyl;

$R_8$ is $C_{1-6}$ alkyl;

$R_4$, $R_5$, $R_9$, $R_{11}$, $R_{12}$ and $R_{14}$ are independently selected from the group consisting of hydrogen, halogen, $C_{1-6}$ alkyl, $C_{1-6}$ alkoxy, —C(=O)NH$_2$, —NO$_2$, —NH$_2$, and —OH;

$R_{10}$ is selected from the group consisting of halogen, $C_{1-6}$ alkyl, $C_{1-6}$ alkoxy, —C(=O)NH$_2$, —NO$_2$, —NH$_2$, and —OH;

$R_{11}$ is selected from the group consisting of hydrogen, halogen, $C_{1-6}$ alkoxy, —C(=O)NH$_2$, —NO$_2$, —NH$_2$, and —OH;

$R_{13}$ is halogen; and n is an integer from 0 to 4.

10. A pharmaceutical composition comprising the compound of claim 9 and a pharmaceutically acceptable carrier or diluent.

11. A compound having a formula selected from the group consisting of:

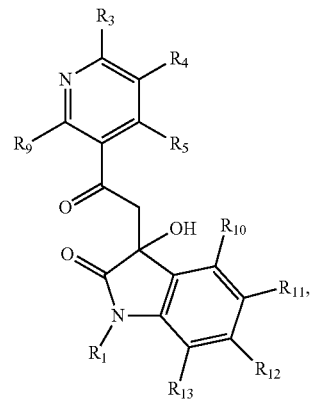

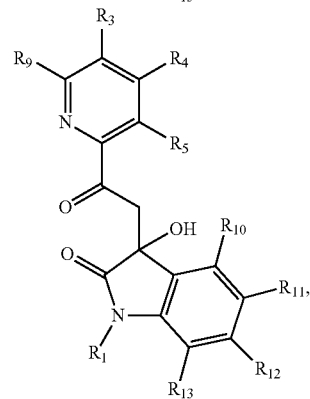

-continued

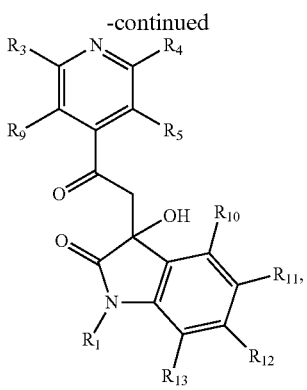

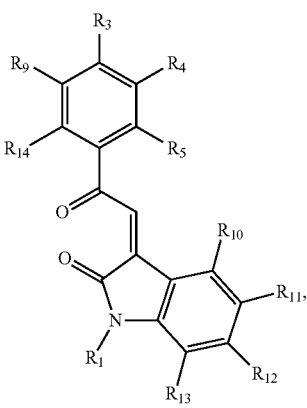

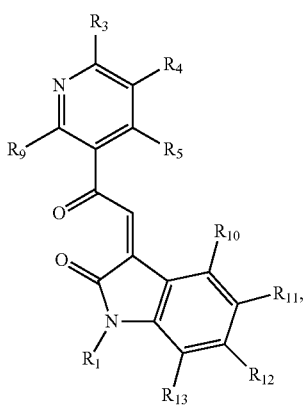

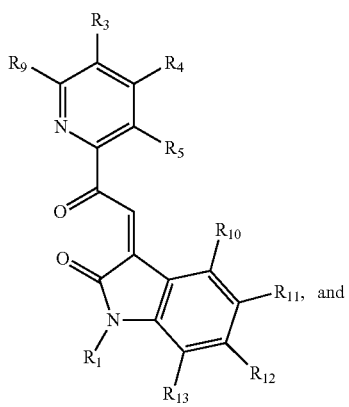

-continued

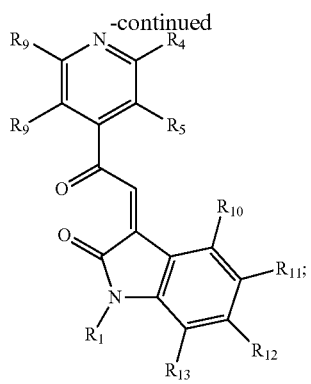

wherein R$_1$ is selected from the group consisting of hydrogen, one amino acid, two amino acids linked together, three amino acids linked together,

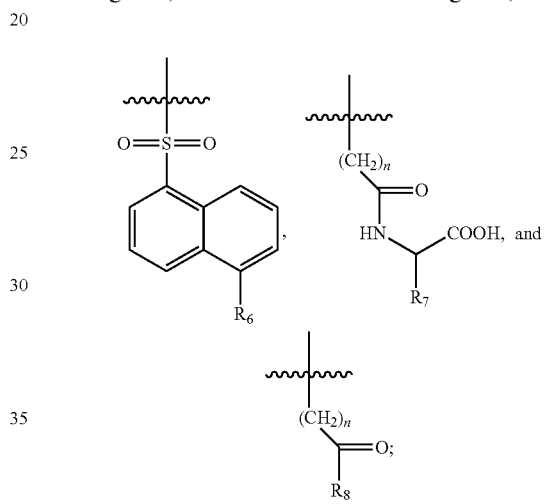

R$_3$ is selected from the group consisting of halogen, C$_{1-6}$ alkyl, C$_{1-6}$ alkoxy, —C(=O)NH$_2$, —NO$_2$, —NH$_2$, and —OH;

R$_4$ is selected from the group consisting of hydrogen, halogen, C$_{1-6}$ alkyl, C$_{1-6}$ alkoxy, —C(=O)NH$_2$, —NH$_2$, and —OH;

R$_6$ is C$_{1-6}$ dialkyl amine;

R$_7$ is selected from the group consisting of hydrogen and C$_{1-6}$ alkyl;

R$_8$ is C$_{1-6}$ alkyl;

R$_5$, R$_{11}$, R$_{12}$, R$_{13}$ and R$_{14}$ are independently selected from the group consisting of hydrogen, halogen, C$_{1-6}$ alkyl, C$_{1-6}$ alkoxy, —C(=O)NH$_2$, —NO$_2$, —NH$_2$, and —OH;

R$_9$ is selected from the group consisting of hydrogen, halogen, C$_{1-6}$ alkyl, —C(=O)NH$_2$, —NO$_2$, —NH$_2$, and —OH;

R$_{10}$ is halogen;

R$_{13}$ is selected from the group consisting of halogen, C$_{1-6}$ alkoxy, —C(=O)NH$_2$, —NO$_2$, —NH$_2$, and —OH;

n is an integer from 0 to 4.

12. A pharmaceutical composition comprising the compound of claim 11 and a pharmaceutically acceptable carrier or diluent.

13. The compound of claim 1, wherein R$_3$ is selected from the group consisting of C$_{1-6}$ alkoxy, —C(=O)NH$_2$, —NO$_2$, and —OH.

14. The compound of claim 1, wherein $R_3$ is $C_{1-6}$ alkoxy.

15. The compound of claim 1, wherein $R_{10}$ is halogen.

16. The compound of claim 1, wherein $R_{10}$ and $R_{13}$ are chlorine.

17. The compound of claim 5, wherein $R_3$ is selected from the group consisting of $C_{1-6}$ alkyl, $C_{1-6}$ alkoxy, —C(=O)NH$_2$, —NO$_2$, —NH$_2$—, and —OH.

18. The compound of claim 5, wherein $R_3$ is $C_{1-6}$ alkoxy.

19. The compound of claim 5, wherein $R_{13}$ is halogen.

20. The compound of claim 5, wherein $R_{10}$ and $R_{13}$ are chlorine.

\* \* \* \* \*

UNITED STATES PATENT AND TRADEMARK OFFICE
CERTIFICATE OF CORRECTION

PATENT NO.        : 9,758,481 B2
APPLICATION NO.   : 14/696005
DATED             : September 12, 2017
INVENTOR(S)       : Toretsky et al.

It is certified that error appears in the above-identified patent and that said Letters Patent is hereby corrected as shown below:

On the Title Page

In Column 2 (item (56)) at Line 16, Under Other Publications, change "Indo1" to --Indol--.

In Column 2 (item (56)) at Line 19, Under Other Publications, change "Indo1" to --Indol--.

In Column 2 (item (56)) at Line 39, Under Other Publications, change "tomorigenesis"," to --tumorigenesis",--.

In Column 2 (item (56)) at Line 42, Under Other Publications, change "pyrazonlin)" to --pyrazolin)--.

In Column 2 (Primary Examiner) at Line 1, Change "Redding" to --Reddig--.

In Column 2 (page 2, item (56)) at Line 19, Under Other Publications, change ""Sequencespecific" to --"Sequence Specific--.

In Column 2 (page 2, item (56)) at Line 24, Under Other Publications, change "Sciene" to --Science--.

In Column 2 (page 2, item (56)) at Line 28, Under Other Publications, change ""NROB1" to --"NR0B1--.

In Column 2 (page 2, item (56)) at Line 35, Under Other Publications, change "KOBAYASHIetal.," to --KOBAYASHI et al.,--.

In Column 2 (page 2, item (56)) at Line 35, Under Other Publications, change "derivativrs" to --derivatives--.

In Column 1 (page 3, item (56)) at Line 12, Under Other Publications, change "assocation" to --association--.

Signed and Sealed this
Second Day of October, 2018

Andrei Iancu
*Director of the United States Patent and Trademark Office*

CERTIFICATE OF CORRECTION (continued)
U.S. Pat. No. 9,758,481 B2

In Column 1 (page 3, item (56)) at Line 45, Under Other Publications, change "Luekemia" to --Leukemia--.

In Column 1 (page 3, item (56)) at Line 61, Under Other Publications, change "oxoehyl]," to --oxoethyl],--.

In Column 1 (page 3, item (56)) at Line 63, Under Other Publications, change "Indo1" to --Indol--.

In Column 2 (page 3, item (56)) at Line 17, Under Other Publications, change "PPWT" to --PFWT--.

In Column 1 (page 4, item (56)) at Line 48, Under Other Publications, change "Classsification" to --Classification--.

In Column 2 (page 4, item (56)) at Line 33, Under Other Publications, change "nik.gov/" to --nih.gov/--.

In the Drawings

Sheet 1 of 66 (FIG. 1A) at Line 7 (approx.), Change "protien" to --Protein--.

Sheet 24 of 66 (FIG. 19) at Line 4 (approx.), Change "substitued" to --substituted--.

Sheet 26 of 66 (FIG. 21) at Line 2 (approx.), Change "cinhonine" to --cinchonine--.

Sheet 27 of 66 (FIG. 22) at Line 2 (approx.), Change "cinhonine" to --cinchonine--.

In the Specification

In Column 13 at Line 48, Change "( )" to --($\tau$)--.

In Column 13 at Line 48, Change "(P2A" to --P2A--.

In Column 13 at Line 49, Change "( )" to --($\sigma$)--.

In Column 15 at Line 41, Change "Reformasky" to --Reformatsky--.

In Column 16 at Line 15, Change "1050" to --$IC_{50}$--.

In Column 16 at Line 28, Change "NO.s:" to --NOs.--.

In Column 18 at Line 47, Change "COST" to --COS7--.

In Column 18 at Line 58, Change "keritinocytes," to --keratinocytes,--.

In Column 37 at Line 28, Change "nitrohenyl" to --nitrophenyl--.

CERTIFICATE OF CORRECTION (continued)
U.S. Pat. No. 9,758,481 B2

In Column 37 at Line 34, Change "oxo2-" to --oxo-2- --.

In Column 39 at Line 62 (approx.), Change "HEPFVTNTPSLI" to --HHPFVTNTPSLI--.

In Column 41 at Line 11 (approx.), Change "spheroblasts." to --spheroplasts.--.

In Column 42 at Lines 24-25, Change "carboxymethylcellulose, ultramylopectin," to --carboxymethyl cellulose, ultra-amylopectin,--.

In Column 42 at Line 58, Change "providone" to --povidone--.

In Column 43 at Line 33, Change "9.5" to --9.5 µm.--.

In Column 43 at Line 40, Change "cyclodextran." to --cyclodextrin.--.

In Column 47 at Line 46, Change "gene bank" to --genbank--.

In Column 50 at Line 26, Change "pseudopaillary" to --pseudopapillary--.

In Column 50 at Line 52, Change "mesobalstic" to --mesoblastic--.

In Column 51 at Line 2, Change "11 q23" to --11q23--.

In Column 51 at Line 52 (approx.), Change "EWS-FLI 1." to --EWS-FLI1.--.

In Column 57 at Lines 38-39, Change "the an" to --an--.

In Column 60 at Line 50, Change "gastrocnemeous." to --gastrocnemius.--.

In Column 61 at Line 34, Change "metastastic" to --metastatic--.

In Column 63 at Line 32, Change "Reformasky" to --Reformatsky--.

In Column 66 at Line 34, Change "QuickChange" to --QuikChange--.

In Column 66 at Line 52, Change "al" to --al.--.

In Column 67 at Line 36, Change "52.53," to --52.53;--.

In Column 67 at Line 36, Change "3.17," to --3.17;--.

In Column 67 at Line 44, Change "55.82," to --55.82;--.

In Column 67 at Line 44, Change "3.98," to --3.98;--.

In Column 67 at Lines 50-51, Change "fluorimeter" to --fluorometer--.

CERTIFICATE OF CORRECTION (continued)
U.S. Pat. No. 9,758,481 B2

In Column 68 at Line 65, Change "(FIG." to --(FIGS.--.

In Column 69 at Line 21, Change "(FIG." to --(FIGS.--.

In Column 69 at Line 23, Change "(FIG." to --(FIGS.--.

In Column 69 at Line 60 (approx.), Change "Antennnapedia" to --Antennapedia--.

In Column 70 at Line 24, Change "(FIG." to --(FIGS.--.

In Column 70 at Line 26, Change "(FIG." to --(FIGS.--.

In Column 71 at Line 67, Change "nontransformed" to --non-transformed--.

In Column 72 at Lines 6-7, Change "cells 42." to --cells42.--.

In Column 73 at Line 7, Change ""Sequencespecific" to --"Sequence Specific--.

In Column 73 at Lines 23-24, Change "(RHA)(Petermann," to --(RHA) (Petermann,--.

In Column 73 at Line 56, Change "NFkappaB" to --NFκB--.

In Column 73 at Line 56, Change "STATE" to --STAT6--.

In Column 73 at Line 62, Change "o." to --O.--.

In Column 73 at Line 63, Change "STATE-dependent" to --STAT6-dependent--.

In Column 76 at Line 7, Change "(2006).)." to --(2006)).--.

In Column 76 at Line 11, Change "hematopoetic" to --hematopoietic--.

In the Claims

In Column 95 at Lines 56-65, In Claim 9, change " 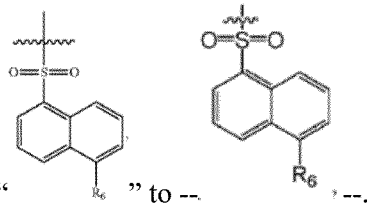 " to -- --.

In Column 98 at Lines 22-32 (approx.), In Claim 11, change " 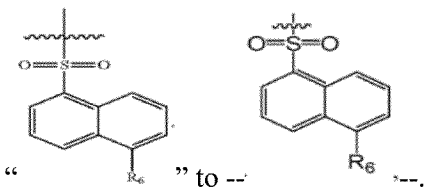 " to -- --.

SEQUENCE LISTING

```
<160> NUMBER OF SEQ ID NOS: 45

<210> SEQ ID NO 1
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 1

Thr Met Arg Gly Lys Lys Lys Arg Thr Arg Ala Asn
 1               5                   10
```

```
<210> SEQ ID NO 2
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 2

Gln His Arg Met Ala Ser Met Ser Pro Thr Leu Pro
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 3

Gly Leu Leu Pro Tyr Arg Pro Arg Glu Ala Asn Phe
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 4

Ala Met Ile Pro Tyr Thr Trp Phe Ser Pro Ser Pro
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 5

Lys Gln Pro Lys Lys Ala Pro Arg Arg Ile Pro Gln
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 6

Ser Ile Pro Thr Thr Trp Phe His Pro Pro Pro Ser
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 7

Gly Val Ser Leu His Asn Thr Asn Trp Asn Ile Tyr
1               5                   10
```

```
<210> SEQ ID NO 8
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 8

Ser Asp Thr Ser Val Asn Trp Leu Thr Leu Trp Tyr
 1               5                  10

<210> SEQ ID NO 9
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 9

Asn Thr Pro Gln Arg Pro Pro Tyr Lys Arg Ser Pro
 1               5                  10

<210> SEQ ID NO 10
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 10

Leu Ala Lys Ser Pro Ser Asn Ser Ala Arg Glu Trp
 1               5                  10

<210> SEQ ID NO 11
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 11

Ala Lys Cys His Ser Asp Val Pro Ser Pro Ala Cys
 1               5                  10

<210> SEQ ID NO 12
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 12

Val His Phe Lys Pro Thr His Leu Pro Ser Pro Pro
 1               5                  10

<210> SEQ ID NO 13
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 13

Ser Thr Ser Gln Ala Leu Ser Arg Phe Pro Ser Phe
 1               5                  10
```

```
<210> SEQ ID NO 14
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 14

Gly Met Met Arg Ala Leu Ser His Pro Ser Ala Ser
 1               5                  10

<210> SEQ ID NO 15
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 15

Gly Thr Leu Thr Thr Pro Arg Leu Asp Leu Ile Met
 1               5                  10

<210> SEQ ID NO 16
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 16

Met Lys Ile Ser Ala Pro Ala Leu Ala Phe Gly Leu
 1               5                  10

<210> SEQ ID NO 17
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 17

Met Phe Ala Lys Ser Pro Pro Tyr Pro Ser Leu Met
 1               5                  10

<210> SEQ ID NO 18
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 18

Phe Asn Trp His Trp Leu Ser Arg Pro Tyr Phe Pro
 1               5                  10

<210> SEQ ID NO 19
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 19

Phe Ala Asn His Leu Thr Asn Ala Val His Ala Leu
 1               5                  10

<210> SEQ ID NO 20
```

```
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 20

Ser Gln Pro Trp Thr Asn Ala Leu Val Val Ser Ser
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 21

Thr Ala Phe Trp Pro Leu Tyr Pro Leu Ser Asp Trp
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 22

Lys Leu Trp Asn Val Pro Trp Pro Pro His Met Arg
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 23

Phe Thr Pro Pro Pro Ala Tyr Gly Arg Asn Glu Gly
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 24

His Trp Ile Pro Gln Thr Leu Pro Ala Ser Phe Ile
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 25

His His Pro Phe Val Thr Asn Thr Pro Ser Leu Ile
1               5                   10

<210> SEQ ID NO 26
<211> LENGTH: 12
```

```
<212> TYPE: PRT
<213> ORGANISM: Artificial Sequence
<220> FEATURE:
<223> OTHER INFORMATION: Synthetic Amino Acid Sequence

<400> SEQUENCE: 26

Pro Asn Arg Leu Gly Arg Arg Pro Val Arg Trp Glu
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 27

His Trp Trp Tyr Pro Leu Leu Pro Val Arg Gln Met
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Synthetic Amino Acid Sequence

<400> SEQUENCE: 28

Tyr Thr Pro Pro Pro Leu Ile Glu Ala Phe Ala Thr
1               5                   10

<210> SEQ ID NO 29
<211> LENGTH: 10
<212> TYPE: PRT
<213> ORGANISM: Homo Sapiens

<400> SEQUENCE: 29

Pro Pro Pro Leu Asp Ala Val Ile Glu Ala
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic Amino Acid Sequence

<400> SEQUENCE: 30

Pro Ala Pro Leu Asp Ala Val Ile Glu Ala
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthetic Amino Acid Sequence

<400> SEQUENCE: 31

Pro Pro Pro Leu Ala Ala Val Ile Glu Ala
1               5                   10

<210> SEQ ID NO 32
<211> LENGTH: 5
<212> TYPE: PRT
<213> ORGANISM: Artificial Sequence
<220> FEATURE:
```

<223> OTHER INFORMATION: Synthetic Amino Acid Sequence

<400> SEQUENCE: 32

Pro Pro Pro Leu Asp
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic Amino Acid Sequence

<400> SEQUENCE: 33

Leu Asp Ala Val Ile Glu Ala
1               5

<210> SEQ ID NO 34
<211> LENGTH: 16
<212> TYPE: PRT
<213> ORGANISM: Drosophilia Melanogaster

<400> SEQUENCE: 34

Arg Gln Ile Lys Ile Trp Phe Gln Asn Arg Arg Met Lys Trp Lys Lys
1               5                   10                  15

<210> SEQ ID NO 35
<211> LENGTH: 26
<212> TYPE: PRT
<213> ORGANISM: Artificial Sequence
<220> FEATURE:
<223> OTHER INFORMATION: Synthetic Amino Acid Sequence

<400> SEQUENCE: 35

Arg Gln Ile Lys Ile Trp Phe Gln Asn Arg Arg Met Lys Trp Lys Lys
1               5                   10                  15

Pro Pro Pro Leu Asp Ala Val Ile Glu Ala
            20                  25

<210> SEQ ID NO 36
<211> LENGTH: 26
<212> TYPE: PRT
<213> ORGANISM: Artificial Sequence
<220> FEATURE:
<223> OTHER INFORMATION: Synthetic Amino Acid Sequence

<400> SEQUENCE: 36

Arg Gln Ile Lys Ile Trp Phe Gln Asn Arg Arg Met Lys Trp Lys Lys
1               5                   10                  15

Pro Pro Pro Leu Ala Ala Val Ile Glu Ala
            20                  25

<210> SEQ ID NO 37
<211> LENGTH: 57
<212> TYPE: DNA
<213> ORGANISM: Homo Sapiens

<400> SEQUENCE: 37
ccgggaagga ttactactca agaaactcga gtttcttgag tagtaatcct tcttttt         57

<210> SEQ ID NO 38
<211> LENGTH: 57
<212> TYPE: DNA
<213> ORGANISM: Homo Sapiens

<400> SEQUENCE: 38
ccggtcgagg aatcagtcat gtaatctcga gattacatga ctgattcctc gattttt    57

<210> SEQ ID NO 39
<211> LENGTH: 10
<212> TYPE: PRT
<213> ORGANISM: Artificial Sequence
<220> FEATURE:
<223> OTHER INFORMATION: Synthetic Amino Acid Sequence

<400> SEQUENCE: 39

Pro Pro Asp Leu Asp Thr Thr Ile Glu Ala
 1               5                  10

<210> SEQ ID NO 40
<211> LENGTH: 10
<212> TYPE: PRT
<213> ORGANISM: Homo Sapiens

<400> SEQUENCE: 40

Pro Pro Pro Leu Asp Ala Val Ile Glu Ala
 1               5                  10

<210> SEQ ID NO 41
<211> LENGTH: 9
<212> TYPE: PRT
<213> ORGANISM: Homo Sapiens

<400> SEQUENCE: 41

Pro Pro Pro Leu Asp Ala Val Ile Glu
 1               5

<210> SEQ ID NO 42
<211> LENGTH: 8
<212> TYPE: PRT
<213> ORGANISM: Homo Sapiens

<400> SEQUENCE: 42

Pro Pro Pro Leu Asp Ala Val Ile
 1               5

<210> SEQ ID NO 43
<211> LENGTH: 7
<212> TYPE: PRT
<213> ORGANISM: Homo Sapiens

<400> SEQUENCE: 43

Pro Pro Pro Leu Asp Ala Val
 1               5

<210> SEQ ID NO 44
<211> LENGTH: 5
<212> TYPE: PRT
<213> ORGANISM: Homo Sapiens

<400> SEQUENCE: 44

Pro Pro Pro Leu Asp
 1               5

<210> SEQ ID NO 45
<211> LENGTH: 4

```
<212> TYPE: PRT
<213> ORGANISM: Homo Sapiens

<400> SEQUENCE: 45

Pro Pro Leu Asp
 1
```